(12) United States Patent
Araki et al.

(10) Patent No.: US 11,306,317 B2
(45) Date of Patent: Apr. 19, 2022

(54) METHOD OF PRODUCING ISOPRENOIDS AND PROTEINS, GENES, AND TRANSFORMANTS FOR THE SAME

(71) Applicants: KIKKOMAN CORPORATION, Noda (JP); NAGASAKI UNIVERSITY, Nagasaki (JP)

(72) Inventors: Yasuko Araki, Noda (JP); Yasutomo Shinohara, Noda (JP); Kiyoshi Kita, Nagasaki (JP)

(73) Assignees: NAGASAKI UNIVERSITY, Nagasaki (JP); KIKKOMAN CORPORATION, Noda (JP)

( * ) Notice: Subject to any disclaimer, the term of this patent is extended or adjusted under 35 U.S.C. 154(b) by 0 days.

(21) Appl. No.: 16/612,413

(22) PCT Filed: May 11, 2018

(86) PCT No.: PCT/JP2018/018405
§ 371 (c)(1),
(2) Date: Nov. 11, 2019

(87) PCT Pub. No.: WO2018/207928
PCT Pub. Date: Nov. 15, 2018

(65) Prior Publication Data
US 2020/0063143 A1     Feb. 27, 2020

(30) Foreign Application Priority Data
May 11, 2017  (JP) .............................. JP2017-094509
Jan. 17, 2018  (JP) .............................. JP2018-005888

(51) Int. Cl.
| | |
|---|---|
| *C12N 15/52* | (2006.01) |
| *C12N 1/14* | (2006.01) |
| *C12P 7/24* | (2006.01) |
| *C12P 7/26* | (2006.01) |
| *C12P 17/04* | (2006.01) |

(52) U.S. Cl.
CPC .............. *C12N 15/52* (2013.01); *C12N 1/14* (2013.01); *C12P 7/24* (2013.01); *C12P 7/26* (2013.01); *C12P 17/04* (2013.01)

(58) Field of Classification Search
CPC ........ C12N 15/52; C12N 1/14; C12N 9/0071; C12N 9/0073; C12N 9/0004; C12N 9/1085; C12N 1/20; C12P 7/24; C12P 7/26; C12P 17/04; C12P 5/007; C07K 14/37; C12Y 114/00
See application file for complete search history.

(56) References Cited

U.S. PATENT DOCUMENTS

| | | |
|---|---|---|
| 2013/0296422 A1 | 11/2013 | Saimoto |
| 2015/0166498 A1 | 6/2015 | Kita |

FOREIGN PATENT DOCUMENTS

| | | |
|---|---|---|
| JP | S45-009832 | 4/1970 |
| JP | S459832 Y1 | 5/1970 |
| JP | S56-025310 | 6/1981 |
| JP | H09-165332 | 6/1997 |
| JP | 2006-213644 | 8/2006 |
| WO | 1148143 A2 * | 10/2001 |

OTHER PUBLICATIONS

Araki et al. Complete biosynthetic pathways of ascofuranone and ascochlorin in Acremonium egyptiacum (synonym: Acremonium sclerotigenum), PNAS, Apr. 23, 2019, 116(17): 8269-8274.*
UniProt accession No. A0A0N8H6E0 (Uncharacterized protein, created Jan. 20, 2016).*
Whisstock et al. Quaterly Reviews of Biophysics, 2003, "Prediction of protein function from protein sequence and structure", 36(3): 307-340.*
Chica et al., Semi-rational approaches to engineering enzyme activity: combining the benefits of directed evolution and rational design. Curr. Opi. Biotechnol., 2005, vol. 16: 378-384.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Genbank[online], Accession No. LKCW01000126.1.
Hosono, K. et al., "LL-Z1272α epoxide, a precursor of ascochlorin produced by a mutant of Ascochytaviciae", The Journal of Antibiotics, 2009, vol. 62, pp. 571-574.
Yu, D. et al., "A specific cytochrome P450 hydroxy lase in herboxidiene biosynthesis", Bioorganic & Medicinal Chemistry Letters, 2014, vol. 24, pp. 4511-4514.
Okada M. et al., "Combinatorial biosynthesis of (+)—daurichromenic acid and its halogenated analoque", Organic Letters, 2017, vol. 19, pp. 3183-3386.
Notification concerning transmittal of international preliminary report on patentability (Form PCT/IB/326) for international patent application No. PCT/JP2018/18405.
Notification concerning transmittal of translation of international preliminary report on patentability (Form PCT/IB/338) for international patent application No. PCT/JP2018/18405.
Extended European Search Report of corresponding EP patent application (Total 10 Pages).
Yasuaki Hijikawa et al, "Re-identification of the ascofuranone-producing fungus Aschochyta viceiae as Acremonium sclerotigenum", The Journal of Anibiotics, vol. 70, No. 3, Nov. 2, 2016 (Nov. 2, 2016), pp. 304-307.

(Continued)

*Primary Examiner* — Iqbal H Chowdhury
(74) *Attorney, Agent, or Firm* — JMB Davis Ben-David

(57) ABSTRACT

The problem to be solved by the present invention is to provide a method of producing isoprenoids including ascofuranone, ilicicolin A, and ascochlorin and derivatives thereof in a high yield as compared to the conventional art, which method enables industrial-scale production of isoprenoids. The problem can be solved by a method of producing isoprenoids such as ascofuranone, ilicicolin A, and ascochlorin, including using a transformant obtained by transformation with biosynthetic genes for ascofuranone, ilicicolin A, or ascochlorin or a knockout organism for these genes to obtain isoprenoids such as ascofuranone, ilicicolin A, and ascochlorin.

6 Claims, 18 Drawing Sheets

Specification includes a Sequence Listing.

(56) References Cited

OTHER PUBLICATIONS

Ping Zhang et al: "Antiinflammatory Sesquiterpenoids from a Sponge-Derived Fungus *Acremonium* sp.", Journal of Natural Products, vol. 72, No. 2, Feb. 27, 2009 (Feb. 7, 2009), pp. 270-275.
Office Action from JPO for Japanese Patent Application No. 2019-517726 (dated Feb. 8, 2022).

* cited by examiner

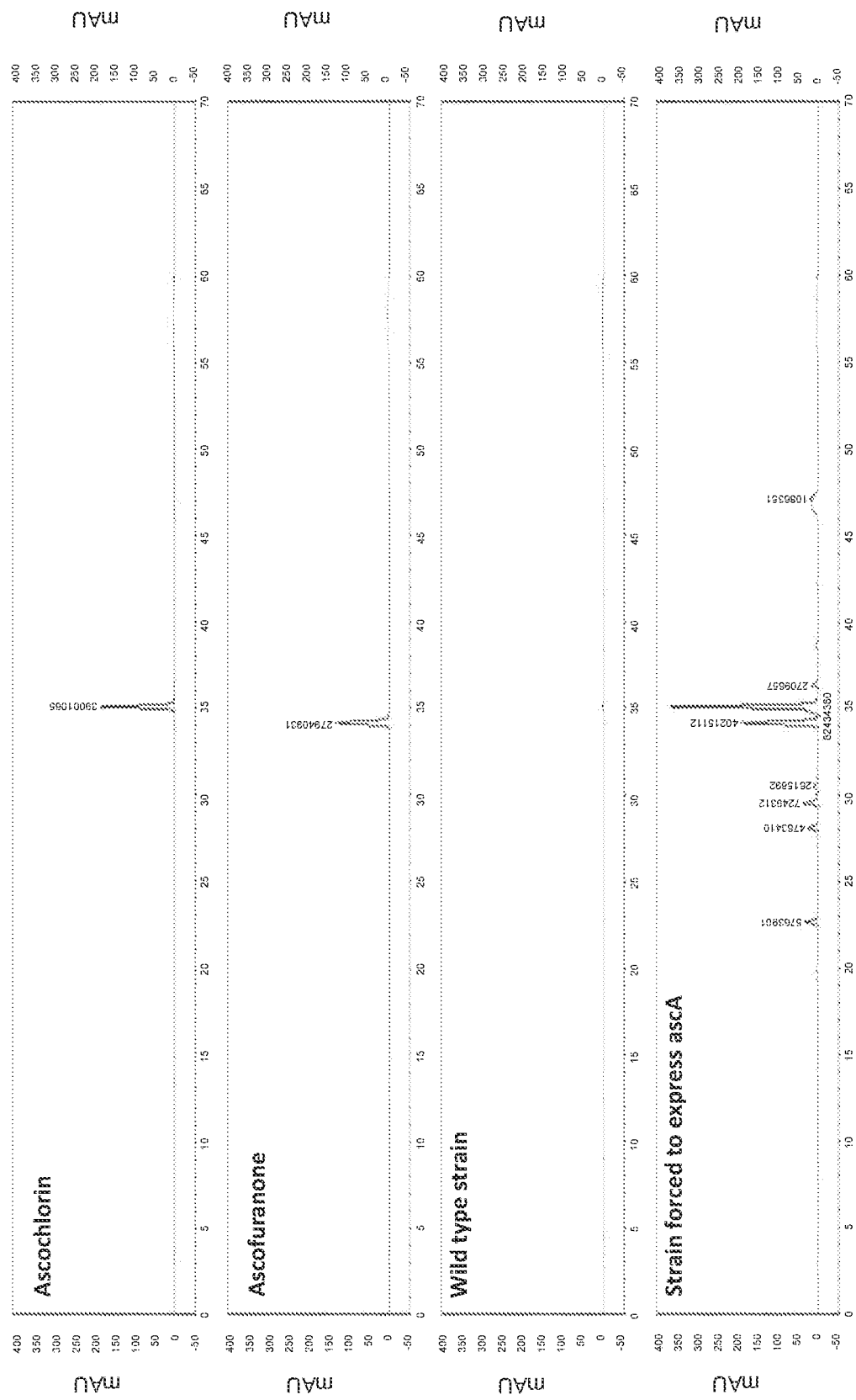

SEQUENCE LISTING

```
<160> NUMBER OF SEQ ID NOS: 67

<210> SEQ ID NO 1
<211> LENGTH: 1011
<212> TYPE: DNA
<213> ORGANISM: Acremonium sclerotigenum

<400> SEQUENCE: 1
atggctgcca agtcaaggag tccaaagcgc gggacttctg agaagacccc gctggtcgag      60
aaagaagcgc cctaccaacc acccacgaag ggcattctct ccaaattgcc cgcttcgtgg     120
gttccgtacg cgcagctcat ccgtctcgag cagccgcacg gaaactacat gatctacttc     180
cctcacatca ttggcctcat gtacgcctct gccatcaggc ctactgagct cagcgtcttg     240
```

| | |
|---|---|
| ggccatcgtg cggctatatt cgccatctgg acattcttga tgcgcggagc cggctgcgct | 300 |
| tggaacgaca acgtcgacca agactttgat cgcaagacgg agcgatgccg acacaggccc | 360 |
| atcgcccgtg gagccatttc aactactcaa ggccacgtct ttactttgat cttgacgctc | 420 |
| cttggttttg ccgccatcca gtcactgccc attgaatgca cctatgtcgg cgtcggcacg | 480 |
| actgtactct ctgcaatcta ccccttrggc aagcgcttca cgcactttgc tcaagtcatc | 540 |
| ctcggaagca cgctggcttc taccatagcc ctctctgcat actcggttgg cttgccggcg | 600 |
| ctgtccaagg actacttcgt cccgacgctg tgcctctcag ctacgattat gcttctcgtc | 660 |
| gtcttttacg acgtcgtgta cgcccgagct gatacgaccg atgatctcaa gtctggtgtc | 720 |
| aagggtatgg cggtccgctt ccgcaatcat cttgagggtc tctttgcctt tatcacgctg | 780 |
| tccattgccg gttcgctgac gacgctggga tacctcgtcg gcatgggaca ttggttctac | 840 |
| ctgttctcag tgggtggatt gacgtttgga cttgtttcca tggtcgccct tacgcactgg | 900 |
| aacatactgc caggctattc ttccgggcga tgctatgcat ttgccatcct gaaccttctg | 960 |
| actggcttca tcatggagta cgccacgaag gactatgttg tgggtgtcta a | 1011 |

<210> SEQ ID NO 2
<211> LENGTH: 3282
<212> TYPE: DNA
<213> ORGANISM: Acremonium sclerotigenum

<400> SEQUENCE: 2

| | |
|---|---|
| atgacggtta acgtcatca caccaacggc gtcaacggcg ccaacgggac caacggtcat | 60 |
| gccaatggaa gcaatggcat caatgacacc aaggccgtga aggaaattgt ccccttcgtt | 120 |
| aagccacaag tgaactttgc ctcagctcaa cgactcgaag gctgtattca ttcattgcca | 180 |
| gagctcgtgg acttcaacag cttgaacaat cagcaccaca cttttttgcgt tcaggcaaag | 240 |
| tcttctgagc catttgacac cattacacat ggcgagttca aggtggccgt gtcgaaatgc | 300 |
| gcggcatggc tcaaggagaa ccttccaatt cgccccagta gcgacgacaa agctctgaca | 360 |
| aagatggcgc ccgttgcgct gtttatggag agtgacattg gtctcgtcat tcacgagttc | 420 |
| gctttgatga gcattggcgt gccgccattg gtactttcac ctcgattgag ccctgtcgcc | 480 |
| atcaatgcac tcctcgaagc tacgggtgct gcttcgttca tcgtatcacc tcgcatgagc | 540 |
| gagcctctaa agggagctct cgccgccctc gcagcaaagg gagtctccac acacattgga | 600 |
| aacccgtaca aggcatacta tcagcctgga gcagatccca agtctgttgc gccttttgag | 660 |
| gttcctcaga accctgagga tgttattctt ctgctccact cgtcaggcac gacaggactt | 720 |
| cccaagccaa ttccaaccac acatcgccag ctcctgttcg cggtgaactg ccacaagttc | 780 |
| gacacggagg agcaagctca gagcctgaac ctgtcaacgc ttcccctgtt ccacggcttc | 840 |
| ggactcgttg ccctgggct ttcgatgtct gcaggcaagc cgacattgta ccctgccagc | 900 |
| gatggcatcc ccaacgccaa gtccatcgtc gatctcatca caagactaa cgctaagagc | 960 |
| atgatgactg tgcctttctt gctggacgac atcacgaatc tgccaaacga ggagggtatc | 1020 |
| aaggctcttg ttcacatgga cttcgtcgga acgggaggtg cagctctcgg agccggtatt | 1080 |
| ggcgaccgcc ttgccaaagg tggtgtgaag ctcctcaact tctacggcac aaccgagaca | 1140 |
| ggaccctat ctcttacatt tgcccccacc gacaactacg actggaagta cttccgcctt | 1200 |
| cgtaccgact gcagtacaa gattgacgag cttgagcccc gtgacggaga aggaggttc | 1260 |
| cgcctcacag tctacccta cggaagcgag ggcttcgaga tttcggacca gctcatccgc | 1320 |

```
aatgagcaat accccgagac agatttcgcc gcggttggtc gcgacgatga tgtgatcgtc    1380
ctggccactg gcgaaaaggc gaaccctctc attcttgaga cgaagctcac cgaggcgccc    1440
atggtcaagg ctgccatcgc cttcggcgag aaccagttca acctgggtgt gatcgtcgag    1500
cctgcagagc ctcttacccc tgatacagaa tcagctttcc gggagagtat ctggccaatt    1560
atcacggcag cttgcgacca gatggacgct ttctcacgca tccctcgcc ggacgccgtc     1620
gtgcttgttc ccgctggtgt ggttattccg cgcaccgaca agggcagtat cgcgcgtaaa    1680
gagacgtacg ccttgttcga taagcagatc aagggcgttt acgagcagct gctcaaggcc    1740
gcagctgatg ccgttgagcc ccttgatctc gacaacctgg agcaaaacct caagagcttg    1800
attcaggagc atctccacat ccaggctccg gcctcagact ggggagtcga ggatagtctc    1860
ttcgatattg gcgtggattc cctgcaggtc ttgcagctgc ccgtatttt ggtcactgca     1920
gcgtccaaga ccgaggcttt caaggatacc gactgcgaga agatgatccc gcctgagttc    1980
gtgtacatga acccatctat tcgcgagatc gcggctgctc ttactaaggg ctccgatggc    2040
ggagatgttt ctcttgagga tgccgctaag gaggtagtcg agctcgcgga gacgtacagc    2100
ctgaagggtg tcagtgccca ggagaaagcg ccgagctcta gcgagggtgc cttcgtcatg    2160
ttgactggtc ccactggaag tctggggtcc cacgttgccg cggatttggc gcgtcgagac    2220
aacgtcgcca aggttgtctg cctggtgcgc aaagacaagg gcacgaacca gcctccgatg    2280
cctggaggaa accccttcga caagaagatt ctcaaggctc gaggcatcca gcttaccgac    2340
gaacaatttg gaaagctcgc taccctcgag gttgacccga ctgcggataa gcttggactt    2400
attcccatgg cctatggcat gatgcaggca aggtcaccc atgttatcca cgccgcgtgg    2460
ccgatgaact atctcatccg cctgcgtaac ttccaatacc agttcaagtt cctgcgcaat    2520
cttctcgagt tcgcttctca gggcccggct cccaccaaga agcgtttcgt cttcatctcg    2580
tcgattgcaa ccgttgcaag gatcggcctc gcgcagcccg gatccatctc agaagccccc    2640
gtctccccgt ccgattctgc atgcgggatt ggatatgccg acgggaagct tgtgtgcgag    2700
aagatcatgg agaaggcagc tcaagattac ggtggtcagc tcgatgtcac atccgtccgt    2760
tgtggacaaa tgaccggctc gaagaagact ggcgtctgga actctaacga gcagattcca    2820
atgctattga agtctgcgca gggtcttgga tccctaccgc agttgtcagg ggagctgtcc    2880
tggatccccg tcgacgatgc cgcgtctacg gtttccgaga ttgcgttttc agatggaagc    2940
atgccaattg tgcaacatct cgagaacccc atccggcagt cttgggacgc tatgctgcaa    3000
agctttgggc gtgagcttgg attgcccgct ggcaaggtcc cgttcggcga gtggctggat    3060
caagttgctg ctgctgatgg agatgacgag actttccccg tcaagaagtt gacattcttc    3120
ttcaagagct tcttccaaag cgttgcttgt ggccaggtcg tcctcgatac tacagtgtct    3180
cggggccaat cgaagacact gaatgccatg actgccgtgg gtgacgagac ggtcaaggcc    3240
tacgcagact actggaagtc tactggatac ctgagcaagt aa                      3282
```

<210> SEQ ID NO 3
<211> LENGTH: 6348
<212> TYPE: DNA
<213> ORGANISM: Acremonium sclerotigenum

<400> SEQUENCE: 3

```
atgacattga tacagacgaa gcattctgct tcggcagctg tcttctcgcc tcagagcaca      60
gcgccaaaac caacccatct cgctcatata cgagcgagac tactagagga tgatcttctc     120
aagccggtga agaggctgtg tgtctcgttg ccaaagacat ggcgggcatt agtctcgaag     180
```

```
caaccggagc ttgggaagaa ccgcaaggct tcagatctta tcgaagcctt cccttcgtgg      240
atcgaggacg ggaagaccga ggtcctcgag actgacatgt cagggctcat caccctgcct      300
cttctcgcag tcatccacat tgtccagtac ctggactaca tccaaagact cgggataagc      360
cactcggaat ttctagaaag tgtcgagagc ggtggtgtcc aaggatattg cataggccta      420
ctgtcggcaa tcgtcgtcag ctctgcggag gacgaggagg ccctaattca cacgctgcc       480 cacggcattc gcctgtcgtt ggcgatcgga gcatttggcg acattggctc ctcgtcagac      540
gaggtcgtct caaacacctt gcaggttcga ttgcgaaacg caggcagcga agaggatcta      600
gttgcgcgtt tccctggttc ctacatctcg accatcacgg acgctaagac aatgagcata      660
atcgctcccc cgcatctcat tgacgcattg aaagaacatg ccgagacgga gggtctgcgc      720
ccgcgggcga tgcacatccg cagcaacctt cacaactcaa gaaacacaga gctcgcccaa      780
caatgcagct cgttgttcga ggattgcccg tttgcatcac ccgataccct gcaagttgcc      840
gtccgctcaa acaagaccgg ctgctactta gagcaggatg ccacgtcgtt ggttgaggag      900
gctgtctcta cagtcctcgc atcccgatgc gattggagtc tagtgatgca gggtcttgca      960
gacgacctaa accagtctgg atccaagcac cattccattc tgctgttcgg catgggcgat     1020
tcggttcctg gagctccttt cagggaacac agcctggata tctccaagat tgatgttttg     1080
tcgctcgtcg agacgcccct ttcagccact ccgccagcca gctccatcga tgacttccct     1140
cccgacagca tagcaatcgt tggctcggcc tgtcggctcc ctggagccaa ctcactggat     1200
gagctctggg atcttattgc cgcagggcga tcaaggctcg aaaaggtccg aaccgaccgt     1260
gtcaacatca aggagtctta ccgcgccagc caggatcctg aatggaccaa gaagcgagag     1320
ttctatggaa actttatcga cgatgtcgac gctttcgacc acgcgttctt caacatctcg     1380
cccagagagg ccaaatacat ggaccctcaa cagaggctac tcctgatggc agcctttgaa     1440
gccatggact ccagcggtta tctccgcagc caccaacgaa atgatggcga cgccgtgggg     1500
tgtttcctgg gtgccagcta cactgagtac accgagaaca ccagcgcgta cagcccatca     1560
gctttcactg ccacatccac cattcgggca ttttttgtctg aaagatcag ctaccacttc      1620 gggtggactg gtccatccga agtgattgat acggcctgct cagccagtat cgtagccgtg     1680
catcgtgctg tgcaagcaat caacgccggt gaatgtccgg tggccctggc cggaggcgtc     1740
aacattatca ccggtgtcaa caactacttc gatcttggca aggccagctt ccttagccag     1800
actggacaat gtaagccctt tgacgactcg ccgacggct actgccgtgc tgatggcgtc      1860
ggcttggttg tcttgaagcc actcagcaag gcggttgcgg acggggacta catccagggt     1920
gtcatcccag ccatcgcaac caaccagggc ggcatcggtg cacctggaat cacggttccc     1980
gacgggatcg ctcagaaggc cctgtaccgt ggcattctcg agaaggctgg cctcaaaggc     2040
gaggacatct cttacgtcga ggcccacggc actggcactc aggtcggaga tccaatcgag     2100
attggctcca tccggggagt ttttggcggt gctcaccgtg cctcgccttt gcatcttgga     2160
tcacttaaag ccaacatagg ccacagtgag accgctgcgg gtgtggcctc tctcttgaag     2220
gttctttcca tggtgcgaaa ccgtggtgtc cctcctttgc aaggcttcaa gcgcttgaac     2280
cacaagattc cggccttgga gctggacaag atggccatcc ccacgaagct actgccctgg     2340
gatagtgacc accgcattgc gtgcatcaac agttacggtg caagtggcag caacagcgca     2400
ctcatctgct ctgagtggct ggaagagccg agcaagctcc ctgatgtgac cggacaacct     2460
cttcaagaat atcctattct tctgagcgca gcgtctaacg agagcttgct gcgctatgcg     2520
```

```
cgtcacctgg ctgattacat caccaagtcg tccgcggatc tgactctggg caacttatcg    2580
tacactctca gccaacgccg taagcaccac cgcattcgct ggtcgacgac tgccaaggac    2640
ctcatcggtc tcatcgagca gcttcgggag tgcacgcccg ccgatttcgt ccaggcacct    2700
cagaagagta gaagattgt tcttaccttc tccgggcaga gccgtacgac gattggcgtc    2760
agcgactcag cacgtctcga gaaccctcgt ttcgagcact acatccagca atgcaacaac    2820
atcctcatgt cctatggttg ccctgatttg ctgccgtacc tgagtcagac agacccgatc    2880
tcggatccga ccatcattca gtgcggcaca gtgactgtgc agtatgcctg cgctcagtgc    2940
tggatcgatg gtggcctcga tgtagctgga attgttggcc attctttggg cgagctaaca    3000
gctctggcta tctcaggtgc cctttctctc gaagatacac tgaaggtggt gtacacccga    3060
gctgaagcca tcaaggcgaa atggggccct gagtctggct ccatgctcgc tatccatgcc    3120
aaccaggaca ctgtcaaatc cattgtcgag atcatcgaga ccatgatcac caaccctgac    3180
gaggcacttg agattgcatg ctacaacagc atcacaagtc acattgttgt tggaaaggag    3240
tcgtccattg agatggcaga gaaggtcatt caacaagatg ctcgctacca cgggctgcgg    3300
taccagcgct tgaacaccag ccatggcttt cactcccgct tcacggagcc tctcctccaa    3360
gacttgatcc acgttgagcg cagcgtagag ttccgcaaac catctattcc cttggagacc    3420
agcactcaga ctccggtcga ctttgcaaag aagcgtcact ccaagtacct ttctaaccat    3480
gctcgggagc ctgtcttctt tgtcgacgcg gcccgccgtc tagagtctcg tctcggcgag    3540
tgcgtgtggc tcgaggctgg atggaacacg cccatcgttg ccatgaccaa acgtgcggtg    3600
gccaacccat cagcccatac cttccaggct gtcacgtctc ctgcagcagt tgcaatggag    3660
ctgtggcggg aaggcatcgc aaccacctac tggagcttct tcaccccccaa ggagagtggt    3720 ttgaagcaca tctggcttcc tccttacagc ttcgaccgac ctaaatactg gttggagcac    3780
gtcgatcgtg ctgtccaaga gcgggatgct gccgcgaacg gctccgcttc gccgccgcct    3840
aagaaggtcc agcaactggt caccctcaag aagaccgagg gcacaaagtc tcagttccgc    3900
ctgcacacaa ctaccgagcg ctacaagcgc attgtgtctg gtcacgctgt tcgcagcaag    3960
cccctgtgcc ctgcttctat gtacatggag tccgccatca tgggtactga gcagcttggt    4020
gcttctctcg tcggcaagac catcactttc gagaatgtct ccttcacgaa gcctttgggg    4080
tgcgatgaaa accttgaggt ttacgtcaac ctcgagcaga acaccgctgc cggtgaagaa    4140
gcttggcatt acgccgtgca atccggaggc aagggcagtc actctgaagg tgacttcttc    4200
gccacaagcg gagagatggc agacattcag ttgtacgaga tgctcatcgc cgacaagatc    4260
gaggctctcc gcaatgatgt tgacgccgaa cgtctgcgca ctgcgacagc ctactctatc    4320
ttctctcgag tggttgagta ctcggatttg ctacggggta tctcgagcat caccatgggt    4380
acccgtcagg ctctcgctca aattaaggtc ccgaagtcca cctttgaggc tcaggagagc    4440
actgtgtccg acttctacga tgcgatcact cttgacacct tcatccaggt cctgggggctt    4500 ctgatcaact ctgacaatga ctccagtgca gatgacgaga tttatgtcgc ttccagtatc    4560
ggaaagatgg ttgtgtcccc caccgagttc aagaagcacg ctacgtggaa tgtttatgcc    4620
acctactccg cttccgacag caaggcatcg agcggtgctg tctttgtctt ctccgaggac    4680
cgcaaattgg tcagcttcgc tacgaagatc caattcatga ggatcaaggc cgcgaagctg    4740
gagaaggtct tggagtcggc gaaccctggc tcgaagacaa agtcgacaaa tggtaacgct    4800
cttccatctg tcccgcgctc tgtgccggct ggcccaactt cggcgcctca gcaagtcgca    4860
ccgaccacca tgccatccgc gccggctcca gtcccagtgg tggcggcagg tgcgagtcca    4920
```

```
tcaaagattg ccgacctcaa gtccttgatc tcggtctaca ccggtgttcc cgttgacgag    4980
atgcaagaca accagaactt tggcgacatg ggacttgact ccctggcatc gatggagctg    5040
gcagacgaga tggagtcaaa gcttggcctg aaggtcgaga ctgaggacct tctcctcggc    5100
agcgttggct ccttgatcaa gttgcttgct ccctcttctg ggcccacagc cgcgttgacg    5160
gagggcctgg tcgagagtta cgatacctgt tcggagtctt ccgattccat tcgcaactcg    5220
accggtttcc acaccacgat cccagctacc ccagctgagc tgcactcaaa cccacctgat    5280
tcgctggatg aagcactgt ctggacgaag ccgaagcact cattgagcgc acggttcaag    5340
cttgacacaa tggtgtacaa ggaggcagag ggcatcgaca ttccagctga tgtctatgtt    5400
ccccaagaac cgcctcaaca acctatgcct gtagcactaa tgatccacgg cggtgggcat    5460
ctcaccctct ctcggcgagc agtccgacca acccagacaa gtacctcct gtctcagggc    5520
attctgcccg ttagcattga ctatcgccta tgcccgcagg tcaatgtcat cgatggccct    5580
gttgctgaca ctcgcgacgc ttgtgaatgg gctcaacggg accttccaaa gataatggcc    5640
tcaaggaaca tcgaggtcga tgcctcgaag ttgattgtca ttggctggtc cactggaggc    5700
acattagcga tgacaacggc ctggacgctg ccatcggctg gacttccccc tcctgttgcg    5760
attttgagct tctattgccc ggtaaattac gaccctgaag cccccatcca gatgggcgag    5820
gagcacgaga agcgcaacat gtctttgagc gaaattcgcc gactactggg tcctcagcct    5880
gctaccagcc acgcttcgca taccaccgac acaaccaagc ttggctgggt gcaggcgaac    5940
gacccacgct cagagctcgt gctagccttg atcaaggagc cgcgcggcat gtccctactg    6000
ttcaacggac ttcctccaac gggtgaggag ctgccagtcc ccgacgccga gcgcgctgca    6060
gctctcagcc ccttggtaca agtccgcaag ggcaactatg acgtgcccac ctatctcatc    6120
tttggcgacg aggatgagat cgctccttt ggcaaggccg tcgagttcgc tcaagcgctc    6180
aaggacgctg gtgtcaagag tggcttccta cccatcaaag gtggtaagca catcttcgac    6240
ctcgggatca gcccgggaag caaggcgtgg gatgagtcca tcggtcctgg gtacgacttc    6300
ttactgggag agcttgagaa cgcccatcgc agatgcagag atgtatag                6348
```

<210> SEQ ID NO 4
<211> LENGTH: 1665
<212> TYPE: DNA
<213> ORGANISM: Acremonium sclerotigenum

<400> SEQUENCE: 4

```
atgtctgcta ttcccaagaa gtgcaccgtg ctggtgattg cggtggccc cggtggcagc      60
tacgccgcca gcgccttggc tcgcgagggc attgacactg tcgttttgga gggtgacaag    120
ttccctcgtt accacattgg cgagagtatg cttgcgtcga tgaggcatct tctgaagttt    180
gtcgagctcg atggcaagtt tgactcttac ggcttcgtca agaagcccgg tgccgccttc    240
aagctcaaca gaacaagcg cgagggctac accgacttcc tcgctgccgg cggccccaac    300
aactacgcct ggaacgtcgt gcgctccgag gcggacaacc tcatgttcca gcacgccggc    360
gagagcggcg ccaagatctt cgacggcgtc tctgtcaagt cgattcagtt cgagaacccc    420
accgaggtcc ccgacggcga gcccaacctg aaccctggca gcctgtgtc ggccacctac    480
cagatcaagg agaccaagga gcagggccag attgactttg actacgtcgt cgatgcttcc    540
ggccgtattg gtatcttgag caccaagtac atgaagaacc gtcgctacaa ccagggtctg    600
aagaacattg ccaactgggg atactgggag ggctgcaaca agtacgcccc cggtacccct    660
```

```
cgcgagaact cgcccttctt cgaggctctg caggacgaga gcggctgggc ttggttcatc      720
cctctccaca acgggaccgt gtcggttggt gtggtcatga accagaagct cgccacccag      780
aagaagcagg aagccgatct tgactccacc gagttctacc acgacaccct gaacaagatc      840
tctcccaacc tgcgggaact gattggcgac ggcaagttcg tgtccaacgt caagaccgcg      900
tccgactact cctacagcgc ctcttcttac tccttcccct acgctcgcat tgtcggcgac      960
gctggttgct tcatcgaccc ctacttctct tccggagtgc acttggcgct gaccagtggt     1020
ctctccgctg ctaccaccat ctctgcctcc atccgggac aggtcgacga ggagctcggc      1080
tccgagtggc acaccaagaa gttctctgac gcttacacgc gtttcttgct ggtcgtgctg     1140
agtgcctaca agcagatcag gcaccaggag gagcctgtcc tctccgactt tgacgaggac     1200
aacttcgacc gcgccttctc cttcttccgt cccatcatcc agggcaccgc cgacgcggcc     1260
aacaacaagc tctcgcaaga ggagctcaac aagacgctcg agttctgcgc cttcgcgttc     1320
gagcccgtcg agaacgacga ggatcgcagc aaggccatgt cggccatgca ggaggccgtt     1380
gacaacggca ctgggtacca ccccgacctg tcccccgagc agctcaaggc cgtcaagcac     1440
atccaggcca acgcgcgat gcgtacctcg gacacgatga acattgagag cttcggcact      1500
gacgcgatca acggctttgt tccgaacctt gtccggggta gcctgggttt gaggaagcag     1560
gaggcgatga gcggtgatat gggtggcgcg aatggtcatg tcgacgagac gaatggtgtg     1620
actgttaatg gacaccacca gcccgagggc gtcaaggctc attga                     1665
```

<210> SEQ ID NO 5
<211> LENGTH: 3195
<212> TYPE: DNA
<213> ORGANISM: Acremonium sclerotigenum

<400> SEQUENCE: 5

```
atgacagaac tgattccagg acctaaaggt ctgccattga ttggcaacgt ccttgacatt        60
gatccagtgg atgctgttgt atgtcttgga cgtattgccg acacctacgg ccacatctac       120
cagctcaaag tcggcggttc agccaagatc ttcatctcga gccgagagct cgtcgatgaa       180
ctatctgacg agagccgctt caccaagctg gtgtcgggcc gctagcaca gcttcgcaat       240
gtctgtcatg actccctttt cacggcgcag tcggacgagc cggcgtggga tcttgcccac       300
aagattctga tgccagcttt cgggcctctt gctattcgag ggatgttcga cgaaatgcac       360
gacatcgcat cgcagctcgt cgtcaagtgg gcgcgattcg ggcctcaaga caccatcgac       420
gtttctggcg actttacacg gctaacactt gatgcaattg cactctgctc catgagcacc       480
cgcttcaact cttcctacaa gcaagatcaa caccccttg tgagctcgat gcttgaggtc        540
ctcgccgagt caggcaagcg agcagtccga ccgccgtttg tcaacgacta catcttccgt       600
ggatcgttaa agcactacaa cactgaaatt gccacaatgc ggcggatcgc aatggatgtc       660
ctagccgagc gtcgcgccaa ccctatggcg tgccagaaga acgacctgct caacgccatg       720
atcaacgggc gggacccgaa gaccggggag gggctatctg acgagagcac gatcaacaat       780
ttgatcgtct tcctcattgc cggtcacgaa accacaagtg gcttactctc tttcttgttc       840
tactacctcc tcacccgtcc cgatgttttc gaaaaggcac aaaaggaggt cgatgagctc       900
gttggacgag gacctgtgac gattgaacac atgtcaaagc tgcattacat cgaagcctgt       960
ctccgggaaa cgcttcgtct gcaccccaca gcaccggtca ttaccttcaa gacgaagccg     1020
gggttcgaaa aggagagcac caccatcgga ggtggcaagt acaagatcga ccgcgatcag     1080
ggcatcgtgg ccctgctggt caatatccag cgcgacccca aggtctgggg cgacgacgcc     1140
```

```
aacgagttca agcctgagcg catgacggat gagaaattca acaacctccc tgccaactgc    1200
tggaagccct tcggcaacgg catccgggga tgcattggcc gcgcgttcgc ctggcaggag    1260
agtctgctga tcacggccat gctgctgcaa aacttcaact tccagctggc ggatccggac    1320
tacaagcttc agatcaagca gacgctcacc atcaagccgg gcaacttctt catgcacgct    1380
aagcttcgag atcacgttga cccgctggag ctggagggca tccttcatgg aggagccaag    1440
aagggctcaa agattgatgg ccatcatctc ggcgcttctc ttgccaccac tgagcaagag    1500
ctgcagccca tgaccattct ttacggctct gactcgggca cttgtgagtc catggcgcag    1560
tcgctggctc gcgcggctag gggtcgtgga tacggtgcga cagtgaaaac tctcgactct    1620
gctgtcgaac aagtccccaa agaccagcct gtggtgatcg tatcgccaag ttacaacggc    1680
cagccaccaa gcaacgctac tgacttcgtc aagtggctag aagcactcga ctccaaggcc    1740
ctcaaggacg tcaagtactc cgtttatggc tgcggcaaca aggattatac ctcaaccttc    1800
catcgcatcc caaagctcct ggacgccgag tttgaaagat gtggcgcaaa gcggatcgcc    1860
gaaactggcc tgggcgatgt caccgttggc gatatcttca gcgactttga gagatggcaa    1920
gacgaccagc tctggccagc gcttggtgtg gcacacatgg atggtgatgc ggatgccgag    1980
tttgacattc atgtcgacag gagtggccgt gccgctgagc ttgaagtcga tgcggatgag    2040
gcgacggtgc agagcaacca ggtcttgaca gcgcccggag agccagagaa gcggtacatc    2100
actttgaagc tgccagaagg aatgcagtac aagagcggag atcacctctc cgtgctacct    2160
ttgaacgatt ggggtgttgt tcgaagggtc ttcgcctggg cgcaactgcc ttgggatgca    2220
gtcgtgacga tccccaaagg aaccaacact tcattaccga ctggtcgcca aatctctgcc    2280
aaagatcttt taagcggata cgttgagctg agccaacctg ctactcgaaa gaacattgcg    2340
aaactcgcag ccagttcgcc atgtcctttc acacagaaga gcctctccaa gcttgaagag    2400
cacttcgaca gcgatattgc tcagaggcga ctctccgttc tcgacatctt ggaggaattc    2460
cctgccatcg atattacctt tggcaacttc atctctatgt taccgccgat gcgtcctcga    2520
cagtattcta ttgcttcgtc gcccatggct gatccatcaa ctgcgacgct gatgtggact    2580
gtactcaact cggaagccta ctctgggtct ggccgacgtt tcttgggggt ctgctcgaca    2640
tacctcgccg ggttggctga aggcgacagg gtccatgtga cggtcaagcc ggcgctgcgc    2700
ttgttccatc ctccttcgga tcccgaaagc atgcccatca tcatggcctg cgccggaacg    2760
ggccttgcac ccttcagggg cttcctcgaa gagcgcgtct gccaaatgaa ggctggtcgc    2820
gcactcgccc cagcttatct cttcgtcggc tgcagagacc cggaaaagga tgctctactc    2880
aaagatgagt tggctcagtg ggagcgagac ggggtggtga agatctacta tgctttctcg    2940
agagccagcg accagagcga cggctgcaaa cacgtccaag accgcatctg gaacgagaga    3000
gatctcgtca gaaagggctt gtttgaaggc aacgccaggt tctttatgtg tggtggctct    3060
ggcgccggca gagcgtcgga ggatgtggtg aagaggatca caaggataaa taaggcgag    3120 agtcaggaga aggcggcgga gagctggttc caggatctga aagcgaatcg ctacgtgacg    3180 gagattttg cataa                                                      3195
```

<210> SEQ ID NO 6
<211> LENGTH: 822
<212> TYPE: DNA
<213> ORGANISM: Acremonium sclerotigenum

<400> SEQUENCE: 6

| | |
|---|---:|
| atggcttttg gtgttgagcc ccccgagcat gtgacgccct ggttcaagcc cgtctacgag | 60 |
| gccacattcc agtttggcgg cgtcgcgtgg acactatgct acatcctcat tgcccgtgag | 120 |
| ggtatgcgca ccaagtccta tggcatgccc ctctttgccc tcgccaacaa cttcgcgtgg | 180 |
| gagatggtct acgctctctg gtcgtggac aacgcctttg agaagaccgc catgacgatc | 240 |
| tggatgttga tcgacacgcc catcatctac tccatcctga agcacggcgt gctggagtgg | 300 |
| cagcatgcgc cgatggtgag caggaacctg aagagcatcc ttgtgggcct gattgccctc | 360 |
| tgtgcggcgg cgcattggag ctggcagagc tggtggattg caacgagat ggggaagaga | 420 |
| gacgacctgg agggcgcaga tttgacgcag atggcctact gggctgtgag catgtgtcag | 480 |
| ttcctggtga gcaccatgtc gctggccatg ttgtgcgtta ggggccactc tggtggcgtg | 540 |
| agctggatga tctggctttc gagattcttg ggtactctca tcggtctcaa catgaactac | 600 |
| gcttgggcat actacacctg gcccgaggcg cacgagtact tcatgtccgc accagccgtc | 660 |
| ttcgtctggg gcgtgaccac cgtgtgcgac atcatctatg gcttcgtgct ttaccacgtc | 720 |
| aagagcaacg agagggagct gtcggatggt cgcaaggtag ctgctgaggc cgatgacgag | 780 |
| caggttgggg gctggagcaa gatgaagact gggaagaact ga | 822 |

<210> SEQ ID NO 7
<211> LENGTH: 1605
<212> TYPE: DNA
<213> ORGANISM: Acremonium sclerotigenum

<400> SEQUENCE: 7

| | |
|---|---:|
| atggggtctc tactattcga cagccctgtt gggcgtttcg tcgcctcgtt ccctgccctg | 60 |
| tcggcggcag ctggactcat cgttgctatt tctttcatct acattcgctt cattaagacg | 120 |
| cccaagctcg atctccccgt ggtgggaaac cctggtgaca gtgggatgc ccagaagcac | 180 |
| attgtcgctg gcgcccgcaa gtaccccgac actccctaca tcctccccat ggatccccct | 240 |
| attgtcgttc tccccattaa gatccaggat gaagtccgca acctccctga gaatgttgtc | 300 |
| tccttcacca aggagcacca gcgcaacttc ttcgcgcagt acaccggtat tggagaccac | 360 |
| cgtcccgaga tgatcactgc catccgtcaa gatctgacaa ggcacatcgt ctctaccatt | 420 |
| cctggtctgc aggaggaggt gcgctacggc ttcgacaagg agtttggcga ttgcaaggac | 480 |
| tggacgcctt tccctctcta catgaaggtt ctccgcattg tcgctctgac ttctggccgt | 540 |
| gtcttcgttg gtcgtcctct ttctcgtgag gaggagtggc tgcagcgcac catcagctac | 600 |
| accatggact gtgtcaaggc ccgcaacgct atccgcgagt accctggtg gaagcgtcgc | 660 |
| tgggtcacca gctccctccc cgagattgcc aagctgactg agcaccgtac tcgtggcggt | 720 |
| gtcttgctca gcccatcat ggacgctcaa ttggccaagg actccaagcg ggagaagatc | 780 |
| atcaacgagg agacgggtga cgaggagggc aacttcattg agtggttgct gaaacacacc | 840 |
| cccggtgacc tcaagatgga tcccgagaat ctggctctga accagatggt tttggcattt | 900 |
| gcttccgttc acactagctc catgtctgtc acccacgcca cctcgagct cgtcacgcga | 960 |
| cctgagtact tcgcccctct ccgtgaggag ctggaggagg tccgtcgcgc ggatggtcac | 1020 |
| actgttgacg acgacggcta catccgtctg aagaaggaat ccattaacaa gctccgcaag | 1080 |
| ctcgacagct tcatgaagga gtcccagcgc ttcaaccctc ccatctcgac tctggtaccc | 1140 |
| cgtatctgca ctgcagactt gaagctgtcc acaggtcaca ctctccccaa gggcacacgc | 1200 |
| atctgcttcc cgtcctacga cgtccaccac aaccccaaga ccaccaccta ctctccagag | 1260 |
| tacaaccctc ctggctacac tcctcccgat cagttcgacg gcctgcgctt cttcaagctg | 1320 |

```
cgcgagatgc ctggcaagga gtcccgtcac cagttcgcca ctgccaacca cgagtccctc    1380
gttttcggct ttggtaacca cacctgccct ggtcgcttct ttgctgcgaa ccagatcaag    1440
attatcctgg ctgagctgtt gatgaactgg gatgtcaggc tgaagggtga cgtcgagcag    1500
aagggaggtc ccgagaagag gccccagaac atggtcgttg atcttgtcat cacgccgaac    1560
ccgatggcta tggttgagat gaagaggcgg agtcgggcgg tttag                    1605
```

<210> SEQ ID NO 8
<211> LENGTH: 1539
<212> TYPE: DNA
<213> ORGANISM: Acremonium sclerotigenum

<400> SEQUENCE: 8

```
atggggctat cactcggtta cagccccgat cgaggcagca ttgggtcttg gatctgtgct      60
gcgccgctaa ttctggctct tttcgtcatc tcgtaccgtc tttttcaatc tgtgatcgac     120
tatcgactgt cgcaccgcaa cggctgcaaa ccaccccccta cgtaccctca caaggattgg     180
tatcttggcc tccaccacgt tttcggcctc ctgaaagcga agaaagaaaa ccgtctgccg     240
actgcattta gcgagctttt cgacgccagt ggccctgatg ttcacactct gggccactat     300
gtccttggca aaaagtctta ctggacaaga gaccccgaga acatcaaagc tgtcctgtcg     360
tccaagttca cgactgggg tcttccgtct gcgaggaagg caactttcag gacatgtctt     420
gggggcggca tctttggtgt cgatggcaaa gagtgggagc actcaagagc aatgctcaag     480
ccttcattca cccggactca gattgggac actgcgactc tgtccaagca cgccgacaac     540
ctcatcgcaa ggattccaga gggggagacg gtggacctag ctgagctatt tcccctcctt     600
accatggatg ttgaacgga aatgctcttc ggcgaaagcg tcgggagcct ggatccagcg     660
gagatcaagc aggccactag gttcactaca tcatttgact acattgttca gacaatgtcc     720
aagcacatgg ccttgcctat ccttacaaag cttcgcgata agacactaca aggatgcgtt     780
gaatttgtcg acgacttcgc agctgatgtg gtaaatcgga ccatcgccaa tgaaagcaaa     840
acggagaagc cgagctccct tgggaagtac atctttccta ctgagctggc caagatgggc     900
ttgccggaga aacaaatcag gatcgaggtt atcaacatca tggttgctgg aagagatacg     960
actgctgcac tcctgagtct catctggtgg tacttagcga aacgacctga tgccgtcatg    1020
aagcttcatc aggagcttga gccgctcgga ggacggccgc caacaggtga agaggtcaag    1080
aagatgaagt acctcagaaa cttcgtcaat gaaatcctga ggctccaccc aatcaacccc    1140
ttgaactccc gtaccgccgc caaagacact accctgccac gcggtgggggg accggacggg    1200 aagtcccctg tattcatacg aaagggaaca cagctcatgt tctcttctgc tgccctgcaa    1260
cgtagaaagg atctgtacgg agaagatgct ttggatctga ggcccgagag atgggagcgc    1320
atccgaccat ccgcgtttga atacattccc ttcggtggcg gtccaaggat ttgtccaggt    1380
caacagcttg cctttgacaga agcatcatac ttcactgcaa gactcttgca agagtttcag    1440
ggagtgactt ccgagtcgag cggaccgttc caggaagcat cgctattct cgtgaccagc    1500 ggagacgggg tcaaggttaa gttccacaag aagcactga                           1539
```

<210> SEQ ID NO 9
<211> LENGTH: 1155
<212> TYPE: DNA
<213> ORGANISM: Acremonium sclerotigenum

<400> SEQUENCE: 9

```
atgccccagc tcgcaggtaa gttaatactg gcagggctca ttcccctggg tgcatgggtc      60
ctccatggtt tcgcctcctg caacggactc atccagatgt tcgaagactt cgggaagcag     120
acagtcctgt cagacggagt gaccgattac actggggctt tcaccggcct tgagggcctg     180
gatcgcctcc tcaggactct gctcaatttt ttctggccag ttgccaacgg acatgattgg     240
gcactgtcgc tgcatgcttt catgtttgct ggccaaggag tcccgctcct ggtgcttaac     300
atgctggaag gggctcgacc tgggaacaag tctctggtcg tcagctacgt taccgtcttc     360
ggaattctgt acatggtggt tggattagcc atcatggccc ccttgtatct cttccttcac     420
ctcttgacat ctcgaaccgc cactgcaccg tccaaggcta agtggccgt ggaccctaac      480
acggcaaaag ccgtcggctt cggcgtgttc gtaggctacg tactgcccac aattttcatg    540
tcattgcctc atccttcgct tctgtccacg gacacaaagg tcttgtcagt tgtcttctgg     600
caagcagtgc cgctgtgggc tcagtgtgt gcatactttg catctacagc tcttggccag      660
tcggcaactt cacggtcgtc cagcaacctg ccttcggcat tgggagcggt atatgccgcc     720
tctctcatca tcgcaactgc cactcacgtt gccacattcg ccatatccgc aaatctatcg     780
gatacctgga gcggcatttt cacctttttg attccaccga tcccttcaa cacggatatg      840
aggatctcat ccttccttga gggcgcaact tggttcttgc agtgggacta cacaatgatg     900
tccttggcat acatggtctg ggccatcggt atccggcacg gggttgaagt acctcggagc     960
tcgcaccact tcgagacact cggaaagatc gccctgcgct cgatggcgaa gttgttggtc    1020
atgggaccca ttggcgcagc gctcagtctt gtatgggaga gagatcaact actgtggcaa    1080
cttgacagcg agagcggtga aagggtgag aaaaataggt ctaggaggat gtcaaggaag     1140
tggatgttct catag                                                     1155

<210> SEQ ID NO 10
<211> LENGTH: 891
<212> TYPE: DNA
<213> ORGANISM: Acremonium sclerotigenum

<400> SEQUENCE: 10
atgacagaca ttcatattca ggacggagat ctctcgagtc tcaaggacaa ggtggtggtg      60
atcacaggtg gctcctcagg tatcggtctt gctactacga accttctgct cgacctcggt     120
gcaaaggtgg tcattggcga tctccaaccg cccacgaccc gtgtggacag cgagcgatgc     180
agctttcaca aagtagatgt gaccgtgtgg tctgaccaac tgacccttttt caaggaagct    240
cgagagctcc atggaagaat tgaccacgtt tttgccaacg caggcgttgg gcctaaagcc     300
gactacctat caacggcact tgaccagaat ggcgatttgg tagagccaac gttcttgacg     360
ctcgatgtca acttgaaggc agtcatctac accgcgacca ttgcttgcta ctacatgcgg     420
gaagagcagc aaagccctgc tggaggaagc atcgtcattg tctcgtctgt tgctggtgtg     480
tcgcgcttca gggcggtcga ctatgccact gccaagcacg gaaatcttgg tttcgcccgc    540
ggtctgcatc agcggttgac ggctgagaac tcgccaactc gcgtcaacct catcgctccg     600
tcgtggacca acacgggctt catgccaccc cagattatgg cggccgttgg cgtcgagcct     660
caagagcctg cctcggtggg tcgagctgcg gcttatctga tggctgatga ctcgagaaaa    720
ggacagatga ttcacattgc gaagggggcga atcgcgagg ttgaagagag cattatgctg     780
cccgctgctg agaaagttgt tgacgtggag aacggggtg tgatggaaga cgacaccctg     840
gctaagatta ttgagaccat gggcatattc aaagcgaagg caacacaatg a              891
```

```
<210> SEQ ID NO 11
<211> LENGTH: 336
<212> TYPE: PRT
<213> ORGANISM: Acremonium sclerotigenum

<400> SEQUENCE: 11

Met Ala Ala Lys Ser Arg Ser Pro Lys Arg Gly Thr Ser Glu Lys Thr
1               5                   10                  15

Pro Leu Val Glu Lys Glu Ala Pro Tyr Gln Pro Thr Lys Gly Ile
            20                  25                  30

Leu Ser Lys Leu Pro Ala Ser Trp Val Pro Tyr Ala Gln Leu Ile Arg
        35                  40                  45

Leu Glu Gln Pro His Gly Asn Tyr Met Ile Tyr Phe Pro His Ile Ile
    50                  55                  60

Gly Leu Met Tyr Ala Ser Ala Ile Arg Pro Thr Glu Leu Ser Val Leu
65                  70                  75                  80

Gly His Arg Ala Ala Ile Phe Ala Ile Trp Thr Phe Leu Met Arg Gly
                85                  90                  95

Ala Gly Cys Ala Trp Asn Asp Asn Val Asp Gln Asp Phe Asp Arg Lys
            100                 105                 110

Thr Glu Arg Cys Arg His Arg Pro Ile Ala Arg Gly Ala Ile Ser Thr
        115                 120                 125

Thr Gln Gly His Val Phe Thr Leu Ile Leu Thr Leu Leu Gly Phe Ala
    130                 135                 140

Ala Ile Gln Ser Leu Pro Ile Glu Cys Thr Tyr Val Gly Val Gly Thr
145                 150                 155                 160

Thr Val Leu Ser Ala Ile Tyr Pro Phe Gly Lys Arg Phe Thr His Phe
                165                 170                 175

Ala Gln Val Ile Leu Gly Ser Thr Leu Ala Ser Thr Ile Ala Leu Ser
            180                 185                 190

Ala Tyr Ser Val Gly Leu Pro Ala Leu Ser Lys Asp Tyr Phe Val Pro
        195                 200                 205

Thr Leu Cys Leu Ser Ala Thr Ile Met Leu Leu Val Val Phe Tyr Asp
    210                 215                 220

Val Val Tyr Ala Arg Ala Asp Thr Thr Asp Asp Leu Lys Ser Gly Val
225                 230                 235                 240

Lys Gly Met Ala Val Arg Phe Arg Asn His Leu Glu Gly Leu Phe Ala
                245                 250                 255

Phe Ile Thr Leu Ser Ile Ala Gly Ser Leu Thr Thr Leu Gly Tyr Leu
            260                 265                 270

Val Gly Met Gly His Trp Phe Tyr Leu Phe Ser Val Gly Gly Leu Thr
        275                 280                 285

Phe Gly Leu Val Ser Met Val Ala Leu Thr His Trp Asn Ile Leu Pro
    290                 295                 300

Gly Tyr Ser Ser Gly Arg Cys Tyr Ala Phe Ala Ile Leu Asn Leu Leu
305                 310                 315                 320

Thr Gly Phe Ile Met Glu Tyr Ala Thr Lys Asp Tyr Val Val Gly Val
                325                 330                 335

<210> SEQ ID NO 12
<211> LENGTH: 1093
<212> TYPE: PRT
<213> ORGANISM: Acremonium sclerotigenum

<400> SEQUENCE: 12

Met Thr Val Asn Gly His His Thr Asn Gly Val Asn Gly Ala Asn Gly
```

-continued

```
1               5                   10                  15
Thr Asn Gly His Ala Asn Gly Ser Asn Gly Ile Asn Asp Thr Lys Ala
                20                  25                  30
Val Lys Glu Ile Val Pro Phe Val Lys Pro Gln Val Asn Phe Ala Ser
                35                  40                  45
Ala Gln Arg Leu Glu Gly Cys Ile His Ser Leu Pro Glu Leu Val Asp
            50                  55                  60
Phe Asn Ser Leu Asn Asn Gln His His Thr Phe Cys Val Gln Ala Lys
 65                 70                  75                  80
Ser Ser Glu Pro Phe Asp Thr Ile Thr His Gly Glu Phe Lys Val Ala
                    85                  90                  95
Val Ser Lys Cys Ala Ala Trp Leu Lys Glu Asn Leu Pro Ile Arg Pro
                100                 105                 110
Ser Ser Asp Asp Lys Ala Leu Thr Lys Met Ala Pro Val Ala Leu Phe
                115                 120                 125
Met Glu Ser Asp Ile Gly Leu Val Ile His Glu Phe Ala Leu Met Ser
            130                 135                 140
Ile Gly Val Pro Pro Leu Val Leu Ser Pro Arg Leu Ser Pro Val Ala
145                 150                 155                 160
Ile Asn Ala Leu Leu Glu Ala Thr Gly Ala Ala Ser Phe Ile Val Ser
                165                 170                 175
Pro Arg Met Ser Glu Pro Leu Lys Gly Ala Leu Ala Ala Leu Ala Ala
                180                 185                 190
Lys Gly Val Ser Thr His Ile Gly Asn Pro Tyr Lys Ala Tyr Tyr Gln
                195                 200                 205
Pro Gly Ala Asp Pro Lys Ser Val Ala Pro Phe Glu Val Pro Gln Asn
210                 215                 220
Pro Glu Asp Val Ile Leu Leu His Ser Ser Gly Thr Thr Gly Leu
225                 230                 235                 240
Pro Lys Pro Ile Pro Thr Thr His Arg Gln Leu Leu Phe Ala Val Asn
                245                 250                 255
Cys His Lys Phe Asp Thr Glu Glu Gln Ala Gln Ser Leu Asn Leu Ser
                260                 265                 270
Thr Leu Pro Leu Phe His Gly Phe Gly Leu Val Ala Pro Gly Leu Ser
            275                 280                 285
Met Ser Ala Gly Lys Pro Thr Leu Tyr Pro Ala Ser Asp Gly Ile Pro
            290                 295                 300
Asn Ala Lys Ser Ile Val Asp Leu Ile Asn Lys Thr Asn Ala Lys Ser
305                 310                 315                 320
Met Met Thr Val Pro Phe Leu Leu Asp Asp Ile Thr Asn Leu Pro Asn
                325                 330                 335
Glu Glu Gly Ile Lys Ala Leu Val His Met Asp Phe Val Gly Thr Gly
                340                 345                 350
Gly Ala Ala Leu Gly Ala Gly Ile Gly Asp Arg Leu Ala Lys Gly Gly
                355                 360                 365
Val Lys Leu Leu Asn Phe Tyr Gly Thr Thr Glu Thr Gly Pro Leu Ser
                370                 375                 380
Leu Thr Phe Ala Pro Thr Asp Asn Tyr Asp Trp Lys Tyr Phe Arg Leu
385                 390                 395                 400
Arg Thr Asp Cys Glu Tyr Lys Ile Asp Glu Leu Glu Pro Arg Asp Gly
                405                 410                 415
Glu Arg Arg Phe Arg Leu Thr Val Tyr Pro Tyr Gly Ser Glu Gly Phe
                420                 425                 430
```

```
Glu Ile Ser Asp Gln Leu Ile Arg Asn Glu Gln Tyr Pro Glu Thr Asp
            435                 440                 445

Phe Ala Ala Val Gly Arg Asp Asp Val Ile Val Leu Ala Thr Gly
450                 455                 460

Glu Lys Ala Asn Pro Leu Ile Leu Glu Thr Lys Leu Thr Glu Ala Pro
465                 470                 475                 480

Met Val Lys Ala Ala Ile Ala Phe Gly Glu Asn Gln Phe Asn Leu Gly
                485                 490                 495

Val Ile Val Glu Pro Ala Glu Pro Leu Thr Pro Asp Thr Glu Ser Ala
                500                 505                 510

Phe Arg Glu Ser Ile Trp Pro Ile Ile Thr Ala Ala Cys Asp Gln Met
            515                 520                 525

Asp Ala Phe Ser Arg Ile Pro Ser Pro Asp Ala Val Val Leu Val Pro
            530                 535                 540

Ala Gly Val Val Ile Pro Arg Thr Asp Lys Gly Ser Ile Ala Arg Lys
545                 550                 555                 560

Glu Thr Tyr Ala Leu Phe Asp Lys Gln Ile Lys Gly Val Tyr Glu Gln
                565                 570                 575

Leu Leu Lys Ala Ala Asp Ala Val Glu Pro Leu Asp Leu Asp Asn
            580                 585                 590

Leu Glu Gln Asn Leu Lys Ser Leu Ile Gln Glu His Leu His Ile Gln
            595                 600                 605

Ala Pro Ala Ser Asp Trp Gly Val Glu Asp Ser Leu Phe Asp Ile Gly
            610                 615                 620

Val Asp Ser Leu Gln Val Leu Gln Leu Arg Arg Ile Leu Val Thr Ala
625                 630                 635                 640

Ala Ser Lys Thr Glu Ala Phe Lys Asp Thr Asp Cys Glu Lys Met Ile
                645                 650                 655

Pro Pro Glu Phe Val Tyr Met Asn Pro Ser Ile Arg Glu Ile Ala Ala
                660                 665                 670

Ala Leu Thr Lys Gly Ser Asp Gly Gly Asp Val Ser Leu Glu Asp Ala
            675                 680                 685

Ala Lys Glu Val Val Glu Leu Ala Glu Thr Tyr Ser Leu Lys Gly Val
            690                 695                 700

Ser Ala Gln Glu Lys Ala Pro Ser Ser Glu Gly Ala Phe Val Met
705                 710                 715                 720

Leu Thr Gly Ala Thr Gly Ser Leu Gly Ser His Val Ala Ala Asp Leu
                725                 730                 735

Ala Arg Arg Asp Asn Val Ala Lys Val Val Cys Leu Val Arg Lys Asp
                740                 745                 750

Lys Gly Thr Asn Gln Pro Pro Met Pro Gly Gly Asn Pro Phe Asp Lys
            755                 760                 765

Lys Ile Leu Lys Ala Arg Gly Ile Gln Leu Thr Asp Glu Gln Phe Gly
            770                 775                 780

Lys Leu Ala Thr Leu Glu Val Asp Pro Thr Ala Asp Lys Leu Gly Leu
785                 790                 795                 800

Ile Pro Met Ala Tyr Gly Met Met Gln Ala Lys Val Thr His Val Ile
                805                 810                 815

His Ala Ala Trp Pro Met Asn Tyr Leu Ile Arg Leu Arg Asn Phe Gln
                820                 825                 830

Tyr Gln Phe Lys Phe Leu Arg Asn Leu Leu Glu Phe Ala Ser Gln Gly
            835                 840                 845
```

Pro Ala Pro Thr Lys Lys Arg Phe Val Phe Ile Ser Ser Ile Ala Thr
850                 855                 860

Val Ala Arg Ile Gly Leu Ala Gln Pro Gly Ser Ile Ser Glu Ala Pro
865                 870                 875                 880

Val Ser Pro Ser Asp Ser Ala Cys Gly Ile Gly Tyr Ala Asp Gly Lys
                885                 890                 895

Leu Val Cys Glu Lys Ile Met Glu Lys Ala Ala Gln Asp Tyr Gly Gly
                900                 905                 910

Gln Leu Asp Val Thr Ser Val Arg Cys Gly Gln Met Thr Gly Ser Lys
                915                 920                 925

Lys Thr Gly Val Trp Asn Ser Asn Glu Gln Ile Pro Met Leu Leu Lys
930                 935                 940

Ser Ala Gln Gly Leu Gly Ser Leu Pro Gln Leu Ser Gly Glu Leu Ser
945                 950                 955                 960

Trp Ile Pro Val Asp Asp Ala Ala Ser Thr Val Ser Glu Ile Ala Phe
                965                 970                 975

Ser Asp Gly Ser Met Pro Ile Val Gln His Leu Glu Asn Pro Ile Arg
                980                 985                 990

Gln Ser Trp Asp Ala Met Leu Gln Ser Phe Gly Arg Glu Leu Gly Leu
                995                 1000                1005

Pro Ala Gly Lys Val Pro Phe Gly Glu Trp Leu Asp Gln Val Ala
1010                1015                1020

Ala Ala Asp Gly Asp Asp Glu Thr Phe Pro Val Lys Lys Leu Thr
1025                1030                1035

Phe Phe Phe Lys Ser Phe Phe Gln Ser Val Ala Cys Gly Gln Val
1040                1045                1050

Val Leu Asp Thr Thr Val Ser Arg Gly Gln Ser Lys Thr Leu Asn
1055                1060                1065

Ala Met Thr Ala Val Gly Asp Glu Thr Val Lys Ala Tyr Ala Asp
1070                1075                1080

Tyr Trp Lys Ser Thr Gly Tyr Leu Ser Lys
1085                1090

<210> SEQ ID NO 13
<211> LENGTH: 2115
<212> TYPE: PRT
<213> ORGANISM: Acremonium sclerotigenum

<400> SEQUENCE: 13

Met Thr Leu Ile Gln Thr Lys His Ser Ala Ser Ala Ala Val Phe Ser
1               5                   10                  15

Pro Gln Ser Thr Ala Pro Lys Pro Thr His Leu Ala His Ile Arg Ala
                20                  25                  30

Arg Leu Leu Glu Asp Asp Leu Leu Lys Pro Val Lys Glu Ala Val Val
            35                  40                  45

Ser Leu Pro Lys Thr Trp Arg Ala Leu Val Ser Lys Gln Pro Glu Leu
        50                  55                  60

Gly Lys Asn Arg Lys Ala Ser Asp Leu Ile Glu Ala Phe Pro Ser Trp
65                  70                  75                  80

Ile Glu Asp Gly Lys Thr Glu Val Leu Glu Thr Asp Met Ser Gly Leu
                85                  90                  95

Ile Thr Leu Pro Leu Leu Ala Val Ile His Ile Val Gln Tyr Leu Asp
                100                 105                 110

Tyr Ile Gln Arg Leu Gly Ile Ser His Ser Glu Phe Leu Glu Ser Val
            115                 120                 125

```
Glu Ser Gly Gly Val Gln Gly Tyr Cys Ile Gly Leu Leu Ser Ala Ile
            130                 135                 140

Val Val Ser Ser Ala Glu Asp Glu Glu Ala Leu Ile Gln His Ala Ala
145                 150                 155                 160

His Gly Ile Arg Leu Ser Leu Ala Ile Gly Ala Phe Gly Asp Ile Gly
                165                 170                 175

Ser Ser Ser Asp Glu Val Val Ser Asn Thr Leu Gln Val Arg Leu Arg
            180                 185                 190

Asn Ala Gly Ser Glu Glu Asp Leu Val Ala Arg Phe Pro Gly Ser Tyr
            195                 200                 205

Ile Ser Thr Ile Thr Asp Ala Lys Thr Met Ser Ile Ile Ala Pro Pro
210                 215                 220

His Leu Ile Asp Ala Leu Lys Glu His Ala Glu Thr Glu Gly Leu Arg
225                 230                 235                 240

Pro Arg Ala Met His Ile Arg Ser Asn Leu His Asn Ser Arg Asn Thr
                245                 250                 255

Glu Leu Ala Gln Gln Cys Ser Ser Leu Phe Glu Asp Cys Pro Phe Ala
            260                 265                 270

Ser Pro Asp Thr Leu Gln Val Ala Val Arg Ser Asn Lys Thr Gly Cys
            275                 280                 285

Tyr Leu Glu Gln Asp Ala Thr Ser Leu Val Glu Glu Ala Val Ser Thr
290                 295                 300

Val Leu Ala Ser Arg Cys Asp Trp Ser Leu Val Met Gln Gly Leu Ala
305                 310                 315                 320

Asp Asp Leu Asn Gln Ser Gly Ser Lys His His Ser Ile Leu Leu Phe
                325                 330                 335

Gly Met Gly Asp Ser Val Pro Gly Ala Pro Phe Arg Glu His Ser Leu
            340                 345                 350

Asp Ile Ser Lys Ile Asp Val Leu Ser Leu Val Glu Thr Pro Leu Ser
            355                 360                 365

Ala Thr Pro Pro Ala Ser Ser Ile Asp Asp Phe Pro Pro Asp Ser Ile
370                 375                 380

Ala Ile Val Gly Ser Ala Cys Arg Leu Pro Gly Ala Asn Ser Leu Asp
385                 390                 395                 400

Glu Leu Trp Asp Leu Ile Ala Ala Gly Arg Ser Arg Leu Glu Lys Val
                405                 410                 415

Arg Thr Asp Arg Val Asn Ile Lys Glu Ser Tyr Arg Ala Ser Gln Asp
            420                 425                 430

Pro Glu Trp Thr Lys Lys Arg Glu Phe Tyr Gly Asn Phe Ile Asp Asp
            435                 440                 445

Val Asp Ala Phe Asp His Ala Phe Phe Asn Ile Ser Pro Arg Glu Ala
450                 455                 460

Lys Tyr Met Asp Pro Gln Gln Arg Leu Leu Leu Met Ala Ala Phe Glu
465                 470                 475                 480

Ala Met Asp Ser Ser Gly Tyr Leu Arg Ser His Gln Arg Asn Asp Gly
                485                 490                 495

Asp Ala Val Gly Cys Phe Leu Gly Ala Ser Tyr Thr Glu Tyr Thr Glu
            500                 505                 510

Asn Thr Ser Ala Tyr Ser Pro Ser Ala Phe Thr Ala Thr Ser Thr Ile
            515                 520                 525

Arg Ala Phe Leu Ser Gly Lys Ile Ser Tyr His Phe Gly Trp Thr Gly
530                 535                 540
```

-continued

```
Pro Ser Glu Val Ile Asp Thr Ala Cys Ser Ala Ser Ile Val Ala Val
545                 550                 555                 560

His Arg Ala Val Gln Ala Ile Asn Ala Gly Glu Cys Pro Val Ala Leu
                565                 570                 575

Ala Gly Gly Val Asn Ile Ile Thr Gly Val Asn Asn Tyr Phe Asp Leu
            580                 585                 590

Gly Lys Ala Ser Phe Leu Ser Gln Thr Gly Gln Cys Lys Pro Phe Asp
        595                 600                 605

Asp Ser Ala Asp Gly Tyr Cys Arg Ala Asp Gly Val Gly Leu Val Val
    610                 615                 620

Leu Lys Pro Leu Ser Lys Ala Val Ala Asp Gly Asp Tyr Ile Gln Gly
625                 630                 635                 640

Val Ile Pro Ala Ile Ala Thr Asn Gln Gly Gly Ile Gly Ala Pro Gly
                645                 650                 655

Ile Thr Val Pro Asp Gly Ile Ala Gln Lys Ala Leu Tyr Arg Gly Ile
            660                 665                 670

Leu Glu Lys Ala Gly Leu Lys Gly Glu Asp Ile Ser Tyr Val Glu Ala
        675                 680                 685

His Gly Thr Gly Thr Gln Val Gly Asp Pro Ile Glu Ile Gly Ser Ile
    690                 695                 700

Arg Glu Val Phe Gly Gly Ala His Arg Ala Ser Pro Leu His Leu Gly
705                 710                 715                 720

Ser Leu Lys Ala Asn Ile Gly His Ser Glu Thr Ala Ala Gly Val Ala
                725                 730                 735

Ser Leu Leu Lys Val Leu Ser Met Val Arg Asn Arg Gly Val Pro Pro
            740                 745                 750

Leu Gln Gly Phe Lys Arg Leu Asn His Lys Ile Pro Ala Leu Glu Leu
        755                 760                 765

Asp Lys Met Ala Ile Pro Thr Lys Leu Leu Pro Trp Asp Ser Asp His
    770                 775                 780

Arg Ile Ala Cys Ile Asn Ser Tyr Gly Ala Ser Gly Ser Asn Ser Ala
785                 790                 795                 800

Leu Ile Cys Ser Glu Trp Leu Glu Pro Ser Lys Leu Pro Asp Val
                805                 810                 815

Thr Gly Gln Pro Leu Gln Glu Tyr Pro Ile Leu Leu Ser Ala Ala Ser
            820                 825                 830

Asn Glu Ser Leu Leu Arg Tyr Ala Arg His Leu Ala Asp Tyr Ile Thr
        835                 840                 845

Lys Ser Ser Ala Asp Leu Thr Leu Gly Asn Leu Ser Tyr Thr Leu Ser
    850                 855                 860

Gln Arg Arg Lys His His Arg Ile Arg Trp Ser Thr Thr Ala Lys Asp
865                 870                 875                 880

Leu Ile Gly Leu Ile Glu Gln Leu Arg Glu Cys Thr Pro Ala Asp Phe
                885                 890                 895

Val Gln Ala Pro Gln Lys Ser Lys Lys Ile Val Leu Thr Phe Ser Gly
            900                 905                 910

Gln Ser Arg Thr Thr Ile Gly Val Ser Asp Ser Ala Arg Leu Glu Asn
        915                 920                 925

Pro Arg Phe Glu His Tyr Ile Gln Gln Cys Asn Asn Ile Leu Met Ser
    930                 935                 940

Tyr Gly Cys Pro Asp Leu Leu Pro Tyr Leu Ser Gln Thr Asp Pro Ile
945                 950                 955                 960

Ser Asp Pro Thr Ile Ile Gln Cys Gly Thr Val Thr Val Gln Tyr Ala
```

```
                965                 970                 975
Cys Ala Gln Cys Trp Ile Asp Gly Gly Leu Asp Val Ala Gly Ile Val
                980                 985                 990
Gly His Ser Leu Gly Glu Leu Thr Ala Leu Ala Ile Ser Gly Ala Leu
                995                1000                1005
Ser Leu Glu Asp Thr Leu Lys Val Val Tyr Thr Arg Ala Glu Ala
        1010                1015                1020
Ile Lys Ala Lys Trp Gly Pro Glu Ser Gly Ser Met Leu Ala Ile
        1025                1030                1035
His Ala Asn Gln Asp Thr Val Lys Ser Ile Val Glu Ile Ile Glu
        1040                1045                1050
Thr Met Ile Thr Asn Pro Asp Glu Ala Leu Glu Ile Ala Cys Tyr
        1055                1060                1065
Asn Ser Ile Thr Ser His Ile Val Val Gly Lys Glu Ser Ser Ile
        1070                1075                1080
Glu Met Ala Glu Lys Val Ile Gln Gln Asp Ala Arg Tyr His Gly
        1085                1090                1095
Leu Arg Tyr Gln Arg Leu Asn Thr Ser His Gly Phe His Ser Arg
        1100                1105                1110
Phe Thr Glu Pro Leu Leu Gln Asp Leu Ile His Val Glu Arg Ser
        1115                1120                1125
Val Glu Phe Arg Lys Pro Ser Ile Pro Leu Glu Thr Ser Thr Gln
        1130                1135                1140
Thr Pro Val Asp Phe Ala Lys Lys Arg His Ser Lys Tyr Leu Ser
        1145                1150                1155
Asn His Ala Arg Glu Pro Val Phe Phe Val Asp Ala Ala Arg Arg
        1160                1165                1170
Leu Glu Ser Arg Leu Gly Glu Cys Val Trp Leu Glu Ala Gly Trp
        1175                1180                1185
Asn Thr Pro Ile Val Ala Met Thr Lys Arg Ala Val Ala Asn Pro
        1190                1195                1200
Ser Ala His Thr Phe Gln Ala Val Thr Ser Pro Ala Ala Val Ala
        1205                1210                1215
Met Glu Leu Trp Arg Glu Gly Ile Ala Thr Thr Tyr Trp Ser Phe
        1220                1225                1230
Phe Thr Pro Lys Glu Ser Gly Leu Lys His Ile Trp Leu Pro Pro
        1235                1240                1245
Tyr Ser Phe Asp Arg Pro Lys Tyr Trp Leu Glu His Val Asp Arg
        1250                1255                1260
Ala Val Gln Glu Arg Asp Ala Ala Asn Gly Ser Ala Ser Pro
        1265                1270                1275
Pro Pro Lys Lys Val Gln Gln Leu Val Thr Leu Lys Lys Thr Glu
        1280                1285                1290
Gly Thr Lys Ser Gln Phe Arg Leu His Thr Thr Glu Arg Tyr
        1295                1300                1305
Lys Arg Ile Val Ser Gly His Ala Val Arg Ser Lys Pro Leu Cys
        1310                1315                1320
Pro Ala Ser Met Tyr Met Glu Ser Ala Ile Met Gly Thr Glu Gln
        1325                1330                1335
Leu Gly Ala Ser Leu Val Gly Lys Thr Ile Thr Phe Glu Asn Val
        1340                1345                1350
Ser Phe Thr Lys Pro Leu Gly Cys Asp Glu Asn Leu Glu Val Tyr
        1355                1360                1365
```

```
Val Asn Leu Glu Gln Asn Thr Ala Ala Gly Glu Glu Ala Trp His
    1370            1375            1380

Tyr Ala Val Gln Ser Gly Gly Lys Gly Ser His Ser Glu Gly Asp
    1385            1390            1395

Phe Phe Ala Thr Ser Gly Glu Met Ala Asp Ile Gln Leu Tyr Glu
    1400            1405            1410

Met Leu Ile Ala Asp Lys Ile Glu Ala Leu Arg Asn Asp Val Asp
    1415            1420            1425

Ala Glu Arg Leu Arg Thr Ala Thr Ala Tyr Ser Ile Phe Ser Arg
    1430            1435            1440

Val Val Glu Tyr Ser Asp Leu Leu Arg Gly Ile Ser Ser Ile Thr
    1445            1450            1455

Met Gly Thr Arg Gln Ala Leu Ala Gln Ile Lys Val Pro Lys Ser
    1460            1465            1470

Thr Phe Glu Ala Gln Glu Ser Thr Val Ser Asp Phe Tyr Asp Ala
    1475            1480            1485

Ile Thr Leu Asp Thr Phe Ile Gln Val Leu Gly Leu Leu Ile Asn
    1490            1495            1500

Ser Asp Asn Asp Ser Ser Ala Asp Asp Glu Ile Tyr Val Ala Ser
    1505            1510            1515

Ser Ile Gly Lys Met Val Val Ser Pro Thr Glu Phe Lys Lys His
    1520            1525            1530

Ala Thr Trp Asn Val Tyr Ala Thr Tyr Ser Ala Ser Asp Ser Lys
    1535            1540            1545

Ala Ser Ser Gly Ala Val Phe Val Phe Ser Glu Asp Arg Lys Leu
    1550            1555            1560

Val Ser Phe Ala Thr Lys Ile Gln Phe Met Arg Ile Lys Ala Ala
    1565            1570            1575

Lys Leu Glu Lys Val Leu Glu Ser Ala Asn Pro Gly Ser Lys Thr
    1580            1585            1590

Lys Ser Thr Asn Gly Asn Ala Leu Pro Ser Val Pro Arg Ser Val
    1595            1600            1605

Pro Ala Gly Pro Thr Ser Ala Pro Gln Gln Val Ala Pro Thr Thr
    1610            1615            1620

Met Pro Ser Ala Pro Ala Pro Val Pro Val Val Ala Ala Gly Ala
    1625            1630            1635

Ser Pro Ser Lys Ile Ala Asp Leu Lys Ser Leu Ile Ser Val Tyr
    1640            1645            1650

Thr Gly Val Pro Val Asp Glu Met Gln Asp Asn Gln Asn Phe Gly
    1655            1660            1665

Asp Met Gly Leu Asp Ser Leu Ala Ser Met Glu Leu Ala Asp Glu
    1670            1675            1680

Met Glu Ser Lys Leu Gly Leu Lys Val Glu Thr Glu Asp Leu Leu
    1685            1690            1695

Leu Gly Ser Val Gly Ser Leu Ile Lys Leu Leu Ala Pro Ser Ser
    1700            1705            1710

Gly Pro Thr Ala Ala Leu Thr Glu Gly Leu Val Glu Ser Tyr Asp
    1715            1720            1725

Thr Cys Ser Glu Ser Ser Asp Ser Ile Arg Asn Ser Thr Gly Phe
    1730            1735            1740

His Thr Thr Ile Pro Ala Thr Pro Ala Glu Leu His Ser Asn Pro
    1745            1750            1755
```

```
Pro Asp Ser Leu Asp Gly Ser Thr Val Trp Thr Lys Pro Lys His
    1760                1765                1770

Ser Leu Ser Ala Arg Phe Lys Leu Asp Thr Met Val Tyr Lys Glu
    1775                1780                1785

Ala Glu Gly Ile Asp Ile Pro Ala Asp Val Tyr Val Pro Gln Glu
    1790                1795                1800

Pro Pro Gln Gln Pro Met Pro Val Ala Leu Met Ile His Gly Gly
    1805                1810                1815

Gly His Leu Thr Leu Ser Arg Arg Ala Val Arg Pro Thr Gln Thr
    1820                1825                1830

Lys Tyr Leu Leu Ser Gln Gly Ile Leu Pro Val Ser Ile Asp Tyr
    1835                1840                1845

Arg Leu Cys Pro Gln Val Asn Val Ile Asp Gly Pro Val Ala Asp
    1850                1855                1860

Thr Arg Asp Ala Cys Glu Trp Ala Gln Arg Asp Leu Pro Lys Ile
    1865                1870                1875

Met Ala Ser Arg Asn Ile Glu Val Asp Ala Ser Lys Leu Ile Val
    1880                1885                1890

Ile Gly Trp Ser Thr Gly Gly Thr Leu Ala Met Thr Thr Ala Trp
    1895                1900                1905

Thr Leu Pro Ser Ala Gly Leu Pro Pro Val Ala Ile Leu Ser
    1910                1915                1920

Phe Tyr Cys Pro Val Asn Tyr Asp Pro Glu Ala Pro Ile Gln Met
    1925                1930                1935

Gly Glu Glu His Glu Lys Arg Asn Met Ser Leu Ser Glu Ile Arg
    1940                1945                1950

Arg Leu Leu Gly Pro Gln Pro Ala Thr Ser His Ala Ser His Thr
    1955                1960                1965

Thr Asp Thr Thr Lys Leu Gly Trp Val Gln Ala Asn Asp Pro Arg
    1970                1975                1980

Ser Glu Leu Val Leu Ala Leu Ile Lys Glu Pro Arg Gly Met Ser
    1985                1990                1995

Leu Leu Phe Asn Gly Leu Pro Pro Thr Gly Glu Glu Leu Pro Val
    2000                2005                2010

Pro Asp Ala Glu Arg Ala Ala Leu Ser Pro Leu Val Gln Val
    2015                2020                2025

Arg Lys Gly Asn Tyr Asp Val Pro Thr Tyr Leu Ile Phe Gly Asp
    2030                2035                2040

Glu Asp Glu Ile Ala Pro Phe Gly Lys Ala Val Glu Phe Ala Gln
    2045                2050                2055

Ala Leu Lys Asp Ala Gly Val Lys Ser Gly Phe Leu Pro Ile Lys
    2060                2065                2070

Gly Gly Lys His Ile Phe Asp Leu Gly Ile Ser Pro Gly Ser Lys
    2075                2080                2085

Ala Trp Asp Glu Ser Ile Gly Pro Gly Tyr Asp Phe Leu Leu Gly
    2090                2095                2100

Glu Leu Glu Asn Ala His Arg Arg Cys Arg Asp Val
    2105                2110                2115

<210> SEQ ID NO 14
<211> LENGTH: 554
<212> TYPE: PRT
<213> ORGANISM: Acremonium sclerotigenum

<400> SEQUENCE: 14
```

```
Met Ser Ala Ile Pro Lys Lys Cys Thr Val Leu Val Ile Gly Gly Gly
1               5                   10                  15

Pro Gly Gly Ser Tyr Ala Ala Ser Ala Leu Ala Arg Glu Gly Ile Asp
            20                  25                  30

Thr Val Val Leu Glu Gly Asp Lys Phe Pro Arg Tyr His Ile Gly Glu
            35                  40                  45

Ser Met Leu Ala Ser Met Arg His Leu Leu Lys Phe Val Glu Leu Asp
    50                  55                  60

Gly Lys Phe Asp Ser Tyr Gly Phe Val Lys Lys Pro Gly Ala Ala Phe
65                  70                  75                  80

Lys Leu Asn Lys Asn Lys Arg Glu Gly Tyr Thr Asp Phe Leu Ala Ala
                85                  90                  95

Gly Gly Pro Asn Asn Tyr Ala Trp Asn Val Val Arg Ser Glu Ala Asp
                100                 105                 110

Asn Leu Met Phe Gln His Ala Gly Glu Ser Gly Ala Lys Ile Phe Asp
            115                 120                 125

Gly Val Ser Val Lys Ser Ile Gln Phe Glu Asn Pro Thr Glu Val Pro
130                 135                 140

Asp Gly Glu Pro Asn Leu Asn Pro Gly Lys Pro Val Ser Ala Thr Tyr
145                 150                 155                 160

Gln Ile Lys Glu Thr Lys Glu Gln Gly Gln Ile Asp Phe Asp Tyr Val
                165                 170                 175

Val Asp Ala Ser Gly Arg Ile Gly Ile Leu Ser Thr Lys Tyr Met Lys
            180                 185                 190

Asn Arg Arg Tyr Asn Gln Gly Leu Lys Asn Ile Ala Asn Trp Gly Tyr
            195                 200                 205

Trp Glu Gly Cys Asn Lys Tyr Ala Pro Gly Thr Pro Arg Glu Asn Ser
210                 215                 220

Pro Phe Phe Glu Ala Leu Gln Asp Glu Ser Gly Trp Ala Trp Phe Ile
225                 230                 235                 240

Pro Leu His Asn Gly Thr Val Ser Val Gly Val Val Met Asn Gln Lys
                245                 250                 255

Leu Ala Thr Gln Lys Lys Gln Glu Ala Asp Leu Asp Ser Thr Glu Phe
                260                 265                 270

Tyr His Asp Thr Leu Asn Lys Ile Ser Pro Asn Leu Arg Glu Leu Ile
            275                 280                 285

Gly Asp Gly Lys Phe Val Ser Asn Val Lys Thr Ala Ser Asp Tyr Ser
290                 295                 300

Tyr Ser Ala Ser Ser Tyr Ser Phe Pro Tyr Ala Arg Ile Val Gly Asp
305                 310                 315                 320

Ala Gly Cys Phe Ile Asp Pro Tyr Phe Ser Ser Gly Val His Leu Ala
                325                 330                 335

Leu Thr Ser Gly Leu Ser Ala Ala Thr Thr Ile Ser Ala Ser Ile Arg
            340                 345                 350

Gly Gln Val Asp Glu Glu Leu Gly Ser Glu Trp His Thr Lys Lys Phe
            355                 360                 365

Ser Asp Ala Tyr Thr Arg Phe Leu Leu Val Val Leu Ser Ala Tyr Lys
    370                 375                 380

Gln Ile Arg His Gln Glu Glu Pro Val Leu Ser Asp Phe Asp Glu Asp
385                 390                 395                 400

Asn Phe Asp Arg Ala Phe Ser Phe Arg Pro Ile Ile Gln Gly Thr
                405                 410                 415
```

Ala Asp Ala Ala Asn Asn Lys Leu Ser Gln Glu Glu Leu Asn Lys Thr
            420                 425                 430

Leu Glu Phe Cys Ala Phe Ala Phe Glu Pro Val Glu Asn Asp Glu Asp
        435                 440                 445

Arg Ser Lys Ala Met Ser Ala Met Gln Glu Ala Val Asp Asn Gly Thr
    450                 455                 460

Gly Tyr His Pro Asp Leu Ser Pro Glu Gln Leu Lys Ala Val Lys His
465                 470                 475                 480

Ile Gln Ala Arg Arg Ala Met Arg Thr Ser Asp Thr Met Asn Ile Glu
            485                 490                 495

Ser Phe Gly Thr Asp Ala Ile Asn Gly Phe Val Pro Asn Leu Val Arg
        500                 505                 510

Gly Ser Leu Gly Leu Arg Lys Gln Glu Ala Met Ser Gly Asp Met Gly
    515                 520                 525

Gly Ala Asn Gly His Val Asp Glu Thr Asn Gly Val Thr Val Asn Gly
530                 535                 540

His His Gln Pro Glu Gly Val Lys Ala His
545                 550

<210> SEQ ID NO 15
<211> LENGTH: 1064
<212> TYPE: PRT
<213> ORGANISM: Acremonium sclerotigenum

<400> SEQUENCE: 15

Met Thr Glu Leu Ile Pro Gly Pro Lys Gly Leu Pro Leu Ile Gly Asn
1               5                   10                  15

Val Leu Asp Ile Asp Pro Val Asp Ala Val Val Cys Leu Gly Arg Ile
            20                  25                  30

Ala Asp Thr Tyr Gly His Ile Tyr Gln Leu Lys Val Gly Gly Ser Ala
        35                  40                  45

Lys Ile Phe Ile Ser Ser Arg Glu Leu Val Asp Glu Leu Ser Asp Glu
    50                  55                  60

Ser Arg Phe Thr Lys Leu Val Ser Gly Pro Leu Ala Gln Leu Arg Asn
65                  70                  75                  80

Val Cys His Asp Ser Leu Phe Thr Ala Gln Ser Asp Glu Pro Ala Trp
            85                  90                  95

Asp Leu Ala His Lys Ile Leu Met Pro Ala Phe Gly Pro Leu Ala Ile
        100                 105                 110

Arg Gly Met Phe Asp Glu Met His Asp Ile Ala Ser Gln Leu Val Val
    115                 120                 125

Lys Trp Ala Arg Phe Gly Pro Gln Asp Thr Ile Asp Val Ser Gly Asp
130                 135                 140

Phe Thr Arg Leu Thr Leu Asp Ala Ile Ala Leu Cys Ser Met Ser Thr
145                 150                 155                 160

Arg Phe Asn Ser Phe Tyr Lys Gln Asp Gln His Pro Phe Val Ser Ser
            165                 170                 175

Met Leu Glu Val Leu Ala Glu Ser Gly Lys Arg Ala Val Arg Pro Pro
        180                 185                 190

Phe Val Asn Asp Tyr Ile Phe Arg Gly Ser Leu Lys His Tyr Asn Thr
    195                 200                 205

Glu Ile Ala Thr Met Arg Arg Ile Ala Met Asp Val Leu Ala Glu Arg
210                 215                 220

Arg Ala Asn Pro Met Ala Cys Gln Lys Asn Asp Leu Leu Asn Ala Met
225                 230                 235                 240

-continued

Ile Asn Gly Arg Asp Pro Lys Thr Gly Glu Gly Leu Ser Asp Glu Ser
            245                 250                 255

Thr Ile Asn Asn Leu Ile Val Phe Leu Ile Ala Gly His Glu Thr Thr
            260                 265                 270

Ser Gly Leu Leu Ser Phe Leu Phe Tyr Tyr Leu Leu Thr Arg Pro Asp
            275                 280                 285

Val Phe Glu Lys Ala Gln Lys Glu Val Asp Glu Leu Val Gly Arg Gly
            290                 295                 300

Pro Val Thr Ile Glu His Met Ser Lys Leu His Tyr Ile Glu Ala Cys
305                 310                 315                 320

Leu Arg Glu Thr Leu Arg Leu His Pro Thr Ala Pro Val Ile Thr Phe
                325                 330                 335

Lys Thr Lys Pro Gly Phe Glu Lys Ser Thr Thr Ile Gly Gly Gly
                340                 345                 350

Lys Tyr Lys Ile Asp Arg Asp Gln Gly Ile Val Ala Leu Leu Val Asn
            355                 360                 365

Ile Gln Arg Asp Pro Lys Val Trp Gly Asp Asp Ala Asn Glu Phe Lys
            370                 375                 380

Pro Glu Arg Met Thr Asp Glu Lys Phe Asn Asn Leu Pro Ala Asn Cys
385                 390                 395                 400

Trp Lys Pro Phe Gly Asn Gly Ile Arg Gly Cys Ile Gly Arg Ala Phe
                405                 410                 415

Ala Trp Gln Glu Ser Leu Leu Ile Thr Ala Met Leu Leu Gln Asn Phe
                420                 425                 430

Asn Phe Gln Leu Ala Asp Pro Asp Tyr Lys Leu Gln Ile Lys Gln Thr
            435                 440                 445

Leu Thr Ile Lys Pro Gly Asn Phe Phe Met His Ala Lys Leu Arg Asp
            450                 455                 460

His Val Asp Pro Leu Glu Leu Glu Gly Ile Leu His Gly Gly Ala Lys
465                 470                 475                 480

Lys Gly Ser Lys Ile Asp Gly Pro Ser Ser Gly Ala Ser Leu Ala Thr
                485                 490                 495

Thr Glu Gln Glu Leu Gln Pro Met Thr Ile Leu Tyr Gly Ser Asp Ser
            500                 505                 510

Gly Thr Cys Glu Ser Met Ala Gln Ser Leu Ala Arg Ala Ala Arg Gly
            515                 520                 525

Arg Gly Tyr Gly Ala Thr Val Lys Thr Leu Asp Ser Ala Val Glu Gln
            530                 535                 540

Val Pro Lys Asp Gln Pro Val Val Ile Val Ser Pro Ser Tyr Asn Gly
545                 550                 555                 560

Gln Pro Pro Ser Asn Ala Thr Asp Phe Val Lys Trp Leu Glu Ala Leu
                565                 570                 575

Asp Ser Lys Ala Leu Lys Asp Val Lys Tyr Ser Val Tyr Gly Cys Gly
            580                 585                 590

Asn Lys Asp Tyr Thr Ser Thr Phe His Arg Ile Pro Lys Leu Leu Asp
            595                 600                 605

Ala Glu Phe Glu Arg Cys Gly Ala Lys Arg Ile Ala Glu Thr Gly Leu
            610                 615                 620

Gly Asp Val Thr Val Gly Asp Ile Phe Ser Asp Phe Glu Arg Trp Gln
625                 630                 635                 640

Asp Asp Gln Leu Trp Pro Ala Leu Gly Val Ala His Met Asp Gly Asp
                645                 650                 655

```
Ala Asp Ala Glu Phe Asp Ile His Val Asp Arg Ser Gly Arg Ala Ala
            660                 665                 670

Glu Leu Glu Val Asp Ala Asp Glu Ala Thr Val Gln Ser Asn Gln Val
        675                 680                 685

Leu Thr Ala Pro Gly Glu Pro Glu Lys Arg Tyr Ile Thr Leu Lys Leu
    690                 695                 700

Pro Glu Gly Met Gln Tyr Lys Ser Gly Asp His Leu Ser Val Leu Pro
705                 710                 715                 720

Leu Asn Asp Trp Gly Val Val Arg Val Phe Ala Trp Ala Gln Leu
                725                 730                 735

Pro Trp Asp Ala Val Thr Ile Pro Lys Gly Thr Asn Thr Ser Leu
        740                 745                 750

Pro Thr Gly Arg Gln Ile Ser Ala Lys Asp Leu Leu Ser Gly Tyr Val
        755                 760                 765

Glu Leu Ser Gln Pro Ala Thr Arg Lys Asn Ile Ala Lys Leu Ala Ala
    770                 775                 780

Ser Ser Pro Cys Pro Phe Thr Gln Lys Ser Leu Ser Lys Leu Glu Glu
785                 790                 795                 800

His Phe Asp Ser Asp Ile Ala Gln Arg Arg Leu Ser Val Leu Asp Ile
                805                 810                 815

Leu Glu Glu Phe Pro Ala Ile Asp Ile Thr Phe Gly Asn Phe Ile Ser
                820                 825                 830

Met Leu Pro Pro Met Arg Pro Arg Gln Tyr Ser Ile Ala Ser Ser Pro
                835                 840                 845

Met Ala Asp Pro Ser Thr Ala Thr Leu Met Trp Thr Val Leu Asn Ser
850                 855                 860

Glu Ala Tyr Ser Gly Ser Gly Arg Arg Phe Leu Gly Val Cys Ser Thr
865                 870                 875                 880

Tyr Leu Ala Gly Leu Ala Glu Gly Asp Arg Val His Val Thr Val Lys
                885                 890                 895

Pro Ala Leu Arg Leu Phe His Pro Pro Ser Asp Pro Glu Ser Met Pro
                900                 905                 910

Ile Ile Met Ala Cys Ala Gly Thr Gly Leu Ala Pro Phe Arg Gly Phe
            915                 920                 925

Leu Glu Glu Arg Val Cys Gln Met Lys Ala Gly Arg Ala Leu Ala Pro
        930                 935                 940

Ala Tyr Leu Phe Val Gly Cys Arg Asp Pro Glu Lys Asp Ala Leu Leu
945                 950                 955                 960

Lys Asp Glu Leu Ala Gln Trp Glu Arg Asp Gly Val Val Lys Ile Tyr
                965                 970                 975

Tyr Ala Phe Ser Arg Ala Ser Asp Gln Ser Asp Gly Cys Lys His Val
                980                 985                 990

Gln Asp Arg Ile Trp Asn Glu Arg Asp Leu Val Arg Lys Gly Leu Phe
            995                 1000                1005

Glu Gly Asn Ala Arg Phe Phe Met Cys Gly Gly Ser Gly Ala Gly
    1010                1015                1020

Lys Ser Val Glu Asp Val Val Lys Arg Ile Tyr Lys Asp Asn Lys
    1025                1030                1035

Gly Glu Ser Gln Glu Lys Ala Ala Glu Ser Trp Phe Gln Asp Leu
    1040                1045                1050

Lys Ala Asn Arg Tyr Val Thr Glu Ile Phe Ala
    1055                1060
```

-continued

```
<210> SEQ ID NO 16
<211> LENGTH: 273
<212> TYPE: PRT
<213> ORGANISM: Acremonium sclerotigenum

<400> SEQUENCE: 16

Met Ala Phe Gly Val Glu Pro Pro Glu His Val Thr Pro Trp Phe Lys
1               5                   10                  15

Pro Val Tyr Glu Ala Thr Phe Gln Phe Gly Val Ala Trp Thr Leu
            20                  25                  30

Cys Tyr Ile Leu Ile Ala Arg Glu Gly Met Arg Thr Lys Ser Tyr Gly
                35                  40                  45

Met Pro Leu Phe Ala Leu Ala Asn Asn Phe Ala Trp Glu Met Val Tyr
        50                  55                  60

Ala Leu Trp Val Val Asp Asn Ala Phe Glu Lys Thr Ala Met Thr Ile
65                  70                  75                  80

Trp Met Leu Ile Asp Thr Pro Ile Ile Tyr Ser Ile Leu Lys His Gly
                85                  90                  95

Val Leu Glu Trp Gln His Ala Pro Met Val Ser Arg Asn Leu Lys Ser
            100                 105                 110

Ile Leu Val Gly Leu Ile Ala Leu Cys Ala Ala Ala His Trp Ser Trp
        115                 120                 125

Gln Ser Trp Trp Ile Gly Asn Glu Met Gly Lys Arg Asp Asp Leu Glu
    130                 135                 140

Gly Ala Asp Leu Thr Gln Met Ala Tyr Trp Ala Val Ser Met Cys Gln
145                 150                 155                 160

Phe Leu Val Ser Thr Met Ser Leu Ala Met Leu Cys Val Arg Gly His
                165                 170                 175

Ser Gly Gly Val Ser Trp Met Ile Trp Leu Ser Arg Phe Leu Gly Thr
            180                 185                 190

Leu Ile Gly Leu Asn Met Asn Tyr Ala Trp Ala Tyr Tyr Thr Trp Pro
        195                 200                 205

Glu Ala His Glu Tyr Phe Met Ser Ala Pro Ala Val Phe Val Trp Gly
    210                 215                 220

Val Thr Thr Val Cys Asp Ile Ile Tyr Gly Phe Val Leu Tyr His Val
225                 230                 235                 240

Lys Ser Asn Glu Arg Glu Leu Ser Asp Gly Arg Lys Val Ala Ala Glu
                245                 250                 255

Ala Asp Asp Glu Gln Val Gly Gly Trp Ser Lys Met Lys Thr Gly Lys
            260                 265                 270

Asn

<210> SEQ ID NO 17
<211> LENGTH: 534
<212> TYPE: PRT
<213> ORGANISM: Acremonium sclerotigenum

<400> SEQUENCE: 17

Met Gly Ser Leu Leu Phe Asp Ser Pro Val Gly Arg Phe Val Ala Ser
1               5                   10                  15

Phe Pro Ala Leu Ser Ala Ala Ala Gly Leu Ile Val Ala Ile Ser Phe
            20                  25                  30

Ile Tyr Ile Arg Phe Ile Lys Thr Pro Lys Leu Asp Leu Pro Val Val
        35                  40                  45

Gly Asn Pro Gly Asp Lys Trp Asp Ala Gln Lys His Ile Val Ala Gly
    50                  55                  60
```

```
Ala Arg Lys Tyr Pro Asp Thr Pro Tyr Ile Leu Pro Met Asp Pro Pro
 65                  70                  75                  80

Ile Val Val Leu Pro Ile Lys Ile Gln Asp Glu Val Arg Asn Leu Pro
                 85                  90                  95

Glu Asn Val Val Ser Phe Thr Lys Glu His Gln Arg Asn Phe Phe Ala
            100                 105                 110

Gln Tyr Thr Gly Ile Gly Asp His Arg Pro Glu Met Ile Thr Ala Ile
        115                 120                 125

Arg Gln Asp Leu Thr Arg His Ile Val Ser Thr Ile Pro Gly Leu Gln
130                 135                 140

Glu Glu Val Arg Tyr Gly Phe Asp Lys Glu Phe Gly Asp Cys Lys Asp
145                 150                 155                 160

Trp Thr Pro Phe Pro Leu Tyr Met Lys Val Leu Arg Ile Val Ala Leu
                165                 170                 175

Thr Ser Gly Arg Val Phe Val Gly Arg Pro Leu Ser Arg Glu Glu Glu
            180                 185                 190

Trp Leu Gln Arg Thr Ile Ser Tyr Thr Met Asp Cys Val Lys Ala Arg
        195                 200                 205

Asn Ala Ile Arg Glu Tyr Pro Trp Trp Lys Arg Arg Trp Val Thr Ser
210                 215                 220

Ser Leu Pro Glu Ile Ala Lys Leu Thr Glu His Arg Thr Arg Gly Gly
225                 230                 235                 240

Val Leu Leu Lys Pro Ile Met Asp Ala Gln Leu Ala Lys Asp Ser Lys
                245                 250                 255

Arg Glu Lys Ile Ile Asn Glu Glu Thr Gly Asp Glu Glu Gly Asn Phe
            260                 265                 270

Ile Glu Trp Leu Leu Lys His Thr Pro Gly Asp Leu Lys Met Asp Pro
        275                 280                 285

Glu Asn Leu Ala Leu Asn Gln Met Val Leu Ala Phe Ala Ser Val His
290                 295                 300

Thr Ser Ser Met Ser Val Thr His Ala Ile Leu Glu Leu Val Thr Arg
305                 310                 315                 320

Pro Glu Tyr Phe Ala Pro Leu Arg Glu Glu Leu Glu Glu Val Arg Arg
                325                 330                 335

Ala Asp Gly His Thr Val Asp Asp Gly Tyr Ile Arg Leu Lys Lys
            340                 345                 350

Glu Ser Ile Asn Lys Leu Arg Lys Leu Asp Ser Phe Met Lys Glu Ser
        355                 360                 365

Gln Arg Phe Asn Pro Pro Ile Ser Thr Ser Gly Thr Arg Ile Cys Thr
        370                 375                 380

Ala Asp Leu Lys Leu Ser Thr Gly His Thr Leu Pro Lys Gly Thr Arg
385                 390                 395                 400

Ile Cys Phe Pro Ser Tyr Asp Val His His Asn Pro Lys Thr Thr Thr
                405                 410                 415

Tyr Ser Pro Glu Tyr Asn Pro Gly Tyr Thr Pro Asp Gln Phe
            420                 425                 430

Asp Gly Leu Arg Phe Phe Lys Leu Arg Glu Met Pro Gly Lys Glu Ser
        435                 440                 445

Arg His Gln Phe Ala Thr Ala Asn His Glu Ser Leu Val Phe Gly Phe
        450                 455                 460

Gly Asn His Thr Cys Pro Gly Arg Phe Phe Ala Ala Asn Gln Ile Lys
465                 470                 475                 480
```

```
Ile Ile Leu Ala Glu Leu Leu Met Asn Trp Asp Val Arg Leu Lys Gly
                485                 490                 495

Asp Val Glu Gln Lys Gly Gly Pro Glu Lys Arg Pro Gln Asn Met Val
            500                 505                 510

Val Asp Leu Val Ile Thr Pro Asn Pro Met Ala Met Val Glu Met Lys
        515                 520                 525

Arg Arg Ser Arg Ala Val
        530

<210> SEQ ID NO 18
<211> LENGTH: 512
<212> TYPE: PRT
<213> ORGANISM: Acremonium sclerotigenum

<400> SEQUENCE: 18

Met Gly Leu Ser Leu Gly Tyr Ser Pro Asp Arg Gly Ser Ile Gly Ser
1               5                   10                  15

Trp Ile Cys Ala Ala Pro Leu Ile Leu Ala Leu Phe Val Ile Ser Tyr
            20                  25                  30

Arg Leu Phe Gln Ser Val Ile Asp Tyr Arg Leu Ser His Arg Asn Gly
        35                  40                  45

Cys Lys Pro Pro Pro Thr Tyr Pro His Lys Asp Trp Tyr Leu Gly Leu
    50                  55                  60

His His Val Phe Gly Leu Leu Lys Ala Lys Lys Glu Asn Arg Leu Pro
65                  70                  75                  80

Thr Ala Phe Ser Glu Leu Phe Asp Ala Ser Gly Pro Asp Val His Thr
                85                  90                  95

Leu Gly His Tyr Val Leu Gly Lys Lys Ser Tyr Trp Thr Arg Asp Pro
            100                 105                 110

Glu Asn Ile Lys Ala Val Leu Ser Ser Lys Phe Asn Asp Trp Gly Leu
        115                 120                 125

Pro Ser Ala Arg Lys Ala Thr Phe Arg Thr Cys Leu Gly Gly Gly Ile
    130                 135                 140

Phe Gly Val Asp Gly Lys Glu Trp Glu His Ser Arg Ala Met Leu Lys
145                 150                 155                 160

Pro Ser Phe Thr Arg Thr Gln Ile Gly Asp Thr Ala Thr Leu Ser Lys
                165                 170                 175

His Ala Asp Asn Leu Ile Ala Arg Ile Pro Glu Gly Glu Thr Val Asp
            180                 185                 190

Leu Ala Glu Leu Phe Pro Leu Leu Thr Met Asp Val Gly Thr Glu Met
        195                 200                 205

Leu Phe Gly Glu Ser Val Gly Ser Leu Asp Pro Ala Glu Ile Lys Gln
    210                 215                 220

Ala Thr Arg Phe Thr Thr Ser Phe Asp Tyr Ile Val Gln Thr Met Ser
225                 230                 235                 240

Lys His Met Ala Leu Pro Ile Leu Thr Lys Leu Arg Asp Lys Thr Leu
                245                 250                 255

Gln Gly Cys Val Glu Phe Val Asp Asp Phe Ala Ala Asp Val Val Asn
            260                 265                 270

Arg Thr Ile Ala Asn Glu Ser Lys Thr Glu Lys Pro Ser Ser Leu Gly
        275                 280                 285

Lys Tyr Ile Phe Pro Thr Glu Leu Ala Lys Met Gly Leu Pro Glu Lys
    290                 295                 300

Gln Ile Arg Ile Glu Val Ile Asn Ile Met Val Ala Gly Arg Asp Thr
305                 310                 315                 320
```

```
Thr Ala Ala Leu Leu Ser Leu Ile Trp Trp Tyr Leu Ala Lys Arg Pro
                325                 330                 335

Asp Ala Val Met Lys Leu His Gln Glu Leu Glu Pro Leu Gly Gly Arg
            340                 345                 350

Pro Pro Thr Gly Glu Glu Val Lys Lys Met Lys Tyr Leu Arg Asn Phe
        355                 360                 365

Val Asn Glu Ile Leu Arg Leu His Pro Ile Asn Pro Leu Asn Ser Arg
    370                 375                 380

Thr Ala Ala Lys Asp Thr Thr Leu Pro Arg Gly Gly Pro Asp Gly
385                 390                 395                 400

Lys Ser Pro Val Phe Ile Arg Lys Gly Thr Gln Leu Met Phe Ser Ser
                405                 410                 415

Ala Ala Leu Gln Arg Arg Lys Asp Leu Tyr Gly Glu Asp Ala Leu Asp
            420                 425                 430

Leu Arg Pro Glu Arg Trp Glu Arg Ile Arg Pro Ser Ala Phe Glu Tyr
        435                 440                 445

Ile Pro Phe Gly Gly Gly Pro Arg Ile Cys Pro Gly Gln Gln Leu Ala
    450                 455                 460

Leu Thr Glu Ala Ser Tyr Phe Thr Ala Arg Leu Leu Gln Glu Phe Gln
465                 470                 475                 480

Gly Val Thr Ser Glu Ser Ser Gly Pro Phe Gln Glu Ala Phe Ala Ile
                485                 490                 495

Leu Val Thr Ser Gly Asp Gly Val Lys Val Lys Phe His Lys Lys His
            500                 505                 510

<210> SEQ ID NO 19
<211> LENGTH: 384
<212> TYPE: PRT
<213> ORGANISM: Acremonium sclerotigenum

<400> SEQUENCE: 19

Met Pro Gln Leu Ala Gly Lys Leu Ile Leu Ala Gly Leu Ile Pro Leu
1               5                   10                  15

Gly Ala Trp Val Leu His Gly Phe Ala Ser Cys Asn Gly Leu Ile Gln
            20                  25                  30

Met Phe Glu Asp Phe Gly Lys Gln Thr Val Leu Ser Asp Gly Val Thr
        35                  40                  45

Asp Tyr Thr Gly Ala Phe Thr Gly Leu Glu Gly Leu Asp Arg Leu Leu
    50                  55                  60

Arg Thr Leu Leu Asn Phe Phe Trp Pro Val Ala Asn Gly His Asp Trp
65                  70                  75                  80

Ala Leu Ser Leu His Ala Phe Met Phe Ala Gly Gln Gly Val Pro Leu
                85                  90                  95

Leu Val Leu Asn Met Leu Glu Gly Ala Arg Pro Gly Asn Lys Ser Leu
            100                 105                 110

Val Val Ser Tyr Val Thr Val Phe Gly Ile Leu Tyr Met Val Val Gly
        115                 120                 125

Leu Ala Ile Met Ala Pro Leu Tyr Leu Phe Leu His Leu Leu Thr Ser
    130                 135                 140

Arg Thr Ala Thr Ala Pro Ser Lys Ala Lys Val Ala Val Asp Pro Asn
145                 150                 155                 160

Thr Ala Lys Ala Val Gly Phe Gly Val Phe Val Gly Tyr Val Leu Pro
                165                 170                 175

Thr Ile Phe Met Ser Leu Pro His Pro Ser Leu Leu Ser Thr Asp Thr
```

```
                180             185             190
Lys Val Leu Ser Val Val Phe Trp Gln Ala Val Pro Leu Trp Ala Ser
            195                 200             205

Val Cys Ala Tyr Phe Ala Ser Thr Ala Leu Gly Gln Ser Ala Thr Ser
            210                 215             220

Arg Ser Ser Ser Asn Leu Pro Ser Ala Leu Gly Ala Val Tyr Ala Ala
225                 230                 235                 240

Ser Leu Ile Ile Ala Thr Ala Thr His Val Ala Thr Phe Ala Ile Ser
                245                 250                 255

Ala Asn Leu Ser Asp Thr Trp Ser Gly Ile Phe Thr Phe Leu Ile Pro
            260                 265                 270

Pro Asn Pro Phe Asn Thr Asp Met Arg Ile Ser Ser Phe Leu Glu Gly
            275                 280                 285

Ala Thr Trp Phe Leu Gln Trp Asp Tyr Thr Met Met Ser Leu Ala Tyr
            290                 295                 300

Met Val Trp Ala Ile Gly Ile Arg His Gly Val Glu Val Pro Arg Ser
305                 310                 315                 320

Ser His His Phe Glu Thr Leu Gly Lys Ile Ala Leu Arg Ser Met Ala
                325                 330                 335

Lys Leu Leu Val Met Gly Pro Ile Gly Ala Ala Leu Ser Leu Val Trp
            340                 345                 350

Glu Arg Asp Gln Leu Leu Trp Gln Leu Asp Ser Glu Ser Gly Glu Lys
            355                 360                 365

Gly Glu Lys Asn Arg Ser Arg Arg Met Ser Arg Lys Trp Met Phe Ser
370                 375                 380
```

<210> SEQ ID NO 20
<211> LENGTH: 296
<212> TYPE: PRT
<213> ORGANISM: Acremonium sclerotigenum

<400> SEQUENCE: 20

```
Met Thr Asp Ile His Ile Gln Asp Gly Asp Leu Ser Ser Leu Lys Asp
1               5                   10                  15

Lys Val Val Ile Thr Gly Gly Ser Gly Ile Gly Leu Ala Thr
                20                  25                  30

Thr Asn Leu Leu Leu Asp Leu Gly Ala Lys Val Val Ile Gly Asp Leu
            35                  40                  45

Gln Pro Pro Thr Thr Arg Val Asp Ser Glu Arg Cys Ser Phe His Lys
50                  55                  60

Val Asp Val Thr Val Trp Ser Asp Gln Leu Thr Leu Phe Lys Glu Ala
65                  70                  75                  80

Arg Glu Leu His Gly Arg Ile Asp His Val Phe Ala Asn Ala Gly Val
                85                  90                  95

Gly Pro Lys Ala Asp Tyr Leu Ser Thr Ala Leu Asp Gln Asn Gly Asp
            100                 105                 110

Leu Val Glu Pro Thr Phe Leu Thr Leu Asp Val Asn Leu Lys Ala Val
            115                 120                 125

Ile Tyr Thr Ala Thr Ile Ala Cys Tyr Tyr Met Arg Glu Glu Gln Gln
            130                 135                 140

Ser Pro Ala Gly Gly Ser Ile Val Ile Val Ser Ser Val Ala Gly Val
145                 150                 155                 160

Ser Arg Phe Arg Ala Val Asp Tyr Ala Thr Ala Lys His Gly Asn Leu
                165                 170                 175
```

```
Gly Phe Ala Arg Gly Leu His Gln Arg Leu Thr Ala Glu Asn Ser Pro
            180                 185                 190

Thr Arg Val Asn Leu Ile Ala Pro Ser Trp Thr Asn Thr Gly Phe Met
        195                 200                 205

Pro Pro Gln Ile Met Ala Ala Val Gly Val Glu Pro Gln Glu Pro Ala
    210                 215                 220

Ser Val Gly Arg Ala Ala Ala Tyr Leu Met Ala Asp Asp Ser Arg Lys
225                 230                 235                 240

Gly Gln Met Ile His Ile Ala Lys Gly Arg Tyr Arg Glu Val Glu Glu
                245                 250                 255

Ser Ile Met Leu Pro Ala Ala Glu Lys Val Val Asp Val Glu Asn Gly
            260                 265                 270

Gly Val Met Glu Asp Asp Thr Leu Ala Lys Ile Ile Glu Thr Met Gly
        275                 280                 285

Ile Phe Lys Ala Lys Ala Thr Gln
    290                 295

<210> SEQ ID NO 21
<211> LENGTH: 1011
<212> TYPE: DNA
<213> ORGANISM: Artificial sequence
<220> FEATURE:
<223> OTHER INFORMATION: modified gene

<400> SEQUENCE: 21
atggccgcta agagcaggtc gccaaaacgc ggtaccagcg agaagactcc tctggtcgag      60
aaagaagctc cctaccagcc tcccaccaag ggaatccttt caaaattgcc agcaagttgg     120
gtgccgtatg cgcagctcat caggctggag caaccacatg caactacat gatttatttc      180 ccgcacatca ttggtctgat gtacgcatcc gcgattcgtc ctaccgaact ttctgttttg     240
ggccatcggg cagcgatctt cgcaatttgg acttttctta tgcggggagc cgggtgcgct    300
tggaacgaca tgtcgatca ggacttcgat cgaaagactg agcgctgtcg tcatcggccc     360
atcgcaagag gagcgattag caccactcag gggcacgtgt tcacacttat cttgacgctc    420
ctgggctttg ccgctatcca atccctgcca attgaatgca catacgtcgg cgtgggtaca    480
acggtgcttt ctgccattta tccgttcgga aagcgtttca cgcattttgc acaagttatc    540
ttggggtcca ccctcgcgtc tactattgcc ttgtcagctt acagtgtcgg tctccctgcc    600
ctgtcaaaag attatttcgt gcccacactc tgtctgagtg ctacgatcat gcttttggtc    660 gtgtttacg acgttgtcta tgcccgcgct gataccactg atgacctcaa gtcgggcgtg     720
aagggtatgg ctgttcgatt cagaaatcac cttgagggct gttcgccctt tatcaccttg    780
agcattgctg gctcgctcac aacgctgggt taccttgttg gaatggggca ttggttctat    840
ctctttagcg tcggcggtct gacatttggt cttgtttcga tggtcgcatt gacgcactgg    900
aacatcctcc ctggatactc ctctgggcgc tgctatgcat tcgcgatcct taatctcctg    960 accggatttta ttatggaata cgcgactaag gactatgtgg ttggcgtctg a            1011

<210> SEQ ID NO 22
<211> LENGTH: 3282
<212> TYPE: DNA
<213> ORGANISM: Artificial sequence
<220> FEATURE:
<223> OTHER INFORMATION: modified gene

<400> SEQUENCE: 22
atgaccgtca acggtcatca cactaacggg gtgaatggcg caaacggtac caatggacat      60
```

```
gcgaacggga gcaatggcat caacgacact aaggccgtca aagagattgt gccatttgtt    120
aagccgcaag tgaatttcgc ttcggcacaa cggctggaag gctgcatcca tagtttgcca    180
gagctcgtgg actttaactc ccttaacaat cagcatcaca ccttctgtgt tcaagcaaag    240
tcctctgagc cgtttgatac catcactcac ggcgagttca aggtggccgt ttccaaatgc    300
gccgcttggc tcaaggagaa tctgcccatt cgaccaagct cggatgacaa ggccctcact    360
aaaatggcgc cagttgccct gtttatggaa tctgacatcg gccttgtcat tcacgagttc    420
gctttgatga gcatcggtgt gcctcccctg gttctttccc ctagattgtc cccgttgct    480 atcaacgcac tcctggaagc tactggcgca gcgagcttca ttgtctcgcc taggatgtca    540
gagcccctca aggtgcact ggccgctctt gcagcgaagg tgtctccac acatatcgga    600 aatccataca aagcttacta tcagccaggt gcagacccga agtctgtcgc gccgttcgaa    660
gtgccgcaaa accctgagga tgtgatcctt ttgctccact caagtggtac cactggactg    720
ccaaaaccga ttcctacaac gcatcggcag ctgcttttg ctgttaattg tcacaagttc    780
gatacagagg aacaggcaca aagtttgaac ctctccacgc tgcctctttt tcatggattc    840
gggcttgtcg ccccccgggtt gagtatgtcc gctggcaaac ctaccttgta tcccgcatct    900
gacggcatcc ccaacgcgaa gagcatcgtc gatctcatta ataagaccaa cgccaaatct    960
atgatgactg tgccatttt gctcgatgac atcaccaatc ttccgaacga ggaagggatt   1020
aaggctttgg ttcacatgga cttcgttgga actggcggtg ccgctcttgg tgcaggtatc   1080
ggagatcgtt tggctaaggg aggggtgaaa ctgcttaatt tctacggtac cactgagacc   1140
ggaccattga gcctcacctt tgccccgact gacaactacg attggaaata tttccgcctt   1200
cgtacagatt gcgaatataa gattgacgag ttggaaccta gagatggcga gcgccgtttt   1260
aggctcacgg tctacccta tgggtcggag ggcttcgaaa tctcagacca gctcattcgc   1320
aatgaacaat accccgagac agatttcgca gcggtgggtc gtgatgacga tgtcatcgtg   1380
ttggctacgg gagagaaggc aaacccactg attcttgaaa caaaactcac ggaggccccg   1440
atggtgaagg ccgctatcgc ttttggtgaa aatcagttca acctcggagt tattgtcgag   1500
cccgcagaac cactgacccc ggacactgaa tcggcgtttc gggagtcaat ctggccaatc   1560
attaccgcag cgtgtgacca aatggatgcc ttctctcgaa ttcccagccc agatgccgtc   1620
gtgctggttc ctgctggtgt tgtcatcccc cgcaccgaca agggatccat tgcacgtaaa   1680
gaaacttacg cgcttttcga taagcagatc aaaggcgtct atgagcaatt gctcaaagcc   1740
gctgcagacg ctgtggaacc tttgacctc gataatttgg agcagaactt gaagtccctc   1800
atccaggaac atctccacat tcaagctcct gcatctgatt ggggcgtcga ggactcactc   1860
ttcgacatcg gcgtggactc gctgcaggtt ctgcaacttc ggcgaattct ggtcacagcg   1920
gcctcaaaga cggaggcctt taaagacacc gattgcgaaa agatgatccc accggagttc   1980
gtctacatga atccttctat ccgcgagatt gctgcagcgc tgaccaaagg aagtgacggc   2040
ggtgatgtct cccttgaaga cgccgctaag gaagtcgttg aactcgctga gacttatagt   2100
ctgaagggag tgtccgcgca ggaaaaagcc ccctcctcta gcgagggcgc attcgttatg   2160
ctcacaggtg cgacgggatc cctggggtct catgtcgcag cggatctggc cagaagggac   2220
aacgttgcta aggtcgtgtg tcttgtcaga aaggataaag gcacaaatca gcctcccatg   2280
cctggcggca acccgtttga caagaaaaatc cttaaggccc gtggtattca gttgacggat   2340
gaacaattcg gaaaactggc aacacttgag gtcgatccaa cggcggacaa gttggggctc   2400
```

| | |
|---|---|
| atcccgatgg catacggcat gatgcaggcg aaggtcaccc atgtgatcca cgccgcttgg | 2460 |
| ccaatgaatt acttgattcg gctccgaaac tttcagtatc aatttaagtt cctgcgcaac | 2520 |
| ctgcttgagt tcgcttctca gggacctgca cctacaaaga aacggtttgt tttcatctcg | 2580 |
| tcaattgcga ccgttgcacg aattggactt gcacaacctg gatctattag cgaagctcct | 2640 |
| gtgtcgccct cagacagtgc ctgcgggatc ggctacgctg atggcaagct ggtttgtgaa | 2700 |
| aagattatgg agaaagcagc gcaggactat ggcggtcaac ttgatgttac aagcgtccgt | 2760 |
| tgcggccaga tgaccggttc gaagaaaact ggagtctgga actcaaatga gcaaatccct | 2820 |
| atgttgctca gtctgccca gggtctggga agccttcctc aattgtcggg agaactgtca | 2880 |
| tggatccccg tggacgatgc cgctagcact gtttcggaga ttgctttctc agacggcagt | 2940 |
| atgcctatcg ttcagcactt ggaaaatccc attagacaga gttgggatgc catgctccaa | 3000 |
| tcctttggaa gggaactggg gcttccagct ggcaaggtgc cgttcgggga gtggttggac | 3060 |
| caagttgcag cggccgatgg cgacgatgag acattccccg tcaagaaact cacgttcttt | 3120 |
| ttcaagtcct tcttccagtc cgtggcttgt ggtcaagttg cctggatac aacggtttct | 3180 |
| cgcggacaga gcaagacact taacgctatg acggcagtcg gtgacgagac cgtgaaggct | 3240 |
| tacgcagatt attggaaatc tactggctac ctcagcaagt ga | 3282 |

<210> SEQ ID NO 23
<211> LENGTH: 6348
<212> TYPE: DNA
<213> ORGANISM: Artificial sequence
<220> FEATURE:
<223> OTHER INFORMATION: modified gene

<400> SEQUENCE: 23

| | |
|---|---|
| atgacactta ttcagacgaa acattcggcc tcagccgctg tgttctcgcc tcaatcaaca | 60 |
| gctccaaagc cgacgcattt ggctcacatc agagcaaggc tcctggaaga tgaccttttg | 120 |
| aagcccgtta agaggccgt cgtgagcttg ccaaaaacat ggagagctct cgtctcgaag | 180 |
| cagcccgagc tgggcaagaa caggaaagca tctgaccctta ttgaggcgtt cccaagctgg | 240 |
| atcgaagatg gcaagaccga ggtccttgaa actgacatgt ccggactgat cacccttccc | 300 |
| ctcctggccg tgatccatat tgttcagtac ctggactata tccaacgcct tggaattagt | 360 |
| cactccgagt cctcgaaaag tgtggagtcc ggcggtgttc agggctactg catcggtctt | 420 |
| ttgagcgcta ttgttgtctc ctctgcggaa gatgaggaag ccctgatcca acatgcagcg | 480 |
| cacggcatcc ggctttcgtt ggccattggg gcttttggcg acatcggtag ctcgtcagac | 540 |
| gaggtggtta gcaataccct tcaggttcgc ttgcgtaacg ccgggtcgga ggaagatctc | 600 |
| gtcgctcgat tcccgggctc ttatatcagc acgattaccg acgcaaaaac catgtccatc | 660 |
| attgcgcctc cccatctcat tgatgctctg aaggaacacg cagagactga aggtctccgg | 720 |
| ccccgagcaa tgcatatcag atcaaacctg cacaatagta ggaacaccga acttgcccag | 780 |
| caatgcagtt ccttgttcga ggattgtccg tttgcatcac ctgacactct gcaggtcgcg | 840 |
| gtgcggagta ataagactgg ctgctacctc gagcaagacg ccacatctct ggtggaggaa | 900 |
| gccgtctcca cggtgcttgc ttctcgatgt gattggagct tggttatgca gggtcttgct | 960 |
| gatgacttga accaatctgg aagcaagcat cactccatcc tcctgtttgg gatgggcgac | 1020 |
| tctgttcccg gtgcaccatt ccgggaacat agccttgaca tctcgaagat tgacgtcctc | 1080 |
| tccctcgtcg agacacccct tgtcagcgacg ccaccggcct ctagcatcga tgacttccct | 1140 |
| cccgattcga tcgcgattgt tggatcagca tgccgactcc caggtgcaaa ttcattggat | 1200 |

```
gagctctggg acctgattgc cgctggaaga tccaggctgg aaaaagtccg cacagaccgt   1260
gtgaacatca aggagtcata cagagctagt caggatcccg agtggacgaa gaaaagggaa   1320
ttctacggca acttcatcga tgacgtggat gctttcgacc atgcattctt aacatcagc    1380 ccccgcgagg ctaagtacat ggacccacag caacgtcttt tgctcatggc agcgtttgag   1440
gcaatggatt cgtcaggcta tctccggtcg caccaacgaa atgatggaga cgccgttggg   1500
tgtttcctgg gcgctagcta cactgaatat acagagaaca cgtcggctta ctcgccctca   1560
gcattcactg cgacaagcac gattcgggca tttctctccg gcaagatctc ttatcatttc   1620
ggatggacgg ggccatcgga agtcatcgac accgcctgca gtgcttccat cgttgccgtc   1680
caccgagcag tgcaggcgat caatgctggc gagtgtcctg tggcactggc gggagggggtt  1740 aacatcatta caggtgtcaa caattacttc gatttgggaa aagcttcgtt tctctcacag   1800
acgggtcaat gcaagccatt cgatgacagc gcagatggat actgtcgtgc ggacggtgtg   1860
ggacttgtcg tgttgaaacc gctctcgaag gccgtggctg atggggacta tatccagggc   1920
gttatccctg caattgcgac caatcaaggc ggtatcggcg ccccgggtat tactgttcct   1980
gatgggattg ctcagaaggc actctaccgg ggcatcctgg agaaagccgg acttaagggg   2040
gaggacattt cctatgtcga agctcatggg accggcactc aagtgggcga tcccatcgag   2100
attggttcta tccgcgaagt cttcggaggg gcgcatcgtg ccagtccact tcacttggga   2160
tcccttaaag caaacattgg acactctgaa actgctgctg gcgtggcttc tctgcttaag   2220
gttttgagca tggtccgcaa tcgtggagtt ccaccgctgc aggggttcaa aagacttaac   2280
cataagattc ccgcactcga gctggacaaa atggcgatcc ccaccaagtt gctcccatgg   2340
gattcagacc accgaatcgc ctgcattaat agttacggcg cctctggtag caactcggct   2400
ttgatctgta gtgagtggct cgaggaaccc tccaagctgc cagatgtcac tggtcagccg   2460
cttcaagaat atcctattct gcttagtgca gcgtccaatg agtctttgct ccggtacgcg   2520
cgacatttgg ccgattatat caccaagagt tccgccgacc ttactttggg caacctcagc   2580
tatacactgt cgcagcgccg taaacatcac cggatccgat ggtccaccac tgctaaggac   2640
ctgatcggtc ttattgaaca actcagagag tgcaccccgg ctgattttgt ccaggcacct   2700
caaaagtcta agaaaattgt gcttactttc agcggccagt cgaggacaac gatcggagtc   2760
tcagacagtg ccagattgga aaaccctagg ttcgagcact acattcagca atgcaacaat   2820
atcctcatgt cctacggttg tccggatctg cttccttatc tgtcgcagac ggatcccatc   2880
tcagacccaa ccatcattca atgtggaaca gtgacggttc agtatgcctg cgctcaatgt   2940
tggattgatg gcggtctcga cgtggccgga atcgttgggc attctcttgg tgaactcacc   3000
gcactggcga tctcaggagc tctcagtctg gaggatacac tcaaggttgt ctacacgcgc   3060
gccgaagcta ttaaggccaa atggggtccg gagtccggat ctatgctggc tatccacgca   3120
aaccaggaca cagtcaagtc tattgtggaa atcattgaga ccatgatcac taatcctgat   3180
gaagctctgg agatcgcatg ctataactca atcacgagtc atattgtggt tggcaaagag   3240
tctagcattg aaatggccga gaaggtcatc cagcaagacg ctcggtacca cgggttgcgc   3300
taccagaggc tcaatacctc gcatggcttc cactcacgat ttactgaacc cttgctccaa   3360
gatctcattc atgttgaacg ctctgtcgag tttcgtaaac cgagtatccc tctggagacc   3420
tctactcaga cacccgttga cttcgctaag aaacggcatt ccaagtacct ttctaaccac   3480
gcacgagagc cagtttttctt tgtcgatgcc gctcggcgac ttgaaagccg gttgggggag   3540
```

```
tgtgtctggt tggaagcagg ctggaatacc ccaatcgtcg cgatgactaa gcgcgcagtg    3600
gctaacccett ctgctcacac cttttcaagcc gtgacttctc ctgcagcggt tgcaatggaa   3660
ctttggcgcg agggtattgc gaccacttat tggtctttct ttaccccgaa agagagcgga    3720
ctgaagcata tctggcttcc tccctacagc ttcgaccgtc ctaagtattg gctcgagcac    3780
gtggatcggg ccgttcagga acgagatgct gctgcaaatg gatctgcttc gccaccgcct    3840
aagaaagtcc agcaacttgt gaccttgaag aaaacagagg gtacgaagtc ccaattcaga    3900
ctccatacaa cgaccgagcg ctacaaacgt atcgtttctg acatgctgt caggagcaag     3960
ccactgtgcc cagccagtat gtatatggag tccgctatta tgggtaccga acagctcgga    4020
gcttcactgg ttgggaaaac gatcaccttc gaaaatgtca gttttacaaa gcctcttggg    4080
tgtgatgaaa acctcgaggt ctacgtgaat ctcgagcaga acacggcggc cggagaggaa    4140
gcgtggcatt atgccgtcca atcgggaggg aagggctcac acagtgaggg tgatttcttt    4200
gcaacctcag gcgagatggc ggacatccag ctttacgaaa tgttgatcgc tgataagatt    4260
gaggcactcc gcaacgatgt ggacgccgaa agactgagga ctgccacagc ttactccatc    4320
ttctccagag tcgtggagta ttccgacctg cttaggggga tctcgtcaat taccatgggc    4380
actcgtcagg cactggcgca aatcaaggtg ccaaaatcta cttttcgaagc acaggagagc    4440
acagtttcgg attttacga cgcgattaca cttgatacgt tcatccaagt tttgggcttg    4500
ctcatcaatt ccgataacga cagttccgca gatgacgaaa tttatgtcgc gtctagcatc    4560
ggcaagatgg ttgtctctcc tacagagttc aagaaacatg ccacatggaa tgtctacgct    4620
acgtattccg catctgacag caaggcgtcg tcaggtgccg ttttcgtctt ttcggaggat    4680
cgcaaactgg tgtcattcgc taccaagatc cagtttatgc gtattaaggc tgcaaaactc    4740
gaaaaggttc tggagtccgc aaacccgggt agcaagacca aatcgactaa cggaaatgcc    4800
cttccgtcag ttcctcgcag tgtccctgct ggaccaacta gcgcccctca gcaagtcgct    4860
ccgactacaa tgccatctgc acctgcacct gtgccagtgg ttgctgctgg tgcatcgccg    4920
tcaaaaattg ctgacctcaa gtcactgatc agtgtttaca caggtgtgcc tgttgatgaa    4980
atgcaggaca accaaaattt cggcgatatg ggtcttgact ccttggcatc tatggagctt    5040
gcggacgaga tggaatctaa acttggttg aaggttgaga cagaagatct gcttttggga    5100
agcgtcgggt cgttgatcaa gttgctggca ccaagttctg gaccaaccgc tgcacttact    5160
gaaggcttgg tcgagtctta tgatacgtgc agcgaatcta gcgactccat tcgcaattct    5220
acaggatttc ataccactat ccctgctacg cctgctgagc tccactccaa ccctcctgat    5280
agcctggacg gctcgacagt ctggacgaag ccaaaacata gtctgtccgc tcgtttcaaa    5340
cttgatacca tggtgtacaa ggaagccgaa ggcatcgata ttcccgctga cgtctatgtg    5400
ccacaggagc cgcctcagca accgatgcct gtcgccctca tgatccatgg cggtggacac    5460
ctcactctgt ctagaagggc tgttcgcccg acgcagacca agtaccttt gagtcaagga    5520
atccttcctg tctccattga ctatcgtttg tgcccgcagg ttaatgtcat cgatggccct    5580
gtggccgata ctcgggacgc ttgtgaatgg gcacaacgag atctccctaa aattatggcc    5640
tcgcgcaaca tcgaggttga tgcttcaaag cttatcgtca ttggtggag taccgggggc    5700
actttggcga tgactacagc ctggaccctt ccttctgcag gactccctcc tcctgtggcg    5760
attctgtctt tctactgccc agttaattat gatcccgagg ctccaatcca gatgggagag    5820
gaacacgaaa agcgtaacat gtctctctct gaaatccgcc gtctcctggg accacagcca    5880
gctacctcac atgcaagtca cacgaccgac actacaaaac tgggttgggt gcaagcaaat    5940
```

```
gatccgcggt ctgaacttgt tttggcgctc atcaaggagc ctcgcggtat gagccttttg    6000
tttaatggac tccctcccac tggagaggaa ttgcctgtcc ctgatgctga gcgtgctgca    6060
gctctctccc ctctcgtgca ggttcgtaag ggaaattacg atgtgccaac ttatctgatt    6120
ttcggggatg aggacgaaat cgccccgttc ggcaaggctg tcgaatttgc acaagcgctt    6180
aaagacgctg gggtgaagag cggcttttgt cctattaaag gtggaaagca tatcttcgat    6240
ctcggtattt cccccggatc taaggcatgg gatgagtcga tcggtccagg atacgacttc    6300
ctcttgggtg aactggaaaa tgcacaccgg cgatgtcgtg atgtctga                 6348
```

<210> SEQ ID NO 24
<211> LENGTH: 1665
<212> TYPE: DNA
<213> ORGANISM: Artificial sequence
<220> FEATURE:
<223> OTHER INFORMATION: modified gene

<400> SEQUENCE: 24

```
atgtccgcca tccccaagaa atgcaccgtg ctcgttattg gcggtggacc aggggggctcc      60 tatgcagctt ctgcacttgc gcgcgaagga atcgacactg tcgtgttgga gggcgataag    120
ttccctcggt atcatattgg cgaaagcatg ttggcttcga tgcgacatct cctcaagttt    180
gtggagctcg acgggaaatt cgattcttac ggctttgtta agaaacccgg tgcagcgttc    240
aagctgaaca agaataaacg cgaaggttac accgactttc ttgccgctgg cggcccaaac    300
aattatgcat ggaacgttgt ccgttcagaa gcggacaatt tgatgttcca gcatgcaggc    360
gagagtggag cgaagatctt cgatggagtc agcgtgaaat cgattcaatt tgaaaaccct    420
actgaggtcc ccgacggcga gccaaacctc aatcctggca gcccgtgag cgccacatac    480 cagatcaagg agacgaaaga acaggggacaa attgatttcg actatgtggt tgatgctagc    540
gggagaatcg gcattctgtc gacaaagtac atgaaaaacc gccgttataa tcaaggcctt    600
aagaacatcg caaattgggg ttactgggaa ggatgcaaca aatatgctcc tggaacgccg    660
cgggagaata gccccttctt tgaagccttg caggacgagt cgggttgggc ttggttcatt    720
ccactccata acgggaccgt ttcggtcggc gtcgtgatga atcaaaagct cgcaactcag    780
aagaaacaag aagcggatct ggactccacc gagttctacc acgatactct taacaagatc    840
tctcccaatc tccgggagct gattggtgac ggaaagttcg tctccaacgt gaaaacagcc    900
tctgattact catatagtgc ttcctcttac tcatttccgt atgcccgaat cgttggtgac    960
gctggatgtt tcattgatcc ttattttagc tcgggtgtcc acctcgcact gacgtcagga   1020
ctgagtgcag cgaccactat ctccgcgtct attcgcggac aggtcgacga ggaacttggg   1080
tccgagtggc atacaaagaa attctctgat gcctacacga gatttctttt ggttgtcttg   1140
tctgcttata gcagatcag gcaccaagag gaaccggtcc tcagcgattt cgacgaagat   1200
aatttcgaca gagccttttc gttctttagg cctatcattc agggcacagc tgatgccgct   1260
aacaataagc tgagccaaga ggaacttaac aaaacgttgg agttctgtgc cttcgctttt   1320
gagccagtgg aaaatgacga ggatcgctca aaggcaatga gtgcgatgca ggaagctgtt   1380
gacaacggga ccggctatca tccgatctc tctcctgagc agctgaaggc agtcaaacac   1440
atccaagccc ggcgagctat gcgaacatca gacacgatga atatcgaaag tttcggaact   1500
gatgccatta acgggtttgt tccgaatctt gtccgcgggt cacttggctt gcgtaagcag   1560
gaagccatga gtggcgacat gggcggcgcc aacggtcatg tcgatgaaac caacggtgtg   1620
```
actgttaatg gacatcacca acctgagggt gtgaaggctc actga            1665

<210> SEQ ID NO 25
<211> LENGTH: 748
<212> TYPE: DNA
<213> ORGANISM: Aspergillus sojae

<400> SEQUENCE: 25

```
tgtggaccag acaggcgcca ctcggccggg ccacaactgc ttgggttttg accgggagcg      60
gaccaattaa ggactcgaac gaccgcgggg ttcaaatgca aacaagtaca acacgcagca     120
aacgaagcag cccaccactg cgttgatgcc cagtttgtct gtccgaaatc caccggaaag     180
gtggaaacat actatgtaac aatcagaggg aagaaaaatt ttttatcgac gaggcaggat     240
agtgactgat ggtggggtca tggtcgggtc tccgagcgaa agagaaccaa ggaaacaaga     300
tcaacgaggt tggtgtaccc aaaaggccgc agcaacaaga gtcatcgccc aaaagtcaac     360
agtctggaag agactccgcc gtgcagattc tgcgtcggtc ccgcacatgc gtggtgggg      420
cattacccct ccatgtccaa tgataagggc ggcggtcgag ggcttaagcc cgcccactaa     480
ttcgccttct cgcttgcccc tccatataag gattcccctc cttcccctcc cacaactttt     540
ttcctctttc tctcttcgtc cgcatcagta cgtatatctt tcccccctac ctctttctca     600
ctcttcctcg attcattcca ctcttctcct tactgacatc tgttttgctc agtacctcta     660
cgcgatcagc cgtagtatct gagcaagctt ttttacagaa tctttctagt atcttacaaa     720
gaactacaaa gttcgcacca ccttcaaa                                        748
```

<210> SEQ ID NO 26
<211> LENGTH: 800
<212> TYPE: DNA
<213> ORGANISM: Aspergillus sojae

<400> SEQUENCE: 26

```
gtaccaggag tacattggag agttctacca ttgttgctgg aatacaatga tgattagaaa      60
ccgaagagtg ttatgattcg gacggatata cgcatggcac gcatacagcg tgatacatag     120
gctgtttgct caagaattag gattttatct gaatccatgt acagagttta cttatgttag     180
tagtcaatga aatcttggct ttctaatttt gtccgatcta caaggggtag tcgatcacag     240
aacgaactag atgtgcaggg aacgatgatc acccgctctt agcaagacct ctagtagttt     300
tcgaccatag cttaacgcg aatcatgacc ctactatttt ctagattgca gaccaagtca     360
catgacaatg tcctctttga agtaggatca gtagctgatt agattccggg aaatgaatta     420
gggctggcgt tccaactact ggggagtgcc gatgttgctg tatgaaagat agtaagatta     480
ctagtgcaca gctgtagtaa ttatttactc tagattatat attccaaata ataagtaatc     540
taagatagta gacagtccta tgatatagct ccgggttcga agtcggcaaa agatatgcaa     600
tcacctgtcg ggatgatata tgtatatctg aaataccgac atcaaccatc cagtcggatc     660
agctaaacga agtatcactt ctttcgccac tgccaatcac tacttctatt aaagttcatg     720
ttacagtata agccacaaga cttatctcca gaactaactt gtgcatagga gctctgccga     780
tagccgggtg gttggatcgg                                                 800
```

<210> SEQ ID NO 27
<211> LENGTH: 1838
<212> TYPE: DNA
<213> ORGANISM: Aspergillus sojae

<400> SEQUENCE: 27

```
ttgggcttat tgctatgtcc ctgaaaggat atcaaaagca ggcaaaaagc caggcataac      60
cccgcgcgga tggtacccta aggataagcc ctaatcttat ctacatgtga ctgcgtcgat     120
gtgtttggtc caaatgaggc atgtggctca ccccacaggc ggagaaacgt gtggctagtg     180
catgacggtc ccctccatag attcaattta atttttcgcg gcaattgtcg tgcagtttgt     240
atctaccgtt cattctacat attaagggtt agtaattgga catcctgatt actttgtcta     300
attactgaaa actcgaagta ctaacctact aaataagtca gtttcaacca ctaagtactc     360
atttatacaa tagttgcaga accccgcgct acccctccat tgccaacatg tcttccaagt     420
cgcaattgac ctacagcgca cgcgctagca agcaccccaa tgcgctcgtg aagaagctct     480
tcgaggttgc cgaggccaag aaaaccaatg tcaccgtttc cgccgacgtg acaaccacca     540
aagagctgct ggatttggct gaccgtatgc gcaccgggga tgccacttac atatgatcta     600
gtaatggtta atggtggaat atataacagg actcggtccg tacattgccg tgatcaaaac     660
tcacatcgat atcctctccg atttcagcga agagaccatc atcggtctga aggcccttgc     720
agagaagcac aatttcctca tcttcgaaga tcgcaagttc atcgatatcg gaaacacagt     780
ccaaaagcag taccatggcg gcactctgcg catctctgag tgggcccaca tcatcaactg     840
cagtattctg cccggtgagg gtatcgtcga ggctctggcc cagactgctt cggccgagga     900
cttcccctat ggctctgaga ggggcctttt gatccttgcg gagatgacat ccaagggatc     960
tttggctacc ggtcaatata ctacttcttc tgttgactat gcccggaagt ataagaagtt    1020
tgtgatggga ttcgtctcga cgcgtcacct gggcgaggtt cagtctgaag ttagctcgcc    1080
ttcggaggag gaggatttcg tcgtcttcac gacaggtgtc aacctctcct cgaagggaga    1140
caaactggga cagcaatacc agactcctga gtctgctgtt ggacgcggtg ccgactttat    1200
cattgctggt cgtggaattt atgctgctcc tgatcccgtg gaggcagcga agcggtacca    1260
gaaagaggga tgggatgcat accagaagcg tgttggtgcg caataagtag tggtgaatac    1320
gtgctctttt tatggcagta tatcgcaagt atgatgcgat tcataaattc agcagtcgaa    1380
ttctacgaga gaacgatgct aagagatacc ctctctatat gaataatatg cctgcctcga    1440
gatatggaca tattcaagat cagagttaag ggtcatgttt caaaatcaca ccaatctcca    1500
acatagacga gaattttttac cggattgtct gaaggtgcag ctggagattg gtctattttc    1560
taagagtggg gtatcactaa tgtacagtcg gtcactatcg tacaaacaat cacaattata    1620
tacaagattt cccatcaccc cttactctaa catggcactt ttatccatcg agtccgagcc    1680
tagccaccat ttggtgcttt cgtagagacc aaagtataac cctgatccga cagcggccat    1740
aaacgtgttg atagcacacc ctcggaatag tcctctcggg ccatctgttc gtataatctc    1800
ccgtacggta ttgatcatcc tttcttctg aggtgcgg                             1838
```

<210> SEQ ID NO 28
<211> LENGTH: 3195
<212> TYPE: DNA
<213> ORGANISM: Artificial sequence
<220> FEATURE:
<223> OTHER INFORMATION: modified gene

<400> SEQUENCE: 28

```
atgaccgagc tgattcctgg gccgaaggga ctgcctctga ttggtaatgt gctggatatt      60
gaccccgtgg acgctgttgt ttgtctcgga cggatcgccg acacctacgg gcatatctat    120
cagctgaaag tgggcggatc cgccaagatc ttcatcagta gccgcgagct ggtcgacgag    180
```

```
ctgagtgatg agagccggtt caccaagctg gtgtctggac ctctggctca gctgcgaaac    240
gtctgtcatg attctctgtt caccgcccag tcagacgagc ctgcctggga tctggcccac    300
aagatcctga tgcctgcttt tggacctctg gctatccgag gcatgttcga cgagatgcac    360
gatatcgctt cccagctggt ggtcaagtgg gctcgatttg gaccacagga caccatcgat    420
gtgtctggcg acttcacccg gctgaccctg gatgccatcg ccctgtgtag tatgagcacc    480
cgattcaaca gtttctacaa gcaggaccag catcccttcg tgtcgtccat gctggaggtc    540
ctggctgagt caggaaagcg cgctgtgcgc ccgccctttg tcaacgatta catcttccga    600
ggcagtctga agcactataa caccgagatc gccaccatgc gccgaatcgc tatggatgtg    660
ctggctgagc gacgcgctaa cccgatggcc tgtcagaaga cgatctgct  gaacgccatg    720 atcaacggac gcgaccctaa gaccggagag gggctgtcgg atgagtccac catcaacaac    780
ctgatcgtct tcctgatcgc cggacatgaa accacctctg gctgctgtc  attcctgttc    840 tactatctgc tgacccgccc agacgtgttc gagaaggccc agaaggaagt ggatgaactg    900
gtgggacgag gacctgtcac catcgagcat atgtcaaagc tgcactacat cgaggcctgt    960
ctgcgcgaaa ccctgcgact gcacccaacc gctcctgtga tcaccttcaa gaccaagccg   1020
ggcttcgaga aggagagtac caccatcggg ggcggaaagt ataagatcga tcgcgatcag   1080
ggaatcgtgg ccctgctggt caacatccag cgcgacccga aggtctgggg cgatgacgcc   1140
aacgagttca gcctgagcg  aatgaccgat gagaagttca caacctgcc  cgccaactgt   1200 tggaagccgt cgggaacgg  catccgcggg tgcatcggac gagcttttgc ttggcaggag   1260
agcctgctga tcaccgccat gctgctgcag aacttcaact tccagctggc cgatccagac   1320
tataagctgc agatcaagca gaccctgacc atcaagcccg gcaacttctt catgcatgcc   1380
aagctgcgcg accacgtgga tccctggag  ctggagggaa tcctgcatgg gggcgccaag   1440 aagggtcaa  agatcgacgg accgtcttct ggggctagtc tggctaccac cgagcaggag   1500
ctgcagccta tgaccatcct gtacggctcg gattccggaa cctgtgagag tatggctcag   1560
agcctggctc gagctgctcg aggacggggg tatggagcta ccgtgaagac cctggactct   1620 gctgtgagc  aggtccctaa ggatcagcca gtggtcatcg tgtctccctc atacaacggc   1680
cagcctccat cgaacgccac cgatttcgtc aagtggctgg aggccctgga ctccaaggcc   1740
ctgaaggatg tgaagtactc tgtctatgga tgtgggaaca aggactatac cagcaccttc   1800
catcgcatcc cgaagctgct ggatgccgag ttcgagcggt gtggcgccaa gcgaatcgcc   1860
gaaaccggcc tgggagatgt gaccgtcgga gacatcttct cggatttcga gcggtggcag   1920
gatgatcagc tgtggcctgc tctgggagtg gctcatatgg atggagacgc cgatgccgag   1980
ttcgacatcc acgtggatcg atctggacga gctgctgagc tggaggtgga tgctgatgag   2040
gccaccgtgc agtcgaacca ggtcctgacc gcccctggag agcagagaa  gcggtacatc   2100 accctgaagc tgccagaggg gatgcagtat aagtctggcg accacctgtc tgtgctgcct   2160
ctgaacgatt ggggcgtggt ccggcgagtc tttgcttggg ctcagctgcc ttgggatgct   2220
gtggtcacca tcccaaaggg aaccaacacc tccctgccaa ccggacggca gatcagtgcc   2280
aaggatctgc tgtctggata tgtggagctg tctcagccag ccacccgaaa gaacatcgcc   2340
aaactggctg cgtcatcacc ttgcccgttc acccaaaagt ctctctcaaa actggaagaa   2400
cattttgaca gtgacatcgc ccaacgacgg ctcagtgttc tggacattct ggaggagttc   2460
cccgccattg acattacttt cggcaacttc atcagcatgc tgccacccat gcgcccacga   2520
cagtacagca tcgccagtag cccaatggcc gatccaagta ccgccaccct gatgtggacc   2580
```

| | |
|---|---|
| gtcctgaaca gtgaggccta ttcgggcagt ggacgccgat tcctgggagt gtgtagcacc | 2640 |
| tatctggccg gactggccga gggcgatcga gtccatgtga ccgtcaagcc tgccctgcga | 2700 |
| ctgttccatc caccttcaga tccagagtcg atgcccatca tcatggcctg tgccggaacc | 2760 |
| ggcctggccc cgttccgcgg attcctggag gagcgggtgt gtcagatgaa ggccggacgc | 2820 |
| gccctggccc ccgcctatct gttcgtcggc tgtcgagacc cagagaagga tgccctgctg | 2880 |
| aaggatgagc tggcccagtg ggagcgagat ggcgtggtca agatctatta cgccttcagt | 2940 |
| cgcgccagcg atcagagtga tgggtgtaag catgtccagg atcgaatctg gaacgagcga | 3000 |
| gatctggtgc gaaagggcct gttcgaggga acgcccgct tcttcatgtg tgggggatca | 3060 |
| ggcgccggaa agtccgtcga ggatgtggtc aagcgcatct acaaggacaa caagggagag | 3120 |
| tcccaggaga aggctgcgga gtcgtggttc caggacctca aggctaatcg ttatgtcact | 3180 |
| gaaatctttg cgtga | 3195 |

<210> SEQ ID NO 29
<211> LENGTH: 822
<212> TYPE: DNA
<213> ORGANISM: Artificial sequence
<220> FEATURE:
<223> OTHER INFORMATION: modified gene

<400> SEQUENCE: 29

| | |
|---|---|
| atggcgtttg gcgtggagcc cccagagcat gtcaccccgt ggttcaagcc ggtttatgag | 60 |
| gcgacttttc agtttggcgg agtggcgtgg accctgtgtt acatcctgat cgcccgcgag | 120 |
| ggcatgcgga ccaagagtta tggaatgccc ctgttcgccc tggccaacaa cttcgcctgg | 180 |
| gagatggtct acgccctgtg ggtggtcgat aacgccttcg agaagaccgc catgaccatc | 240 |
| tggatgctga tcgacacccc tatcatctat tccatcctga agcatggagt gctggagtgg | 300 |
| cagcacgccc caatggtcag tcgcaacctg aagagcatcc tggtggggct gatcgctctg | 360 |
| tgtgctgctg cccattggag ttggcagagc tggtggatcg ggaacgagat gggaaagcga | 420 |
| gatgacctgg agggagctga tctgacccag atggcctact gggccgtgtc gatgtgtcag | 480 |
| ttcctggtga gtaccatgtc cctggccatg ctgtgtgtgc ggggacactc tggcggagtc | 540 |
| tcatggatga tctggctgtc tcgattcctg ggaaccctga tcgggctgaa catgaactac | 600 |
| gcctgggcct actatacctg gcccgaggcc atgagtatt tcatgtcagc tcctgctgtg | 660 |
| tttgtctggg gcgtgaccac cgtctgtgat atcatctacg gcttcgtgct gtatcacgtc | 720 |
| aagtcgaacg agcgagagct gtccgacggc cgcaaggtgg ccgctgaggc tgatgacgag | 780 |
| caagtcggtg gtggtctaa gatgaaaact gggaagaact ga | 822 |

<210> SEQ ID NO 30
<211> LENGTH: 1605
<212> TYPE: DNA
<213> ORGANISM: Artificial sequence
<220> FEATURE:
<223> OTHER INFORMATION: modified gene

<400> SEQUENCE: 30

| | |
|---|---|
| atgggctccc tgctctttga ttcccccgtt gggcgttttg tcgcttcatt tcctgctctc | 60 |
| tcggcggctg ctggactcat tgttgccatc agtttcatct acatccgctt catcaagacc | 120 |
| cctaagctgg acctgccagt ggtgggaaac ccaggcgaca gtgggatgc tcagaagcat | 180 |
| atcgtggctg gagctcgaaa gtaccctgac accccatata tcctgccgat ggatcccccg | 240 |

```
atcgtggtcc tgcctatcaa gatccaggat gaggtccgaa acctgcccga gaacgtggtc      300
agtttcacca aggagcatca gcgaaacttc ttcgcccagt ataccggaat cggggaccac      360
cgaccggaga tgatcaccgc catccggcag gatctgaccc gacacatcgt gagccaccatc    420 cctggactgc aggaagaggt gcgctacggg ttcgacaagg agttcggcga ctgtaaggat     480
tggaccccct tcccgctgta tatgaaggtg ctgcgaatcg tggctctgac cagtggacga     540
gtgtttgtgg gacgcccgct gtcacggagg aagagtggc tgcagcggac catctcgtac      600
accatggatt gtgtgaaggc ccgaaacgcc atccgcgagt atccatggtg gaagcgccga    660
tgggtcacca gtagcctgcc cgagatcgcc aagctgaccg agcatcgaac ccgaggcgga    720
gtgctgctga agcctatcat ggacgcccag ctggccaagg atagcaagcg agagaagatc    780
atcaacgagg aaaccggaga cgaggaaggc aacttcatcg agtggctgct gaagcacacc    840
ccaggcgacc tgaagatgga tcccgagaac ctggccctga accagatggt gctggccttc    900
gcctcggtcc atacctcgtc catgtccgtg acccatgcta tcctggaact ggtgacccgg    960
ccggagtact ttgcccctct gcgagaagag ctggaggaag tgcgacgcgc tgacggccat   1020
accgtcgatg acgatggata tatccgcctg aagaaggagt ctatcaacaa gctgcggaag   1080
ctggatagtt tcatgaagga gagccagcga ttcaaccctc caatctctac ctcaggcacc   1140
cgcatctgta ccgccgacct gaagctgtca accggacaca ccctgccaaa ggggacccgg   1200 atctgttttcc cctcgtacga tgtgcatcac aacccgaaga ccaccaccta ctcccctgag   1260
tataacccgc ccgggtatac ccctccagac cagttcgatg gcctgcgctt cttcaagctg   1320
cgggagatgc aggaaaagga gagtcgacat cagttcgcca ccgccaacca cgagagcctg   1380
gtgttcggct tcggaaacca tacctgtccc ggacgcttct tcgccgccaa ccagatcaag   1440
atcatcctgg ccgagctgct gatgaactgg gacgtgcgcc tgaagggaga gtgtgagcag   1500
aagggcggcc cagagaagcg gccgcagaac atggtggtcg atctggttat taccccccaat   1560 ccaatggcga tggttgaaat gaagcgtcgt tctcgggctg tgtga               1605
```

<210> SEQ ID NO 31
<211> LENGTH: 23
<212> TYPE: DNA
<213> ORGANISM: Artificial sequence
<220> FEATURE:
<223> OTHER INFORMATION: primer

<400> SEQUENCE: 31
tgtggaccag acaggcgcca ctc                                              23

<210> SEQ ID NO 32
<211> LENGTH: 25
<212> TYPE: DNA
<213> ORGANISM: Artificial sequence
<220> FEATURE:
<223> OTHER INFORMATION: primer

<400> SEQUENCE: 32
tttgaaggtg gtgcgaactt tgtag                                            25

<210> SEQ ID NO 33
<211> LENGTH: 39
<212> TYPE: DNA
<213> ORGANISM: Artificial sequence
<220> FEATURE:
<223> OTHER INFORMATION: primer

<400> SEQUENCE: 33

```
cgcaccacct tcaaaatgac acttattcag acgaaacat                                    39
```

```
<210> SEQ ID NO 34
<211> LENGTH: 39
<212> TYPE: DNA
<213> ORGANISM: Artificial sequence
<220> FEATURE:
<223> OTHER INFORMATION: primer

<400> SEQUENCE: 34
atgtactcct ggtactcaga catcacgaca tcgccggtg                                    39
```

```
<210> SEQ ID NO 35
<211> LENGTH: 325
<212> TYPE: PRT
<213> ORGANISM: Neonectria ditissima

<400> SEQUENCE: 35
```

Met Ala Pro Lys Thr Ser Thr Ala Gln Gly Arg Tyr Thr Pro Pro Thr
1               5                   10                  15

Lys Gly Ile Leu Ser Lys Leu Pro Ala Ser Trp Val Pro Tyr Ala Glu
            20                  25                  30

Leu Ile Arg Leu Glu Gln Pro His Gly Ile Tyr Met Ile Tyr Phe Pro
        35                  40                  45

His Ile Val Gly Leu Met Tyr Ala Cys Ser Ala Arg Pro Ser Ala Val
    50                  55                  60

Pro Ala His Glu Leu Ala His Arg Leu Val Val Phe Val Trp Thr
65                  70                  75                  80

Phe Phe Met Arg Gly Ala Gly Cys Ala Trp Asn Asp Ile Thr Asp Gln
                85                  90                  95

Asp Phe Asp Arg Lys Thr Glu Arg Cys Arg Asn Arg Pro Val Ala Arg
            100                 105                 110

Gly Ala Ile Ser Thr Thr Gln Gly His Ile Tyr Thr Leu Val Leu Thr
        115                 120                 125

Ala Leu Gly Phe Leu Thr Leu Gln Thr Leu Pro Val Glu Cys Thr Leu
    130                 135                 140

Cys Ala Leu Ala Thr Ala Val Leu Thr Ile Ile Tyr Pro Phe Gly Lys
145                 150                 155                 160

Arg Phe Thr Asn Phe Ala Gln Val Ile Leu Gly Ser Thr Leu Ala Ser
                165                 170                 175

Thr Ile Ala Leu Ser Ala Tyr Ala Val Glu Leu Pro Ala Leu Ser Pro
            180                 185                 190

Gly Tyr Val Val Pro Thr Leu Cys Leu Thr Ala Thr Ile Leu Leu Leu
        195                 200                 205

Val Val Phe Tyr Asp Thr Ile Tyr Ala Arg Gln Asp Thr Ala Asp Asp
    210                 215                 220

Leu Lys Thr Gly Val Lys Gly Met Ala Val Leu Phe Arg Asn His Ile
225                 230                 235                 240

Glu Thr Leu Leu Ala Val Leu Ala Leu Ser Ile Ala Gly Leu Leu Ala
                245                 250                 255

Thr Thr Gly Thr Leu Leu Asn Met Gly Pro Tyr Phe Phe Ala Phe Ser
            260                 265                 270

Val Val Gly Leu Ala Thr Gly Leu Leu Thr Met Ile Ala Leu Ile Arg
        275                 280                 285

Trp His Leu Phe Pro Ser Phe Ala Lys Tyr Ser Gly Trp Phe Tyr Ala
    290                 295                 300

```
Leu Ala Ile Val Asn Leu Leu Gly Gly Cys Val Val Glu Tyr Leu Asn
305                 310                 315                 320

Lys Ala Pro Ala Leu
            325

<210> SEQ ID NO 36
<211> LENGTH: 1057
<212> TYPE: PRT
<213> ORGANISM: Neonectria ditissima

<400> SEQUENCE: 36

Met Ala Pro Thr Ile Arg Pro Phe Val Lys Pro Ala Val Asn Phe Ala
1               5                   10                  15

Ser Ile Gln Arg Leu Asp Gly Cys Leu His Ser Leu Pro Glu Leu Val
            20                  25                  30

Asp Phe Asn Ala Gln Asn Asn Ala Asp His Pro Phe Cys Ile Gln Ala
        35                  40                  45

Lys Ser Asp Gly Leu Asp Thr Phe Thr His Ala Asp Phe Lys Thr Ala
    50                  55                  60

Val Ser Asn Cys Ala Ala Trp Ile Lys Glu Asn Val Pro Leu Arg Ala
65                  70                  75                  80

Ser Thr Asp Pro Asn Gly Leu Thr Lys Met Ala Pro Val Ala Leu Phe
                85                  90                  95

Met Gln Ser Asp Phe Gly Leu Val Ile His Glu Phe Ala Leu Leu Ser
            100                 105                 110

Ile Gly Val Pro Pro Leu Ile Leu Ser Pro Arg Leu Pro Pro Ile Ala
        115                 120                 125

Ile Met His Leu Leu Gln Glu Thr Ala Ala Ser Ser Phe Ile Val Ser
    130                 135                 140

Gln Arg Leu Ser Glu Pro Ala Lys Pro Ala Leu Ala Ala Leu Asn Ala
145                 150                 155                 160

Lys Gly Ile Ser Thr His Ile Gly Leu Asn Tyr Asp Ser Phe His Glu
                165                 170                 175

Ala Gly Ala Val Ala Ser Lys Pro Lys Phe Asp Leu Pro Thr Glu Leu
            180                 185                 190

Asp Ser Val Val Leu Leu His Ser Ser Gly Thr Thr Gly Met Pro
        195                 200                 205

Lys Pro Ile Pro Ile Thr His Arg Gln Leu Leu Phe Ala Val Asn Cys
210                 215                 220

His Gly Phe Asp Thr Glu Glu Glu Ala Gln Gly Leu Asn Val Ser Ser
225                 230                 235                 240

Leu Pro Leu Phe His Gly Phe Gly Leu Val Ala Pro Gly Leu Ser Met
                245                 250                 255

Ser Ala Gly Lys Thr Thr Val Tyr Pro Ala Ser Asp Gly Ile Pro Asn
            260                 265                 270

Ala Leu Ser Ile Val Glu Leu Val Lys Arg Thr Asn Ala Lys Ser Leu
        275                 280                 285

Met Thr Val Pro Phe Leu Leu Asp Asp Val Val Asn Asn Glu Glu Ala
    290                 295                 300

Ile Lys Val Leu Ala Gly Leu Asp Phe Val Gly Thr Gly Gly Ala Ala
305                 310                 315                 320

Leu Gly Ala Gly Val Gly Asp Lys Leu Ala Gln Gly Gly Val Lys Leu
                325                 330                 335

Leu Asn Phe Tyr Gly Thr Thr Glu Ser Gly Pro Leu Ser Asp Thr Phe
```

```
            340             345             350
Val Pro Lys Asp Asn Tyr Ser Trp Lys Tyr Phe Arg Leu Arg Lys Asp
            355             360                 365

Val Asn Tyr Lys Val Asp Glu Leu Asp Pro Lys Asp Gly Gln Arg Met
    370             375             380

Phe Arg Leu Thr Val Phe Pro Tyr Gly Gly Thr Glu Gly Ile Glu Ile
385             390             395                             400

Ala Asp Gln Leu Ile Arg Asn Glu Gln Tyr Pro Glu Thr Asp Phe Ala
                405             410                 415

Ala Val Gly Arg Asp Asp Val Ile Val Leu Ala Thr Gly Glu Lys
            420             425             430

Ala Asp Pro Leu Ile Leu Glu Thr Met Leu Ser Glu Ala Pro Ser Val
        435             440             445

Lys Ser Ala Ile Ala Phe Gly Glu Asn Arg Phe Asn Leu Gly Val Val
    450             455             460

Val Glu Pro Ala Ser Pro Ile Ala Glu Gly Glu Ala Ala Phe Lys
465             470             475                         480

Glu Ser Ile Trp Pro Ile Ala Ala Ala Gly Gln Lys Met Glu Ser
                485             490             495

Tyr Ser Arg Ile Pro Ser Gln Asp Val Val Ile Val Pro Ser Ser
            500             505                 510

Val Thr Ile Pro Arg Thr Asp Lys Gly Ser Ile Pro Arg Lys Glu Val
            515             520             525

Tyr Ala Leu Phe Glu Lys Asp Ile Asn Glu Val Tyr Glu Lys Leu Ala
    530             535             540

Arg Gly Val Glu Glu Ser Val Glu Ala Leu Asp Leu Asp Asn Leu Glu
545             550             555                             560

Gln Asn Leu Lys Gln Leu Val Glu Thr His Ser Arg Leu Gln Val Ser
                565             570             575

Pro Ser Asp Trp Thr Val Glu Asp Ser Leu Phe Asp Leu Gly Leu Asp
            580             585             590

Ser Leu Gln Ala Leu Gln Leu Arg Arg Val Leu Ile Thr Ala Ala Ser
    595             600             605

Lys Thr Glu Val Phe Lys Asn Thr Asp Val Ala Lys Met Ile Pro Val
    610             615             620

Glu Phe Leu Tyr Leu Asn Ser Ser Val Arg Glu Met Ala Thr Ala Leu
625             630             635                             640

Thr Arg Ser Gly Ser Ala Gly Asp Ala Thr Glu Ser Trp Ser Glu Val
                645             650             655

Asn Lys Phe Val Glu Gln Tyr Thr Leu Ala Gln Ser Val Asp Thr Lys
            660             665             670

Asp Lys Leu Pro Ser Thr Pro Glu Asn Ala Val Val Leu Leu Thr Gly
        675             680             685

Ser Ser Gly Ser Leu Gly Ser His Ile Leu Ala Asn Leu Ala Arg Ser
    690             695             700

Pro Asn Val Lys Arg Val Val Leu Leu Arg Lys Gly Lys Ala Ala
705             710             715                         720

Ala Pro Pro Val Pro Gly Gln Lys Tyr Asp Arg Ser Gly Leu Thr Ala
                725             730             735

Arg Gly Ile Lys Leu Ser Glu Ala Glu Trp Ala Lys Ile Ser Ser Leu
            740             745             750

Asp Val Asp Pro Thr Gln Glu Gln Leu Gly Leu Asn Pro Met Val Tyr
    755             760             765
```

Gly Ala Leu Gln Gln Asn Val Thr Gln Ile Ile His Ala Ala Trp Pro
    770                 775                 780

Met Asn Tyr Leu Ile Arg Leu Pro Ser Phe Gln Tyr Gln Phe Lys Phe
785                 790                 795                 800

Leu Gln Asn Leu Leu Gln Leu Ala Met Asp Gly Asn Gly Asp Thr Lys
                805                 810                 815

Arg Arg Phe Val Phe Val Ser Ser Ile Ala Ala Val Ala Lys Val Gly
                820                 825                 830

Leu Ala Ser Gly Gly Lys Leu Ile Ala Glu Ser Pro Val Asp Pro Val
                835                 840                 845

Asp Ala Ala Cys Gly Ile Gly Tyr Ala Asp Gly Lys Leu Ala Cys Glu
                850                 855                 860

Lys Ile Leu Glu Arg Ala Ala Lys Thr Phe Ala Gly Gln Leu Glu Val
865                 870                 875                 880

Thr Tyr Val Arg Cys Gly Gln Met Thr Gly Ala Arg Glu Thr Gly Val
                885                 890                 895

Trp Asn Ser Gly Glu Gln Ile Pro Met Leu Leu Arg Thr Ala Gln Ser
                900                 905                 910

Val Gly Ser Leu Pro Gln Leu Gln Gly Thr Leu Ser Trp Ile Pro Val
                915                 920                 925

Asp Asp Ala Ala Val Ile Ser Asp Met Thr Phe Ser Ala Gly Ile
                930                 935                 940

Pro Pro Ile Ala Gln His Leu Glu Asn Pro Val Arg Gln Ala Trp Ser
945                 950                 955                 960

Asp Val Ile Glu Ser Ile Arg Gln Gln Leu Lys Leu Ala Asn Ala Ser
                965                 970                 975

Val Pro Phe Asp Ala Trp Leu Asp Gln Val Ala Ser Ala Glu Gly Glu
                980                 985                 990

Glu Asp Ala Tyr Pro Ile Arg Lys Leu His Asp Phe Phe Lys His Ser
                995                 1000                1005

Phe Arg Ala Val Ala Cys Gly Gln Val Ile Leu Asp Thr Ala Val
        1010                1015                1020

Ala Arg Asn Ser Ser Thr Thr Leu Arg Ser Ala Ala Val Asp
        1025                1030                1035

Glu Ala Thr Ile Gln Gly Tyr Ile Arg His Trp Lys Glu Thr Gly
        1040                1045                1050

Tyr Leu Gln Lys
        1055

<210> SEQ ID NO 37
<211> LENGTH: 1880
<212> TYPE: PRT
<213> ORGANISM: Neonectria ditissima

<400> SEQUENCE: 37

Ala Tyr Ile Ser Thr Ile Ser Asp Ser His Thr Arg Ser Leu Ile Ala
1               5                   10                  15

Pro Gln Asp Gln Ile Ser Ser Leu Arg Ala Tyr Ala Glu Lys Glu Gly
                20                  25                  30

Leu Ser Pro Lys Thr Met His Ile Gln Gly Lys Leu His Asp Thr Asn
                35                  40                  45

Asn Ala Asp Leu Ala Asn Glu Cys Ile Glu Trp Cys Asn Thr Leu Pro
        50                  55                  60

Glu Leu Pro Phe Pro Ser Gly Lys Ala Leu Gln Val Pro Val Arg Ser

```
                65                  70                  75                  80
Asn Arg Ser Gly Gly Leu Leu Ala Thr Val Thr Gln Ser Leu Ser Asn
                    85                  90                  95

Glu Val Ile Gln Thr Ile Leu Ala Ser Thr Cys Asp Trp Ser Leu Val
                    100                 105                 110

Ile Arg Gly Leu Ala Ser Asp Leu Gln Gln Thr Asp Arg Arg Glu His
                    115                 120                 125

Thr Leu Ala Leu Phe Gly Ile Gly Asn Ser Val Pro Leu Ala Pro Phe
                    130                 135                 140

Arg Gln His Glu Leu Asp Ile Thr Lys Leu Asp Met Ser Ser Ile Ser
145                 150                 155                 160

Thr Thr Ser Thr Ala Phe Asn Pro Ile Ser Phe Pro Pro Asn Ala Ile
                    165                 170                 175

Ala Val Val Gly Ala Gly Cys Arg Leu Pro Gly Ala Ser Ser Leu Glu
                    180                 185                 190

Glu Leu Trp Glu Leu Ile Ser Glu Gly Lys Ser Arg Leu Glu Thr Leu
                    195                 200                 205

Arg Ser Asp Arg Ala Asn Val Gln Gly Ser Tyr Arg Ala Ser Gln Asp
210                 215                 220

Lys Asn Trp Ala Ser Lys Arg Gln Phe Tyr Gly Asn Tyr Ile Asp Asp
225                 230                 235                 240

Ile Asp Ala Phe Asp His Ser Phe Phe Gly Ile Ser Pro Arg Glu Ala
                    245                 250                 255

Lys Tyr Met Asp Pro Gln Gln Arg Leu Leu Leu Met Val Ala Phe Asp
                    260                 265                 270

Ala Leu Asp Ser Ser Gly Tyr Met Arg Gln His Arg Arg Glu Glu Gly
                    275                 280                 285

Asp Ala Val Gly Cys Phe Ile Gly Ala Ser Tyr Thr Glu Tyr Leu Glu
                    290                 295                 300

Asn Thr Ser Ser Tyr Ser Pro Ser Ala Phe Thr Ala Thr Gly Thr Ile
305                 310                 315                 320

Arg Ala Phe Leu Ser Gly Lys Ile Ser Tyr His Phe Gly Trp Ser Gly
                    325                 330                 335

Pro Ser Glu Val Ile Asp Thr Ala Cys Ser Ser Ile Val Ala Val
                    340                 345                 350

His Arg Ala Cys Gln Ala Ile Asn Ala Gly Glu Cys Ser Ser Ala Leu
                    355                 360                 365

Ala Gly Gly Val Asn Leu Ile Thr Gly Ile Asn Asn Tyr Phe Asp Leu
                    370                 375                 380

Gly Lys Ala Ser Phe Leu Ser Gln Thr Gly Gln Cys Lys Pro Phe Asp
385                 390                 395                 400

Asp Ser Ala Asp Gly Tyr Cys Arg Ala Asp Gly Val Gly Leu Val Val
                    405                 410                 415

Leu Lys Pro Leu Ser Lys Ala Ile Ser Asp Gly Asp His Ile Met Gly
                    420                 425                 430

Val Ile Pro Ala Thr Ala Thr Asn Gln Gly Gly Ile Asp Ala Pro Gly
                    435                 440                 445

Ile Thr Val Pro Asp Gly Ser Ala Gln Lys Ala Leu Tyr Gln Asn Val
                    450                 455                 460

Leu Leu Lys Ser Gly Ile Lys Gly His Gln Val Ser Tyr Val Glu Ala
465                 470                 475                 480

His Gly Thr Gly Thr Gln Val Gly Asp Pro Ile Glu Ile Lys Ser Ile
                    485                 490                 495
```

```
Arg Asp Val Phe Gly Gly Pro Thr Arg Thr Asn Pro Val Tyr Leu Gly
            500                 505                 510

Ser Leu Lys Ala Asn Ile Gly His Ser Glu Thr Ala Ala Gly Val Ala
            515                 520                 525

Ser Leu Leu Lys Val Leu Ala Met Phe Arg His Gln Gly Ile Pro Pro
            530                 535                 540

Leu Gln Gly Phe Lys Ser Leu Asn His Lys Ile Pro Ala Leu Glu Pro
545                 550                 555                 560

Asp Gly Met Ser Ile Pro Thr Thr Leu Leu Pro Trp Asp Ala Lys Tyr
                565                 570                 575

Pro Arg Ile Ala Ala Val Asn Ser Tyr Gly Ala Ser Gly Ser Asn Ser
                580                 585                 590

Ala Leu Leu Cys Ser Glu Trp Ser Gly Ala Ser Lys Pro Ala Ser Arg
            595                 600                 605

Gln Thr Ser Phe Pro Ile Leu Leu Ser Ala Ala Ser Pro Glu Ser Leu
            610                 615                 620

Arg Arg Tyr Thr Asp Asp Leu Ala Ser Tyr Leu Ser Lys Ser Ser Ala
625                 630                 635                 640

Ala Gly Leu Lys Val Gly Asp Leu Ala Leu Thr Leu Ser Glu Arg Arg
                645                 650                 655

Lys His His Arg Val Arg Trp Ser Thr Thr Val Ala Ser Leu Pro Asp
            660                 665                 670

Leu Val Ser Gln Leu Gln Lys Gly Pro Glu Asp Leu Val Glu Ile Pro
            675                 680                 685

Lys Ala Ser Lys Lys Val Val Leu Thr Phe Ser Gly Gln Ser Arg Thr
            690                 695                 700

Ser Ile Gly Leu Asp Pro Ser Val Arg Gln Ser Tyr Pro Leu Phe Glu
705                 710                 715                 720

Lys Tyr Ile Thr Gln Cys Asn Asp Ile Leu Gln Gly Phe Gly Cys Ser
                725                 730                 735

Asp Ile Leu Ser Ala Leu Ser Asp Pro Gly Pro Ile Thr Asn Pro Val
                740                 745                 750

Ile Leu Gln Cys Gly Thr Val Ala Val Gln Tyr Ala Cys Ala Gln Cys
            755                 760                 765

Trp Ile Asp Gly Gly Leu Arg Val Asp Ala Ile Ile Gly His Ser Leu
            770                 775                 780

Gly Glu Leu Thr Ala Leu Ala Val Ser Gly Val Leu Ser Leu Ser Asp
785                 790                 795                 800

Ala Leu Lys Val Val Tyr Thr Arg Ala Glu Leu Ile Asn Glu Lys Trp
                805                 810                 815

Gly Pro Glu Arg Gly Thr Met Leu Ala Ile His Ala Pro Leu Asp Val
                820                 825                 830

Val Gln Ser Val Met Glu Val Val Asp Thr Leu Val Ser Glu Glu Asp
            835                 840                 845

Asp Glu Leu Glu Ile Ala Cys Phe Asn Ser Val Ser Ser His Ile Val
            850                 855                 860

Val Gly Thr Glu Ala Trp Val Ala Met Ala Glu Arg Ile Leu Gln Gln
865                 870                 875                 880

Asp Ala Lys Tyr Gln Gly Ile Arg Phe Gln Arg Leu Ser Val Ser His
                885                 890                 895

Gly Phe His Ser Arg Phe Thr Glu Pro Leu Leu Ser Asp Leu Val Asp
                900                 905                 910
```

```
Leu Glu Glu Thr Leu Glu Phe Arg Glu Pro Thr Ile Pro Leu Glu Thr
            915                 920                 925

Ser Thr Gln Thr Pro Phe Val Phe Gly Thr Lys Asp Ser Thr Tyr Leu
    930                 935                 940

Ala Asp His Ala Arg Asp Pro Val His Phe Val Ser Ala Val Gln Arg
945                 950                 955                 960

Val Glu Gln Arg Leu Gly Pro Cys Val Trp Leu Glu Ala Gly Trp Gly
            965                 970                 975

Ser Pro Ile Val Ala Met Ala Lys Lys Ala Val Ala Asp Pro Lys Leu
            980                 985                 990

His Thr Phe Gln Ala Val Thr Ser Pro Ala Ala Val Ala Ala Asn Leu
            995                 1000                1005

Trp Arg Glu Gly Ile Thr Ile Thr Asp Trp Gly Phe Leu Thr Pro
        1010            1015            1020

Lys Asp Ser Gly Leu Gly Pro Val Trp Leu Pro Pro Tyr Ser Phe
        1025            1030            1035

Asp Gln Pro Lys Ala Trp Leu Asp His Val Asp Asn Ala Ile Glu
        1040            1045            1050

Glu Gln Asn Lys Val Pro Val Gln Leu Glu Ala Lys Ser Asn Thr
        1055            1060            1065

Gln Leu Leu Ser Tyr Lys Gly Ala Val Ala Asp Gly Ser His Asn
        1070            1075            1080

Phe Thr Leu His Thr Asn Thr Glu Arg Phe Val Lys Ile Val Gln
        1085            1090            1095

Gly His Ala Val Arg Arg Lys Pro Leu Cys Pro Ala Ser Met Tyr
        1100            1105            1110

Met Glu Ala Ala Val Met Gly Thr Asp Lys Leu Gly Val Glu Leu
        1115            1120            1125

Arg Ser Lys Thr Ile Thr Phe Arg Asn Val Thr Phe Ala Arg Pro
        1130            1135            1140

Leu Gly Cys Gly Glu Gly Leu Asp Val Glu Leu Cys Leu Gly Lys
        1145            1150            1155

Leu Pro Asn Ser Ala Glu Ser Trp His Tyr Ala Val Gln Ser Thr
        1160            1165            1170

Ser Lys Ser Ala Tyr Ser Glu Gly Asp Phe Ser Val Ser Ser Ser
        1175            1180            1185

Pro Pro Asp Asp Met Glu Leu Tyr Gly Met Leu Val Thr Asp Gly
        1190            1195            1200

Ile Thr Ala Leu Lys Asn Asp Pro Asp Thr Glu Lys Leu Arg Lys
        1205            1210            1215

Ser Thr Ala Tyr Ser Leu Phe Ser Lys Ile Val Glu Tyr Ala Asp
        1220            1225            1230

Leu Leu Arg Gly Ile Thr Ser Ile Thr Leu Gly Gln Lys Gln Ala
        1235            1240            1245

Leu Ala Lys Ile Glu Val Pro Lys Ser Thr Phe Ala Thr Ser Glu
        1250            1255            1260

Ser Thr Val Ser Asp Tyr Tyr Asp Ala Ile Thr Leu Asp Thr Phe
        1265            1270            1275

Val Gln Val Leu Gly Leu Leu Ile Asn Cys Asn Asn Ala Ser Asp
        1280            1285            1290

Ser Gly Asp Glu Ile Tyr Ile Ala Ser Cys Ile Asp Lys Met Val
        1295            1300            1305

Val Ser Pro Thr Asp Phe Gln Lys Pro Gln Thr Trp Thr Val Tyr
```

-continued

```
            1310                1315                1320

Ala Thr Tyr Ser Ala Ala Asp Ser Lys Thr Leu Ser Gly Ser Val
    1325                1330                1335

Phe Val Phe Ser Glu Glu Gly Lys Leu Thr Ala Phe Gly Thr Lys
    1340                1345                1350

Ile Gln Phe Met Arg Thr Gln Ala Ala Arg Leu Glu Arg Val Leu
    1355                1360                1365

Glu Ala Ala Asn Pro Arg Pro Ala Val Asn Gly Leu Ser Leu Ser
    1370                1375                1380

Thr Asn Ile Pro Ile Pro Ala Gly Gly Gln Gln Val Asp Leu Ala
    1385                1390                1395

Leu Val Asn Pro Lys Ile Ser Ile His Ala Pro Ser Pro Thr Ser
    1400                1405                1410

Ala Asn Ile Ala Leu Glu Val Glu Val Gly Lys Ile Asp Val Leu
    1415                1420                1425

Lys Ser Leu Ile Ala Ala Tyr Ser Gly Val Lys Glu Ala Asp Ile
    1430                1435                1440

Gln Asp Asp Val Ser Phe Ala Ser Met Gly Leu Asp Ser Leu Ala
    1445                1450                1455

Ser Met Glu Leu Ala Ser Glu Ile Glu Ser Thr Leu Gly Ile Arg
    1460                1465                1470

Val Asn Ser Glu Asp Leu Leu Thr Gly Asp Ile Arg Ser Leu Leu
    1475                1480                1485

Lys Ser Phe Pro Ser Glu Gly Asn Met Glu Ser Leu Ser Gln Ser
    1490                1495                1500

Leu Glu Asn Ala Ser Arg Ser Ser Asp Lys Ser Thr Ala Ser Asn
    1505                1510                1515

Gly Thr Ser Ile Asp Gly Asp Cys Asp Asp Pro Thr Ala Met Ser
    1520                1525                1530

Thr Pro Pro Asp Leu Gly Phe Gln Lys Ile Asp Thr Glu Thr Gly
    1535                1540                1545

Asn Thr Pro Trp Thr Arg Pro Ser Thr Pro Leu Ser Thr Arg Phe
    1550                1555                1560

Lys Ile Glu Thr Val Thr Tyr Lys Glu Val Asp Gly Val Arg Ile
    1565                1570                1575

Pro Ala Asp Leu Tyr Ile Pro Ser Glu Ala Pro Ser Gln Pro Met
    1580                1585                1590

Pro Ile Ala Leu Met Ile His Gly Gly Gly His Leu Thr Leu Ser
    1595                1600                1605

Arg Arg Ala Val Arg Pro Ala Gln Thr Asn Phe Leu Leu Gln Asn
    1610                1615                1620

Gly Leu Phe Pro Ile Ser Ile Asp Tyr Arg Leu Ala Pro His Val
    1625                1630                1635

Asn Val Val Asp Gly Ser Met Ala Asp Thr Arg Asp Ala Cys Ile
    1640                1645                1650

Trp Ala Arg Arg Glu Leu Pro Lys Leu Met Ala Leu Lys Gly Ile
    1655                1660                1665

Thr Leu Asp Pro Thr Lys Leu Val Val Ile Gly Trp Ser Thr Gly
    1670                1675                1680

Gly Thr Leu Ala Met Thr Thr Ser Trp Thr Leu Lys Asp Leu Gly
    1685                1690                1695

His Ser Pro Pro Leu Ala Val Leu Ser Phe Tyr Cys Pro Val Glu
    1700                1705                1710
```

```
Tyr Asn Pro Asp Ala Pro Thr Leu Met Gly His Asp His Pro Pro
    1715                1720                1725

Arg Thr Met Ser Leu Ser Glu Ile Arg Ser Cys Leu Pro Ala Gly
    1730                1735                1740

Pro Ser Thr Ser His Ala Phe Asn Thr Leu Asp Thr Thr Lys Leu
    1745                1750                1755

Gly Trp Leu Asp Glu Gly Asp Pro Arg Ser Glu Leu Val Leu Ala
    1760                1765                1770

Leu Ile Lys Glu Glu Asn Gly Met Ser Leu Leu Phe Asp Gly Leu
    1775                1780                1785

Pro Ser Glu Gly Glu Gln Phe Pro Arg Ala Asn Ser Ser Arg Thr
    1790                1795                1800

Thr Ala Phe Ser Pro Leu Thr Gln Ala Arg Asn Gly Asn Tyr Ser
    1805                1810                1815

Thr Pro Thr Tyr Val Ile Phe Gly Asp Glu Asp Glu Ile Ala Pro
    1820                1825                1830

Phe Glu Lys Ala Val Glu Phe Glu Asp Val Leu Asn Ser Asn Gly
    1835                1840                1845

Val Pro Cys Gly Phe Leu Pro Val Thr Gly Gly Lys His Ile Phe
    1850                1855                1860

Asp Leu Gly Leu Ser Pro Gly Ser Glu Gly Trp Asp Ile Val Leu
    1865                1870                1875

Tyr Thr
    1880

<210> SEQ ID NO 38
<211> LENGTH: 534
<212> TYPE: PRT
<213> ORGANISM: Neonectria ditissima

<400> SEQUENCE: 38

Met Ala Ala Gln Ile Pro Lys Lys Thr Thr Val Leu Val Ile Gly Gly
1               5                   10                  15

Gly Pro Gly Gly Ser Tyr Ala Ala Ala Leu Ala Arg Glu Gly Ile
            20                  25                  30

Asp Thr Val Val Leu Glu Gly Asp Lys Phe Pro Arg Tyr His Ile Gly
            35                  40                  45

Glu Ser Met Leu Ala Ser Ile Arg His Leu Leu Arg Phe Val Glu Leu
    50                  55                  60

Asp Ala Lys Phe Asp Ser Tyr Gly Phe Leu Lys Lys Ala Asn Thr Asp
65                  70                  75                  80

Phe Leu Ala Ala Gly Gly Pro Asp Asn Tyr Ala Trp Asn Val Ile Arg
                85                  90                  95

Ser Glu Ser Asp Lys Leu Met Phe Asp His Ala Ala Glu Ser Gly Ala
            100                 105                 110

His Val Phe Asp Gly Val Gln Val Lys Ser Val Glu Phe Glu Gly Gly
        115                 120                 125

Val Val Pro Gly Glu Asp Gly Val Glu Ser Leu Asn Pro Gly Arg Pro
    130                 135                 140

Ile Ser Ala Thr Tyr Leu Ile Lys Glu Thr Glu Thr Gly Gln Ile
145                 150                 155                 160

Ala Phe Asp Tyr Val Ile Asp Ala Ser Gly Arg Ile Gly Ile Leu Ser
                165                 170                 175

Thr Lys Tyr Met Lys Asn Arg Arg Tyr Asn Gln Gly Leu Lys Asn Val
```

```
            180                 185                 190
Ala Asn Trp Ala Tyr Trp Lys Gly Thr Asn Pro Tyr Ala Pro Gly Thr
        195                 200                 205

Thr Arg Glu Asn Ser Pro Phe Phe Glu Ala Leu Gln Asp Glu Ser Gly
        210                 215                 220

Trp Ala Trp Phe Ile Pro Leu His Asn Gly Thr Thr Ser Val Gly Ile
225                 230                 235                 240

Val Glu Asn Gln Lys Leu Ser Ile Glu Lys Lys Gln Ala Ser Lys Thr
                245                 250                 255

Asp Asn Ser Gln Asp Phe Tyr Leu Glu Asn Leu Lys Leu Ala Pro Asn
            260                 265                 270

Leu Leu Ala Leu Ile Gly Asp Ala Thr Gln Val Asp Lys Val Lys Ala
        275                 280                 285

Ala Ser Asp Tyr Ser Tyr Cys Ala Ser Ser Tyr Ala Phe Pro Tyr Ala
        290                 295                 300

Arg Ile Val Gly Asp Ala Gly Cys Phe Ile Asp Pro Tyr Phe Ser Ser
305                 310                 315                 320

Gly Val His Leu Ala Leu Val Gly Leu Ser Ala Ala Thr Ile
                325                 330                 335

Cys Ala Ser Ile Arg Gly Asp Val Glu Ser Ser Ala Ala Asp Trp
                340                 345                 350

His Ser Lys Lys Ile Ala Asp Ala Tyr Thr Arg Phe Leu Leu Val Val
        355                 360                 365

Leu Ser Ala Tyr Arg Gln Ile Arg Ser Gln Glu Pro Val Leu Thr
370                 375                 380

Asp Ile Asn Glu Asp His Phe Asp Arg Ala Phe Ala Met Phe Arg Pro
385                 390                 395                 400

Ile Ile Gln Gly Thr Ala Asp Val Gly Asn Lys Lys Leu Ser Gln Glu
                405                 410                 415

Glu Leu Lys Lys Thr Leu Glu Phe Cys Ala Thr Ala Phe Glu Pro Val
            420                 425                 430

Lys Thr Glu Glu Asp Arg Thr Ala Ala Ile Glu Glu Ile Thr Asn Asn
        435                 440                 445

Pro Asn Gly Thr Gly Tyr His Ala Asp Leu Ser Ala Ser Gln Arg Asn
        450                 455                 460

Ala Val Asn His Ile Arg Ala Arg Lys Met Met Arg Thr Glu Asp Thr
465                 470                 475                 480

Val Asn Ile Asp Ser Phe Gly Ser Asp Ala Ile Ala Gly Tyr Val Pro
                485                 490                 495

His Leu Lys Arg Gly Ser Leu Gly Leu Lys Gln Val Ala Lys Gly Gly
            500                 505                 510

Leu Asp Ala Val Pro Gly Gln Met Thr Pro Val His Ser His Thr Thr
        515                 520                 525

Ala Val Glu Val Arg Ala
        530

<210> SEQ ID NO 39
<211> LENGTH: 1064
<212> TYPE: PRT
<213> ORGANISM: Neonectria ditissima

<400> SEQUENCE: 39

Met Pro Ser Lys Ile Pro Gly Pro Arg Gly Leu Pro Leu Leu Gly Asn
1               5                   10                  15
```

-continued

```
Ile Ala Asp Ile Asp Pro Ser Asp Ala Val Ala Ser Leu Gly Arg Ile
             20                  25                  30
Ala Glu Thr Tyr Gly Pro Ile Tyr Lys Leu Asn Leu Val Gly Ser Glu
         35                  40                  45
Lys Leu Phe Ile Ser Ser Arg Glu Leu Met Asp Glu Val Ser Asp Glu
 50                  55                  60
Lys Arg Phe Thr Lys Leu Val Ser Gly Pro Leu Phe Gln Leu Arg Asn
 65                  70                  75                  80
Ala Val Gly Asp Ser Leu Phe Thr Ala His Ser Asn Glu Pro Asn Trp
                 85                  90                  95
Asp Val Ala His Arg Val Leu Met Pro Ala Met Gly Pro Leu Ala Ile
                100                 105                 110
Arg Gly Met Phe Asp Glu Met His Asp Val Ala Thr Gln Leu Leu Thr
            115                 120                 125
Lys Trp Ala Arg Phe Gly Pro Lys Glu Thr Ile Asp Val Thr Ser Asp
130                 135                 140
Phe Thr Arg Leu Thr Leu Asp Thr Ile Ala Leu Cys Ser Met Gly Thr
145                 150                 155                 160
Arg Phe Asn Ser Phe Tyr His Glu Glu Met His Pro Phe Val Gly Ser
                165                 170                 175
Met Ile Gly Leu Leu Glu Glu Ser Gly Lys Arg Ala Pro Arg Pro Asn
            180                 185                 190
Trp Val Asn Tyr Leu Met Pro Ala Ser Gln Ala Lys Tyr Glu Ala Asp
            195                 200                 205
Ile His Thr Leu Gln Gln Val Gly Ala Asn Leu Leu Ala Asp Arg Arg
210                 215                 220
Val Asn Pro Thr Asp Lys Lys Asp Ile Leu Asn Ala Leu Ile Asn Gly
225                 230                 235                 240
Ile Asp Pro Lys Thr Gly Lys Gly Met Ser Asp Ser Ile Leu Asn
                245                 250                 255
Asn Met Ile Val Phe Leu Ile Ala Gly His Glu Thr Thr Ser Gly Leu
            260                 265                 270
Leu Ser Phe Leu Phe Tyr Tyr Leu Leu Lys Lys Ala Asp Val Phe Glu
            275                 280                 285
Lys Ala Gln Lys Glu Val Asp Glu Val Val Gly Arg Gly Pro Val Thr
 290                 295                 300
Ile Glu His Leu Ser Glu Leu Pro Tyr Leu Glu Ala Cys Leu Arg Glu
305                 310                 315                 320
Val Leu Arg Leu His Pro Thr Ala Pro Val Ile Thr Leu Gln Pro Arg
                325                 330                 335
Pro Asp Leu Val Gln Glu Asn Leu Thr Ile Gly Lys Ala Glu Tyr Ala
            340                 345                 350
Val Gly Pro Gly Gln Pro Ile Val Ala Leu Leu Thr Gln Val His Arg
        355                 360                 365
Asp Pro Ala Val Trp Gly Pro Asp Ala Asn Glu Phe Arg Ala Glu Arg
370                 375                 380
Met Ser Asp Glu Asn Phe Ser Arg Leu Pro Lys Asn Ser Trp Lys Pro
385                 390                 395                 400
Phe Gly Asn Gly Ile Arg Gly Cys Ile Gly Arg Ala Phe Ala Trp Gln
                405                 410                 415
Glu Ser Leu Leu Val Thr Val Met Leu Leu Gln Thr Phe Asn Phe Arg
            420                 425                 430
Leu Lys Asp Pro Glu Tyr Glu Leu Lys Ile Lys Gln Thr Leu Thr Ile
```

```
            435                 440                 445
Lys Pro Gly Asp Phe Tyr Met His Ala Thr Leu Arg Asp His Leu Asp
450                 455                 460

Ser Val Gln Leu Gly Lys Ser Leu Tyr Gly Asn Ser Gln Pro Ser Asn
465                 470                 475                 480

Gly His Ser Lys Gln Ser Glu Val Glu Thr Lys Pro Thr Ala Thr Pro
                485                 490                 495

His Ala Ser Lys Lys Met Thr Ile Leu Tyr Gly Ser Asp Ser Gly Thr
                500                 505                 510

Cys Glu Thr Met Ala Gln Ala Leu Ala Arg Ala Pro Thr Arg Gly
                515                 520                 525

Tyr Asp Ala Thr Leu Ser Ser Leu Asp Ala Ala Val Asp Asp Leu Pro
530                 535                 540

Arg Glu Gln Pro Val Ile Leu Ile Cys Ser Ser Tyr Asn Gly His Pro
545                 550                 555                 560

Pro Asn Asn Ala Ala Gly Phe Val Ala Trp Leu Glu Gly Leu Lys Ser
                565                 570                 575

Asp Asn His Val Leu Lys Gly Ile Thr Phe Ala Val Tyr Gly Cys Gly
                580                 585                 590

Asn Arg Asp Tyr Gly Pro Thr Phe His Arg Ile Pro Lys Leu Leu Asp
                595                 600                 605

Ser Glu Leu Gly Asn Asn Gly Ala Thr Arg Leu Met Asp Ile Gly Leu
                610                 615                 620

Gly Asp Val Thr Val Gly Asp Ile Phe Ser Asp Phe Glu Ala Trp Gln
625                 630                 635                 640

Asp Asp Arg Leu Trp Pro Ala Leu Gly Ala Tyr Ala Val Gly Asn Val
                645                 650                 655

Asp Gly Ala Phe Asp Ile Lys Ile Asp Arg Ser Tyr Arg Pro Ser Asp
                660                 665                 670

Leu Arg Glu Asp Phe Asn Glu Ala Val Val Leu Thr Asn Ser Val Val
                675                 680                 685

Thr Ala Pro Ser Glu Pro Glu Lys Arg Thr Met Thr Leu Lys Leu Pro
690                 695                 700

Asp Ala Val Lys Tyr Thr Ala Gly Asp His Ile Ala Val Leu Pro Leu
705                 710                 715                 720

Asn Asp Ser Asp Thr Val Arg Arg Val Leu Arg Trp Ala Lys Leu Pro
                725                 730                 735

Trp Asp Ala Val Ile Thr Ile Pro Thr Gly Ser Asn Thr Thr Leu Pro
                740                 745                 750

Thr Gly Arg Ala Ile Ser Ala Pro Asp Leu Leu Ser Gly Tyr Val Glu
                755                 760                 765

Leu Ser Arg Pro Ala Thr Arg Lys Val Ile Pro Pro Asn Val Ala Thr
770                 775                 780

Ile Thr Ala Arg Ala Ala Asp Glu Lys Thr Arg Asn Lys Met Leu Ala
785                 790                 795                 800

Leu Glu Glu Asp Phe Asp Asn Ser Val Thr Leu Gln Arg Arg Ser Val
                805                 810                 815

Leu Asp Ile Leu Glu Asp Thr Pro Glu Ile Ser Leu Pro Phe Ala Glu
                820                 825                 830

Phe Leu Ala Met Leu Pro Pro Met Arg Ala Arg Lys Tyr Ser Val Ala
                835                 840                 845

Ser Ser Pro Leu Ala Asp Ala Ser Thr Val Thr Leu Leu Trp Ser Val
850                 855                 860
```

```
Val Asp Lys Glu Ser Pro Leu Asn Pro Val Met Arg Arg Gly Val
865                 870                 875                 880

Ala Ser Thr Tyr Leu Ala Arg Leu Asn Gln Gly Asp Ser Ile His Val
                885                 890                 895

Ala Val Lys Pro Ala Leu Arg Leu Phe His Pro Pro Thr Asp Val Glu
                900                 905                 910

Asn Thr Pro Val Ile Met Ala Cys Ala Gly Thr Gly Leu Ala Pro Phe
            915                 920                 925

Arg Ala Phe Val Gln Glu Arg Ser Val His Ala Gln Ala Gly Arg Asn
            930                 935                 940

Leu Ala Pro Ala Tyr Leu Phe Ile Gly Cys Arg Asp Pro Ser Lys Asp
945                 950                 955                 960

Thr Leu Leu Gln Glu Glu Leu Arg Gln Trp Glu Lys Leu Asp Ile Val
                965                 970                 975

Lys Val Phe Tyr Ala Phe Ser Gln Ala Ser Glu Gln Ser Ser Gly Cys
                980                 985                 990

Lys Tyr Val Gln Asp Arg Ile Trp  Lys Glu Arg Glu Ile  Val Glu Arg
                995                 1000                1005

Val Ile  Val Asn Gly Lys Gly  Ile Ile Tyr Val Cys  Gly Gly Ala
    1010                1015                1020

Gly Val  Gly Lys Gly Val Glu  Val Met Lys Arg  Ile Tyr Ser
    1025                1030                1035

Leu Glu  Thr Arg Ala Asn Thr  Ala Glu Gln Trp Val  Gln Asp Leu
    1040                1045                1050

Lys Ser  Ser Arg Tyr Ala Arg  Glu Ile Phe Ser
    1055                1060
```

```
<210> SEQ ID NO 40
<211> LENGTH: 267
<212> TYPE: PRT
<213> ORGANISM: Neonectria ditissima

<400> SEQUENCE: 40

Met Gly Phe Asn Asp Ile Pro Pro Ala His Val Ser Ala Trp Tyr Gln
1               5                   10                  15

Pro Val Tyr Asn Ala Thr Phe Gly Phe Ala Gly Leu Ser Trp Thr Leu
                20                  25                  30

Cys Tyr Met Leu Tyr Ala Arg Gln Gly Leu Arg Thr Lys Ser Tyr Gly
            35                  40                  45

Met Pro Leu Phe Ala Leu Ala Asn Asn Phe Ala Trp Glu Met Val Tyr
        50                  55                  60

Ala Leu Ser Val Ala Asp Ala Pro Arg Glu Lys Thr Ala Met Val Ile
65                  70                  75                  80

Trp Met Leu Ile Asp Met Pro Ile Ile Tyr Ser Thr Leu Arg Tyr Gly
                85                  90                  95

Arg Glu Glu Trp Ser His Ala Pro Met Val Ser Arg Asn Leu Gly Lys
                100                 105                 110

Ile Leu Val Thr Leu Val Met Leu Cys Ala Val Ala His Tyr Ser Phe
            115                 120                 125

Ala Ser Trp Trp Met Gly Asn His Ile Ala Met Lys Ser Gly Lys Val
        130                 135                 140

Tyr Arg Gly Val Glu Gly Gln Asp Ala Thr Glu Met Ala Phe Trp Ala
145                 150                 155                 160

Val Ser Val Cys Gln Val Ile Val Ser Thr Ser Ser Leu Ala Gln Leu
```

-continued

```
                165                 170                 175
Ile Thr Arg Gln His Thr Gly Gly Val Ser Trp Ser Ile Trp Ala Leu
                180                 185                 190

Arg Phe Cys Gly Thr Leu Val Gly Leu Asn Ile Asn Tyr Gly Trp Ala
                195                 200                 205

Trp Tyr Thr Trp Thr Glu Ala His Gly Tyr Phe Met Ser Ala Pro Gly
                210                 215                 220

Val Phe Leu Trp Gly Ile Thr Thr Leu Cys Asp Val Val Tyr Ala Ile
225                 230                 235                 240

Val Phe Ala Gln Val Arg Arg Asn Glu Arg Val Leu Pro Asp Gly Arg
                245                 250                 255

Lys Ala Ala Pro Leu Gln Ser Ile Lys Arg Gly
                260                 265
```

<210> SEQ ID NO 41
<211> LENGTH: 533
<212> TYPE: PRT
<213> ORGANISM: Neonectria ditissima

<400> SEQUENCE: 41

```
Met Glu Ser Leu Ser Ser Ala Gly Glu Ser Ala Val Gln Ala Ile Thr
1               5                   10                  15

Ser Phe Pro Ala Leu Ser Ser Val Val Ala Leu Phe Leu Ala Val Leu
                20                  25                  30

Val Tyr Gln Ser Cys Val Lys Thr Arg Ala Pro Thr Pro Ala Leu Pro
                35                  40                  45

Val Val Gly Lys Pro Gly Ser His Ile Thr Lys Asp Val Ile Leu Glu
                50                  55                  60

Gly Ser Arg Lys Tyr Pro Asp Thr Pro Phe Ile Leu Pro Met Ser Pro
65                  70                  75                  80

Pro Ile Val Val Leu Pro Ile Gly Ile Gln Asp Glu Val Arg Asn Leu
                85                  90                  95

Pro Glu Ser Arg Val Ser Phe Thr Gln Glu His Gln Arg Asn Phe Phe
                100                 105                 110

Ala Gln Tyr Thr Gly Ile Gly Asp His Arg Pro Glu Met Ile Lys Ala
                115                 120                 125

Ile Arg Ile Asp Leu Thr Arg His Ile Ala Ser Thr Leu Pro Ala Leu
                130                 135                 140

Gln Glu Glu Val Arg Phe Gly Phe Asp Lys Glu Phe Gly Asp Cys Lys
145                 150                 155                 160

Asp Trp Thr Pro Leu Pro Val Tyr Leu Lys Val Leu Arg Val Val Ala
                165                 170                 175

Leu Met Asn Gly Arg Ile Phe Val Gly Arg Pro Leu Ser Arg Glu Glu
                180                 185                 190

Glu Trp Ile Gln Ser Thr Ile Ser Tyr Thr Ile Asp Cys Val Lys Ala
                195                 200                 205

Arg Asn Ala Ile Arg Glu His Pro Val Trp Lys Arg Arg Trp Val Thr
                210                 215                 220

Ser Ser Leu Pro Glu Ile Ala Lys Leu Thr His His Arg Thr Arg Gly
225                 230                 235                 240

Gly Glu Leu Leu Glu Pro Ile Met Lys Ala Gln Leu Ala Lys Pro Ser
                245                 250                 255

Phe Lys Glu Lys Leu His Asn Pro Glu Ser Gly Asp Glu Glu Gly Asn
                260                 265                 270
```

```
Phe Ile Glu Trp Ile Leu Lys Tyr Thr Pro Glu Leu Arg Asn Asp
            275                 280                 285

Pro Val Asn Leu Ala Val Asn Gln Met Val Leu Ser Phe Ala Ala Ile
        290                 295                 300

His Thr Ser Ser Met Ala Thr Thr His Ala Ile Leu Asp Leu Ala Ala
305                 310                 315                 320

Arg Arg Glu Tyr Ile Gln Pro Leu Arg Asp Glu Ile Asp Gln Val Arg
                325                 330                 335

Ala Ala Asp Gly Asp Glu Arg Asp Asp Asp Gly Phe Val Arg Leu Lys
            340                 345                 350

Lys Glu Ser Ile Asn Lys Leu Arg Lys Leu Asp Ser Phe Met Lys Glu
        355                 360                 365

Ser Gln Arg Phe Ser Pro Pro Ile Tyr Thr Ser Gly Thr Arg Ile Cys
    370                 375                 380

Thr Ser Asp Ile His Leu Ser Thr Gly His Thr Leu Pro Lys Asp Thr
385                 390                 395                 400

Arg Ile Cys Phe Ser Ser Phe Ala Val Gln Thr Asp Pro Lys Thr Thr
                405                 410                 415

Thr Phe Ser Pro Glu Tyr Asn Pro Ala Gly Tyr Thr Pro Pro Asp Gln
            420                 425                 430

Phe Asp Gly Met Arg Phe Tyr Asn Leu Arg Asn Met Pro Gly Lys Glu
        435                 440                 445

Ser Arg His Gln Phe Ala Thr Ala Gly Pro Glu Ser Leu Thr Phe Gly
    450                 455                 460

Tyr Gly Asn His Thr Cys Pro Gly Arg Phe Phe Ala Ser Asn Glu Ile
465                 470                 475                 480

Lys Ile Ile Leu Val Glu Leu Leu Met Asn Trp Asp Phe Arg Leu Lys
                485                 490                 495

Gly Asp Val Glu Leu Lys Gly Gly Ala Glu Lys Arg Pro Pro Asn Val
            500                 505                 510

Glu Val Asp Leu Val Ile Thr Pro Asn Pro Met Ala Met Leu Glu Phe
        515                 520                 525

Lys Arg Arg Arg Ala
    530

<210> SEQ ID NO 42
<211> LENGTH: 1065
<212> TYPE: DNA
<213> ORGANISM: Aspergillus sojae

<400> SEQUENCE: 42
atggcagcca tcaccgacca caacgtcgtc tacgcggacg gcaaaaagat ccactaccta      60
gcagcaggcc ctgcaaatgg ccctctagtt ctctttatcc atggctggcc aggcagcgcg     120
atcacctgga aggcgcaaat cgatgccttc gcatccgtgg ggttccgcgc gattgcccct     180
gatatgccag gctatgggca gtcgactgcc cgccgcgtgg ccgatgacta ctgtcaagaa     240
gccgtcgtag agggcatgct ggctttgcta gccgacacag gccgcgatgc agcgatctgg     300
gtcggccacg actggggcgc aggcgtcaca tcctccgttg cgacgcaaca ccccgaggtg     360
gttaaagcgt tggtgactat gtctgtgcca ttccacacta tcgagcgtgg ctggcagggc     420
ttccttccct atgtaaaccg cgagctctac ccagcggacg aatacgagtt cggccagtgg     480
gactatatga agaactggga ggagaacttc gaaaaaaccg tggaatggtt cgacagtgac     540
attgcaggaa tgtgcaaagc ttccttgcaa ccgtccaagc ccccaactag ccgttttgcc     600
```

| | |
|---|---:|
| cagctgtttg ccaccgtgcg caagagcggt ggatggatgg gcggggcgcc aaagcccccg | 660 |
| agtgtggaga tgacagggcc tccggtgctc cctgctgagg tcttcgactc ttttgttcag | 720 |
| gatatgcaga gaaccggctt ctgggccgga tctgcgtact accttcacca tgcgcggaac | 780 |
| gcggaataca atggaaagcg cgaggggaag ttgaaccaac cagtcctgtt tatccatgac | 840 |
| gccagggatg tgatatgtga caccataacg tctcgcctgg tcgagccgat gagagagaac | 900 |
| tgtagcaatt tgactgaggt tacgatcgac gcaggacact ttgcgcatta tgaaaagccg | 960 |
| gaagaggtac aggccgccat tttcaggttc attgtggaag agctgccgag tgagtggcct | 1020 |
| gggttttgga ctgccgggta tactaagaag aagtcggttc tgtga | 1065 |

<210> SEQ ID NO 43
<211> LENGTH: 2163
<212> TYPE: DNA
<213> ORGANISM: Aspergillus sojae

<400> SEQUENCE: 43

| | |
|---|---:|
| atggcgcaac tcgacactct cgatttggtt gtcctggtgg cgcttttggt gggtagcgtt | 60 |
| gcctacttca ccaaaggcac ttactgggct gtcgccaaag atccttatgc ctcctccggt | 120 |
| ccagcgatga atggcgccgc caaggcagga agactagaga tatcttgga gaaaatggaa | 180 |
| gaaactggca agaattgcgt cattttctac ggttcccaga ctggaactgc agaggactac | 240 |
| gcctcgaggt tggccaagga aggatctcag agattcggtc tcaaaactat ggttgctgat | 300 |
| ttggaagatt acgactacga aaacttggac aaattcccgg aagacaaggt cgccttttt | 360 |
| gttctcgcga cttatggtga gggcgagcct acgataatg ctgtcgagtt ttaccagttc | 420 |
| atcaccggtg aagatgttgc ttttgaaagt ggcgcgtccg ctgaagagaa gccgctgtcc | 480 |
| actctcaagt atgtcacctt cggccttggt aacaatacct atgagcacta caacgctatg | 540 |
| gttcgcaatc tcgacgtcgc tctgcaaaag cttggtgctc aacgtattgg ttctgctggt | 600 |
| gaaggtgatg acgcgctgg cacgatggaa gaagacttct ggcttggaa ggaacctatg | 660 |
| tggaccgcgc tttccgaggc gatgggtctc caggagcgcg aggccgttta tgagccggtg | 720 |
| ttcaatgtca cagaagatga gtctaagagc gccgaagacg agacggtcta tctcggcgag | 780 |
| ccgactaagg gtcatctcga aggtcaaccc aagggcccat tctcggccca aacccgttc | 840 |
| attgcgccta tcgtcgagtc tcgtgagcta ttcaccgtaa aggatcgtaa ctgtctgcac | 900 |
| atggaaatta gcatcgccgg aagcaacctc acctatcaaa ccggtgacca cattgctgta | 960 |
| tggccgacaa atgctggtgc tgaggtggat cggttcctgc aggttttgg acttgaggag | 1020 |
| aagcgccatt cggttattaa tatcaagggc attgatgtga ctgctaaggt tccgatcccg | 1080 |
| accctacca cctatgatgc cgctgttcgt tactacatgg aagtctgtgc ccctgtttcc | 1140 |
| cggcagtttg tctcgagtct ggctgctttt gctcccgatg aggcgaccaa gacagaaatt | 1200 |
| cagcgtttgg gcagcgacaa ggattacttc acgataaga tcaccaacca atgcttcaat | 1260 |
| attgcccagg ctctccaaag catcacgtcc aagccttct ctgccgttcc attctcgttg | 1320 |
| ctcatcgaag gcctcaataa gctccagcct cgttattatt ccatctcgtc atcttccctc | 1380 |
| gtccagaagg ataagatcag tatcactgcc gttgtggaat ccgtccgttt gcctggtgcc | 1440 |
| tcccaccttg tcaagggtgt gaccacgaat tacctccttg cgctcaagca aaagcagaat | 1500 |
| ggtgaacctt ctcctgaccc tcacggcttg acgtacgcta tcactggtcc gcgcaacaag | 1560 |
| tatgatggta ttcacgttcc ggttcacgtc cgccactcga atttcaaact gccatctgat | 1620 |
| ccctcgagac caattatcat ggttggacct ggtaccggtg tcgcaccttt ccgtggcttt | 1680 |

```
atacaggaac gtgccgcctt ggcggctaaa ggcgagaaag tcggcacaac tgttttgttc   1740
tttgggtgcc gtaatcgcaa tgaggatttc ctgtatcagg acgaattcaa ggtatggttt   1800
ccccgctttc tacacttccc ccttcggata cccatggacc attagctcta acgtgtttga   1860
ctacaggctt atgaggagca acttggtgat tcattgaaga tcatcactgc attttcccgc   1920
gagacttctc aaaaggttta tgtccaacat cggttgcgcg aacaagctga gctggtcagc   1980
gaccttctga agcagaaagc cacattctac gtttgtggag atgccgccaa catgcgcgt    2040 gaggtcaatc tggtgcttgg ccagattatt gcccaacagc gtggtcttcc cgccgagaag   2100
ggcgaggaga tggtcaagca tatgcgcagc agtggaagct accaggagga tgtttggtca   2160
tga                                                                 2163

<210> SEQ ID NO 44
<211> LENGTH: 657
<212> TYPE: DNA
<213> ORGANISM: Acremonium sclerotigenum

<400> SEQUENCE: 44
gcgccttcct ccatcggctt tatcgccttg ggtgctcgcg acgtagcttg tgctcacagg     60
ttactgtact tgcttctacg acgaaatgat actgcgatga cgatgatatc ttgggacgca    120
tgacgagtcg ggcgttggga tttaccgacc tcaccgtcgt atgtcaggac aacaaaagga    180
taactctaga tgtagagaaa atctgaacac ttttcctttg tagccacctc tttcagctgc    240
ccttgcacgt gtgaacctgg gtgttaatat ccttgtgctg ttcgtgcgcc gacctcaact    300
ttatgtcctg cgcctcagct atgtgacctt gggacaccct tagctcgaca attgacggca    360
gtctatgcgc tgattacaat aaatgctctg acgctattgt agatgctact aatttacatg    420
ttgtacagat cgcctgccgt cgtgctaaat catccctgaa gggtcccgtg aaacgccgtg    480
atgagatgcg aagctgactc tcaatttttct cctcacgtc tggagcccat cggcccgatg    540
gacttacctt gcgtagccaa atcctctgcc aaccccccct gcaacaactt gatcagcaat    600
tttgcttata tagtatccct cacttctcca acgtgtgact cccttttgca agcaata       657

<210> SEQ ID NO 45
<211> LENGTH: 2046
<212> TYPE: DNA
<213> ORGANISM: Acremonium sclerotigenum

<400> SEQUENCE: 45
atggcggata caaagattc gtggaggaag accgaggaag atgaggatga tcaggaaatc      60
gatgagacag tgagtgaggg ttcacccttc gcaaggccgc gacttacacc gtgaacagag    120
ctacaaggcg caaaaggatg ctatcttgct tgcgattgaa gtgagcgagt cgatgttgac    180
accaccaccc aaatcagatt ccaaaaaggc cgacaaggac agtccattac aggctgctct    240
taaatgcgcc tacaatctaa tggagcagcg catcatctcc aacccaagg acatgatggg     300 tatactgctc tttggcaccg agaagtcaaa gtttcaggac gacggcagtg ggcgaggcgg    360
tctgggttat ccccactgct acctcttcac tgaccttgac attcctgcag ctgacgacgt    420
aaaagcgctg aaggcgcttg ctgaggatga agaggatgaa gaggaaattc tgaagccaac    480
tgaagagact gtgtcgatgt caaatgtcct attttgcgcg aaccagatct tcacgacgaa    540
agcggccaac ttcggcagcc gtcgcttgtt catcgttacc gacaacgatg atccacagaa    600
agaggacaag gccgcccggt cagctgctgc agtgcgcgcc aaagacttgt atgatctagg    660
```

```
cgttaccatc gatctatttc cgattacccg gggcgacagc aggttccagc tcgacagatt    720
ctacgatgta aggacgttgt tagaaagcaa acggcagctc ttactgaccg tcaacaggac    780
atcatctacc aagatacgat agctggcgaa gccaacctga ctgaagtgcg atcatcaaaa    840
tcaggcgacg gtctgacgct tctgaactca ctgatctcca acatcaattc aaaacagacc    900
gcaaaacggg ctctcttctc gaacctggcg ttcgaaattg ccccgggact gaggatatca    960
gtgaagggat acaacgtcat ccaccgacag acgccagcaa ggacatgcta tgtgtggctc   1020
gacggcgaaa agccacaaat agcctctggc gagaccacga ggatggcaga ggacagcgct   1080
cgtacggtcg agaagactga aatcaagaag gcgtacaagt ttggaggcga gttcgtctac   1140
ttcaccccag aggagcagaa gaagctgcga gacttcggat cacccatcat tcgtgttatc   1200
ggatttaagc cgaggtcgtc gctgcccaga tgggccagtg ttaagaaaag tacttttatc   1260
ttcccgagcg aagaggactt cgtcggttcc actcgcgtgt acgccgctct gtggcagaag   1320
ttgctacggg atgacaagat tggtcttgcc tggacgatca ccaggccaa cgcgcagcca   1380
gtattggcag ccatcatccc atcaaaagag cataccgatg acgacaatgg gacgccctac   1440
ctgcccgcag gactttggat ctacccacta cccctttgccg atgatctccg tgagatcaag   1500
ccgccgggcg agctgtgtcg aagctcagat gaactgaaga gccagatgcg tgtcatcgtg   1560
cagcagctgc agctaccgaa agccatgtac aacccgatga agtaccccaa cccagcactg   1620
cagtggcact acaagatcct tcaagccatg gctttggagg aagaagtacc cgaagtggct   1680
gaagacgcca cgcagccgaa gtacaaagct atcagtaagc gagctggggg ctacttggag   1740
gattggtctg agacacttga gaatgaggca gtcgcggcac gcaacaggcg agctacttct   1800
gccaagcgag agcctgataa cgatatcccc acgcgtccgg caaagaagag ccgggcaggc   1860
tccgagaagc ctagcccagc cggtctcacc aacctgcaga tcaagtcttt ggtaggagac   1920
ggtggtatca cgaagatgac ggttgcgcag ttgaaagatg tgctcgggtc taaagggctg   1980
agtacgagcg ggaagaagat ggagctcgta gagcgaatcg agcaatgggt ggaggagaat   2040
gcctga                                                              2046
```

<210> SEQ ID NO 46
<211> LENGTH: 2404
<212> TYPE: DNA
<213> ORGANISM: Acremonium sclerotigenum

<400> SEQUENCE: 46

```
cggctctcga cccctactcc gttcgcaagg tccgtctcct cgttggtccc tgcttgccct     60
gccttgccct gccttgccct tccttgcctg gccttgcctt cagttgcctc catgtcctca    120
agccacccgg gtctgccccg tcaagcgcgt ccacgcccgg ccctagctg aagtggctct     180
gccgtaccta gctcgctcgc attccctcaa ccctacttga gcacacccat atctcacctg    240
ccgtcttgca tttccaggct gatctttcga actgcagcac tttcagactg gtgcctggct    300
gctgaacact ttgtctgtgc ttcgccgccg cagctctata ttgggaagac agcctcaact    360
cctggctgcc accattgcac tctgccctgc tcaggtggtc accgcttcga ccctcggata    420
gcatatcaac ccagctccgc ccgcgcgcca gcctgcatag cctcgccctt ctcctcaatt    480
gccttcgcag ctccagatcc tcctcaagat ctgtccagcc gctggcaccc aggcgtcgag    540
gcgggtacgc acattgcgag ctggtctagc agtttctgca tcccggccgt tggccatccc    600
ctcgttgtga cttggccaat catcgacatc gccagctctt accaactctc catctcccaga    660
gaaccgattt tgagctcgac aactctcgtt catcctcacc atggcgcccc acccgacgtt    720
```

```
gaagatgcct tactcgaggc ggtcggagac cgtttcgcac cctttgagcc aatatctcta      780
caagctcatg gacctgaaag cctctaacct gtgtcttagc gctgatgtgc caacggcccg      840
cgagctgctc tactttgccg acaaggttgg cccgtccatc gtcgttttga agacgcacta      900
cgacatggtc gcaggctggg acttctcgcc agaaacgggc acgggcgcac gtctcgcagc      960
gctagctcgt aagcatgggt ttctgatctt cgaggaccga aaattcggcg acattggcaa     1020
cacggtagag ctgcagtata tcagggcac ggcgcgcatc attaactggg cgcatatcgt      1080
taatgtcaat atggtgcctg gcaaggcctc cgtagcgtcc ctcgccaaag cagccgcgca     1140
ttggctgcag aggttacctt acgaggtcaa gacctcggtc acggttggca caccgaggaa     1200
ggatgaggac accgaagatg aagaggaaga cgagacgggc aaccagaaga atggcaccag     1260
tctgacacgg aaggagagca gcgagggccg caagggcagc atcgtctccg tcaccacggt     1320
cacgcaacag tacgagtccg cacactctcc aagatacggc aagacgatcg cagaggaggg     1380
cgacgaggag ctcttctccg gctggagga gccgcctctg aatcggggtc tcctcatcct      1440
ggctcagatg tcgagcgccg ggaacttcat gaacgccgag tacacccaag cctgcgtcga     1500
ggcggcgagg gaacacaagg acttcgtcat gggattcgtt tcacaggaag gactgaacag     1560
catgccagag gacgacttca tccacatgac gcccggttgc cagctgccac cggagcacga     1620
catggatgcg gaggtaaagg gcgatgggaa gggtcagcag tacaacacac cggacaagat     1680
cattggcctg ggggcagata tcgttattgt agggaggggt atcatcaagg ctggcgatcc     1740
ggagcatgaa gccgaccgat accgttcggc ggcctggaag gcctacagcg agcgtgttcg     1800 ctgagggggtc aaaaacctag ataattctgg ccaagcgctc tatgtggtta atggatgatc     1860
tatatatgga cgggcgaggc tgcttacacc ccctttgttt gaacgggcgg gatgacgatg     1920
tgggtttgga tgtgccgtgt ctcatctggt ggagttgcag tactacactg agacgacacc     1980
aattattttc caatcacata gcctctcaca tgtataagaa gacaaagtca tgaatcctat     2040
caaatcactt gcgacgtatt tttgaatgtt tcaaatgcag gcaacggcgg gacaccaact     2100
ggttatgcat agaccgtcgg aattaaagcc agcattctcc gctccctccg gaatccgact     2160
cccgtcactc aagcgcaccg ttcgtaacgc aggtcaatcc cgctcacaca actcatctca     2220
caccgagcga ttactctcat tgctgacctc acccgctccc gctcccgcga caaacctcca     2280
tccaggatcc ttcactttcc tgcccttttgc acatggcttc gcaccgataa cgagtcaaga     2340
caactcccgc cccagaaatg gacgccatgg ggatccagca cgagaaccgc cagcctctcc     2400
gtgt                                                                  2404
```

<210> SEQ ID NO 47
<211> LENGTH: 320
<212> TYPE: PRT
<213> ORGANISM: Trichoderma reesei

<400> SEQUENCE: 47

Met Pro Pro Ala Val Val Lys Asn Ser Ala Tyr Thr Pro Pro Thr Lys
1               5                   10                  15

Gly Ile Leu Ser Cys Leu Pro Ser Ser Trp Val Pro Tyr Ala Glu Leu
            20                  25                  30

Ile Arg Leu Asp Lys Pro His Gly Ile Tyr Met Thr Ile Tyr Pro Tyr
        35                  40                  45

Ala Leu Gly Leu Leu Tyr Ala Ser Gln Leu Thr Ser Glu Ser Leu Pro
    50                  55                  60

```
Pro Asn Val Val Leu Ser Arg Phe Leu Asn Leu Ala Ile Trp Thr Phe
 65                  70                  75                  80

Leu Ile Arg Ser Ala Gly Cys Ala Trp Asn Asp Asn Val Asp Gln Asp
                 85                  90                  95

Phe Asp Arg Gln Thr Ala Arg Cys Arg Asp Arg Pro Ile Ala Arg Gly
            100                 105                 110

Ala Ile Ser Thr Leu Gln Gly His Val Phe Thr Thr Ala Leu Leu Ala
        115                 120                 125

Leu Gly Phe Leu Ser Ile Gln Asn Phe Pro Leu Glu Ser Lys Ile Asp
130                 135                 140

Gly Ala Ala Thr Val Leu Leu Thr Cys Ile Tyr Pro Phe Gly Lys Arg
145                 150                 155                 160

Phe Thr His Phe Ala Gln Val Thr Leu Gly Leu Thr Leu Ser Val Ala
                165                 170                 175

Ile Ile Phe Gly Pro His Ser Val Gly Ala Asn Pro Leu Ser Gln Gly
            180                 185                 190

Asn Phe Leu Pro Thr Thr Cys Leu Val Ser Ser Ile Ile Leu Leu Val
        195                 200                 205

Ile Phe Tyr Asp Val Val Tyr Ala Arg Gln Asp Thr Val Asp Asp Leu
210                 215                 220

Lys Ser Gly Val Lys Gly Met Ala Val Leu Phe Arg Asn Trp Ile Thr
225                 230                 235                 240

Thr Leu Leu Leu Thr Leu Ile Ile Ala Ile Leu Thr Leu Leu Tyr Ile
                245                 250                 255

Thr Ala Arg Ser Leu Asp Leu Gly Trp Val Phe Phe Gly Leu Ser Val
            260                 265                 270

Ala Gly Pro Ala Val Ser Leu Leu Thr Thr Ile Ala Leu Ile Ala Ser
        275                 280                 285

Lys Ser Ser Ser Arg Tyr Ala Gly Lys Phe Tyr Val Leu Ala Ile
290                 295                 300

Ala Ser Leu Leu Ser Gly Phe Thr Ile Glu Tyr Leu Arg Thr Ile Met
305                 310                 315                 320

<210> SEQ ID NO 48
<211> LENGTH: 1052
<212> TYPE: PRT
<213> ORGANISM: Trichoderma reesei

<400> SEQUENCE: 48

Met Arg Ser Phe Val Lys Ala Asn Val Asp Phe Ser Ser Ala Glu Arg
  1               5                  10                  15

Lys Glu Asp Tyr Ile His Ser Leu Pro Glu Leu Val Asp Phe Asn Ala
                 20                  25                  30

Val Gln Asn Pro Asn His Leu Leu Cys Ile Gln Ala Arg Ser Asn Ala
             35                  40                  45

Pro Trp Val Lys Ile Thr Asn Ala Gln Phe Lys Val Ala Ile Asp Gln
         50                  55                  60

Cys Ala Thr Trp Ile Ala Glu Asn Val Lys Leu Pro Lys Ala Arg Thr
 65                  70                  75                  80

Lys His Asp Leu Thr Gly Arg Leu Pro Val Ala Leu Leu Met Glu Ser
                 85                  90                  95

Asp Phe Gly Leu Leu Val His Gln Phe Ala Leu Val Ser Met Gly Ile
            100                 105                 110

Pro Pro Leu Val Leu Ser Ala Arg Leu Ser Pro Glu Ala Ile Phe His
        115                 120                 125
```

```
Leu Leu Arg Ser Thr Glu Ala Ser Ser Leu Ile Val Ser Gln Arg Val
    130                 135                 140

Ala Met Ile Thr Lys Gly Ala Phe Gly Asn Val Lys Thr Ser Asp Phe
145                 150                 155                 160

His Val Ala Gln Pro Tyr Ser Thr Phe Cys Asn Val Pro Ala Asp Lys
                165                 170                 175

Ser Val Arg Lys Gln Ser Val Tyr Pro Asp Asn Ile Asp Ala Asn Ile
                180                 185                 190

Val Leu Leu His Ser Ser Gly Thr Thr Gly Leu Pro Lys Pro Ile Ala
            195                 200                 205

Leu Ser His Arg Gln Leu Met Phe Ser Val Ser His Gly Asp Phe Glu
210                 215                 220

Thr Glu Glu Ala Gln Gly Ile Val Ile Ser Thr Leu Pro Leu Phe
225                 230                 235                 240

His Gly Phe Gly Leu Leu Ala Pro Gly Leu Ser Met Ala Ile Gly Lys
                245                 250                 255

Thr Val Cys Phe Pro Ala Ser Asp Glu Val Pro Asp Ala Gln Ser Ile
                260                 265                 270

Val Asp Leu Ile Asn Met Ser Gly Ala Thr Gly Met Leu Thr Val Pro
            275                 280                 285

Phe Leu Leu Glu Asn Met Ala Ala Leu Pro Asn Gly Thr Gly Leu Arg
290                 295                 300

Ala Leu Ala Lys Leu Asp Phe Val Gly Thr Gly Ser Ala Leu Ser
305                 310                 315                 320

Ala Asp Phe Gly Val Ser Ala Ser Ala Ala Gly Val Lys Leu Leu Asn
                325                 330                 335

Leu Tyr Gly Thr Thr Glu Thr Gly Pro Leu Thr Lys Thr Phe Ala Pro
                340                 345                 350

Lys Ser Gly Tyr Asp Trp Lys Tyr Phe Arg Leu Arg Gln Asp Met Leu
            355                 360                 365

Phe Lys Val Thr Glu Leu Pro Pro Val Asp Gly Glu Lys Arg Phe Arg
370                 375                 380

Leu Thr Val Phe Pro Phe Gly Ala Asp Lys Pro Phe Glu Ile Ala Asp
385                 390                 395                 400

Gln Leu Ile Arg Ser Glu Lys Phe Pro Glu Thr Asp Phe Ala Ala Val
                405                 410                 415

Gly Arg Asp Asp Asp Val Val Leu Ala Thr Gly Glu Lys Val Asn
                420                 425                 430

Pro Leu Leu Leu Glu Thr Ala Leu Thr Asp Ser Gly Leu Val Lys Ser
                435                 440                 445

Ala Ile Val Phe Gly Glu Asn Gln Phe Gln Ile Gly Val Val Val Glu
450                 455                 460

Pro Ala Thr Pro Leu Asn Pro Asp Gln Lys Glu Glu Phe Arg Lys Lys
465                 470                 475                 480

Ile Trp Pro Ile Ile Val Arg Val Gly Glu Arg Met Asp Thr Thr Ala
                485                 490                 495

Arg Ile Tyr Ser Pro Asn Ala Val Ile Val Pro Ser Ser Val Thr
                500                 505                 510

Ile Pro Arg Thr Asp Lys Gly Ser Ile Ala Arg Lys Glu Val Phe Gln
            515                 520                 525

Leu Leu Glu Lys Glu Ile Ser Gln Val Tyr Glu Asp Leu Glu Asn Gly
530                 535                 540
```

-continued

```
Ser Ile Glu Glu Thr Pro Leu Asp Tyr Asp Lys Leu Glu Gln Glu Leu
545                 550                 555                 560

Lys Gly Leu Ile Gln Lys Arg Leu Lys Leu Arg Val His Pro Gly Lys
            565                 570                 575

Trp Thr Val Asp Asp Asn Leu Phe His Leu Gly Leu Asp Ser Leu Gln
                580                 585                 590

Ala Thr Thr Leu Arg Arg Ile Leu Leu Ser Ala Ala Ser Lys Thr Pro
        595                 600                 605

Pro Asp Val Ile Gly Lys Asp Phe Ile Tyr Val Asn Pro Ser Val Lys
    610                 615                 620

Ala Ile Ala Asn Ala Leu Arg Pro Ala Asn Gly Pro Ile Gly Thr Glu
625                 630                 635                 640

Ser Ala Ser Val Ala Gln Glu Val Asp Asp Tyr Ala Gln Gln Tyr Ser
            645                 650                 655

Ile Lys Gly Phe Glu Val Gln Asp Ile Val Pro Lys Ala Ser Pro Lys
                660                 665                 670

Leu Ile Arg Gly Ala Val Val Leu Leu Thr Gly Ser Ser Gly Gly Leu
        675                 680                 685

Gly Ser His Ala Leu Gly Lys Leu Ala Glu Ser Thr Gln Val Ala Lys
    690                 695                 700

Ile Val Cys Leu Gln Arg Lys Arg Pro Gly Thr Val Ile Asn Pro Ile
705                 710                 715                 720

Pro Gly Ala Ala Lys Val Asp Arg Ala Ser Ile Glu Ala Lys Gly Ile
            725                 730                 735

Lys Leu Thr Asp Asp Gln Trp Ala Lys Ile Thr Ala Leu Glu Ile Asp
                740                 745                 750

Pro Thr Ile Asp Asn Leu Gly Leu Pro Ala Met Val Met Gly Met Val
        755                 760                 765

Ser Lys Thr Val Thr His Ile Leu His Ala Ala Trp Pro Met Asp Phe
    770                 775                 780

His Met Arg Leu Pro Ser Phe Gly Tyr Gln Phe Ser Tyr Leu Lys Asn
785                 790                 795                 800

Leu Leu Arg Ile Ala Val Gln Ala Pro Gln Lys Val Arg Phe Leu Phe
            805                 810                 815

Val Ser Ser Ile Ser Ala Leu Ala Lys Leu Gly Leu Ile Thr Pro Gly
                820                 825                 830

Arg Pro Ile Pro Glu Glu Pro Leu Asp Val Glu Ser Ala Ala Cys Gly
        835                 840                 845

Ile Gly Tyr Ala Asp Ala Lys Leu Val Cys Glu Lys Ile Leu Glu Glu
    850                 855                 860

Ala Ala Ser Leu Tyr Asn Ser Asn Val Glu Val Val Ile Ala Arg Cys
865                 870                 875                 880

Gly Gln Leu Ser Gly Ala Arg Lys Thr Gly Ala Trp Asn Val Ser Glu
            885                 890                 895

Gln Ile Pro Met Leu Ile Arg Thr Ser Gln Gly Leu Gly Ile Leu Pro
                900                 905                 910

Ile Leu Glu Gly Thr Val Ser Trp Ile Pro Val Asp Ala Ala Ala
        915                 920                 925

Thr Val Ala Glu Leu Leu Phe Ala Pro Asp Ala Pro Gly Leu Val Thr
    930                 935                 940

His Val Glu Asn Pro Val Arg Gln Ser Trp Ser Glu Val Phe Gln Ile
945                 950                 955                 960

Ile Gly Asn Glu Leu Arg Ile Thr Lys Thr Leu Ser Phe Asp Asp Trp
```

```
                        965                 970                 975
Leu Gly Glu Val Thr Ser Thr Ala Glu Arg Asp Val Glu Asp Tyr Pro
            980                 985                 990

Val Arg Lys Leu Tyr Glu Phe Phe Lys Leu Tyr Phe Arg Ile Ala Ser
        995                 1000                1005

Ser Gly Ala Val Val Met Gly Thr Asp Met Ser Arg Lys Asn Ser
    1010                1015                1020

Ala Thr Leu Arg Cys Leu Lys Ala Leu Asp Arg Gly Thr Ile Ala
    1025                1030                1035

Gly Tyr Val Arg Tyr Trp Arg Ser Val Gly Tyr Leu Arg Gln
    1040                1045                1050

<210> SEQ ID NO 49
<211> LENGTH: 2116
<212> TYPE: PRT
<213> ORGANISM: Trichoderma reesei

<400> SEQUENCE: 49

Met Ala Asn Val Ser Gly Ile Val Phe Ser Pro Gln Ser Arg Ala Pro
1               5                   10                  15

Ser Lys Ala Tyr Leu Glu Tyr Ile His Asn Ser Leu Thr Arg Ser Ser
            20                  25                  30

Ile Tyr Ser Pro Ile Cys Glu Ala Ile Ser Asn Leu Ser Ala Thr Trp
        35                  40                  45

Trp Ala Ile Ala Asn Ser Gln Pro Lys Ile Ala Ser Leu Glu Gln Gly
    50                  55                  60

Leu Asn Phe Ala Lys Asp Phe Ser Ala Trp Ile Glu Thr Gly Asn Ser
65                  70                  75                  80

Ser Arg Leu Glu Thr Ser Met Ser Gly Ile Val Thr Leu Pro Leu Leu
                85                  90                  95

Val Ile Ile His Thr Ile Gln Tyr Leu Glu Tyr Leu Arg Gln Asn Cys
            100                 105                 110

Ile Thr His Ser Glu Leu Leu Pro His Leu Arg Ala Gly Gly Val Gln
        115                 120                 125

Gly Phe Cys Ala Gly Leu Met Met Ala Ile Val Val Ala Ala Ser Lys
    130                 135                 140

Asp Glu Thr Gln Leu Val Glu Asn Ser Ala Lys Ala Val Arg Ile Ala
145                 150                 155                 160

Phe Ala Ile Gly Ser Tyr Gly Glu Ile Gly Cys Asp Ala Asn Ser Ile
                165                 170                 175

Ile Ser Thr Thr Met Val Val Arg Leu Lys Arg Gly Ser Glu Arg Glu
            180                 185                 190

Gln Ile Ile Arg Glu Phe Pro Glu Ser Arg Ile Ser Ala Val Ser Asp
        195                 200                 205

Pro Lys Thr Val Ser Ile Ile Ala Ser Ser Gln Ile Ala Ala Met
    210                 215                 220

Gln Ala Tyr Ile Glu Glu Leu Gly Leu Ser Phe Lys Met Val His Met
225                 230                 235                 240

Arg Ser Asn Ile His Asn Pro Lys Asn Val Ala Leu Ala Lys Glu Leu
                245                 250                 255

Leu Gly Leu Cys Leu Arg Asp Ala Asp Trp Gln Leu Pro Asn Ser Asp
            260                 265                 270

Cys Ile Gln Val Ala Val Arg Ser Asn Ser Thr Gly Gln Ile Leu Ser
        275                 280                 285
```

-continued

Gly Cys Ser Leu Thr Ala Glu Val Ile Asn Thr Ile Leu Thr Ser Cys
290                 295                 300

Cys Asp Trp Asp Arg Val Met Asn Asn Val Ala Gln Asp Leu Arg Arg
305                 310                 315                 320

Phe Gly Lys Ser His Arg Ile Ala Met Val Gly Leu Gly Asp Cys Leu
            325                 330                 335

Pro Leu Pro Pro Phe Gln Lys Ile Gly Ile Glu Ile Thr Lys Val Asp
            340                 345                 350

Val Met Ser Asn Thr Glu Asp Ala Arg Arg Arg Thr Asn Asp Ala Asn
            355                 360                 365

Ile Ser Arg Arg Ala Thr Phe Pro Ser Asp Ser Val Ala Val Val Gly
370                 375                 380

Ala Ala Cys Arg Leu Pro Gly Ala Asn Thr Leu Asp Glu Leu Trp Asp
385                 390                 395                 400

Leu Ile Ser Arg Gly Glu Ser Arg Leu Glu Thr Leu Arg Gln Asp Arg
                405                 410                 415

Val Arg Leu Glu Glu Ser Phe Arg Ala Ser Gln Asp Lys Asp Trp Thr
            420                 425                 430

Thr Arg Arg Gln Trp Phe Gly Asn Phe Val Asp Cys Val Asp Glu Phe
            435                 440                 445

Asp His Gly Phe Phe Gly Ile Ser Glu Lys Glu Ala Ala Tyr Met Asp
450                 455                 460

Pro Gln Gln Arg Leu Leu Leu Thr Cys Ala Tyr Glu Ala Leu Asp Ser
465                 470                 475                 480

Ser Gly Tyr Leu His His His Ala Arg Ala Asn Gly Asp Pro Ile Gly
            485                 490                 495

Cys Phe Ile Gly Ala Ser Tyr Thr Glu Tyr Asn Glu Asn Thr Asn Ala
            500                 505                 510

Tyr Ala Pro Ser Ala Phe Ala Ala Thr Gly Thr Ile Arg Ala Phe Leu
            515                 520                 525

Ser Gly Lys Ile Ser His Tyr Phe Gly Trp Thr Gly Pro Ser Glu Val
530                 535                 540

Ile Asp Thr Ala Cys Ser Ala Ser Leu Val Ala Val His His Ala Ile
545                 550                 555                 560

Arg Ala Ile Gln Ser Gly Asp Cys Ser Met Ala Leu Ala Gly Gly Val
                565                 570                 575

Asn Ile Leu Thr Gly Val His Asn Tyr Ile Asp Leu Gly Arg Ala Gly
            580                 585                 590

Phe Leu Ser Arg Thr Gly Gln Cys Lys Pro Phe Asp Glu Ser Ala Asp
            595                 600                 605

Gly Tyr Cys Arg Ala Asp Gly Val Gly Ile Val Val Leu Lys Pro Leu
610                 615                 620

Lys Gln Ala Ile Ala Asp Gly Asn His Ile Met Gly Val Ile Ser Ala
625                 630                 635                 640

Thr Ala Thr Asn Gln Gly Gly Leu Ser Gln Gly Ile Thr Val Pro His
                645                 650                 655

Gly Asp Ala Gln Arg Ala Leu Tyr Cys Arg Ile Leu Lys Thr Ala Asn
            660                 665                 670

Ile Glu Pro Asp Gln Val Thr Tyr Val Glu Ser His Gly Thr Gly Thr
            675                 680                 685

Gln Val Gly Asp Pro Ile Glu Val Ser Ser Ile Arg Glu Val Phe Gly
690                 695                 700

Gly Pro Ser Arg Gln Ser Val Val Tyr Ile Ala Ser Leu Lys Ala Asn

-continued

```
            705                 710                 715                 720
Val Gly His Ser Glu Thr Ala Ala Gly Val Ala Ser Leu Leu Lys Val
                    725                 730                 735

Leu Thr Met Phe Ala His Lys Ala Ile Pro Pro Gln Ala Gly Phe Lys
                    740                 745                 750

Thr Leu Asn Pro Lys Ile Pro Ala Val Glu Pro Asp Asn Met Met Ile
                    755                 760                 765

Ala Ala Gln Leu Met Pro Trp Asp Ser Lys Ile Arg Met Ala Cys Val
    770                 775                 780

Asn Ser Tyr Gly Ala Ser Gly Ser Asn Ala Ala Leu Ile Cys Ala Glu
785                 790                 795                 800

Trp Thr Ala Glu Ile Ala Arg Pro Arg Ala Gly Ala Pro Thr Tyr Pro
                    805                 810                 815

Val Phe Leu Ser Ala His Thr Lys Asp Ala Leu Arg Asp Ser Ala Ile
                    820                 825                 830

Arg Leu Ala Ser Tyr Phe Gln Ser Pro Gly Lys Ala Leu Ser Ile Gly
                    835                 840                 845

Ser Val Ala Phe Thr Leu Ser Glu Arg Arg Lys His His Arg Tyr Arg
850                 855                 860

Trp Ser Thr Ser Ala His Ser Leu Ser Asp Leu Thr Arg Gln Leu His
865                 870                 875                 880

Ala Gly Val Met Glu Gly Ile Val Glu Ser Pro Asn Thr Arg Met Pro
                    885                 890                 895

Val Val Leu Ala Phe Ser Gly Gln Ser Arg Thr Lys Ile Gly Leu Asp
                    900                 905                 910

Pro Thr Leu Cys Glu Leu Tyr Pro Gln Phe Arg Arg Tyr Leu Glu Asn
                    915                 920                 925

Cys Asn Asp Ile Leu Arg Ser Leu Gly Tyr Ser Asp Ile Met Ser Ser
    930                 935                 940

Leu Ile Gln Thr Asp Ala Val Thr Asp Val Val Ile Leu His Ala Gly
945                 950                 955                 960

Thr Phe Ala Val Gln Tyr Ala Cys Ala Arg Ser Trp Leu Glu Gly Gly
                    965                 970                 975

Leu Gln Val Asp Ala Val Ile Gly His Ser Leu Gly Glu Leu Thr Ala
                    980                 985                 990

Leu Ala Val Ser Gly Val Leu Ser  Leu Glu Asp Ala Leu  Gly Leu Val
                    995                 1000                1005

Ala Lys  Arg Ala Leu Leu Ile  Glu Arg Lys Trp Gly  Ser Glu Pro
    1010                1015                1020

Gly Ser  Met Leu Ala Ile Tyr  Ser Asp Leu Glu Thr  Val Gln Gln
    1025                1030                1035

Ile Val  Ala Ser Ser His Thr  Thr Val Val Glu Asp  Gly Leu Glu
    1040                1045                1050

Ile Ala  Cys His Asn Ser Pro  Asn Ala His Val Val  Val Gly Lys
    1055                1060                1065

Arg Ala  Ser Ile Ala Arg Val  Lys Lys Leu Ile Asp  Ser Asn Pro
    1070                1075                1080

Gln Phe  Gln Gly Thr Arg His  Gln Arg Leu Asp Val  Ser His Gly
    1085                1090                1095

Phe His  Ser Arg Leu Thr Asp  Pro Leu Leu Pro Asp  Leu Ile Lys
    1100                1105                1110

Phe Ala  Asn Ser Leu Thr Phe  Asn Glu Pro Leu Ile  Pro Leu Glu
    1115                1120                1125
```

-continued

```
Thr Cys Thr Glu Ser Pro Val Leu Ser Ile Thr Pro Lys Tyr Ile
1130                1135                1140

Ala Glu His Ser Arg His Ala Val Tyr Phe Thr His Ala Ile Arg
1145                1150                1155

Arg Leu Glu Arg Arg Leu Gly Pro Cys Thr Trp Leu Glu Ala Gly
1160                1165                1170

Trp His Thr Pro Ile Ile Pro Met Ala Lys Lys Ala Val Ala Met
1175                1180                1185

Pro Glu Ile His Asn Phe Gln Ser Leu Ser Gly Ser Ala Val Ala
1190                1195                1200

Val Ser Asn Val Thr Ala Ala Leu Trp Lys Gln Gly His Ser Ile
1205                1210                1215

Ser Trp Trp Gly Phe Leu Ser Pro Gly Asp Ser Gln Leu Asp Gln
1220                1225                1230

Ile Trp Leu Pro Pro Phe Ser Phe Gln Pro Ser His His Trp Leu
1235                1240                1245

Glu His Val Asp Arg Val Thr Lys Val Gln His Pro Asp Ser Lys
1250                1255                1260

Val Leu Gln Gln Arg Ser Arg Leu Val Ser Phe Val Lys Val Ser
1265                1270                1275

Ala Thr Gly Asp Glu Phe Gln Leu Leu Arg Gln Cys Glu Lys Tyr
1280                1285                1290

Ser Asn Ile Val Lys Gly His Ala Val Arg Gln Arg Pro Leu Cys
1295                1300                1305

Pro Ala Ser Leu Tyr Met Glu Ile Ala Val Met Cys Ala Gln Glu
1310                1315                1320

Arg Gly Phe Asp Phe Asn Glu His Thr Ile Lys Phe Arg Glu Ile
1325                1330                1335

Val Phe Ser Asn Gly Leu Gly Cys Asp Asn Ser Arg Asp Val Arg
1340                1345                1350

Val Val Leu Ala Gln Asn Leu Asp Ser Thr Ala Asp Gly Ala Trp
1355                1360                1365

Asn Phe Ser Val Asn Ser Ser Lys Lys Gly Asp Ala Lys Ser Val
1370                1375                1380

Arg Thr Met His Ala Ile Gly Gln Phe Ala Ala Leu Ser Glu Ala
1385                1390                1395

Ser Asp Phe Arg Ile Tyr Glu Gly Leu Ile Ser Asp Arg Met Ala
1400                1405                1410

Leu Leu Pro Lys Asp Pro Asn Ala Glu His Leu Lys Arg Arg Thr
1415                1420                1425

Ala Tyr Ala Val Phe Ser Arg Val Val Glu Tyr Ala Glu Leu Leu
1430                1435                1440

Arg Gly Ile Ser Ser Ile Thr Leu Ser Glu Asp Gln Ala Ile Ala
1445                1450                1455

Glu Ile Glu Leu Pro Ala Glu Ala Ser Thr Asn Cys Asp Ser Thr
1460                1465                1470

Val Asp Arg Phe Met Asp Ala Ile Ser Leu Asp Thr Phe Ile Gln
1475                1480                1485

Val Leu Gly Leu Leu Ile Asn Ser Arg Leu Asn Thr Val Gly His
1490                1495                1500

Glu Ile Phe Val Ala Thr Ser Ile Glu Asn Met Thr Ile Leu Pro
1505                1510                1515
```

```
Cys Asp Phe Lys Thr Gln Lys Arg Trp Ser Val Tyr Ala Met Phe
    1520            1525                1530

Gly Met Lys Gly Asp Arg Gln Ala Ile Gly Asp Val Phe Val Phe
    1535            1540                1545

Ser Pro Glu Gly Arg Leu Val Ile Leu Gly Ser Gln Ile Ser Phe
    1550            1555                1560

Thr Arg Ile Lys Ala Ser Ile Leu Glu Glu Leu Leu Asp Arg Asn
    1565            1570                1575

Tyr Ser Glu Ser Val Met Val Lys Ala Gln Arg Ala Glu Gly Pro
    1580            1585                1590

Ala Ala Ser Gly Val Met His Arg Ile Arg Thr Gly Glu Ala Ile
    1595            1600                1605

Ala Ala Gly Ser Ser Val Leu Pro Val Asp Ser Leu Pro Ala Lys
    1610            1615                1620

Ser Glu Glu Pro Ala Tyr Asn Phe Asp Asp Ala Lys Val Leu Ile
    1625            1630                1635

Ala Ser Tyr Ile Gly Leu Thr Ala Ser Glu Ile Arg Lys Glu Glu
    1640            1645                1650

Ser Phe Ser Ser Leu Gly Leu Asp Ser Leu Ser Ser Val Glu Leu
    1655            1660                1665

Ala Asp Glu Leu Arg Val Lys Phe Gly Ile Glu Val Ser Pro Ser
    1670            1675                1680

Asp Leu Leu Thr Met Gln Val Gly Glu Leu Glu Gln Gly Gly Pro
    1685            1690                1695

Ser Gln Gly Thr Asp Ser Ile Asp Val Gln Glu Gln Asp Leu Pro
    1700            1705                1710

Gln Ser Ile Asn Arg Arg Val Asn Gly Leu Ala Asn Gly Arg Val
    1715            1720                1725

Ala Gln Ala Ser Gly Leu Arg Asn Gly Leu His Asp Gly Cys Ser
    1730            1735                1740

Asn Asn Asn Val Ser Gly Gln Val Lys Asp His Ala Tyr Ser Tyr
    1745            1750                1755

Ala Ser Lys Thr Asn Gly His Leu Glu Lys Pro Leu Arg Arg Pro
    1760            1765                1770

His Tyr Ala Arg His Arg Val Gln Thr Val Thr Tyr Lys Glu Val
    1775            1780                1785

Asp Gly Ile His Ile Leu Ala Asp Met Phe Ile Pro Leu Glu Pro
    1790            1795                1800

Pro Ser Glu Ala Met Pro Ile Ala Leu Met Ile His Gly Gly Gly
    1805            1810                1815

His Leu Thr Leu Ser Arg Lys Ala Ile Arg Pro Ser Gln Thr Ser
    1820            1825                1830

Phe Leu Leu Ala Asn Gly Leu Leu Pro Ile Ser Leu Asp Tyr Arg
    1835            1840                1845

Leu Cys Pro His Val Asn Val Leu Asp Gly Pro Met Ala Asp Val
    1850            1855                1860

Arg Asp Ala Tyr Ala Trp Ala Arg Lys Glu Val Pro Leu Leu Leu
    1865            1870                1875

Arg Glu Ala Gly Met Cys Val Asp Gly Ser Lys Ile Val Val Val
    1880            1885                1890

Gly Trp Ser Thr Gly Gly His Leu Ala Met Thr Thr Ala Trp Thr
    1895            1900                1905

Ala Pro Ala Ala Gly Leu Pro Pro Pro Leu Ala Val Leu Ala Phe
```

-continued

```
                1910                1915                1920
Tyr Cys Pro Thr His Tyr Asp Pro Ser Asp Ser Leu Arg Met
        1925                1930                1935
Gly Lys Asp Tyr His Ser Arg Thr Met Ser Met Ser Glu Ile Arg
        1940                1945                1950
Lys Ala Leu Gly Thr Gln Thr Ala Ser Ser His Ala Phe Ser Ser
        1955                1960                1965
Thr Asp Thr Thr Gly Leu Gly Trp Leu Glu Pro Gly Asp Pro Arg
        1970                1975                1980
Ser Glu Leu Val Leu Ala Leu Val Lys Glu Gln Asn Gly Val Ser
        1985                1990                1995
Leu Leu Leu Asp Gly Val Pro Thr Asp Gly Asn Thr Phe Gln Ala
        2000                2005                2010
Pro Glu Pro Glu Arg Val Thr Ala Ile Ser Pro Leu Ser Gln Val
        2015                2020                2025
Arg Leu Gly Thr Tyr Arg Thr Pro Thr Phe Val Ile Ile Gly Asp
        2030                2035                2040
Glu Asp Glu Val Val Pro Phe His Ser Ser Val Asp Phe Val Asp
        2045                2050                2055
Ala Leu Arg Thr Gln Gly Ile Arg His Gly Phe Ile Pro Val Pro
        2060                2065                2070
Gly Gln Arg His Ile Phe Asp Leu Thr Leu Ala Pro Gly Met Ala
        2075                2080                2085
Lys Trp Glu Glu Tyr His Lys Tyr Thr Ala Leu Pro Val Glu His
        2090                2095                2100
Gln Asn Gly Ile Pro Gln Ser Met Arg Asp Ile Asp Thr
        2105                2110                2115

<210> SEQ ID NO 50
<211> LENGTH: 518
<212> TYPE: PRT
<213> ORGANISM: Trichoderma reesei

<400> SEQUENCE: 50

Met Ala Val Pro Glu Lys Cys Thr Val Leu Val Ile Gly Gly Gly Pro
1               5                   10                  15
Ala Gly Ser Tyr Ala Ala Ser Ala Leu Ala Arg Glu Gly Val Asp Thr
                20                  25                  30
Val Leu Leu Glu Ala Asp Lys Phe Pro Arg Tyr His Ile Gly Glu Ser
            35                  40                  45
Met Leu Ala Ser Met Arg His Phe Leu Arg Phe Ile Asp Val Asp Ser
        50                  55                  60
Val Phe Asp Ser Tyr Gly Phe Thr Lys Lys Val Gly Ala Ala Phe Lys
65                  70                  75                  80
Leu Asn Pro Lys Lys Arg Glu Gly Tyr Thr Asp Phe Leu Ala Ala Gly
                85                  90                  95
Gly Pro Gln Asn Tyr Ala Trp Asn Val Val Arg Ser Glu Ala Asp His
                100                 105                 110
Leu Leu Phe Gln His Ala Ala Ser Ser Gly Ala Lys Thr Phe Asp Gly
            115                 120                 125
Val Gln Val Lys Ser Ile Asn Phe Ile Gly Glu Pro Cys Glu Gly Phe
        130                 135                 140
Gly Glu Leu Pro Tyr Asp Tyr Pro Gly Arg Pro Tyr Ser Ala Thr Tyr
145                 150                 155                 160
```

```
Leu Met Lys Asp Asp Lys Thr Ser Arg Glu Ile Lys Phe Asp Tyr Ile
            165                 170                 175

Ile Asp Ala Ser Gly Arg Val Gly Leu Leu Ser Thr Lys Tyr Leu Lys
        180                 185                 190

Asn Arg Lys Tyr Asn Gln Gly Leu Lys Asn Val Ala Thr Trp Gly Tyr
    195                 200                 205

Trp Lys Gly Ala Ala Ala Tyr Gly Val Gly Thr Pro Arg Gln Asn Ser
210                 215                 220

Pro Phe Phe Glu Ala Leu Gln Asp Glu Ser Gly Trp Ala Trp Leu Ile
225                 230                 235                 240

Pro Leu His Asn Gly Thr Thr Ser Val Gly Ile Val Met Asn Gln Lys
                245                 250                 255

Met Ser Ala Asn Arg Lys Ser Gln Ala Gly Ser Pro Asp Ser Lys Thr
            260                 265                 270

Phe Tyr Leu Gly Asn Leu Lys Gln Leu Ala Pro Glu Leu Ser Lys Leu
        275                 280                 285

Leu Glu Asn Ala Glu Leu Leu Thr Asp Ile Lys Ser Ala Ser Asp Tyr
    290                 295                 300

Ser Tyr Ser Ala Thr Ala Tyr Ala Ile Pro Tyr Ala Arg Ile Ala Gly
305                 310                 315                 320

Asp Ala Gly Cys Phe Ile Asp Pro Tyr Phe Ser Ser Gly Val His Leu
                325                 330                 335

Ala Phe Val Gly Gly Leu Ser Ala Ala Thr Thr Ile Ser Ala Ala Ile
            340                 345                 350

Lys Gly Gln Val Ser Glu Val Glu Ala Ala Asp Trp His Ser Lys Lys
        355                 360                 365

Val Ala Asp Ser Tyr Ile Arg Phe Leu Leu Val Leu Ser Ala Tyr
370                 375                 380

Arg Gln Ile Arg Ser Gln Glu Glu Ala Val Leu Ser Asp Phe Asp Glu
385                 390                 395                 400

Asp Asn Tyr Asp Arg Ala Phe Ala Phe Arg Pro Ile Ile Gln Gly
                405                 410                 415

Ile Ala Asp Val Asp Thr Lys Leu Ser Lys Glu Glu Leu Lys Lys Thr
            420                 425                 430

Leu Glu Phe Cys Ser Asn Ala Phe Glu Pro Val Lys Pro Glu Asp Arg
        435                 440                 445

Ser Ser Met Leu Glu Gln Leu Gly Lys Cys Pro Asn Thr Ala Tyr Gln
    450                 455                 460

Val Asp Leu Ser Pro Asp Gln Arg Thr Val Asp His Ile Arg Ala
465                 470                 475                 480

Arg Gln Met Met Arg Thr Glu Asp Thr Met Asn Ile Ser Ser Phe Gly
                485                 490                 495

Thr Asp Ser Ile Asn Gly Phe Val Pro Lys Leu Lys Thr Gly Asp Leu
            500                 505                 510

Gly Leu Val Ala Lys Ala
        515

<210> SEQ ID NO 51
<211> LENGTH: 39
<212> TYPE: DNA
<213> ORGANISM: Artificial sequence
<220> FEATURE:
<223> OTHER INFORMATION: primer

<400> SEQUENCE: 51
```
cgcaccacct tcaaaatgcg ttcgtttgtg aaggccaac        39

<210> SEQ ID NO 52
<211> LENGTH: 38
<212> TYPE: DNA
<213> ORGANISM: Artificial sequence
<220> FEATURE:
<223> OTHER INFORMATION: primer

<400> SEQUENCE: 52
atgtactcct ggtactcact gcctcagata gcctaccg        38

<210> SEQ ID NO 53
<211> LENGTH: 3309
<212> TYPE: DNA
<213> ORGANISM: Trichoderma reesei

<400> SEQUENCE: 53
atgcgttcgt ttgtgaaggc caacgttgat ttctcctctg cagagagaaa ggaggactat        60
atacactctc tgccagagtt ggttgacttc aatgctgtta aaacccccaa tcaccttctt       120
tgcatccagg cccgatcaaa cgcgccatgg gtcaaaatca ccaatgctca attcaaggtc       180
gcgattgacc aatgcgccac atggattgcg aaaaacgtca agctgcccaa ggccaggaca       240
aagcatgatc ttacagggag actgccggtt gctctgctga tggagagtga ctttggtctc       300
ctggtgcacc agttcgctct tgtgtctatg ggcattcccg tgcgtaattt cattccgagc       360
ctcctccgtg cttctctgac ttggctagcc acttgtcctc tccgctcgtc tgagtcctga       420
agccatcttc cacctcctgc gaagtactga agcttcatct ctcattgttt ctcaaagggt       480
cgccatgatc accaaaggag cttttcggaa tgtcaagacc agtgactttc atgttgctca       540
gccgtacagc acttttctgca atgtcccggc agacaaaagc gtcaggaagc agtcggttta       600
cccggataac attgacgcca acattgtgct tctgcactcc tctggaacta caggccttcc       660
gaagccaatc gctctgagcc acagacagct catgttttcc gtcagtcacg gtgacttcga       720
aacagaagag gaggctcaag gaattgtcat ctctacattg cccctgttcc atggcttcgg       780
gcttcttgca ccaggactct cgatggctat tggaaagaca gtgtgctttc cgcctcgga       840 cgaagttccc gatgctcaat caattgtcga tcttatcaac atgtctggcg caactggcat       900
gctgactgtg ccttttccttc tcgaaaacat ggctgctctg ccgaacggaa ccggtctgag       960
ggctctggcc aaattggact tgttggaac cggaggaagt gctctgagtg ctgacttcgg      1020
agtatctgcg tcagctgcgg gcgtcaagct actgaacctc tacgggacaa ctgaaacggg      1080
cccgttgacg aagacatttg cgcctaaatc gggttacgac tggaaatact tcagactccg      1140
acaggatatg ctgttcaagg tcacggagct cccccccagtt gacggcgaga aaaggttcag      1200
gctgacggta ttcccatttg gtgccgataa gccattcgag attgccgatc aactcattcg      1260
aagcgagaag ttccccgaga cggattttgc cgctgtcgga cgcgacgacg atgtcgttgt      1320
tcttgcaact ggcgagaagg tcaacccatt attattggaa accgccctga ctgattctgg      1380
actggtcaaa tcagcgattg tatttggcga gaaccagttc cagataggtg tcgtcgtcga      1440
gcctgcaact cctctaaatc ccgaccgaaa ggaggaattc aggaaaaaga tttggcctat      1500
cattgtacgc gtaggagaac gcatggacac caccgcgaga atctactcgc ccaatgccgt      1560
gattgtcgtt ccgtcatccg tcacaatccc gagaaccgac aaaggatcaa ttgctcgaaa      1620
agaggtcttc caactgctcg aaaaggaaat ttcacaggtt tatgaggacc tcgagaacgg      1680
ctccattgaa gaaacaccac tcgactacga taaactcgag caagaactca agggactgat      1740

```
tcagaaaaga ctcaaactga gagtccatcc tgggaaatgg acagttgatg acaacttgtt    1800
tcatctgggc ctcgactctc tacaagccac aacgctgcga cgcatccttc tttcagctgc    1860
ttcaaaaacg cctccagacg tcattgggaa agattttatc tatgtaaatc cctccgtcaa    1920
agccatcgca aacgctctga gacccgccaa cggccccatt ggcacggaga gcgcatcggt    1980
tgcacaggaa gtagatgatt atgcccagca gtattccatc aagggctttg aagtgcaaga    2040
tatagtgcca aaagcttctc ccaagcttat ccggggagca gtggtgcttc tgacaggcag    2100
ctcaggtggc ctgggatccc acgcgctggg gaaacttgcc gagtccaccc aagttgccaa    2160
gatcgtctgc ttgcaacgaa agcggccagg caccgtcatc aaccccattc aggggcagc     2220 caaggtcgac agagcctcta ttgaagccaa gggcattaaa ttgaccgacg atcaatgggc    2280
aaagattacg cgctagaaa ttgatccaac catagacaac ttggggcttc ctgcgatggt     2340
catgggcatg gtgtcgaaga cggtcaccca tatcttgcac gcagcttggc ccatggattt    2400
ccacatgcgg ctgccatcct tcggctacca gttttcatat ctcaagaatc ttttgagaat    2460
cgctgttcaa gcgccgcaaa aggtccgttt tctctttgtc tcgtccattt ccgccctcgc    2520
caagctaggg ctcatcactc ctggaagacc catcccagaa gagcccctgg atgtggaaag    2580
cgccgcctgt ggcatcggat acgccgatgc aaagttggtt tgtgagaaga ttctcgaaga    2640
ggcagcctca ctctacaata gcaatgtgga ggtagtaatc gcccgatgcg gacagctgag    2700
tggcgctcgg aagacgggag cgtggaacgt cagtgagcag attcctatgc ttatccgcac    2760
ctctcagggc ctaggaattc tgcccatatt ggaaggagta tgcactttc ctacctcacc      2820 ccattcattc catgactgtc aacgagtata cacgcccctc ggtcacgact cgataagcac    2880
taacttttga taccagac tgtttcctgg atcccggtag atgatgctgc agcaacggtg       2940
gcagaacttc tattcgcgcc agacgctcca ggcctggtca cgcacgtaga gaacccggtc    3000
agacagtcct ggtccgaggt ctttcagatc atcggtaacg agctccgcat cacaaagacg    3060
ctctcctttg acgactggct gggggaggtc acatcaacgg ccgaaaggga cgtcgaggat    3120
tatcccgtaa ggaagctgta cgagttcttc aagctttatt tccgtatcgc gtcttcaggg    3180
gcagttgtca tggggactga tatgagccgc aagaactcag ctacactacg ttgtctcaag    3240
gccctggaca gaggaaccat tgctggatat gttaggtact ggagatcggt aggctatctg    3300
aggcagtga                                                            3309
```

<210> SEQ ID NO 54
<211> LENGTH: 1487
<212> TYPE: DNA
<213> ORGANISM: Aspergillus sojae

<400> SEQUENCE: 54

```
taagtactca tttatacaat agttgcagaa ccccgcgcta cccctccatt gccaacatgt      60
cttccaagtc gcaattgacc tacagcgcac gcgctagcaa gcaccccaat cgctcgtga     120 agaagctctt cgaggttgcc gaggccaaga aaaccaatgt caccgtttcc gccgacgtga    180
caaccaccaa agagctgctg gatttggctg accgtatgcg caccggggat gccacttaca    240
tatgatctag taatggttaa tggtggaata tataacagga ctcggtccgt acattgccgt    300
gatcaaaact cacatcgata tcctctccga tttcagcgaa gagaccatca tcggtctgaa    360 ggccccttgca gagaagcaca atttcctcat cttcgaagat cgcaagttca tcgatatcgg    420
aaacacagtc caaaagcagt accatggcgg cactctgcgc atctctgagt gggcccacat    480
```

```
catcaactgc agtattctgc ccggtgaggg tatcgtcgag gctctggccc agactgcttc    540
ggccgaggac ttcccctatg gctctgagag gggccttttg atccttgcgg agatgacatc    600
caagggatct ttggctaccg gtcaatatac tacttcttct gttgactatg cccggaagta    660
taagaagttt gtgatgggat tcgtctcgac gcgtcacctg ggcgaggttc agtctgaagt    720
tagctcgcct tcggaggagg aggatttcgt cgtcttcacg acaggtgtca acctctcctc    780
gaagggagac aaactgggac agcaatacca gactcctgag tctgctgttg gacgcggtgc    840
cgactttatc attgctggtc gtggaattta tgctgctcct gatcccgtgg aggcagcgaa    900
gcggtaccag aaagagggat gggatgcata ccagaagcgt gttggtgcgc aataagtagt    960
ggtgaatacg tgctcttttt atggcagtat atcgcaagta tgatgcgatt cataaattca   1020
gcagtcgaat tctacgagag aacgatgcta agagataccc tctctatatg aataatatgc   1080
ctgcctcgag atatggacat attcaagatc agagttaagg gtcatgtttc aaaatcacac   1140
caatctccaa catagacgag aattttacc ggattgtctg aaggtgcagc tggagattgg    1200 tctatttct aagagtgggg tatcactaat gtacagtcgg tcactatcgt acaaacaatc    1260
acaattatat acaagatttc ccatcacccc ttactctaac atggcacttt tatccatcga   1320
gtccgagcct agccaccatt tggtgctttc gtagagacca agtataacc ctgatccgac    1380 agcggccata acgtgttga tagcacaccc tcggaatagt cctctcgggc catctgttcg    1440
tataatctcc cgtacggtat tgatcatcct tttcttctga ggtgcgg                 1487

<210> SEQ ID NO 55
<211> LENGTH: 39
<212> TYPE: DNA
<213> ORGANISM: Artificial sequence
<220> FEATURE:
<223> OTHER INFORMATION: Primer

<400> SEQUENCE: 55
cgcaccacct tcaaaatgct atcagccatg gccaatgta                            39

<210> SEQ ID NO 56
<211> LENGTH: 39
<212> TYPE: DNA
<213> ORGANISM: Artificial sequence
<220> FEATURE:
<223> OTHER INFORMATION: Primer

<400> SEQUENCE: 56
atgtactcct ggtacctacg tgtcgatgtc ccgcatact                            39

<210> SEQ ID NO 57
<211> LENGTH: 6782
<212> TYPE: DNA
<213> ORGANISM: Trichoderma reesei

<400> SEQUENCE: 57
atgctatcag ccatggccaa tgtatcagga atcgtctttt ctccccagag ccgtgcgccg     60
tcaaaggcgt atctggagta tccacaac tcacttacca gatcgtccat atactcgccc     120
atttgcgaag caatctccaa cctttccgcg acgtggtggg ctattgcaaa cagccagcca   180
aagatcgcct ccctggagca aggcctgaat tttgcaaaag acttttcagc atggattgag   240
acgggaaatt cttcaaggct ggagaccagc atgtcgggga tcgtcacgtt acctctgctg   300
gtcatcatac atacgattca gtatctcgag tatctacggc aaaactgtat cacacactcg   360
gaactgctac ctcatttgcg ggcaggtggg gtccaaggat tctgtgctgg attgatgatg   420
```

```
gccattgttg tggctgcgtc aaaggacgaa acacaactgg ttgagaactc cgccaaagct    480
gttcggatag cctttgcgat tgggtcatat ggagagattg ggtgtgatgc aaactcaatt    540
atttctacta ctatggtggt gcggttgaaa cggggctctg agagggagca aatcatccgc    600
gagttcccag aggtgtgata atctactcag ctccatctca ggagcacgca tgctaaagaa    660
gaatataaca gtcccgtatc tctgctgtat ccgaccccaa gacagtaagc atcattgctt    720
catcatccca aattgccgcc atgcaggcat atatagagga actaggcctc tccttcaaga    780
tggttcacat gcgaagcaac atacacaatc cgaaaaatgt cgctcttgcg aaagagctgc    840
tgggactctg cctacgcgat gccgactggc agttgcccaa cagcgattgt attcaggttg    900
ctgtacgatc caatagcaca ggtcagattc tttcaggctg ttcgctcaca gccgaggtta    960
tcaacaccat tcttacctct tgctgtgact gggacagagt catgaacaat gtagcgcaag   1020
atctccgccg attcgggaaa tctcatcgca tagcaatggt tggcctggga gactgcttac   1080
cgctcccgcc atttcagaag attggcatcg aaattaccaa ggtggatgtc atgagcaaca   1140
cggaggatgc aaggcgacgg acaaatgatg ctaatatctc aagacgggct acttttcctt   1200
ccgattcggt cgccgtagta ggcgcggctt gtcgattacc aggagcaaat accctcgacg   1260
aactctggga tctcatttct cgaggcgaat cgcggctgga aacgctgcgc caagatcggg   1320
tcaggctcga agagtctttt cgggcatcac aggacaagga ctggaccaca agacgacaat   1380
ggttcggaaa tttcgttgat tgtgtcgatg aatttgatca tggcttcttt ggcataagtg   1440
aaaaggaagc ggcatatatg gatccccagc agcggctttt gctcacttgt gcgtacgagg   1500
ctctggactc cagtggctac cttcatcatc atgcccgagc aaatggcgat ccgataggt   1560 gcttcattgg cgcgagctat accgagtata acgagaacac caacgcatac gctccctctg   1620
catttgccgc aacagggacc attcgagctt ttctttcagg caagatcagc cattactttg   1680
gctggacggg gccgtccgag gtcattgaca cggcatgctc ggcgtcgctg gttgctgttc   1740
atcacgcaat tagggcgatt cagtctgggg attgctccat ggcccttgca ggcggtgtga   1800
atatccttac cggagttcac aactacattg atctcggcag agcgggatt ctcagtagaa   1860 cgggccagtg taaaccattt gatgaatcag cggatggcta ttgccgtgca gacggagtcg   1920
ggatcgttgt gttgaagcca ctcaagcaag caattgctga cgggaatcac attatgggcg   1980
tcatttctgc gacagctaca aaccaggcg gcttgtctca gggtatcaca gttccgcatg   2040
gagatgctca gagggcgctc tattgtcgaa tcctcaagac tgccaatatt gagccagatc   2100
aggtgacata tgtcgagtca cacggaacag gtactcaggt cggcgatcct atcgaagtct   2160
ccagcattcg cgaggtcttt ggagggccat cgcggcaatc agtggtgtac attgcgtccc   2220
tcaaagccaa gtaggacac agtgaaactg ctgctggagt tgctagcctt ctgaaggtcc   2280
tcacaatgtt tgctcacaaa gccattcctc cgcaagctgg attcaagaca ctgaatccca   2340
agattcccgc tgttgagccg gataacatga tgattgccgc tcagctcatg ccgtgggatt   2400
cgaagatacg catggcctgt gtcaacagtt atggggcctc agggagcaat gcggcgctga   2460
tctgtgcaga atggaccgct gagatagcaa gaccgagagc gggtgcgccg acttacccag   2520
tctttctgag tgcgcataca aaagatgctc tgagagactc agccatccga ctggcctctt   2580
actttcagag tcccggaaaa gccttgagta ttggcagcgt agcctttaca ttgagcgaac   2640
gcagaaaaca ccaccgttat cgatggtcca cctctgcaca tagtctgtcc gacctgacca   2700
gacaactgca cgcgggtgtg atggaaggca ttgttgagtc tcccaacaca cgaatgccgg   2760
```

```
ttgttctggc cttttcaggt caatctagga cgaagatcgg cctcgacccg acactctgcg    2820
aattatatcc ccagttccgc cgttatctag agaactgcaa tgacatactg cgaagcttgg    2880
gctattcaga catcatgtct tcacttattc agaccgacgc cgtcacagac gttgtcattc    2940
tccatgcggg cacattcgct gttcaatatg cctgtgcgag aagttggcta aaggcggat     3000
tgcaggttga cgcagtgatc ggtcacagtc tcggcgaatt gacggcgttg gctgtatccg    3060
gcgtgctgtc actggaggat gctctgggtc tggtcgcgaa gcgagctcta ttgatagaga    3120
gaaaatgggg ctcagaaccg ggatccatgt tggcgattta ctcagatctc gagactgtgc    3180
agcagatcgt tgcaagctca cacacgacag tcgtggagga tggccttgag atcgcctgcc    3240
acaacagccc taacgctcat gttgttgttg aaagcgagc gtctattgcg agagttaaaa     3300
agcttataga cagcaatccg cagtttcaag gcacgcgaca tcagcgtctc gatgtgagcc    3360
acggctttca ctcgagattg acagacccgt tgctcccaga tctaatcaag ttcgccaata    3420
gcttgacgtt caatgagcct cttattccgc tagagacatg tacggagtcg cctgttctta    3480
gcatcacacc gaagtacatt gcagagcatt cgagacacgc agtgtatttt acacatgcca    3540
ttcggcgtct tgagcgccgt cttggcccat gcacctggtt ggaggcagga tggcatactc    3600
cgatcatccc catggcaaag aaagctgtcg caatgcctga gatacacaac tttcaatcat    3660
tgagtggctc ggcagtggcc gtctccaatg taacggctgc tctatggaaa caaggccatt    3720
caatttcctg gtggggtttt ctctccccag gagactcaca actcgaccaa atctggctgc    3780
cgccattttc gttccaacca tcccaccatt ggctcgaaca tgttgatcga gtgacgaaag    3840
tccagcatcc tgacagcaag gtgcttcagc agcgatctcg acttgtgagc ttcgtcaaag    3900
tatcggccac aggcgacgag ttccagctcc tcaggcagtg tgaaaaatac agcaacatag    3960
tcaaaggcca cgctgtgcgc caaaggcctc tttgtccagc ttccttgtac atggaaattg    4020
ccgtcatgtg tgctcaggag agaggttttg actttaacga gcacacgatc aaattccgcg    4080
agattgtctt ctccaacggc ctgggatgcg acaacagccg tgatgtgaga gtcgtgttgg    4140
cacaaaatct agactcaact gctgatggtg catggaattt ctcagtcaac agctcaaaaa    4200
aaggtgatgc gaagtctgta aggacgatgc atgcgattgg acagtttgct gctttatcag    4260
aggcgtccga ctttcgtata tacgaggggc tcatctcgga ccgcatggct ctcctcccca    4320
aggatccaaa cgcagaacac ctaaagagaa gaacggcgta tgctgtgttc tcgagagttg    4380
ttgagtatgc tgaacttctc agaggtatct cctcgatcac tttgtctgaa gatcaagcta    4440
tcgctgagat cgagctccca gctgaagcgt cgacgaactg cgatagcact gtcgaccgct    4500
ttatggacgc gatatctctg gatacattca tacaggttct cggcctgttg atcaactcaa    4560
gactcaacac tgtaggccac gagatctttg ttgcgacaag catcgagaac atgacaattc    4620
tcccttgcga cttcaagacc cagaaacgct ggagtgtgta cgccatgttc ggtatgaagg    4680
gtgatcgaca agccattgga gacgtctttg tattctctcc cgaaggcagg ctcgtcattc    4740
ttgggtcgca gataagtttc accaggatca aggcaagcat actagaagaa ttgcttgaca    4800
gaaactactc agaatccgtc atggtcaaag ctcagcgagc cgagggccca gctgcgtctg    4860
gtgtgatgca tcgcattcgc actggtgagg ctatcgctgc aggcagttct gtccttcctg    4920
ttgattcgct gccggcgaag tctgaagaac cagcttacaa cttcgacgac gcgaaggtgc    4980
ttatagcaag ttatattggt cttacggcgt ctgagattcg caaagaggaa agtttcagta    5040
gtctaggcct agactcactg tcttcagtcg aacttgccga tgagttgcga gttaagttcg    5100
gaattgaagt ttcgccaagt gacttgctca caatgcaagt gggcgagctt gaacaagggg    5160
```

```
gtccatcaca aggcacagac tcaattgatg tacaggaaca ggacctaccg cagtccataa    5220
acagacgtgt gaatggactt gcgaatggac gtgtcgctca agccagtggg ctgagaaacg    5280
gccttcatga tggatgcagc aataacaatg tgagcggtca agtgaaagac cacgcctata    5340
gctatgccag caagacaaac ggacatctag agaagcctct gagacgaccg cactacgcaa    5400
ggcaccgcgt tcagacggta acttacaaag aagtcgacgg catccacatt ctggcagaca    5460
tgttcattcc gctagagcca ccctcggagg ctatgcccat aggtacgcgg tagctggcca    5520
actcatccct gaaataagtc aactgacatg ttccattatc gatagcgctc atgatccacg    5580
gaggcggcca tttgacgctg tcgaggaaag ccattcggcc gtcccagaca tcctttctcc    5640
tagcaaatgg cttattgccc attagcctag actatcgact ttgccctcac gtcaatgtcc    5700
ttgatggacc tatggcagat gttcgagatg cctatgcctg gcaagaaaaa gaggttccat    5760
tgctgctgcg agaggcaggc atgtgcgtgg atggctcaaa gattgtcgtc gtcggctggt    5820
caacaggagg gcatttggca atgactactg cttggactgc tccagccgca ggtttgcctc    5880
ctcctttggc tgttttggca ttttactgcc ctacacatta cgatccttcg ggtatgttta    5940
gacatttcca ttggaaagac tttcgcaact ttgctaacaa ttaataaaag atgattcctt    6000
aagaatgggc aaagactacc attcccgcac aatgtcaatg tccgagatcc gaaaggcttt    6060
aggcacgcaa acagtatgtt cattcttttc gtcgctccac atatcatcat tactcatgca    6120
gacgtacagg catcgagtca cgcattcagt agtactgata caaccggtct gggctggctt    6180
gaaccaggag atccccgctc agagctggtg ctggctcttg tcaaagaaca gaacggtgtg    6240
tctcttttac tagatggtgt tcctactgat ggaaacacct tccaagctcc tgagcccgag    6300
cgagttacag ctatcagccc gctgtctcag gtccgcctcg gcacctatcg cacaccgacg    6360
tttgtcatca tcggcgacga ggatgaagtt gtccccttcc actcttcggt tgactttgtt    6420
gatgccctga gaacagggg tatcagacac gggttcatcc cggtaccggg tcagcgacac    6480
attttcgacc tgacgcttgc accggggatg gcgaaatggg aagagtgggt ggctccaggc    6540
tacaaattct tgtttgacat ccttggtatt tcttccgatt gatacectct tccctcgagg    6600 agagtatggt gttgggcctg gctgtggggt tggcacaggc ggctagaagt ctcgcgtcaa    6660
gtttgggctc ttcttaaaaa tgggcaatta cgcattcatt gaacagatat cacaagtaca    6720
cggctctccc cgtggagcac caaaatggca ttccacaaag tatgcgggac atcgacacgt    6780
ag                                                                   6782
```

<210> SEQ ID NO 58
<211> LENGTH: 39
<212> TYPE: DNA
<213> ORGANISM: Artificial sequence
<220> FEATURE:
<223> OTHER INFORMATION: Primer

<400> SEQUENCE: 58
cgcaccacct tcaaaatgcc tccagcggta gtcaagaac                            39

<210> SEQ ID NO 59
<211> LENGTH: 39
<212> TYPE: DNA
<213> ORGANISM: Artificial sequence
<220> FEATURE:
<223> OTHER INFORMATION: Primer

<400> SEQUENCE: 59

```
atgtactcct ggtacctaca taatcgttct gagatactc                            39

<210> SEQ ID NO 60
<211> LENGTH: 963
<212> TYPE: DNA
<213> ORGANISM: Trichoderma reesei

<400> SEQUENCE: 60
atgcctccag cggtagtcaa gaactctgct tacactcctc ccacgaaagg catcctctct     60
tgcctgccat cctcatgggt tccctatgct gagctcattc gcctggacaa gccacatggc   120
atatatatga ctatatatcc ttacgccttg ggcctacttt atgccagcca acttacctca   180
gagtcgttgc ctccaaacgt ggtcctgagt cgatttctca acttggcgat atggaccttc   240
ttgatacgaa gcgccggctg tgcttggaac gacaacgttg atcaagactt tgacagacaa   300
actgcccggt gccgcgacag accgattgca cgaggcgcaa tctcgactct tcaaggtcat   360
gtcttcacca ccgctctatt ggctctcggg tttttgtcaa ttcaaaactt tcctcttgaa   420
tccaagattg atgcgctgc aactgtctta ttgacatgca tctacccctt gggaagaga    480
ttcacgcatt tcgctcaggt taccttgggc ctaacgctgt ccgttgctat catattcggg   540
ccgcattctg tgggcgccaa ccccttgtca cagggcaatt tcttgccaac gacctgcctt   600
gtgtcgtcca tcattttgct cgtcatcttc tatgacgtag tctatgctcg tcaggatacg   660
gtcgatgatc tcaagtccgg agtcaaaggc atggccgtcc tctttcgcaa ctggatcacc   720
acgttgcttt tgaccctcat catagccatc ctaactcttc tatacatcac tgcacggtct   780
cttgacttgg gttgggtctt ctttggcttg tccgttgcag ggccagccgt cagcctcctc   840
acaacgattg ccctcatcgc cagcaaatcg agcagttcaa gatatgcggg caagttctat   900
gtgctagcca ttgccagcct gctcagtggc tttactatag agtatctcag aacgattatg   960
tag                                                                  963

<210> SEQ ID NO 61
<211> LENGTH: 1557
<212> TYPE: DNA
<213> ORGANISM: Artificial sequence
<220> FEATURE:
<223> OTHER INFORMATION: modified gene

<400> SEQUENCE: 61
atggcagttc ctgaaaagtg taccgtgttg gttattggcg gcggtcctgc tggctcttac     60
gctgcctctg cccttgcccg agagggtgta gataccgtgt tgctcgaagc cgacaaattt   120
ccacgatatc acatagggga gagcatgctg gcctcgatgc gccatttcct gcgatttatc   180
gacgttgact ccgttttcga ttcctacggc tttacaaaga aggtgggggc cgcctttaag   240
ctcaacccga agaaacgcga gggttacacg gattttctcg cagcgggcgg tcctcaaaac   300
tatgcgtgga atgtcgtgcg gtccgaggcc gatcatctgc tgtttcagca tgccgcctcc   360
tccggggcca aaacttttga cggcgtccag gttaaaagta tcaacttcat tggggagcca   420
tgtgagggtt tcggcgaact accgtatgat tacccaggcc gtccctacag cgccacatac   480
ctcatgaaag acgacaaaac atcgcgcgag atcaagtttg attatatcat agatgcttcc   540
ggtcgcgtgg gactcctcag cacgaaatat ctcaagaatc gtaagtataa tcagggcctt   600
aaaaacgttg ccacctgggg ttattggaaa ggcgctgccg cttatggcgt cggcacgcca   660
cggcaaaaact cgccttttttt tgaggcccctt caggatgagt ccgggtgggc gtggctgatt   720
cccctgcaca atggcactac gtccgtcggt atcgtaatga atcaaaagat gtctgctaac   780
```

```
cgcaaaagtc aggcgggatc cccagactct aaaaccttct acctcggtaa tctcaagcaa    840
ctagctcctg agctctctaa acttctggag aacgcggagt tgcttactga cattaagagc    900
gcctcggatt actcatattc agctaccgct tacgctattc cgtatgctcg aatcgctggg    960
gatgctgggt gcttcatcga tccctacttc tcgtctggag tccatctggc tttcgtcggt   1020
ggtctgtctg cagcgactac aatcagcgcg gcaatcaagg gacaagtgag cgaagtagag   1080
gcggcggact ggcactctaa gaaggtcgcg gacagttata tccgtttcct gttggtcgtc   1140
cttagcgctt accgtcaaat ccggagccaa gaagaggcag tcttgtcaga tttcgatgag   1200
gacaactacg atagggcatt cgcattcttc cggcccatca tacagggaat tgcagatgtc   1260
gatacaaaat tgtcgaagga agaacttaag aagacacttg aattctgctc aaacgcattc   1320
gaacctgtta agccggaaga taggagttca atgttggaac agcttggaaa gtgccccaat   1380
accgcatacc aggttgactt gtcgcccgac cagagaaccg tggtggacca cattagggca   1440
agacagatga tgagaaccga agatactatg aacatttcaa gtttcggaac ggacagtatt   1500
aatggattcg tgccgaagct aaagactgga gacctaggac tagttgcaaa ggcgtga      1557
```

<210> SEQ ID NO 62
<211> LENGTH: 1000
<212> TYPE: DNA
<213> ORGANISM: Acremonium sclerotigenum

<400> SEQUENCE: 62

```
aggctcagtg acgtcggagg ggcggcgggg cagtaactcg aagaggggga ggggctcgcc     60
caaaataatg gaggggcaat tcgagggctg gagatgacct ccgccgagat gcgcaataca    120
acgcacagag tcctgggatt gtagagtccg atctagaccg aatcttgtct ttagataatg    180
atagtaaaat ccccacgtcg aaaggcataa gatatccggg gctcaaagtc aagttcgtga    240
ctcacgccgc ggatgggcat caggggctcc attgaaatga gctcactggg accggcgcta    300
cgaaaaaata tccagaaaaa cgaaaattct gtgtctcgga gcctgaggat gaaccaagct    360
gctcgaacac tgcaccaagc agcacccggc ctaaaatgcc ctctgcacgc gtcttgcacc    420
cagctaaagc cacagattag tctagattag atcgggaacg tcaaggagct gcaaggcagt    480
cgagtttcca ggctgaagct ggcacacgac tccaggggggc gacacttggg cacacaactg    540
attggaacct aacacctgtc cgcaactgca agtgctggaa ccatgatgag gtgaaagttc    600
aaacagtgaa aatttgaaca gcccacttac gcgctggcac caatcacact cggggacttg    660
ttgccatagt ggggcagcct atcgaccccct catcttttga ggtcacttcc cctccaccat    720
ggtgatcctc ttttaaaccc ttcctcccct cccactcgca cagccgaatt ttctttcctc    780
tttgtccgca cacaccgatc gaacaagctt cgtcacctgc gcagtaagcc tccctcctct    840
cgcctgacga cctcgacgcg ctcctcagaa ccgtcgccat ccttactttc cgctcctcta    900
cgcaccatcg cgcgcgcttt cgagaatcgc tcggctgacc ttcgttgctc gaaatagaca    960
caaaaccaac caacaaaact catctctcaa taccgcaatc                         1000
```

<210> SEQ ID NO 63
<211> LENGTH: 800
<212> TYPE: DNA
<213> ORGANISM: Acremonium sclerotigenum

<400> SEQUENCE: 63

```
gcgccttcct ccatcggctt tatcgccttg ggtgctcgcg acgtagcttg tgctcacagg     60
```

| | |
|---|---|
| ttactgtact tgcttctacg acgaaatgat actgcgatga cgatgatatc ttgggacgca | 120 |
| tgacgagtcg ggcgttggga tttaccgacc tcaccgtcgt atgtcaggac aacaaaagga | 180 |
| taactctaga tgtagagaaa atctgaacac ttttcctttg tagccacctc tttcagctgc | 240 |
| ccttgcacgt gtgaacctgg gtgttaatat ccttgtgctg ttcgtgcgcc gacctcaact | 300 |
| ttatgtcctg cgcctcagct atgtgacctt gggacaccct tagctcgaca attgacggca | 360 |
| gtctatgcgc tgattacaat aaatgctctg acgctattgt agatgctact aatttacatg | 420 |
| ttgtacagat cgcctgccgt cgtgctaaat catccctgaa gggtcccgtg aaacgccgtg | 480 |
| atgagatgcg aagctgactc tcaatttct tcctcacgtc tggagcccat cggcccgatg | 540 |
| gacttacctt gcgtagccaa atcctctgcc aacccccct gcaacaactt gatcagcaat | 600 |
| tttgcttata tagtatccct cacttctcca acgtgtgact cccttttgca agcaatagtt | 660 |
| cgctagaaag tgtcaaaaga tgcgctgtaa cacctcgagg tgaacgcaat atgagcgcca | 720 |
| tctagctgtg cggcgagtgc cttggagtac atgatctcat gttcttctgg tgcccaactc | 780 |
| cgtgttcctg agccccgtg | 800 |

<210> SEQ ID NO 64
<211> LENGTH: 804
<212> TYPE: DNA
<213> ORGANISM: Neonectria ditissima

<400> SEQUENCE: 64

| | |
|---|---|
| atgggcttca acgacatccc ccccgctcac gtgtcggctt ggtaccagcc cgtgtacaat | 60 |
| gcaacctttg ggtttgccgg gctatcctgg acactatgct acatgctcta cgcgcgccaa | 120 |
| ggcctgcgca ccaaatccta cggcatgccg ctgttcgccc tcgccaacaa ctttgcctgg | 180 |
| gaaatggtct acgcactgtc cgtggcagac gcgccgcgcg agaagacggc catggtcatc | 240 |
| tggatgctca tcgacatgcc catcatctac agtaccctca ggtacggcag agaagagtgg | 300 |
| tcgcatgccc cgatggtcag taggaaccta ggcaagatcc tcgtcacatt ggtcatgctg | 360 |
| tgtgccgtgg cgcattatag ctttgcgtcg tggtggatgg gcaaccacat cgctatgaag | 420 |
| agtggaaaag tctaccgcgg tgttgaaggc caagacgcca ctgaaatggc ttttgggcc | 480 |
| gtctccgttt gtcaagtcat tgtgtctact tcgtctctgg cacaattgat caccagacaa | 540 |
| cacaccggag gagttagttg gtcgatctgg gctctaaggt tctgcggtac gctggtaggc | 600 |
| ctcaacatca actacggttg ggcttggtac acttggacag aggctcatgg atattttatg | 660 |
| agtgctccgg gtgtttttct ctggggaatt accactctat gtgatgttgt ttatgcaatc | 720 |
| gtctttgctc aagttaggcg caacgagagg gttttgccgg atgggcgcaa ggcggcgccg | 780 |
| ttgcagtcga tcaagcgcgg ctga | 804 |

<210> SEQ ID NO 65
<211> LENGTH: 1590
<212> TYPE: DNA
<213> ORGANISM: Acremonium sclerotigenum

<400> SEQUENCE: 65

| | |
|---|---|
| atgggtaact ctgccaacga agacaagttg cgctacgcct gtgaccgctg tcactcgcaa | 60 |
| aagcttcgtt gccctcgatc tgtcgagcca gaaaaggcca accggaagag gccgtgctcg | 120 |
| agatgtcgaa aggcaggagt accttgtgtg gtcagcctgc gaggcaaggt cggtcgaccg | 180 |
| tcaaaggcca cgaagaagaa gtctgcacga tcgcctcgag cgacgtccac gccggaagct | 240 |
| gagtttccgc cctacgacat caactcagtt ctgagcggag aggtcgatgg cagcattcca | 300 |

```
tgggcttcac catccggaga ccgcatgatg gatatgtttg acctggcctc tggttctggc    360
tcagtcacca catcagcatc cccaaaaacc atggctgagg actaccagcc agagggggcaa   420 cgaccattcc ccgatccatt aatgggccca ggcttgatcc aagtgagtgg caacgacact    480
agaggccttt cgaatccgaa ctcacaaaac aaggtgccct acgagccatt cctcatggaa    540
tttgacacgg atgccgacta ccctactttc tgcataccgc caagtctcac cgatatgccc    600
gcaggggtcg agttcaacca accacaagac aagaccttca actcctcaca aatggacagc    660
ttcatggacg ttaagaccga cgcatcaatg atgatgcctc acgcagacat ggacatgact    720
tcaccaaagg ggacgggacc aactattgac ccagtcaccg tcgatccgag aatgtccttt    780
tcggcccatg ctgcacagtc accaggcgac atttttgcga gcgacgactt cgaagcaggg    840
gctgagttct caagcacagc atcgtatcag aagctatcag acctgaacct acgcatcttg    900
caatgcgggt caacggcaca agcaggcact gctcctcaga acagctctca acttctgaag    960
gacgttgtcg ggttttctgg cgagctcatc gatattgcaa gacagagcat gcctcatttc   1020
gtgggctgca caaggtcgtc atcccgtgcc tccactacgt ccaagggaag ctctatggaa   1080
agcgatgagg cgacggttc tatcgacacc gcctttagcc agtcgtcgtg gggatccttg    1140
aagcctggct ctgcgtctgg accacaagca acaagccaat ccgtaccaga gtccgctgta   1200
atcttcttgc ttctcggatg ctacacccaa atcttgcacc tgttcgagct cacgacgaac   1260
tgtttgtggg ctcagcactg cgaggctgga caaccagctc cgcagaacga cgacacctct   1320
ggcaccatcg gttcgttgct ggaggcatcg atcgctatac acaccgtcac atatcttctg   1380
agccggttgc accgagcttt ggcagcccca gagatggacg cttccaccga tgcggcagac   1440
tcgcacggct ggaagaagtc cttcgtaggt ggcaaggagt tggaagatgg gttgcttggt   1500
cgggcatttg gtgagatccg cgagcgtgaa cagtggctca tgaggcggac gaagcacctg   1560
cagcagagga ttaacaagtg ccacatctga                                     1590
```

<210> SEQ ID NO 66
<211> LENGTH: 512
<212> TYPE: PRT
<213> ORGANISM: Acremonium sclerotigenum

<400> SEQUENCE: 66

```
Met Gly Asn Ser Ala Asn Glu Asp Lys Leu Arg Tyr Ala Cys Asp Arg
1               5                   10                  15

Cys His Ser Gln Lys Leu Arg Cys Pro Arg Ser Val Glu Pro Glu Lys
                20                  25                  30

Ala Asn Pro Glu Glu Pro Cys Ser Arg Cys Arg Lys Ala Gly Val Pro
            35                  40                  45

Cys Val Val Ser Leu Arg Gly Lys Val Gly Arg Pro Ser Lys Ala Thr
        50                  55                  60

Lys Lys Lys Ser Ala Arg Ser Pro Arg Ala Thr Ser Thr Pro Glu Ala
65                  70                  75                  80

Glu Phe Pro Pro Tyr Asp Ile Asn Ser Val Leu Ser Gly Glu Val Asp
                85                  90                  95

Gly Ser Ile Pro Trp Ala Ser Pro Ser Gly Asp Arg Met Met Asp Met
            100                 105                 110

Phe Asp Leu Ala Ser Gly Ser Gly Ser Val Thr Thr Ser Ala Ser Pro
        115                 120                 125

Lys Thr Met Ala Glu Asp Tyr Gln Pro Glu Gly Gln Arg Pro Phe Pro
        130                 135                 140
```

Asp Pro Leu Met Gly Pro Gly Leu Ile Gln Val Pro Tyr Glu Pro Phe
145                 150                 155                 160

Leu Met Glu Phe Asp Thr Asp Ala Asp Tyr Pro Thr Phe Cys Ile Pro
            165                 170                 175

Pro Ser Leu Thr Asp Met Pro Ala Gly Val Glu Phe Asn Gln Pro Gln
        180                 185                 190

Asp Lys Thr Phe Asn Ser Ser Gln Met Asp Ser Phe Met Asp Val Lys
    195                 200                 205

Thr Asp Ala Ser Met Met Met Pro His Ala Asp Met Asp Met Thr Ser
210                 215                 220

Pro Lys Gly Thr Gly Pro Thr Ile Asp Pro Val Thr Val Asp Pro Arg
225                 230                 235                 240

Met Ser Phe Ser Ala His Ala Ala Gln Ser Pro Gly Asp Ile Phe Ala
            245                 250                 255

Ser Asp Asp Phe Glu Ala Gly Ala Glu Phe Ser Ser Thr Ala Ser Tyr
        260                 265                 270

Gln Lys Leu Ser Asp Leu Asn Leu Arg Ile Leu Gln Cys Gly Ser Thr
    275                 280                 285

Ala Gln Ala Gly Thr Ala Pro Gln Asn Ser Ser Gln Leu Leu Lys Asp
290                 295                 300

Val Val Gly Phe Ser Gly Glu Leu Ile Asp Ile Ala Arg Gln Ser Met
305                 310                 315                 320

Pro His Phe Val Gly Cys Thr Arg Ser Ser Arg Ala Ser Thr Thr
            325                 330                 335

Ser Lys Gly Ser Ser Met Glu Ser Asp Glu Gly Asp Gly Ser Ile Asp
        340                 345                 350

Thr Ala Phe Ser Gln Ser Ser Trp Gly Ser Leu Lys Pro Gly Ser Ala
    355                 360                 365

Ser Gly Pro Gln Ala Thr Ser Gln Ser Val Pro Glu Ser Ala Val Ile
370                 375                 380

Phe Leu Leu Leu Gly Cys Tyr Thr Gln Ile Leu His Leu Phe Glu Leu
385                 390                 395                 400

Thr Thr Asn Cys Leu Trp Ala Gln His Cys Glu Ala Gly Gln Pro Ala
            405                 410                 415

Pro Gln Asn Asp Asp Thr Ser Gly Thr Ile Gly Ser Leu Leu Glu Ala
        420                 425                 430

Ser Ile Ala Ile His Thr Val Thr Tyr Leu Leu Ser Arg Leu His Arg
    435                 440                 445

Ala Leu Ala Ala Pro Glu Met Asp Ala Ser Thr Asp Ala Ala Asp Ser
450                 455                 460

His Gly Trp Lys Lys Ser Phe Val Gly Gly Lys Glu Leu Glu Asp Gly
465                 470                 475                 480

Leu Leu Gly Arg Ala Phe Gly Glu Ile Arg Glu Arg Glu Gln Trp Leu
            485                 490                 495

Met Arg Arg Thr Lys His Leu Gln Gln Arg Ile Asn Lys Cys His Ile
        500                 505                 510

<210> SEQ ID NO 67
<211> LENGTH: 554
<212> TYPE: PRT
<213> ORGANISM: Neonectria ditissima

<400> SEQUENCE: 67

Met Ala Val Ala Ser Thr Met Leu Lys Gln Leu Leu Ile Pro Leu Val

```
1               5                   10                  15
Ile Leu Leu Val Ala Thr Arg Val Arg Thr Trp Tyr Thr His Arg Lys
             20                  25                  30
Arg Cys Ser Ser Asn Gly Cys Leu Pro Pro Ala Tyr Pro His Lys
             35                  40              45
Asp Gly Ile Leu Gly Leu Val His Leu Arg Thr Leu Ile Lys Ala Arg
             50                  55                  60
Gln Glu Lys Arg Leu Pro Thr Ala Phe Ser Ser Ile Phe Thr Asp Thr
 65                  70                  75                  80
Gly Ala Gly Val His Thr Leu Thr Tyr Thr Thr Leu Gly Ser Thr Thr
                 85                  90                  95
Tyr Trp Thr Val Asp Ala Asp Asn Ile Lys Ala Val Leu Ser Ser Ser
                100                 105                 110
Phe Arg Asp Trp Gly Leu Pro Arg Ala Arg Val Asp Ala Phe Ala Ala
             115                 120                 125
Cys Trp Gly Gly Ile Phe Gly Ala Asp Gly Ala Glu Trp Glu His
             130                 135                 140
Ser Arg Ala Met Leu Arg Pro Ser Phe Asn Arg Arg Gln Gly Gln Asp
145                 150                 155                 160
Thr Glu Met Leu Glu Arg His Val Gln Asn Leu Leu Ala Arg Ile Thr
                165                 170                 175
His Gly Gln Thr Val Asp Leu Ala Glu Leu Phe Pro Leu Leu Thr Met
             180                 185                 190
Asp Ile Ala Thr Asp Leu Leu Phe Gly Glu Ser Ala Gly Cys Leu Asp
             195                 200                 205
Pro Ala Lys Ser Ala Gln Gly Met Glu Phe Thr Ala Ala Phe Asn Tyr
 210                 215                 220
Val Met Gln Lys Met Ser Val Gln Val Ser Phe Pro Leu Leu Ala Lys
225                 230                 235                 240
Val Pro Asp Arg Arg Leu Lys Ser Cys Val Asn Cys Ile Asn Thr Phe
             245                 250                 255
Thr Asp Ala Phe Val Thr Arg Ala Leu Ser Phe Arg Asp Asn Met Ser
             260                 265                 270
Lys Ala Lys Val Ser Gly Asp His Glu Gly Arg Tyr Gly Lys Lys Cys
             275                 280                 285
Val Phe Leu Asp Glu Leu Ala Lys Gly Asp Tyr Ser Pro Arg Arg Leu
             290                 295                 300
Arg Ala Glu Leu Leu Ser Val Met Val Ala Gly Arg Asp Thr Thr Ala
305                 310                 315                 320
Ser Leu Leu Ser Ile Ile Trp Trp His Leu Ala Arg Arg Pro Asp Ile
                325                 330                 335
Val Glu Lys Leu Arg Glu Glu Ile Ser Pro Leu Lys Ser Arg Pro Pro
             340                 345                 350
Ser Pro Asn Glu Leu Lys Ser Met Thr Tyr Leu Arg Asp Val Ile Asn
             355                 360                 365
Glu Val Leu Arg Leu Tyr Pro Ile Asn Pro Ile Asn Ser Arg Val Ala
             370                 375                 380
Ile Arg Asp Thr Thr Leu Pro Arg Gly Gly Lys Asp Gly Leu Ser
385                 390                 395                 400
Pro Val Phe Ile Ala Lys Gly Gln Arg Leu Ile Phe Ser Ser Ser Ala
             405                 410                 415
Leu His Arg Arg Lys Asp Ile Tyr Gly Gln Asp Ala Met Gln Leu Arg
             420                 425                 430
```

-continued

```
Pro Glu Arg Trp Glu Thr Val Arg Pro Ser Thr Trp Glu Tyr Ile Pro
        435             440             445

Phe Gly Gly Gly Pro Arg Val Cys Ile Gly Gln Gln Leu Ala Gln Thr
    450             455             460

Glu Ala Ala Tyr Thr Thr Val Arg Leu Leu Gln Glu Phe Ser Ser Val
465             470             475             480

Lys Pro Arg Ser Glu Gly Pro Phe Gln Glu Gly Phe Ala Met Ala Leu
            485             490             495

Ser Ser Gly Asp Gly Cys Arg Leu Leu Arg Leu Ala Arg His Ala Arg
            500             505             510

Pro Gly Phe Gln Gly Gly Asp Tyr Leu Lys His Arg Gly Leu Val His
        515             520             525

Ile Pro Val Leu Leu Pro Ser Glu Thr Lys Val His Leu Tyr Ile Phe
    530             535             540

Gly Gln Pro Asn Gly Gln Glu Lys Leu Gly
545             550
```

METHOD OF PRODUCING ISOPRENOIDS AND PROTEINS, GENES, AND TRANSFORMANTS FOR THE SAME

CROSS-REFERENCE TO RELATED APPLICATIONS

This is the U.S. National Stage of International Patent Application No. PCT/JP2018/018405 filed on May 11, 2018, which was published in Japanese under PCT Article 21(2), and which in turn claims priority to Japanese Patent Application No. 2017-94509 filed on May 11, 2017 and Japanese Patent Application No. 2018-005888 filed on Jan. 17, 2018, which are incorporated herein by reference in their entirety.

TECHNICAL FIELD

The present invention relates to genes for synthesizing isoprenoids including ascofuranone, ascochlorin, and ilicicolin A and methods of producing isoprenoids by utilizing the genes.

BACKGROUND ART

In developed countries including Japan and developing countries in which densely populated areas are scattered, infectious diseases caused by viruses, protozoans, and the like often matter. In Japan, among other countries, lifestyle-related diseases such as type 2 diabetes mellitus, hypercholesterolemia, cancer, and complications caused by these diseases lead to increased health care cost and reduced labor force and seriously matter.

Thus, it is desirable to develop substances effective in treating and preventing these diseases. Ascochlorin and ascofuranone, which are bioactive substances included in isoprenoids, are known as one of such effective substances. Ascochlorin and ascofuranone inhibit electron transport chain to decrease the intracellular ATP concentration and therefore are considered as a potential mean for treating and preventing, for example, African sleeping sickness, which is a protozoan infection caused by *Trypanosoma*, a protozoan mediated by tsetse flies (see, for example, Patent Literature 1, incorporated herein by reference in its entirety).

Once patients suffer from African sleeping sickness, the protozoan grows in blood during the early stage of infection. In the chronic stage, central nerves are damaged to cause symptoms such as mental confusion and generalized convulsion, eventually lapsing into drowsiness and leading to death. African sleeping sickness annually kills 10000 or more people in Africa. It is estimated that 70 million or more people are potentially at risk for infection. At the present time, there is no preventive method via vaccination against African sleeping sickness and patients with African sleeping sickness are exclusively treated with drug therapy. However, there is a problem that the therapeutic agents effective against African sleeping sickness have a strong side effect.

It is expected that ascochlorin or ascofuranone is used to prevent and treat African sleeping sickness by specifically inhibiting electron transport chain in *Trypanosoma*. When invading mammalian bodies, the protozoan synthesizes ATP in the glycolysis pathway mainly in glycosomes. While the ATP synthesis requires regeneration of NAD catalyzed by trypanosome alternative oxidase (TAO), ascochlorin and ascofuranone inhibit this action of TAO. Since mammals which may be infected with *Trypanosoma* have no enzyme similar to TAO, *Trypanosoma* can be specifically eliminated. Particularly, ascofuranone and its derivatives have been reported to inhibit TAO even at a very low concentration.

It is also known that ascochlorin, ascofuranone, and derivatives thereof have an antitumor activity, hypoglycemic effect, hypolipidemic effect, glycosylation inhibiting effect, antioxidative effect, and the like (see, for example, Patent Literature 2, incorporated herein by reference in its entirety). Furthermore, ilicicolin A (LL-Z1272α), which is an intermediate of the biosynthetic pathways to ascochlorin and ascofuranone, is also expected to act as an active ingredient in a novel pharmaceutical agent based on its action of an effective antiprotozoal agent (Patent Literature 3, which is incorporated herein by reference in its entirety), an immunosuppressive agent, an antirheumatic drug, an anticancer agent, an antirejection agent, an antiviral agent, an anti-*H. pylori* agent, an antidiabetic agent, and the like (Patent Literature 4, incorporated herein by reference in its entirety). Ilicicolin A is also known as a biosynthetic intermediate for other isoprenoids in addition to ascochlorin and ascofuranone and is a compound useful as a source for those isoprenoids.

Methods of producing ascofuranone and ascochlorin among isoprenoids are known. Such methods include culturing filamentous fungi belonging to the genus *Ascochyta* and separating and collecting them accumulated in hyphae (see, for example, Patent Literatures 5 and 6, incorporated herein by reference in their entirety). It should be noted that Non Patent Literature 1 (incorporated herein by reference in its entirety) describes that *Ascochyta viciae*, which was known as an ascofuranone-producing strain, actually is *Acremonium sclerotigenum*.

CITATION LIST

Patent Literature

Patent Literature 1: Japanese Patent Laid-Open No. 09-165332
Patent Literature 2: Japanese Patent Laid-Open No. 2006-213644
Patent Literature 3: International Publication No. 2012/060387
Patent Literature 4: International Publication No. 2013/180140
Patent Literature 5: Japanese Patent Publication No. 56-25310
Patent Literature 6: Japanese Patent Publication No. 45-9832

Non Patent Literature

Non Patent Literature 1: J Antibiot (Tokyo). 2016 Nov. 2. Re-identification of the ascofuranone-producing fungus *Ascochyta viciae* as *Acremonium sclerotigenum*.

SUMMARY OF INVENTION

Technical Problem

The yields of ascochlorin and ascofuranone will greatly depend on the filamentous fungus to be used if methods that use filamentous fungi known to produce these substances, such as the methods described in the Patent Literatures 5 and 6, are performed. However, there are problems that the existing methods are unable to stably produce a large amount of ascochlorin and ascofuranone because contents of ascochlorin and ascofuranone in microorganisms known so far are too small for industrial-scale production and the contents will greatly vary with slight differences in culture conditions. Moreover, methods of producing ilicicolin A in large amounts are still unknown.

Possible strategies proposed to produce a large amount of isoprenoids including, for example, ascochlorin and ascofuranone, and ilicicolin A, an intermediate thereof include isolation or breeding of wild-type strains that stably produce isoprenoids in a high concentration and establishment of transformed strains having one or more genes involved in biosynthesis of isoprenoids inserted therein by utilizing biotechnological techniques. However, the wild-type strains that stably produce isoprenoids in a high concentration are virtually unknown so far, and the biosynthetic pathways to isoprenoids remain largely unknown.

Biosynthetic genes for ascochlorin, ascofuranone, and ilicicolin A among isoprenoids also still remain largely unknown.

Accordingly, the problem to be solved by the present invention is to provide a method of stably producing isoprenoids including ascofuranone, ilicicolin A, and ascochlorin and derivatives thereof in a high yield as compared to the conventional art, which method enables industrial-scale production of isoprenoids.

Solution to Problem

The inventors have conducted intensive studies directed toward solving the problem as described above. Consequently, the inventors successfully identified a gene cluster (7 genes from ascB gene to ascH gene) that encodes enzymes catalyzing reactions involved in biosynthesis of ascochlorin and ilicicolin A and subsequently a gene cluster (3 genes from ascI gene to ascK gene) that encodes enzymes catalyzing reactions involved in biosynthesis of ascofuranone in *Acremonium sclerotigenum*, which is a species of filamentous fungi.

Next, the inventors generated DNA constructs for overexpressing proteins encoded by the gene clusters as described above. The resulting DNA constructs were then introduced into microorganisms belonging to the genera *Aspergillus* and *Acremonium* to achieve transformation and successfully generate transformed filamentous fungi that overexpress the proteins encoded by the gene clusters as described above, wherein these microorganisms are species of filamentous fungi and were used as host organisms. Furthermore, filamentous fungi belonging to the genus *Acremonium* with knockout of ascF, ascG, and ascI were also successfully generated.

The transformed filamentous fungi as described above can be cultured according to methods of culturing typical filamentous fungi and have the proliferative rate that is not different from that of their host organisms. These results revealed that the transformed filamentous fungi and knockout filamentous fungi as described above can be used to produce isoprenoids including ascofuranone, ilicicolin A, and ascochlorin.

On the other hand, ascA gene in the ascochlorin biosynthetic gene cluster is believed to be a transcription factor and therefore it is expected that ascA gene would have no effect on the biosynthesis of ascochlorin even if not introduced and expressed. In fact, as described above, it is found that the transformed filamentous fungi produced by introducing 7 genes from ascB to ascH genes into microorganisms of the genus *Aspergillus* having no ascA gene can biosynthesize ascochlorin.

Despite such fact, the inventors successfully generated transformed filamentous fungi that overexpress ascA gene by introducing ascA gene to *Acremonium sclerotigenum* which has ascochlorin and ascofuranone biosynthetic genes. Surprisingly, the inventors found that the transformed filamentous fungi that overexpress ascA gene can be also used to produce a large amount of ascofuranone in addition to ascochlorin.

The present invention has been completed based on these successful experiences and findings as described above.

Accordingly, according to one aspect of the present invention, genes, transformants, knockout organisms, and production methods as described in [1] to [11] below are provided.

[1] An ascI gene including any one of nucleotide sequences of (1) to (5) below that encode an amino acid sequence of an enzyme having an activity of catalyzing monooxygenation of ilicicolin A epoxide:

(1) a nucleotide sequence set forth in SEQ ID NO: 8 in the Sequence Listing or a nucleotide sequence that hybridizes, under stringent conditions, with a nucleotide sequence complementary to the nucleotide sequence set forth in SEQ ID NO: 8 in the Sequence Listing;

(2) a nucleotide sequence having 60% or more sequence identity to the nucleotide sequence set forth in SEQ ID NO: 8;

(3) a nucleotide sequence encoding an amino acid sequence of an enzyme that has an activity of catalyzing monooxygenation of ilicicolin A epoxide;

(4) a nucleotide sequence encoding an amino acid sequence having 60% or more sequence identity to the amino acid sequence set forth in SEQ ID NO: 18 or 67; and (5) a nucleotide sequence encoding an amino acid sequence having one or several amino acids deleted, substituted, and/or added in the amino acid sequence set forth in SEQ ID NO: 18 or 67.

[2] An ascJ gene including any one of nucleotide sequences of (1) to (5) below that encode an amino acid sequence of an enzyme having an activity of catalyzing a reaction in which ascofuranol is produced from hydroxylated ilicicolin A epoxide:

(1) a nucleotide sequence set forth in SEQ ID NO: 9 in the Sequence Listing or a nucleotide sequence that hybridizes, under stringent conditions, with a nucleotide sequence complementary to the nucleotide sequence set forth in SEQ ID NO: 9 in the Sequence Listing;

(2) a nucleotide sequence having 60% or more sequence identity to the nucleotide sequence set forth in SEQ ID NO: 9;

(3) a nucleotide sequence encoding an amino acid sequence of an enzyme that has an activity of catalyzing a reaction in which ascofuranol is produced from a compound produced from ilicicolin A epoxide in a reaction catalyzed by AscI protein;

(4) a nucleotide sequence encoding an amino acid sequence having 60% or more sequence identity to the amino acid sequence set forth in SEQ ID NO: 19; and (5) a nucleotide sequence encoding an amino acid sequence having one or several amino acids deleted, substituted, and/or added in the amino acid sequence set forth in SEQ ID NO: 19.

[3] An ascK gene including any one of nucleotide sequences of (1) to (5) below that encode an amino acid sequence of an enzyme having an activity of catalyzing a reaction in which ascofuranone is produced from ascofuranol:

(1) a nucleotide sequence set forth in SEQ ID NO: 10 in the Sequence Listing or a nucleotide sequence that hybridizes, under stringent conditions, with a nucleotide sequence complementary to the nucleotide sequence set forth in SEQ ID NO: 10 in the Sequence Listing;
(2) a nucleotide sequence having 60% or more sequence identity to the nucleotide sequence set forth in SEQ ID NO: 10;
(3) a nucleotide sequence encoding an amino acid sequence of an enzyme that has an activity of catalyzing a reaction in which ascofuranone is produced from ascofuranol;
(4) a nucleotide sequence encoding an amino acid sequence having 60% or more sequence identity to the amino acid sequence set forth in SEQ ID NO: 20; and
(5) a nucleotide sequence encoding an amino acid sequence having one or several amino acids deleted, substituted, and/or added in the amino acid sequence set forth in SEQ ID NO: 20.

[4] A transformant including at least one selected from the group consisting of the ascI, ascJ, and ascK genes according to [1] to [3] inserted thereinto, and expressing the gene or genes, provided that the transformant is not human.

[5] The transformant according to [4] further including at least one selected from the group consisting of the ascF, ascE, ascD, ascB, and ascC genes inserted thereinto, and expressing the inserted gene or genes.

[6] An ascG gene knockout organism derived from a wild-type organism having ascG gene, wherein the gene includes any one of nucleotide sequences of (1) to (5) below that encode an amino acid sequence of an enzyme having an activity of catalyzing a cyclization reaction of ilicicolin A epoxide, provided that the organism is not human:
(1) a nucleotide sequence set forth in SEQ ID NO: 6 in the Sequence Listing or a nucleotide sequence that hybridizes, under stringent conditions, with a nucleotide sequence complementary to the nucleotide sequence set forth in SEQ ID NO: 6 in the Sequence Listing;
(2) a nucleotide sequence having 60% or more sequence identity to the nucleotide sequence set forth in SEQ ID NO: 6;
(3) a nucleotide sequence encoding an amino acid sequence of an enzyme that has an activity of catalyzing a cyclization reaction of ilicicolin A epoxide;
(4) a nucleotide sequence encoding an amino acid sequence having 60% or more sequence identity to the amino acid sequence set forth in SEQ ID NO: 16 or 40; and
(5) a nucleotide sequence encoding an amino acid sequence having one or several amino acids deleted, substituted, and/or added in the amino acid sequence set forth in SEQ ID NO: 16 or 40.

[7] A method of producing ascofuranone, including a step of using the knockout organism according to [6] to obtain ascofuranone. A method of producing an ascofuranone analog, an ascofuranone precursor, and an analog of the ascofuranone precursor, including a step of using the knockout organism according to [6] to obtain the ascofuranone analog, the ascofuranone precursor, and the analog of the ascofuranone precursor.

[8] An ascF gene knockout organism derived from a wild-type organism having ascF gene, wherein the gene includes any one of nucleotide sequences of (1) to (5) below that encode an amino acid sequence of an enzyme having an activity of catalyzing an epoxidation reaction of ilicicolin A, provided that the organism is not human:
(1) a nucleotide sequence set forth in SEQ ID NO: 5 in the Sequence Listing or a nucleotide sequence that hybridizes, under stringent conditions, with a nucleotide sequence complementary to the nucleotide sequence set forth in SEQ ID NO: 5 in the Sequence Listing;
(2) a nucleotide sequence that having 60% or more sequence identity to the nucleotide sequence set forth in SEQ ID NO: 5;
(3) a nucleotide sequence that encoding an amino acid sequence of an enzyme that has an activity of catalyzing an epoxidation reaction of ilicicolin A;
(4) a nucleotide sequence encoding an amino acid sequence having 60% or more sequence identity to the amino acid sequence set forth in SEQ ID NO: 15 or 39; and
(5) a nucleotide sequence encoding an amino acid sequence having one or several amino acids deleted, substituted, and/or added in the amino acid sequence set forth in SEQ ID NO: 15 or 39.

[9] A method of producing ilicicolin A, including a step of using the knockout organism according to [8] to obtain ilicicolin A. A method of producing an ilicicolin A analog, an ilicicolin A precursor, and an analog of the ilicicolin A precursor, including a step of using the knockout organism according to [8] to obtain the ilicicolin A analog, the ilicicolin A precursor and the analog of the ilicicolin A precursor.

[10] An ascI gene knockout organism derived from a wild-type organism having the ascI gene according to [1], provided that the organism is not human.

[11] A method of producing ascochlorin, including a step of using the knockout organism according to [10] to obtain ascochlorin. A method of producing an ascochlorin analog, an ascochlorin precursor, and an analog of the ascochlorin precursor, including a step of using the knockout organism according to [10] to obtain the ascochlorin analog, the ascochlorin precursor and the analog of the ascochlorin precursor.

In another aspect of the present invention, genes, transformants, and production methods as described in [12] to [22] below are provided.

[12] An ascF gene including any one of nucleotide sequences of (1) to (5) below that encode an amino acid sequence of an enzyme having an activity of catalyzing an epoxidation reaction of ilicicolin A:
(1) a nucleotide sequence set forth in SEQ ID NO: 5 in the Sequence Listing or a nucleotide sequence that hybridizes, under stringent conditions, with a nucleotide sequence complementary to the nucleotide sequence set forth in SEQ ID NO: 5 in the Sequence Listing;
(2) a nucleotide sequence having 60% or more sequence identity to the nucleotide sequence set forth in SEQ ID NO: 5;
(3) a nucleotide sequence encoding an amino acid sequence of an enzyme that has an activity of catalyzing an epoxidation reaction of ilicicolin A;
(4) a nucleotide sequence encoding an amino acid sequence having 60% or more sequence identity to the amino acid sequence set forth in SEQ ID NO: 15 or 39; and
(5) a nucleotide sequence encoding an amino acid sequence having one or several amino acids deleted, substituted, and/or added in the amino acid sequence set forth in SEQ ID NO: 15 or 39.

[13] An ascG gene including any one of nucleotide sequences of (1) to (5) below that encode an amino acid sequence of an enzyme having an activity of catalyzing a cyclization reaction of ilicicolin A epoxide:
(1) a nucleotide sequence set forth in SEQ ID NO: 6 in the Sequence Listing or a nucleotide sequence that hybridizes, under stringent conditions, with a nucleotide sequence complementary to the nucleotide sequence set forth in SEQ ID NO: 6 in the Sequence Listing;

(2) a nucleotide sequence having 60% or more sequence identity to the nucleotide sequence set forth in SEQ ID NO: 6;
(3) a nucleotide sequence encoding an amino acid sequence of an enzyme that has an activity of catalyzing a cyclization reaction of ilicicolin A epoxide;
(4) a nucleotide sequence encoding an amino acid sequence having 60% or more sequence identity to the amino acid sequence set forth in SEQ ID NO: 16 or 40; and
(5) a nucleotide sequence encoding an amino acid sequence having one or several amino acids deleted, substituted, and/or added in the amino acid sequence set forth in SEQ ID NO: 16 or 40.

[14] An ascH gene including any one of nucleotide sequences of (1) to (5) below that encode an amino acid sequence of an enzyme having an activity of catalyzing a reaction in which ascochlorin is produced via dehydrogenation of a compound produced from ilicicolin A in the reactions catalyzed by AscF and AscG proteins:
(1) a nucleotide sequence set forth in SEQ ID NO: 7 in the Sequence Listing or a nucleotide sequence that hybridizes, under stringent conditions, with a nucleotide sequence complementary to the nucleotide sequence set forth in SEQ ID NO: 7 in the Sequence Listing;
(2) a nucleotide sequence having 60% or more sequence identity to the nucleotide sequence set forth in SEQ ID NO: 7;
(3) a nucleotide sequence encoding an amino acid sequence of an enzyme that has an activity of catalyzing a reaction in which ascochlorin is produced via dehydrogenation of a compound produced from ilicicolin A in the reactions catalyzed by AscF and AscG proteins;
(4) a nucleotide sequence encoding an amino acid sequence having 60% or more sequence identity to the amino acid sequence set forth in SEQ ID NO: 17 or 41; and
(5) a nucleotide sequence encoding an amino acid sequence having one or several amino acids deleted, substituted, and/or added in the amino acid sequence set forth in SEQ ID NO: 17 or 41.

[15] An ascE gene including any one of nucleotide sequences of (1) to (5) below that encode an amino acid sequence of an enzyme having an activity of catalyzing a reaction in which ilicicolin A is produced from LL-Z127213:
(1) a nucleotide sequence set forth in SEQ ID NO: 4 in the Sequence Listing or a nucleotide sequence that hybridizes, under stringent conditions, with a nucleotide sequence complementary to the nucleotide sequence set forth in SEQ ID NO: 4 in the Sequence Listing;
(2) a nucleotide sequence having 60% or more sequence identity to the nucleotide sequence set forth in SEQ ID NO: 4;
(3) a nucleotide sequence encoding an amino acid sequence of an enzyme that has an activity of catalyzing a reaction in which ilicicolin A is produced from LL-Z1272β;
(4) a nucleotide sequence encoding an amino acid sequence having 60% or more sequence identity to the amino acid sequence set forth in SEQ ID NO: 14 or 38; and
(5) a nucleotide sequence encoding an amino acid sequence having one or several amino acids deleted, substituted, and/or added in the amino acid sequence set forth in SEQ ID NO: 14 or 38.

[16] An ascD gene including any one of nucleotide sequences of (1) to (5) below that encode an amino acid sequence of an enzyme having an activity of catalyzing a reaction in which 0-orsellinic acid is produced from acetyl-CoA:
(1) a nucleotide sequence set forth in SEQ ID NO: 3 in the Sequence Listing or a nucleotide sequence that hybridizes, under stringent conditions, with a nucleotide sequence complementary to the nucleotide sequence set forth in SEQ ID NO: 3 in the Sequence Listing;
(2) a nucleotide sequence having 60% or more sequence identity to the nucleotide sequence set forth in SEQ ID NO: 3;
(3) a nucleotide sequence that encoding an amino acid sequence of an enzyme that has an activity of catalyzing a reaction in which 0-orsellinic acid is produced from acetyl-CoA;
(4) a nucleotide sequence encoding an amino acid sequence having 60% or more sequence identity to the amino acid sequence set forth in SEQ ID NO: 13 or 37; and
(5) a nucleotide sequence encoding an amino acid sequence having one or several amino acids deleted, substituted, and/or added in the amino acid sequence set forth in SEQ ID NO: 13 or 37.

[17] An ascB gene including any one of nucleotide sequences of (1) to (5) below that encode an amino acid sequence of an enzyme having an activity of catalyzing a reaction in which ilicicolinic acid B is produced from O-orsellinic acid:
(1) a nucleotide sequence set forth in SEQ ID NO: 1 in the Sequence Listing or a nucleotide sequence that hybridizes, under stringent conditions, with a nucleotide sequence complementary to the nucleotide sequence set forth in SEQ ID NO: 1 in the Sequence Listing;
(2) a nucleotide sequence that having 60% or more sequence identity to the nucleotide sequence set forth in SEQ ID NO: 1;
(3) a nucleotide sequence encoding an amino acid sequence of an enzyme that has an activity of catalyzing a reaction in which ilicicolinic acid B is produced from O-orsellinic acid;
(4) a nucleotide sequence encoding an amino acid sequence having 60% or more sequence identity to the amino acid sequence set forth in SEQ ID NO: 11 or 35; and
(5) a nucleotide sequence encoding an amino acid sequence having one or several amino acids deleted, substituted, and/or added in the amino acid sequence set forth in SEQ ID NO: 11 or 35.

[18] An ascC gene including any one of nucleotide sequences of (1) to (5) below that encode an amino acid sequence of an enzyme having an activity of catalyzing a reaction in which LL-Z1272β is produced from ilicicolinic acid B:
(1) a nucleotide sequence set forth in SEQ ID NO: 2 in the Sequence Listing or a nucleotide sequence that hybridizes, under stringent conditions, with a nucleotide sequence complementary to the nucleotide sequence set forth in SEQ ID NO: 2 in the Sequence Listing;
(2) a nucleotide sequence having 60% or more sequence identity to the nucleotide sequence set forth in SEQ ID NO: 2;
(3) a nucleotide sequence encoding an amino acid sequence of an enzyme that has an activity of catalyzing a reaction in which LL-Z1272β is produced from ilicicolinic acid B;
(4) a nucleotide sequence encoding an amino acid sequence having 60% or more sequence identity to the amino acid sequence set forth in SEQ ID NO: 12 or 36; and
(5) a nucleotide sequence encoding an amino acid sequence having one or several amino acids deleted, substituted, and/or added in the amino acid sequence set forth in SEQ ID NO: 12 or 36.

[19] A transformant including at least one selected from the group consisting of the ascF, ascG, ascH, ascE, ascD, ascB, and ascC genes according to [12] to [18] inserted thereinto, and expressing the inserted gene or genes, provided that the transformant is not human.

[20] A method of producing ilicicolin A, including a step of using the transformant according to [19] to obtain ilicicolin A.

[21] A method of producing ascochlorin, including a step of using the transformant according to [19] to obtain ascochlorin.

[22] A method of producing ascofuranone, including a step of using the transformant according to [19] to obtain ascofuranone.

In another aspect of the present invention, proteins, genes, transformants, and methods as described in [23] to [31] below are provided.

[23] An AscA protein including any one of amino acid sequences of (a) to (c) below that has an activity of enhancing the expression of one or more of any of the genes according to [1] to [3] and [12] to [18]:

(a) the amino acid sequence set forth in SEQ ID NO: 66 in the Sequence Listing;

(b) an amino acid sequence having one or several amino acids deleted, substituted, or added in the amino acid sequence set forth in SEQ ID NO: 66 in the Sequence Listing; and (c) an amino acid sequence having 60% or more sequence identity to the amino acid sequence set forth in SEQ ID NO: 66 in the Sequence Listing.

[24] An ascA gene including any one of nucleotide sequences of (A) to (D) below that encode an amino acid sequence of a protein having an activity of enhancing the expression of one or more of any of the genes of [1] to [3] and [12] to [18]:

(A) a nucleotide sequence encoding the amino acid sequence of the protein according to [23];

(B) the nucleotide sequence set forth in SEQ ID NO: 65 in the Sequence Listing;

(C) a nucleotide sequence that hybridizes, under stringent conditions, with a nucleotide sequence complementary to the nucleotide sequence set forth in SEQ ID NO: 65 in the Sequence Listing; and (D) a nucleotide sequence having 80% or more sequence identity to the nucleotide sequence set forth in SEQ ID NO: 65 in the Sequence Listing.

[25] A method of increasing production of isoprenoids from filamentous fungi, including a step of enhancing the expression of the AscA protein according to [23] or the ascA gene according to [24] in the filamentous fungi having one or more of any of the genes according to [1] to [3] and [12] to [18] to increase production of isoprenoids from the filamentous fungi.

[26] The method according to [25], wherein the isoprenoids are at least one compound selected from the group consisting of ascofuranone, ascochlorin, and ilicicolin A.

[27] A transformant obtained by transformation to enhance the expression of the ascA gene according to [24], provided that the transformant is not human.

[28] The transformant according to [27], wherein the transformant is derived from a microorganism belonging to the genus *Acremonium* as a host organism.

[29] A method of producing isoprenoids, including enhancing the expression of the AscA protein according to [23] or the ascA gene according to [24] in filamentous fungi having one or more of any of the genes according to [1] to [3] and [12] to [18] to obtain isoprenoids.

[30] A method of producing isoprenoids, including a step of culturing the transformant according to any one of [27] to [28] to obtain isoprenoids.

[31] The method according to [29] or [30], wherein the isoprenoids are at least one compound selected from the group consisting of ascofuranone, ascochlorin, and ilicicolin A.

Advantageous Effects of Invention

According to the present invention, isoprenoids such as ascofuranone, ilicicolin A, and ascochlorin can be stably produced in a high yield. Consequently, according to the present invention, industrial-scale production of isoprenoids such as ascofuranone, ilicicolin A, and ascochlorin can be achieved.

BRIEF DESCRIPTION OF DRAWINGS

FIG. 19 shows the results from HPLC analysis of the extracts from wild-type strain and the strain forced to express AscA as described in the Examples below.

DESCRIPTION OF EMBODIMENTS

Figure 1:
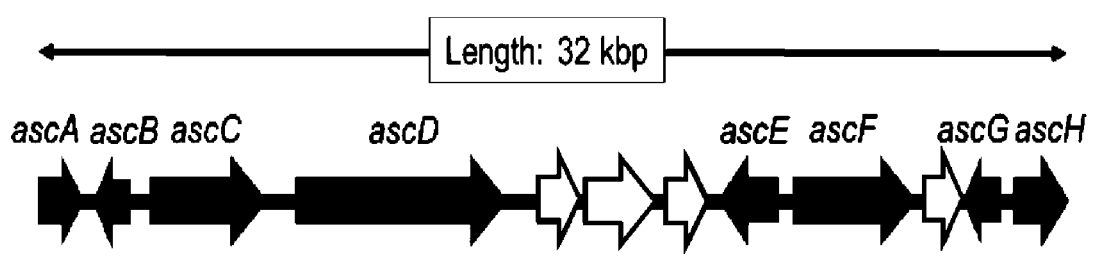
FIG. 1 shows an ascochlorin biosynthetic gene cluster predicted from the transcriptome analysis.

While the genes, transformants, knockout organisms, and production methods of an aspect of the present invention will be now described in detail, the technical scope of the present invention is not limited only by the description in this section, and the present invention may be modified insofar as it can achieve its purpose. The technical scope of the present invention is also not bound by any presumption or inference in the present specification.

(Isoprenoids)

"Isoprenoids" as used herein are not particularly limited provided that they are a compound having, as a component, isoprene as generally known. Isoprenoids include, for example, ilicicolinic acid B (grifolic acid), ilicicolinic acid A, ilicicolin B (LL-Z1272β), ilicicolin A (LL-Z1272α), ilicicolin A epoxide, ilicicolin C, ascochlorin, hydroxy-ilicicolin A epoxide, ascofuranol, ascofuranone, and derivatives thereof. However, in the present specification, the term "isoprenoids" may mainly refer to ascofuranone, ilicicolin A, ascochlorin, and derivatives thereof. The term "ascochlorin precursor" may refer to ilicicolin A epoxide and ilicicolin C. The term "ascofuranone precursor" may refer to ilicicolin A epoxide, hydroxy-ilicicolin A epoxide, and ascofuranol. The term "ilicicolin A precursor" may refer to ilicicolinic acid B, ilicicolinic acid A, and ilicicolin B.

The term "derivative" as used herein includes all of the modified compounds that are obtained via ilicicolinic acid B, ilicicolinic acid A, ilicicolin B, ilicicolin A, ilicicolin A epoxide, ilicicolin C, ascochlorin, hydroxy-ilicicolin A epoxide, ascofuranol, ascofuranone, or the like by using a chemical synthesis method, enzymatic synthesis method, fermentation method, or any other method combined therewith. However, the term "derivative" includes all of compounds having structures similar to those of the compounds as described above, and modified compounds thereof that can be biosynthesized using any one of enzymes as described herein without going through ilicicolinic acid B, ilicicolinic acid A, ilicicolin B, ilicicolin A, ilicicolin A epoxide, ilicicolin C, ascochlorin, hydroxy-ilicicolin A epoxide, ascofuranol, ascofuranone, or the like. Ascofuranone, ascochlorin, ilicicolin A, and precursors thereof are all a meroterpenoid compound which is a complex between a polyketide compound and a terpenoid compound. As noted herein, meroterpenoid compounds are biosynthesized by biosynthesizing a polyketide skeleton by a polyketide synthase such as AscD and then transferring an isoprenoid compound of C10, C15, C20 or the like to the polyketide skeleton by a prenyltransferase such as AscB to form a complex between the polyketide compound and the terpenoid compound. In other words, various ilicicolinic acid B analog compounds can be biosynthesized by different combinations of AscD and AscB which have a modified substrate specificity or have a high identity but altered substrate specificity. By way of example, colletochlorin B may be included in the "derivative" as used herein because colletochlorin B, which has the number of isoprene skeleton of one less than that of ilicicolin A, i.e., has a structure of C10 monoterpene, is an analogous compound similar to ilicicolin A, and colletochlorin B can be synthesized by combining AscD as described herein and AscB with a modified specificity or two enzymes that have a high identity to AscB but have different substrate specificities or using organic chemical synthetic methods to obtain a compound having the terpene moiety corresponding to a structure of C10 monoterpene in ilicicolinic acid B, before further reactions catalyzed by AscC and AscE.

(Amino Acid Sequences of Enzymes (1) to (11))

The ascB gene according to one aspect of the present invention includes a nucleotide sequence encoding an amino acid sequence of an enzyme (hereinafter also referred to as "enzyme (1)") having an activity of catalyzing a reaction in which ilicicolinic acid B is produced from o-orsellinic acid.

The ascC gene according to one aspect of the present invention includes a nucleotide sequence encoding an amino acid sequence of an enzyme (hereinafter also referred to as "enzyme (2)") having an activity of catalyzing a reaction in which LL-Z1272β is produced from ilicicolinic acid B.

The ascD gene according to one aspect of the present invention includes a nucleotide sequence encoding an amino acid sequence of an enzyme (hereinafter also referred to as "enzyme (3)") having an activity of catalyzing a reaction in which o-orsellinic acid is produced from acetyl-CoA.

The ascE gene according to one aspect of the present invention includes a nucleotide sequence encoding an amino acid sequence of an enzyme (hereinafter also referred to as "enzyme (4)") having an activity of catalyzing a reaction in which ilicicolin A is produced from LL-Z1272β. The enzyme (4) may be an enzyme having an activity of catalyzing a reaction in which ilicicolinic acid A is produced from ilicicolinic acid B.

The ascF gene according to one aspect of the present invention includes a nucleotide sequence encoding an amino acid sequence of an enzyme (hereinafter also referred to as "enzyme (5)") having an activity of catalyzing an epoxidation reaction of ilicicolin A.

The ascG gene according to one aspect of the present invention includes a nucleotide sequence encoding an amino acid sequence of an enzyme (hereinafter also referred to as "enzyme (6)") having an activity of catalyzing a cyclization reaction of ilicicolin A epoxide. The compound produced from ilicicolin A epoxide in the reaction catalyzed by the enzyme (6) is ilicicolin C.

The ascH gene according to one aspect of the present invention includes a nucleotide sequence encoding an amino acid sequence of an enzyme (hereinafter also referred to as "enzyme (7)") having an activity of catalyzing a reaction in which ascochlorin is produced via dehydrogenation of a compound produced from ilicicolin A in the reactions catalyzed by AscF and AscG proteins.

The ascI gene according to one aspect of the present invention includes a nucleotide sequence encoding an amino acid sequence of an enzyme (hereinafter also referred to as "enzyme (8)") having an activity of catalyzing monooxygenation of ilicicolin A epoxide. The monooxygenation of ilicicolin A epoxide refers to a reaction in which a hydrogen atom (—H) in ilicicolin A epoxide is substituted with a hydroxy group (—OH). The compound produced from ilicicolin A epoxide in the reaction catalyzed by the enzyme (8) is hydroxy-ilicicolin A epoxide.

The ascJ and ascK genes according to one aspect of the present invention include nucleotide sequences encoding amino acid sequences of enzymes (hereinafter referred to as "enzyme (9)" and "enzyme (10)" respectively) having an activity of catalyzing a reaction in which ascofuranone is produced from a compound produced from ilicicolin A epoxide in a reaction catalyzed by AscI protein.

While the technical scope of the present invention is not bound by any presumption or inference, enzyme (1) may have a function similar to that of prenyltransferase; enzyme (2) may have a function similar to that of oxidoreductase; enzyme (3) may have a function similar to that of polyketide synthase; enzyme (4) may have a function similar to that of halogenase; enzyme (5) may be P450/P450 reductase and have a function similar to that of epoxidase; enzyme (6) may have a function similar to that of terpene cyclase; enzyme (7) may be P450 enzyme and have a function similar to that of dehydrogenase; enzyme (8) may have a function similar to that of p450 mono-oxygenase; enzyme (9) may have a function similar to that of terpene cyclase; and enzyme (10) may have a function similar to that of dehydrogenase. However, as described in the Examples below, enzyme (9) and enzyme (10) can synthesize ascofuranone from the product in the reaction catalyzed by AscI protein by expressing both of the genes encoding these enzymes. Regardless of specific mechanisms of action, when the expression of genes encoding two enzymes allows a particular reaction to occur, in the present specification it is described that one enzyme "conjugates" the other enzyme. However, enzyme (9) may be defined as an enzyme having an activity of catalyzing a reaction in which ascofuranol is produced from hydroxy-ilicicolin A epoxide. Enzyme (10) may be defined as an enzyme having an activity of catalyzing a reaction in which ascofuranone is produced from ascofuranol.

AscA protein according to one aspect of the present invention is a protein having an activity of enhancing the expression of one or more of the genes encoding enzymes (1) to (10). AscA protein can enhance the expression of one or more of the genes encoding enzymes (1) to (10) to promote biosynthesis of isoprenoids in organisms having these genes and thus increase the production of isoprenoids in the organisms. AscA protein may function as a positive transcription factor for the genes encoding enzymes (1) to (10). It should be noted that the gene encoding AscA protein may be included in ascochlorin or ascofuranone biosynthetic genes. For convenience herein, AscA protein is considered as an enzyme and may be referred to as "enzyme (11)" although AscA protein is exactly a transcription factor and is not an enzyme.

Enzymes (1) to (11) have amino acid sequences that are not particularly limited provided that they have an enzymatic activity as described above.

For example, one aspect of enzyme (1) having the enzymatic activity as described above represents the amino acid sequences set forth in SEQ ID NOS: 11, 35, and 47; one aspect of enzyme (2) having the enzymatic activity as described above represents the amino acid sequences set forth in SEQ ID NOS: 12, 36, and 48; one aspect of enzyme (3) having the enzymatic activity as described above represents the amino acid sequences set forth in SEQ ID NOS: 13, 37, and 49; one aspect of enzyme (4) having the enzymatic activity as described above represents the amino acid sequences set forth in SEQ ID NOS: 14, 38, and 50; one aspect of enzyme (5) having the enzymatic activity as described above represents the amino acid sequences set forth in SEQ ID NOS: 15 and 39; one aspect of enzyme (6) having the enzymatic activity as described above represents the amino acid sequences set forth in SEQ ID NOS: 16 and 40; one aspect of enzyme (7) having the enzymatic activity as described above represents the amino acid sequences set forth in SEQ ID NOS: 17 and 41; one aspect of enzyme (8) having the enzymatic activity as described above represents the amino acid sequence set forth in SEQ ID NO: 18; one aspect of enzyme (9) having the enzymatic activity as described above represents the amino acid sequence set forth in SEQ ID NO: 19; one aspect of enzyme (10) having the enzymatic activity as described above represents the amino acid sequence set forth in SEQ ID NO: 20; and one aspect of enzyme (11) having the enzymatic activity as described above represents the amino acid sequence set forth in SEQ ID NO: 66.

The enzymes having the amino acid sequences set forth in SEQ ID NOS: 11 to 20 and 66 are all derived from *Acremonium sclerotigenum*, which is a species of filamentous fungi belonging to the genus *Acremonium*, and are named respectively AscA, AscB, AscC, AscD, AscE, AscF, AscG, AscH, AscI, AscJ, and AscK protein by the present inventors. The nucleotide sequences of the genes encoding these enzymes are set forth in SEQ ID NOS: 1 to 10 and 65.

The enzymes having the amino acid sequences set forth in SEQ ID NOS: 35 to 41 and 67 are all derived from *Neonecrtria ditissima* and are named respectively Nd-AscB, Nd-AscC, Nd-AscD, Nd-AscE, Nd-AscF, Nd-AscG, Nd-AscH, and Nd-AscI protein by the present inventors. The nucleotide sequence of the gene encoding Nd-AscG protein is set forth in SEQ ID NO: 64.

The enzymes having the amino acid sequences set forth in SEQ ID NOS: 47 to 50 are all derived from *Trichoderma reesei* and are named respectively Tr-AscB, Tr-AscC, Tr-AscD, and Tr-AscE protein by the present inventors. The nucleotide sequences of the genes encoding Tr-ascC, Tr-AscD, and Tr-AscB proteins are set forth in SEQ ID NOS: 53, 57, and 60, respectively.

AscA, AscB, AscC, AscD, AscE, AscF, AscG, AscH, AscI, AscJ, and AscK proteins are encoded by genes encoding these enzymes present on chromosomal DNA of the genus *Acremonium, Neonectria*, or *Trichoderma*. The genes present on chromosomal DNA of such source organisms, and proteins and enzymes encoded by the genes may be referred to as, respectively, "wild-type gene", "wild-type protein", and "wild-type enzyme" herein.

The amino acid sequences of enzymes (1) to (11) may consist of an amino acid sequence having one or several amino acids deleted, substituted, and/or added in the amino acid sequences of respective wild-type enzymes provided that they have respective enzymatic activities of enzymes (1) to (11) as described above. The range of "one or several amino acids" in the phrase "having one or several amino acids deleted, substituted, and/or added" in the amino acid sequences is not particularly limited, but means for example 1, 2, 3, 4, 5, 6, 7, 8, 9, 10, 11, 12, 13, 14, 15, 16, 17, 18, 19, or 20, preferably about 1, 2, 3, 4, 5, 6, 7, 8, 9, or 10, and more preferably about 1, 2, 3, 4, or 5 amino acids per unit when 100 amino acids in an amino acid sequence are considered as one unit. The term "amino acid deleted" means a loss or disappearance of an amino acid residue in a sequence; the term "amino acid substituted" means replacement of an amino acid residue with another amino acid residue in a sequence; the term "amino acid added" means addition of a new amino acid residue inserted into a sequence.

Embodiments of the "one or several amino acids deleted, substituted, and/or added" include an aspect in which one or several amino acids have been substituted with other chemically similar amino acids. For example, the aspects include substitution of a hydrophobic amino acid with another hydrophobic amino acid and substitution of a polar amino acid with another polar amino acid having the same electric charge. Such chemically similar amino acids for each amino acid are known in the art. By way of specific example, nonpolar (hydrophobic) amino acids include alanine, valine, isoleucine, leucine, proline, tryptophan, phenylalanine, methionine, and the like. Polar (neutral) amino acids include glycine, serine, threonine, tyrosine, glutamine, asparagine, cysteine, and the like. Basic amino acids with positive charge include arginine, histidine, lysine, and the like. Acidic amino acids with negative charge include aspartic acid, glutamic acid, and the like.

Amino acid sequences of wild-type enzymes having one or several amino acids deleted, substituted, and/or added include an amino acid sequence having a sequence identity higher than a certain level to the amino acid sequences of the wild-type enzymes and include for example an amino acid sequence having 60% or more, preferably 65% or more, preferably 70% or more, preferably 75% or more, preferably 80% or more, preferably 85% or more, more preferably 90% or more, and even preferably 95% or more sequence identity to the amino acid sequences of the wild-type enzymes.

The methods of obtaining enzymes (1) to (11) are not particularly limited, but include, for example, a method including culturing a transformant obtained by transformation to enhance the expression of the genes encoding enzymes (1) to (11) and then collecting enzymes (1) to (11) from the culture. The means of collecting enzymes (1) to (11) in the culture are not particularly limited, but include, for example, according to conventional methods, removing impurities from the culture supernatant to provide a protein concentrate containing enzymes (1) to (11) by ammonium sulfate precipitation or the like and then isolating enzymes (1) to (11) by gel filtration chromatography, SDS-PAGE, or the like based on the molecular weights of enzymes (1) to (11). The theoretical molecular weights calculated from components of AscB, AscC, AscD, AscE, AscF, AscG, AscH, AscI, AscJ, AscK, and AscA proteins having amino acid sequences set forth in SEQ ID NOS: 11 to 20 and 66 are about 37000, 120000, 230000, 61000, 120000, 31000, 61000, 57000, 42000, 32000, and 55000, respectively.

(Genes Encoding Enzymes (1) to (11))

ascB, ascC, ascD, ascE, ascF, ascG, ascH, ascI, ascJ, ascK, and ascA genes (which may be collectively referred to as "genes encoding enzymes (1) to (11)" hereinafter) are not particularly limited provided that they include nucleotide sequences encoding amino acid sequences of enzymes (1) to (11) having the enzymatic activities as described above. Enzymes (1) to (11) are produced by expressing the genes encoding enzymes (1) to (11) in organisms. The term "gene expression" as used herein means production of proteins or enzymes encoded by genes via transcription, translation, and the like, in a form having an original function or activity, particularly in an enzymatically active form. The term "gene expression" also includes high expression of gene, which means increased production of proteins or enzymes encoded by the genes due to gene insertion, as compared to the original expression level in host organisms.

The genes encoding enzymes (1) to (11) may be genes that can produce enzymes (1) to (11) via splicing after transcription of the genes or may be genes that can produce enzymes (1) to (11) without undergoing splicing after transcription of the genes when introduced into host organisms.

The genes encoding enzymes (1) to (11) may not be completely identical to a gene that is originally retained by a source organism (i.e., wild-type gene). The genes encoding enzymes (1) to (11) may be DNA that has nucleotide sequences that hybridize, under stringent conditions, with of nucleotide sequences complementary to the nucleotide sequences of wild-type genes as long as they are genes encoding enzymes having the enzymatic activities as described above.

The term "nucleotide sequence that hybridizes under stringent conditions" as used herein means a nucleotide sequence obtained by colony hybridization, plaque hybridization, Southern blot hybridization, or the like using DNA having the nucleotide sequences of wild-type genes as a probe.

The term "stringent condition" as used herein refers to a condition specifically distinguished between signals of a specific hybrid and a non-specific hybrid although the condition will vary depending on the hybridization system and the type, sequence, and length of probe to be used. Such condition can be determined by altering hybridization temperature, washing temperature, and salt concentration. For example, if a non-specific hybrid is disadvantageously detected as an intense signal, a hybridization specificity can be increased by elevating hybridization and washing temperatures and optionally lowering salt concentration during washing steps. If even any specific hybrids cannot be detected as a signal, the hybrids can be stabilized by lowering hybridization and washing temperatures and optionally increasing salt concentration during washing steps.

Specific examples of stringent conditions include, for example, hybridization performed overnight (for about 8 to 16 hours) using a DNA probe as a probe and 5×SSC, 1.0% (w/v) blocking reagent for nucleic acid hybridization (Boehringer Mannheim), 0.1% (w/v) N-lauroylsarcosine, and 0.02% (w/v) SDS. Washing is performed twice with 0.1 to 0.5×SSC and 0.1% (w/v) SDS, preferably 0.1×SSC and 0.1% (w/v) SDS for 15 minutes. The hybridization and washing temperatures are 65° C. or more, and preferably 68° C. or more.

DNA having a nucleotide sequence that hybridizes under stringent conditions include, for example, a DNA obtained by performing hybridization under stringent conditions as described above using a filter on which a DNA or fragments of the DNA having a nucleotide sequence of wild-type gene derived from a colony or plaque are immobilized; and a DNA that can be identified by performing hybridization at a temperature from 40 to 75° C. in the presence of 0.5 to 2.0 M NaCl, preferably at 65° C. in the presence of 0.7 to 1.0 M NaCl followed by washing a filter with 0.1 to 1×SSC solution (1×SSC solution contains 150 mM sodium chloride and 15 mM sodium citrate) at 65° C. Probe preparation and hybridization techniques can be performed according to methods as described in Molecular Cloning: A Laboratory Manual, 2nd-Ed., Cold Spring Harbor Laboratory, Cold Spring Harbor, N.Y., 1989, Current Protocols in Molecular Biology, Supplement 1-38, John Wiley & Sons, 1987-1997 (these literatures are also referred to as "technical literatures" hereinafter and are incorporated herein by reference in their entirety). It is understood that those skilled in the art would appropriately determine a condition for obtaining a DNA that has a nucleotide sequence hybridizing with a nucleotide sequence complementary to the nucleotide sequences of wild-type genes under stringent conditions by taking account of conditions such as salt concentration and temperature of buffers as well as various other conditions including probe concentration, probe length, reaction time, and the like.

DNA including nucleotide sequences that hybridizes under stringent conditions include DNA having a sequence identity higher than a certain level to nucleotide sequences of DNA having nucleotide sequences of wild-type genes used as a probe, for example, DNA having 60% or more, preferably 65% or more, preferably 70% or more, preferably 75% or more, preferably 80% or more, preferably 85% or more, more preferably 90% or more, and even more preferably 95% or more sequence identity to the nucleotide sequences of wild-type genes.

Nucleotide sequences of DNA that hybridize, under stringent conditions, with DNA consisting of nucleotide sequences complementary to nucleotide sequences of wild-type genes include, for example, a nucleotide sequence having one to several, preferably 1 to 40, preferably 1 to 35, preferably 1 to 30, preferably 1 to 25, preferably 1 to 20, more preferably 1 to 15, more preferably 1, 2, 3, 4, 5, 6, 7, 8, 9, or 10, and even more preferably 1, 2, 3, 4, or 5 bases deleted, substituted, and/or added per unit in the nucleotide sequences of wild-type genes when 100 bases in a nucleotide sequence are considered as one unit. The term "nucleotide deleted" means a loss or disappearance of a nucleotide in a sequence; the term "nucleotide substituted" means replacement of a nucleotide with another nucleotide in a sequence; the term "nucleotide added" means addition of a new nucleotide inserted into a sequence.

An enzyme encoded by a nucleotide sequence of DNA that hybridizes, under stringent conditions, with DNA consisting of nucleotide sequences complementary to nucleotide sequences of wild-type genes may be an enzyme that has an amino acid sequence having one or several amino acids deleted, substituted, and/or added in the amino acid sequence of the enzyme encoded by the nucleotide sequence of the wild-type gene, but has the same activity as that of the enzyme encoded by the nucleotide sequence of the wild-type gene.

The genes encoding enzymes (1) to (11) may be nucleotide sequences that encode an amino acid sequence that is the same as or similar to the amino acid sequence of an enzyme encoded by a wild-type gene and may include nucleotide sequences different from that of the wild-type gene because some codons encode the same amino acid. Such codon-modified nucleotide sequences for nucleotide sequences of wild-type genes include, for example, nucleotide sequences set forth in SEQ ID NOS: 21 to 24, 28 to 30, and 61. The codon-modified nucleotide sequences are preferably, for example, nucleotide sequences with codons that have been modified to be easily expressed in a host organism.

(Means for Calculating Sequence Identity)

While methods of determining sequence identity of nucleotide and amino acid sequences are not particularly limited, the sequence identity is determined by aligning a nucleotide sequence of a wild-type gene or an amino acid sequence of a protein or enzyme encoded by a wild-type gene with a nucleotide or amino acid sequence of interest, and using programs that calculate the match rate between the sequences, for example, using generally known methods.

The programs that calculate the match rate between two amino acid sequences or nucleotide sequences include, for example, the algorithm of Karlin and Altschul (Proc. Natl. Acad. Sci. USA 87: 2264-2268, 1990; Proc. Natl. Acad. Sci. USA 90: 5873-5877, 1993, incorporated herein by reference in their entirety) known in the art. BLAST program using this algorithm was developed by Altschul et al. (J. Mol. Biol. 215: 403-410, 1990, incorporated herein by reference in its entirety). Gapped BLAST which determines sequence identity more sensitively than BLAST is also known (Nucleic Acids Res. 25: 3389-3402, 1997, incorporated herein by reference in its entirety). Thus, those skilled in the art can search for sequences having high sequence identity to a given sequence in the database using, for example, the programs as described above. These programs are available, for example, on the website of The National Center for Biotechnology Information on the Internet at blast.ncbi.nlm-.nih.gov/Blast.cgi.

While each of the methods as described above can be generally used to search for sequences having sequence identity in the database, Genetyx network version 12.0.1 (Genetyx) can be also used for homology analysis as a means for determining sequence identity of an individual sequence. This method is based on the Lipman-Pearson method (Science 227: 1435-1441, 1985, incorporated herein by reference in its entirety). Upon analysis of sequence identity of nucleotide sequences, regions encoding proteins (CDS or ORF) are used if possible.

(Sources of Genes Encoding Enzymes (1) to (11))

The genes encoding enzymes (1) to (11) are derived from biological species having a producing ability of isoprenoids such as, for example, ilicicolin A, ascofuranone, and ascochlorin or biological species in which the expression of enzymes (1) to (11) is found. Source organisms of genes encoding enzymes (1) to (11) include, for example, microorganisms and the like. Filamentous fungi are preferable among other microorganisms because they are known to have many strains with a producing ability of ascochlorin or ascofuranone. Specific examples of the filamentous fungi having a producing ability of ascochlorin or ascochlorin analogs include filamentous fungi belonging to the genera *Acremonium, Neonectria, Fusarium, Cylindrocarpon, Verticillium, Nectria, Cylindrocladium, Colletotrichum, Cephalosporium, Nigrosabulum*, and the like, and more specifically include *Acremonium sclerotigenum, Neonectria ditissima, Verticillium hemipterigenum, Colletotrichum nicotianae*, and the like. Specific examples of the filamentous fungi having a producing ability of ascofuranone include filamentous fungi belonging to the genera *Acremonium, Paecilomyces, Verticillium*, and the like, and more specifically include *Acremonium sclerotigenum, Neonectria ditissima, Trichoderma reesei, Paecilomyces variotii, Verticillium hemipterigenum*, and the like. Specific examples of the filamentous fungi having a producing ability of ilicicolin A include filamentous fungi belonging to the genus *Trichoderma*, and more specifically include *Trichoderma reesei*. It should be noted that the aforementioned specific examples of filamentous fungi having a producing ability of ascochlorin and filamentous fungi having a producing ability of ascofuranone may be a specific example of filamentous fungi having a producing ability of ilicicolin A.

As described above, while the source organisms of the genes encoding enzymes (1) to (11) are not particularly limited, enzymes (1) to (11) expressed in transformants are preferably not inactivated but have an activity in growth conditions of host organisms. Therefore, the source organism of the genes encoding enzymes (1) to (11) are preferably microorganisms which are grown under conditions similar to conditions under which host organisms to be transformed with the genes encoding enzymes (1) to (11) are grown.

(Cloning of the Genes Encoding Enzymes (1) to (11) by Genetic Engineering Techniques)

The genes encoding enzymes (1) to (11) can be inserted into various suitable known vectors. The vectors can be further introduced into suitable known host organisms to generate transformants into which recombinant vectors (recombinant DNA) containing the genes encoding enzymes (1) to (11) have been introduced. Those skilled in the art can appropriately select methods of obtaining the genes encoding enzymes (1) to (11), methods of obtaining nucleotide sequences of the genes encoding enzymes (1) to (11) and amino acid sequence information of enzymes (1) to (11), methods of producing various vectors, methods of producing transformants, and the like. In the present specification, transformation and transformants include transduction and transductants respectively. A non-limiting example of cloning of the genes encoding enzymes (1) to (11) is described below.

Cloning of the genes encoding enzymes (1) to (11) can appropriately employ gene cloning techniques generally used. For example, chromosomal DNA and mRNA can be extracted from microorganisms or various cells having a producing ability of enzymes (1) to (11) according to conventional methods, for example, the methods as described in the technical literatures. The extracted mRNA can be used as a template to synthesize cDNA. The chromosomal DNA and cDNA thus obtained can be used to produce a library of chromosomal DNA and cDNA.

For example, the genes encoding enzymes (1) to (11) can be obtained by cloning them using chromosomal DNA or cDNA from source organisms having the genes as a template. The source organisms of the genes encoding enzymes (1) to (11) are as described above. Specific examples include *Acremonium sclerotigenum* and the like. For example, *Acremonium sclerotigenum* is cultured and the resulting fungal cells are dehydrated and physically ground to fine powder in a mortar or the like while cooling in liquid nitrogen. Subsequently, a chromosomal DNA fraction is extracted from the fine powder of the fungal cells using typical techniques. For chromosomal DNA extraction techniques, commercially available chromosomal DNA extraction kits such as DNeasy Plant Mini Kit (QIAGEN) can be employed.

The chromosomal DNA as described above is then used as a template to amplify DNA by a polymerase chain reaction (hereinafter denoted as "PCR") using synthetic primers complementary to 5'- and 3'-terminal sequences. The primers are not particularly limited provided that DNA fragments containing the genes can be amplified. In other methods, DNA containing gene fragments of interest are amplified by suitable PCR such as 5' RACE and 3' RACE and these amplified DNA fragments are then ligated to obtain DNA containing full-length genes of interest.

Methods of obtaining the genes encoding enzymes (1) to (11) are also not particularly limited. The genes encoding enzymes (1) to (11) can be constructed using not only genetic engineering techniques but also, for example, chemical synthesis methods.

Nucleotide sequences of amplification products amplified by PCR and chemically synthesized genes can be confirmed, for example, as follows. DNA sequences to be confirmed are inserted into suitable vectors to produce recombinant DNA according to typical methods. Commercially available kits such as TA Cloning Kit (Invitrogen); commercially available plasmid vector DNA such as pUC19 (Takara Bio), pUC18 (Takara Bio), pBR322 (Takara Bio), pBluescript SK+ (Stratagene), and pYES2/CT (Invitrogen); and commercially available bacteriophage vector DNA such as XEMBL3 (Stratagene) can be used for cloning into the vectors. Host organisms, for example, *Escherichia coli*, preferably *Escherichia coli* JM109 strain (Takara Bio) or *Escherichia coli* DH5α strain (Takara Bio) are transformed with the recombinant DNA. The recombinant DNA present in the resulting transformants are purified using QIAGEN Plasmid Mini Kit (QIAGEN) or other suitable kits.

The nucleotide sequence of each gene inserted into the recombinant DNA is determined by the dideoxy method (Methods in Enzymology, 101, 20-78, 1983, incorporated herein by reference in its entirety) or the like. Sequencers used to determine the nucleotide sequences are not particularly limited but include, for example, Li-COR MODEL 4200L sequencer (Aloka), 370DNA sequencing system (Perkin Elmer), CEQ2000XL DNA analysis system (Beckman), and the like. The determined nucleotide sequences may then be used to estimate the amino acid sequences of the translated proteins, i.e., the enzymes (1) to (11).

(Construction of Recombinant Vectors Containing the Genes Encoding Enzymes (1) to (11))

Recombinant vectors containing the genes encoding enzymes (1) to (11) (recombinant DNA) can be constructed by ligating a PCR amplification product containing any of the genes encoding enzymes (1) to (11) with any of various vectors in such a manner that the recombinant vector can express the genes encoding the enzymes (1) to (11). For example, such recombinant vectors may be constructed by excising a DNA fragment containing any of the genes encoding enzymes (1) to (11) with a suitable restriction enzyme and ligating the DNA fragment with a plasmid excised with a suitable restriction enzyme. Alternatively, the recombinant vectors may also be obtained by ligating a DNA fragment that contains the genes and has sequences homologous to a plasmid attached to the both ends of the DNA fragment to another DNA fragment derived from the plasmid amplified by inverse PCR, using a commercially available recombinant vector preparation kit such as In-Fusion HD Cloning Kit (Clontech).

(Methods of Producing Transformants)

Methods of producing transformants are not particularly limited, but include, for example, a method in which the genes encoding enzymes (1) to (11) may be inserted into the host organisms according to conventional methods in such a manner that the enzymes are expressed in the host organisms. Specifically, constructed is a DNA construct having any of the genes encoding enzymes (1) to (11) inserted between an expression-inducing promoter and a terminator. Subsequently, a host organism is transformed with the DNA construct containing the genes encoding enzymes (1) to (11) to obtain a transformant that overexpresses the genes encoding the enzymes (1) to (11). In the present specification, a DNA fragment consisting of an expression-inducing promoter—the genes encoding enzymes (1) to (11)—a terminator and a recombinant vector containing the DNA fragment, which are prepared to transform a host organism, are collectively referred to as "DNA construct".

The method of introducing the genes encoding enzymes (1) to (11) into a host organism in such a manner that the genes are expressed in the host organism is not particularly limited, but includes, for example, a method of inserting the gene directly into a chromosome of the host organism utilizing homologous or non-homologous recombination; and a method of introducing a plasmid vector having the gene inserted into the host organism.

In the method using homologous recombination, a DNA construct that has been ligated between sequences homologous to the regions upstream and downstream of a recombination site on a chromosome can be inserted into the genome of the host organism. The high expression promoter is not particularly limited, but includes for example, a promoter region of translation elongation factor TEF1 gene (tef1), a promoter region of α-amylase gene (amy), a promoter region of alkaline protease gene (alp), a promoter region of glyceraldehyde-3-phosphate dehydrogenase (gpd), and the like.

In the method using non-homologous recombination, a DNA construct may be randomly inserted into any region in a genome of a host organism without requiring homologous sequences, and multiple copies of the DNA construct may be inserted. DNA constructs for transformation may be either linear or cyclic. The high expression promoter is not particularly limited, but includes for example, a promoter region of translation elongation factor TEF1 gene (tef1), a promoter region of α-amylase gene (amy), a promoter region of alkaline protease gene (alp), a promoter region of glyceraldehyde-3-phosphate dehydrogenase (gpd), and the like.

In the method using a vector, a DNA construct is incorporated into a plasmid vector for use in transformation of host organisms according to conventional methods and the resulting plasmid vector can be used to transform a corresponding host organism according to conventional methods.

Such suitable vector-host systems are not particularly limited provided that they allow the production of enzymes (1) to (11) in host organisms. Examples of the vector-host systems include a system based on pUC19 and a filamentous fungus; and a system based on pSTA14 (Mol. Gen. Genet. 218, 99-104, 1989, incorporated herein by reference in its entirety) and a filamentous fungus.

While the DNA construct is preferably introduced into a chromosome of host organisms, it may be used without introduction into the chromosome by incorporating the DNA construct into an autonomously replicating vector (Ozeki et al. Biosci. Biotechnol. Biochem. 59, 1133 (1995), incorporated herein by reference in its entirety).

The DNA construct may contain a marker gene that allows the selection of transformed cells. The marker gene is not particularly limited, but includes, for example, genes compensating for the nutritional requirements of the host organisms, such as pyrG, pyrG3, niaD, and adeA; and drug resistance genes such as those against pyrithiamine, hygromycin B, and oligomycin. Also, the DNA construct preferably contains a promoter, a terminator, and other regulatory sequences (such as an enhancer and polyadenylation sequence) that enable the overexpression of the genes encoding the enzyme (1) to (11) in the host organisms. The promoter is not particularly limited, but includes a suitable expression-inducing promoter and constitutive promoter, for example, tef1 promoter, alp promoter, amy promoter, gpd promoter, and the like. The terminator is also not particularly limited but includes, for example, alp terminator, amy terminator, tef1 terminator, and the like.

The expression regulatory sequences for the genes encoding enzymes (1) to (11) in the DNA construct are not necessarily required if the DNA fragments containing the genes encoding enzymes (1) to (11) to be inserted contain sequences having an expression regulatory function. Also, when transformation is performed by the co-transformation method, the DNA construct may not contain any marker genes.

Purification tags may be added to the DNA construct. For example, six or more codons encoding histidine may be added to a linker sequence which may be appropriately added to a site upstream or downstream of any of the genes encoding enzymes (1) to (11) to enable the purification on a nickel column.

The DNA construct may contain a homologous sequence necessary for marker recycling. For example, pyrG marker can be excised on the medium containing 5-fluoroorotic acid (5FOA) by adding a sequence homologous to a sequence upstream of the insertion site (5' region for homologous recombination) to a site downstream of pyrG marker, or adding a sequence homologous to a sequence downstream of the insertion site (3' region for homologous recombination) to a site upstream of pyrG marker. The homologous sequences suitable for marker recycling are preferably 0.5 kb or longer in length.

One aspect of the DNA construct is, for example, a DNA construct in which a tef1 gene promoter Ptef, any of the genes encoding the enzymes (1) to (11), a tef1 gene terminator Ttef or an alp gene terminator, and pyrG marker gene are ligated to the In-Fusion Cloning Site located in the multiple cloning site of pUC19.

One aspect of the DNA construct for inserting the gene by homologous recombination is a DNA construct in which the 5' sequence for homologous recombination, tef1 gene promoter, any of the genes encoding enzymes (1) to (11), alp gene terminator, pyrG marker gene, and the 3' sequence for homologous recombination are ligated together.

One aspect of the DNA construct for inserting the gene by homologous recombination and recycling the marker is a DNA construct in which the 5' sequence for homologous recombination, tef1 gene promoter, any of the genes encoding enzymes (1) to (11), alp gene terminator, a homologous sequence for marker recycling, pyrG marker gene, the 3' sequence for homologous recombination are ligated together.

Methods for transforming filamentous fungi used as host organisms may be appropriately selected from methods known to those skilled in the art. Examples of the methods include the protoplast PEG method in which protoplasts of host organisms are prepared followed by the treatment with polyethylene glycol and calcium chloride (see, for example, Mol. Gen. Genet. 218, 99-104, 1989, Japanese Patent Laid-Open No. 2007-222055, and the like, which are incorporated herein by reference in their entirety). The culture medium to regenerate the transformant is appropriately selected depending on the host organisms and the transformation marker gene to be used. For example, when *Aspergillus oryzae* (*A. oryzae*) or *Aspergillus sojae* (*A. sojae*) is used as a host organism and pyrG gene is used as a transformation marker gene, the transformant can be regenerated, for example, in a Czapek-Dox minimal medium (Difco) containing 0.5% agar and 1.2 M sorbitol.

Alternatively, in order to obtain the transformant, the promoters for the genes encoding enzymes (1) to (11) originally present on the chromosomes of host organisms may be substituted with a high expression promoter such as tef1 by homologous recombination. Again, a transformation marker gene such as pyrG is preferably inserted with the high expression promoter. For example, a transformation cassette consisting of the region upstream of any of the genes encoding enzymes (1) to (11)—a transformation marker gene—a high expression promoter—all or part of any of the genes encoding the enzymes (1) to (11) as described in the Examples and FIG. 1 of Japanese Patent Laid-Open No. 2011-239681 may be used for this purpose. In this case, the region upstream of any of the genes encoding enzymes (1) to (11) and all or part of any of the genes encoding enzymes (1) to (11) are used for homologous recombination. The all or part of any of the genes encoding enzymes (1) to (11) to be used may include a region ranging from the start codon to any position in the genes. For filamentous fungi, the region suitable for homologous recombination is preferably 0.5 kb or longer in length.

Successful production of the transformant can be confirmed by culturing the transformant under a condition that induces the activity of enzymes (1) to (11) and subsequently detecting the presence of products of interest, for example, isoprenoids such as ascochlorin, ilicicolin A, and ascofuranone in the resulting culture or determining that the detected products of interest is more than the products of interest present in a culture of the host organism cultured under the same condition.

Alternatively, successful production of the transformant may be also confirmed by extracting the chromosomal DNA from the transformant and performing PCR using the chromosomal DNA as a template to detect the presence of any PCR product that can be amplified if the transformation has occurred. In this case, for example, PCR is performed using a forward primer complementary to the nucleotide sequence of the promoter used and a reverse primer complementary to the nucleotide sequence of the transformation marker gene in combination to confirm the presence of product with the expected length.

When the transformation is carried out by homologous recombination, PCR is preferably performed using a forward primer located upstream of the upstream homologous region used and a reverse primer located downstream of the downstream homologous region used to confirm the presence of product with the expected length that can be amplified if the homologous recombination has occurred.

(Method of Generating Knockout Organisms)

The term "knockout" means loss of functional expression of a protein encoded by a gene due to deletion of a part or all of the gene, introduction of mutation or insertion of any sequence into the gene, or deletion of a promoter required to the expression of the gene. The term "knockout" as used herein may include organisms with loss of almost all of functional expression of the protein encoded by the gene even if the protein does not exactly lose its full functional expression, that is, the protein encoded by the gene may be functionally expressed. "Knockout organisms" may be referred to as "disruptants" or "deletants" herein.

Methods of generating knockout organisms are not particularly limited, but any method may be used, including, for example, deletion of a part or all of a gene using homologous recombination as described in the Examples below and deletion, insertion, and/or substitution of a gene by genome editing techniques such as TALEN and CRISPR-Cas9. One aspect of the DNA construct for knockout of the gene by homologous recombination is, but not limited to, a DNA construct in which the 5' sequence for homologous recombination, pyrG marker gene, and the 3' sequence for homologous recombination are ligated together.

One aspect of the DNA construct for inserting the gene by homologous recombination and recycling the marker is a DNA construct in which the 5' sequence for homologous recombination, a homologous sequence for marker recycling, pyrG marker gene, the 3' sequence for homologous recombination are ligated together.

(Host Organisms)

Host organisms are not particularly limited provided that they can produce enzymes (1) to (11) or isoprenoids using the DNA construct containing the genes encoding enzymes (1) to (11) or transformation with the DNA construct containing the genes encoding the enzymes (1) to (11). Examples of the host organisms include microorganisms, including microorganisms belonging to the genera *Aspergillus, Acremonium, Neonectria, Fusarium, Escherichia, Saccharomyces, Pichia, Schizosaccharomyces, Zygosaccharomyces, Trichoderma, Penicillium, Rhizopus, Neurospora, Mucor, Neosartorya, Byssochlamys, Talaromyces, Ajellomyces, Paracoccidioides, Uncinocarpus, Coccidioides, Arthroderma, Trichophyton, Exophiala, Capronia, Cladophialophora, Macrophomina, Leptosphaeria, Bipolaris, Dothistroma, Pyrenophora, Neofusicoccum, Setosphaeria, Baudoinia, Gaeumannomyces, Marssonina, Sphaerulina, Sclerotinia, Magnaporthe, Verticillium, Pseudocercospora, Colletotrichum, Ophiostoma, Metarhizium, Sporothrix,* and *Sordaria,* and plants including those belonging to the genus *Arabidopsis.* The host organisms are preferably the microorganisms and plants. The host organisms may be filamentous fungi having a producing ability of isoprenoids such as ilicicolin A, ascochlorin, and ascofuranone or having the genes encoding enzymes (1) to (11) on their genomic DNA.

The host organisms that do not have a producing ability of isoprenoids due to the absence of ascochlorin or ascofuranone biosynthetic genes can be transformed with the genes encoding enzymes (1) to (11). In other words, transformants that includes the ascochlorin or ascofuranone biosynthetic genes inserted thereinto by transformation to allow the heterologous expression of isoprenoids, for example, transformed filamentous fungi are also available for host organisms. However, in any case, human is excluded from the host organisms.

Examples of the organisms having a producing ability of isoprenoids include filamentous fungi belonging to the genera *Acremonium, Trichoderma, Fusarium, Cylindrocarpon, Verticillium, Nectria,* and *Paecilomyces,* and more specifically include *Acremonium sclerotigenum, Neonectria ditissima, Trichoderma reesei, Paecilomyces variotii,* and *Verticillium hemipterigenum.*

In consideration of safety and ease of culture, the preferable microorganisms are those belonging to the genus *Aspergillus* among filamentous fungi including *Aspergillus oryzae, Aspergillus sojae, Aspergillus niger, Aspergillus tamarii, Aspergillus awamori, Aspergillus usami, Aspergillus kawachii,* and *Aspergillus saitoi.*

Preferably, filamentous fungi that have been transformed to suppress Ku gene, such as Ku70 and Ku80, involved in non-homologous recombination mechanism are used for the generation of transformants by homologous recombination because filamentous fungi including microorganisms belonging to the genera *Acremonium* and *Aspergillus* tend to have a low frequency of homologous recombination.

Such suppression of Ku gene can be achieved by any method known to those skilled in the art. Examples of the method include disruption of Ku gene by a Ku gene disruption vector and inactivation of Ku gene by antisense RNA method using an antisense expression vector for Ku gene. The transformed microorganisms belonging to the genus *Aspergillus* thus obtained have a significantly increased frequency of homologous recombination as compared to original microorganisms belonging to the genus *Aspergillus* which have not undergone genetic engineering for the suppression of Ku gene. Specifically, the frequency of homologous recombination increases at least 2 times, preferably at least 5 times, preferably at least 10 times, and preferably at least about 50 times.

Preferably, filamentous fungi that have been transformed to suppress a marker gene such as pyrG are used as a host organism. The marker gene to be suppressed can be appropriately selected depending on the marker gene to be incorporated into the DNA construct.

(Specific Examples of the Genes Encoding Enzymes (1) to (11))

Examples of the genes encoding enzymes (1) to (11) derived from *Acremonium sclerotigenum* include ascB, ascC, ascD, ascE, ascF, ascG, ascH, ascI, ascJ, ascK, and ascA genes having the nucleotide sequences set forth in SEQ ID NOS: 1 to 10 and 65, respectively. Amino acid sequences of AscB, AscC, AscD, AscE, AscF, AscG, AscH, AscI, AscJ, AscK, and AscA proteins are set forth in SEQ ID NOS: 11 to 20 and 66, respectively.

The methods of obtaining the genes encoding enzymes (1) to (11) from *Acremonium sclerotigenum* and any organism other than *Acremonium sclerotigenum* are not particularly limited. For example, BLAST homology search may be conducted on the genomic DNA of a target organism using the nucleotide sequences (SEQ ID NOS: 1 to 10 and 65) of ascB, ascC, ascD, ascE, ascF, ascG, ascH, ascI, ascJ, and ascK genes to identify genes having a nucleotide sequence with a high sequence identity to the nucleotide sequences of ascA, ascB, ascC, ascD, ascE, ascF, ascG, ascH, ascI, ascJ, ascK, and ascA genes. Alternatively, the genes encoding enzymes (1) to (11) may be obtained by identifying proteins having amino acid sequences having a high sequence identity to the amino acid sequences (SEQ ID NOS: 11 to 20 and 66) of AscB, AscC, AscD, AscE, AscF, AscG, AscH, AscI, AscJ, AscK, and AscA proteins from the total proteins in target organisms and identifying the genes encoding the identified proteins. Examples of amino acid sequences having a high sequence identity to amino acid sequences of AscB, AscC, AscD, AscE, AscF, AscG, AscH, and AscI proteins derived from *Acremonium* sclerotigenum include the amino acid sequences set forth in SEQ ID NOS: 35 to 41 and 67 derived from the genus *Neonectria*. Examples of amino acid sequences having a high sequence identity to amino acid sequences of AscB, AscC, AscD, and AscE proteins derived from *Acremonium sclerotigenum* include the amino acid sequences set forth in SEQ ID NOS: 47 to 50 derived from the genus *Trichoderma*.

The genes encoding enzymes (1) to (11) derived from *Acremonium* sclerotigenum or the genes encoding enzymes having a sequence identity to enzymes (1) to (11) can be used for transformation to introduce them into any host cells, such as microorganisms belonging to the genera *Aspergillus* and *Acremonium*, as a host organism.

(Transformants)

One aspect of the transformants is a transformant (hereinafter also referred to as "transformant (1)") that includes any one of ascA, ascB, ascC, ascD, ascE, ascF, ascG, ascH, ascI, ascJ, and ascK genes, or a combination thereof inserted thereinto by transformation of filamentous fungi or plants as a host organism to express the inserted gene(s). When the host organism is an organism having a producing ability of ascochlorin and ascofuranone such as *Acremonium sclerotigenum*, it is desirable that the inserted gene is constitutively highly expressed as compared to forced expression or endogenous expression or the inserted gene is conditionally expressed in late phase of culture following cell proliferation. Such a transformant can produce ilicicolin A, ascochlorin, or ascofuranone, which are not substantially produced or are produced in trace amounts, even if produced, in the host organism, in a detectable amount or more due to the action of AscA, AscB, AscC, AscD, AscE, AscF, AscG, AscH, AscI, AscJ, and/or AscK expressed.

Another aspect of the transformant is a transformant (hereinafter also referred to as "transformant (2)") that includes a DNA construct inserted thereinto by transformation of filamentous fungi or plants as a host organism to express the inserted genes and wherein the DNA construct is designed to allow the overexpression or underexpression of a biosynthetic gene cluster (containing a promoter sequence or the like except ORF) derived from wild-type organisms including all or some of ascB, ascC, ascD, ascE, ascF, ascG, ascH, ascI, ascJ, and ascK genes and a transcription factor, such as AscA, that regulates transcription of the biosynthetic gene cluster. When the host organism has a producing ability of ascochlorin or ascofuranone such as *Acremonium sclerotigenum*, it is desirable that the inserted gene is constitutively highly expressed as compared to forced expression or endogenous expression or is conditionally expressed in late phase of culture following cell proliferation. When cultured or grown under a condition suitable for the host organism or transformant, such a transformant can produce ilicicolin A, ascochlorin, or ascofuranone, which are not substantially produced or are produced in trace amounts, even if produced, in the host organism, in a detectable amount or more due to the action of transcription factors expressed in an altered level.

One embodiment of the transformant includes, but is not limited to, a transformant that includes ascF, ascE, ascD, ascB, and ascC genes in addition to ascI, ascJ, and ascK genes inserted thereinto, and expresses the inserted genes; and a transformant that has ascF gene in addition to ascI, ascJ, and ascK genes inserted thereinto, and expresses the inserted genes, wherein the transformants are obtained by transformation of *Aspergillus sojae* or the like as a host organism.

One embodiment of the transformant includes, but is not limited to, a transformant that includes one or more of ascA to I genes inserted thereinto, and expresses the inserted gene(s), wherein the transformant is generated using *Acremonium sclerotigenum, Neonectria ditissima, Trichoderma reesei*, or the like as a host organism.

(Knockout Organisms)

One aspect of the knockout organisms is a knockout organism (hereinafter also referred to as "knockout organism (1)") obtained by knocking out ascG gene in a wild-type organism that has ascB, ascC, ascD, ascE, ascF, ascG, and ascI genes and produces both ascochlorin and ascofuranone, such as *Acremonium sclerotigenum*. Such a knockout organism expresses no AscG protein, which is an enzyme involved in biosynthesis of ascochlorin and therefore produces only ascofuranone or ascofuranone precursors instead of ascochlorin. For example, such a knockout organism may produce a large amount of ascofuranone or ascofuranone precursors as compared to the wild-type organism.

Another aspect of the knockout organisms is a knockout organism (hereinafter also referred to as "knockout organism (2)") obtained by knocking out ascF gene in a wild-type organism that produces ascochlorin or ascochlorin precursors and has ascB, ascC, ascD, ascE, and ascF genes, such as *Acremonium sclerotigenum* and *Nectria ditissima*. When cultured or grown under a condition suitable for the wild-type organism, such a knockout organism may produce a large amount of ilicicolin A as compared to the wild-type organism.

Another aspect of the knockout organisms is a knockout organism (hereinafter also referred to as "knockout organism (3)") obtained by knocking out ascI gene in a wild-type organism that produces both ascochlorin and ascofuranone and has ascB, ascC, ascD, ascE, ascF, ascG, and ascI genes, such as *Acremonium sclerotigenum*, or in a wild-type organism that has ascB, ascC, ascD, ascE, ascF, ascG, and ascI genes, such as *Nectria ditissima*. Such a knockout organism expresses no AscI protein, which is an enzyme involved in biosynthesis of ascofuranone and therefore produces only ascochlorin instead of ascofuranone. For example, such a knockout organism may produce a large amount of ascochlorin as compared to the wild-type organism.

Another aspect of the knockout organisms is a knockout organism (hereinafter also referred to as "knockout organism (4)") obtained by knocking out genes involved in biosynthesis of proteins subsequent to ilicicolin A in a wild-type organism that produces ilicicolin A derivatives and has ascB, ascC, ascD, and ascE genes and genes involved in biosynthesis of proteins subsequent to ilicicolin A, such as *Trichoderma reesei*. When cultured or grown under a condition suitable for the wild-type organism, such a knockout organism may produce a large amount of ilicicolin A as compared to the wild-type organism.

(Production Method)

One aspect of the production method according to the present invention is a method of producing ilicicolin A, ascochlorin, or ascofuranone, at least including a step of culturing the transformant (1) or transformant (2) under a condition suitable for host cells to obtain ilicicolin A, ascochlorin, or ascofuranone.

Another aspect of the production method according to the present invention is a method of producing ilicicolin A, ascochlorin, or ascofuranone, at least including a step of applying a precursor of ilicicolin A, ascochlorin, or ascofuranone, such as LL-Z1272β and ilicicolin A (LL-Z1272α), to the transformant (1) or transformant (2) to obtain ilicicolin A, ascochlorin, or ascofuranone. For example, the method of applying ilicicolin A to a transformant is not particularly limited provided that it is a method of producing ascochlorin or ascofuranone by contacting ilicicolin A with the transformant to produce ascochlorin or ascofuranone by the action of enzymes contained in the transformant. For example, the transformant may be cultured in a medium containing ilicicolin A and suitable for growing the transformant under a culture condition suitable for growing the transformant to produce ascochlorin. The culture method is not particularly limited, but includes, for example, the solid or liquid culture technique performed under an aerated or non-aerated condition when the host organism is a filamentous fungus.

Another aspect of the production method according to the present invention is a method of producing ilicicolin A, ascochlorin, or ascofuranone, at least including a step of applying a precursor of ilicicolin A, ascochlorin, or ascofuranone, such as LL-Z1272β and ilicicolin A to an enzyme extracted from transformant (1) or transformant (2) to obtain ilicicolin A, ascochlorin, or ascofuranone.

Another aspect of the production method according to the present invention is a method of producing ascofuranone or ascofuranone precursors, at least including a step of culturing knockout organism (1) under a condition suitable for the wild-type organism to obtain ascofuranone or ascofuranone precursors.

Another aspect of the production method according to the present invention is a method of producing ilicicolin A, at least including a step of culturing or growing knockout organism (2) or (4) under a condition suitable for the wild-type organism to obtain ilicicolin A.

Another aspect of the production method according to the present invention is a method of producing ascochlorin or ascochlorin precursors, at least including a step of culturing or growing knockout organism (3) under a condition suitable for the wild-type organism to obtain ascochlorin or ascochlorin precursors.

While the production methods will now be described mainly for filamentous fungi used as a host organism or wild-type organism, the production method in each aspect of the present invention is not limited to those as described below.

The culture medium that can be used may be any standard culture medium for culturing host organisms or wild-type organisms (hereinafter collectively referred to as "host organisms and the like"), which is a synthetic or natural medium that contains a carbon source, a nitrogen source, inorganic materials, and other nutrients at an appropriate ratio. When the host organisms and the like are microorganisms belonging to the genus *Acremonium* or *Aspergillus*, the culture medium that may be used includes, but is not particularly limited to, the GPY medium as described in the Examples below.

The condition for culturing a transformant or a knockout organism (hereinafter collectively referred to as "transformants and the like") may be any culture condition for host organisms and the like generally known by those skilled in the art. For example, when the host organisms and the like are filamentous fungi belonging to the genus *Acremonium* or *Aspergillus*, the initial pH of the culture medium may be adjusted to 5 to 10, the culture temperature may be adjusted to 20 to 40° C., and the culture duration may be appropriately selected and may vary from several hours to several days, preferably from 1 to 7 days, and more preferably from 2 to 4 days. The culture means are not particularly limited, but include, for example, an aerated, agitated, submerged culture, a shake culture, a static culture, and the like. The culture condition is preferably adjusted so that sufficient amounts of dissolved oxygen are present. An example of the culture medium and culture condition for culturing microorganisms belonging to the genus *Acremonium* or *Aspergillus* includes a shake culture performed at 30° C. at 160 rpm for 3 to 5 days in a GPY medium as described in the Examples below.

The method of extracting products of interest (isoprenoids) such as ascochlorin, ascofuranone, and ilicicolin A from the culture after completion of the culture is not particularly limited. The fungal cells collected from the culture by filtration, centrifugation, or other manipulations may be directly used for extraction. Alternatively, the fungal cells collected may be dried and further disrupted. The method of drying fungal cells is not particularly limited, but includes, for example, lyophilization, solar drying, hot air drying, vacuum drying, aeration drying, drying under reduced pressure, and the like.

The solvent used for extraction is not particularly limited provided that it may be any solvent that can dissolve the products of interest. Examples of the solvent include organic solvents, such as methanol, ethanol, isopropanol and acetone; hydrous organic solvents consisting of the mixture of any of these organic solvents and water; and water, warm water, and hot water. The products of interest are extracted in appropriate disruption of the fungal cells after addition of the solvent.

Instead of the heat treatment as described above, the fungal cells may be subjected to cell disruption processes that disrupt the cells using cell disruption means such as an ultrasonicator, a French press, a DYNO-MILL, and a mortar; processes for lysing the fungal cell walls with Yatalase or other cell wall-lysing enzymes; or processes for lysing the fungal cells with a surfactant such as SDS and Triton X-100. These processes may be used either alone or in combination.

The resulting extract can be subjected to purification processes including centrifugation, filtration, ultrafiltration, gel filtration, separation by differential solubility, solvent extraction, chromatography (such as adsorption chromatography, hydrophobic chromatography, cation exchange chromatography, anion exchange chromatography, and reversed-phase chromatography), crystallization, active carbon treatment, membrane treatment, and other purification processes to purify the products of interest.

The qualitative or quantitative analysis techniques that may be conducted include, for example, LC-MS, LC-ICP-MS, MS/MS, and other techniques. Those skilled in the art would appropriately select the conditions for the analysis. For example, the conditions as described in the Examples below may be used.

In each aspect of the production method according to the present invention, various other steps or manipulations may be performed before, during, or after the above-described step as long as the production method can solve the problems for the present invention.

(Methods)

One aspect of the methods according to the present invention is a method of increasing the production of isoprenoids by filamentous fungi, including a step of enhancing the expression of AscA protein or ascA gene in filamentous fungi having one or more of any of the ascB to ascK genes, or alternatively, ascochlorin biosynthetic genes and/or ascofuranone biosynthetic genes to increase the production of isoprenoids by the filamentous fungi. Another aspect of the methods according to the present invention is a method of producing isoprenoids, including a step of enhancing the expression of AscA protein or ascA gene in filamentous fungi having ascochlorin biosynthetic genes and/or ascofuranone biosynthetic genes to obtain isoprenoids. Another aspect of the methods according to the present invention is a method of producing isoprenoids, including a step of culturing a transformant that has been transformed to enhance the expression of ascA gene to obtain isoprenoids.

The means for enhancing the expression of AscA protein or ascA gene are not particularly limited, but include, for example, the use of transformants as a filamentous fungus that have been transformed to enhance the expression of ascA gene; and the enhancement of the expression of ascA gene that is originally present in the filamentous fungi by adjusting the culture condition for the filamentous fungi having ascochlorin biosynthetic genes and/or ascofuranone biosynthetic genes including ascA gene or introducing other transcription factors.

Whether the production of isoprenoids by filamentous fungi is increased or not can be determined by comparing the amount of isoprenoids produced by the filamentous fungi that have ascochlorin biosynthetic genes and/or ascofuranone biosynthetic genes and have not been modified to enhance the expression of AscA protein or ascA gene with the amount of isoprenoids produced by the filamentous fungi that have ascochlorin biosynthetic genes and/or ascofuranone biosynthetic genes and have been modified to enhance the expression of AscA protein or ascA gene.

(Applications)

Isoprenoids such as ascochlorin, ascofuranone, and ilicicolin A obtained by utilizing the genes, transformants, knockout organisms, and production methods according to one aspect of the present invention are functional biological materials that can be expected to have various bioactivities such as an antiprotozoal activity, antitumor activity, hypoglycemic effect, hypolipidemic effect, glycosylation inhibiting effect, and antioxidative effect, and can be applied for pharmaceutical agents, quasi drugs, and others and raw materials for manufacturing these products by exploiting their characteristics.

The present invention will now be described in further detail with reference to the Examples which are not intended to limit the present invention. The present invention may take various forms as long as it can solve the problems for the present invention.

Examples (Search for Ascochlorin Biosynthetic Genes)

An ascofuranone-producing fungus, *Acremonium sclerotigenum* (*Acremonium sclerotigenum* F-1392 strain; J. Antibiot. 70: 304-307 (2016), incorporated herein by reference in its entirety) was used to obtain two culture samples, wherein one culture sample had the production 400 times higher than that in the other culture sample.

From these samples, 50 to 100 mg of fungal cells was collected, and total RNA was collected using TRIzol Reagent (Thermo Fisher Scientific) according to the standard protocol.

mRNA was isolated from the collected total RNA using Dynabeads mRNA DIRECT Micro Kit (Thermo Fisher Scientific) and a transcriptome library (cDNA library) was constructed using Ion Total RNA-seq Kit v2 (Thermo Fisher Scientific).

Quality of the total RNA, mRNA, and cDNA and concentration of the transcriptome library were determined using Agilent RNA 6000 pico kit and Agilent 2100 bioanalyzer system (both from Agilent).

RNA sequencing analysis of the resulting cDNA library was performed on a system from Thermo Fisher Scientific as follows.

The resulting each cDNA library was diluted to 20 pmol/L and amplified by emulsion PCR using Ion OneTouch 2. The amplified library was concentrated on Ion OneTouch ES and RNA sequencing analysis was performed by Ion PGM system. Ion PGM Template OT2 200 Kit was used for Ion OneTouch 2 while Ion PGM sequencing 200 Kit v2 was used for Ion PGM.

Ion PGM Ion 316 v2 chip was used for RNA sequencing. The resulting sequence information was mapped onto the genomic sequence database of *Acremonium sclerotigenum*. Difference in the gene expression level between the two samples was analyzed.

The fold differences of gene expression level between the high and low production samples was calculated based on the number of the mapped cDNA reads that was normalized by the length of each gene (RPKM: reads per kilobase of exon per million mapped sequence reads).

The genes having the expression level ≥300 times higher than that in the low production sample were searched from genes expressed in the high production sample. The only one region where two or more genes are contiguous and the genes having the expression level ≥300 times higher than that in the low production sample are clustered was found. This region was predicted to be an ascofuranone biosynthetic gene cluster. The genes having the expression level ≥300 times higher than that in the low production sample were named ascA to H (see FIG. 1).

Blast Search and Domain Search using Pfam were performed for the protein encoded by each of the genes. The results indicated that AscA to H were predicted to have functions as shown in Table 1. Among them, AscA was predicted to be a transcription factor and therefore AscB to H proteins (SEQ ID NOS: 11 to 17) encoded by ascB to H genes (SEQ ID NOS: 1 to 7) were expected to be involved in the biosynthesis of ascofuranone.

TABLE 1

| Gene | Proposed function |
| --- | --- |
| ascA | transcriptional regulator |
| ascB | prenyl transferase |

TABLE 1-continued

| Gene | Proposed function |
| --- | --- |
| ascC | oxidoreductase |
| ascD | polyketide synthase |
| ascE | halogenase |
| ascF | p450/p450reductase |
| ascG | terpene cyclase |
| ascH | p450 |

(Generation of Transformants Expressing AscD, AscB, AscC, and AscE)

The expression cassette containing any of ascB, ascC, ascD, and ascE genes set forth in SEQ ID NOS: 15 to 18 which have been codon-optimized for the expression in the Aspergillus was introduced into a pyrG disruptant/ku70 disruptant of the Aspergillus, Aspergillus sojae (Aspergillus sojae NBRC4239 strain).

Specifically, in the expression cassette for expressing each asc gene, Ptef which is a promoter sequence of translation elongation factor gene tef1 (748 bp upstream of tef1 gene, SEQ ID NO: 25) was used as a promoter, and Talp which is a terminator sequence of alkaline protease gene alp (800 bp downstream of alp gene, SEQ ID NO: 26) was used as a terminator. The transformation marker gene pyrG which complements the uracil/uridine auxotrophy (a total of 1,838 bp containing 407 bp upstream of the gene, 896 bp of the coding region, and 535 bp downstream of the gene; SEQ ID NO: 27) was used as a selection marker.

For example, as reported in the literature described by Yoon et al. (Appl Microbiol Biotechnol. 2009 March; 82 (4): 691-701. doi: 10.1007/s00253-008-1815-5. Epub 2008 Dec. 24. Construction of quintuple protease gene disruptant for heterologous protein production in Aspergillus oryzae, which is incorporated herein by reference in its entirety), if a sequence homologous to a sequence upstream or downstream of the gene insertion site (homologous recombination region) is incorporated into the DNA to be used for transformation, pyrG marker can be excised on the medium containing 5-fluoroorotic acid (5FOA) to allow repeated use of pyrG marker (marker recycling). Thus, 5' sequence for homologous recombination (5' arm), Ptef, asc gene, Talp, a homologous sequence for marker recycling (a sequence homologous to the sequence downstream of the gene; loop out region), pyrG, and 3' sequence for homologous recombination (3' arm) were ligated together in this order. The ligated product was used as a DNA for transformation to perform pyrG marker recycling. The expression cassette of each asc gene was inserted onto a chromosome of Aspergillus sojae in the order of ascD, ascB, ascC, and ascE.

The DNA was ligated using In-Fusion HD Cloning Kit (Clontech). For example, for the ligation of Ptef and ascD gene, DNA fragments of Ptef and ascD were amplified by PCR using the primer set of SEQ ID NOS: 31 and 32 and the primer set of SEQ ID NOS: 33 and 34, respectively. Ptef and ascD gene were able to be ligated in the In-fusion reaction because the forward primer for ascD gene had a 15-bp sequence homologous to Ptef added to its 5'-end.

A pyrG disruptant/ku70 disruptant from Aspergillus sojae NBRC4239 strain was transformed with the DNA for transformation thus prepared of 5' arm-Ptef-ascD-Talp-loop out region-pyrG-3' arm, 5' arm-Ptef-ascB-Talp-loop out region-pyrG-3' arm, 5' arm-Ptef-ascC-Talp-loop out region-pyrG-3' arm, and 5' arm-Ptef-ascE-Talp-loop out region-pyrG-3' arm to obtain As-D, As-DB, As-DBC, and As-DBCE strains into which one copy of the expression cassette containing any of ascD, ascB, ascC, and ascE genes were introduced, respectively.

Subsequently, As-D, As-DB, As-DBC, and As-DBCE strains were inoculated into GPY medium (2% (w/v) glucose, 1% (w/v) polypeptone, 0.5% (w/v) yeast extract, 0.5% (w/v) potassium dihydrogen phosphate, 0.05% (w/v) magnesium sulfate heptahydrate) supplemented with 1% (w/v) NaCl and cultured at 30° C. for 4 days. The cultured fungal cells were collected on filter paper followed by dehydration via suction filtration.

The collected fungal cells were immersed in acetone overnight and filtered to obtain the acetone extract from As-DBCE strain. The resulting acetone extract was concentrated to dryness and dissolved in methanol. Subsequently, HPLC analysis and MS analysis (negative mode) were performed. In As-D strain, a new peak that was not observed in host strain (NBRC4239 strain) was detected at the same elution position as in the standard preparation of o-orsellinic acid. In As-DB strain, a new peak that was not observed in As-D strain was detected and analyzed by MS, revealing that the m/z value of the new peak was 371 which corresponds to ilicicolinic acid B. In As-DBC strain, a new peak that was not observed in As-DB strain was detected and analyzed by MS, revealing that the m/z value of the new peak was 355 which corresponds to L-Z1272β. Furthermore, in As-DBCE strain, a new peak that was not observed in As-DBC strain was slightly detected at the same elution position as in the standard preparation of ilicicolin A (see FIG. 2).

Figure 2:
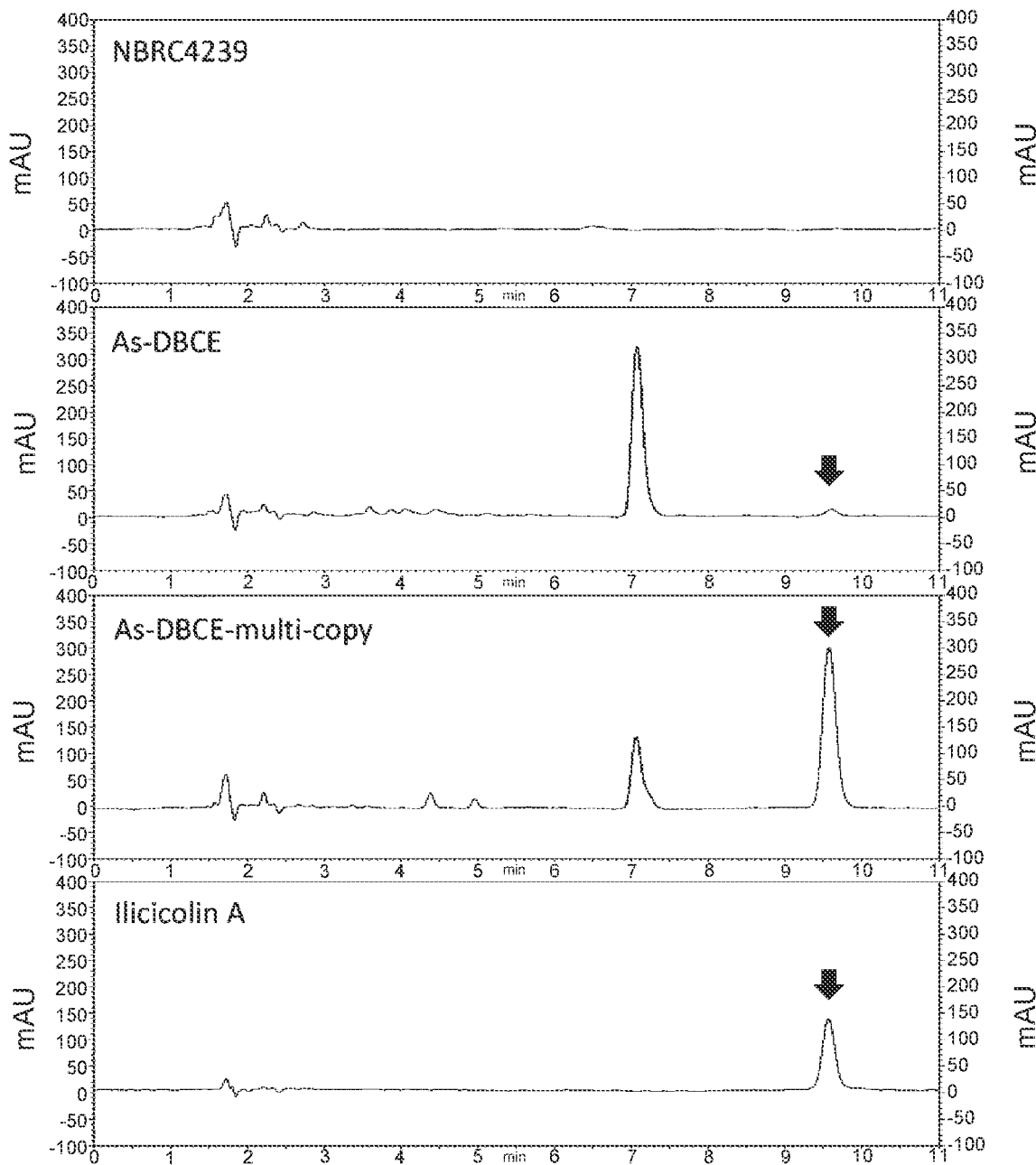
FIG. 2 shows the results from HPLC analysis of the extract from As-DBCE strain and the standard preparation of ilicicolin A, as described in the Examples below.

HPLC shown in FIG. 2 was performed using methanol:water:acetic acid (450:50:10) as a mobile phase (at 1 ml/min) on the ODS column (particle size 3 μm, 4.6 mm×100 mm TSKgel ODS-100V (TOSOH)).

Furthermore, high accumulation of ilicicolin A was observed in As-DBCE-multi-copy strain into which multiple copies of ascD, ascB, ascC, and ascE genes were introduced using pyrG3 gene (SEQ ID NO: 54) as described in Japanese Patent Application No. 2017-206809 (see FIG. 2). The pyrG3 gene is a selection marker gene that is used in filamentous fungi to incorporate a multiple copy of any gene into chromosomes and has a decreased expression level by modifying the promoter region of pyrG.

LC/MS analysis (negative mode) showed that the compound corresponding to the peak has an m/z value of 389 which is the same as that of the standard preparation of ilicicolin A. LC/MS/MS analysis also showed that the compound has a peak pattern similar to that of the standard preparation of ilicicolin A. This demonstrated that ilicicolin A was biosynthesized by AscD, AscB, AscC, and AscE proteins expressed. The peak observed at the elution position at about 7 min in FIG. 2 had the same elution position as the peak observed in As-DBC strain had. The peak was analyzed by MS, revealing that it had the same m/z value as that of LL-Z1272β.

(Generation of Transformants Expressing AscD, AscB, AscC, AscE, AscF, AscG, and AscH)

As in As-DBCE strain, the expression cassette containing any of ascF, ascG, and ascH genes set forth in SEQ ID NOS: 22 to 24 which have been codon-optimized for the expression in the Aspergillus was introduced into As-DBCE strain to obtain As-DBCEF strain having the expression cassette for AscF introduced thereinto; As-DBCEFG strain having the expression cassettes for AscF and AscG introduced thereinto; and As-DBCEFGH strain having the expression cassettes for AscF, AscG, and AscH introduced thereinto. These strains were cultured and analyzed by HPLC in the same way as described above.

The HPLC analysis was performed using Liquid A: acetonitrile+0.1% (v/v) formic acid and Liquid B: water+0.1% (v/v) formic acid under the gradient condition of 40 to 100% Liquid A (for 50 min) at a flow rate of 0.25 ml/min on an ODS column, L-column2 ODS (particle size 3 µm, 2.1 mm×100 mm; Chemicals Evaluation Research Institute).

Figure 3:
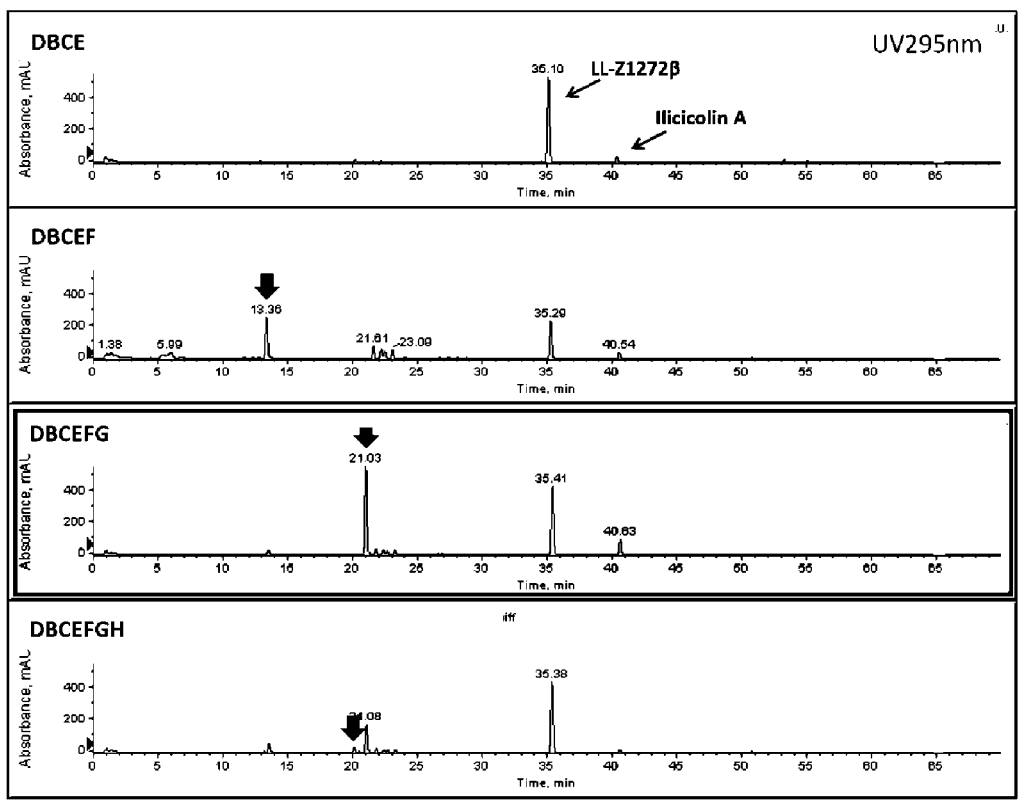
FIG. 3 shows the results from HPLC analysis of the extracts from As-DBCE, As-DBCEF, As-DBCEFG, and As-DBCEFGH strains, as described in the Examples below.

As shown in FIG. 3, a new peak that was not observed in As-DBCE strain was detected in As-DBCEF strain. Also, a new peak that was not observed in As-DBCEF strain was detected in As-DBCEFG strain. Moreover, a new peak that was not observed in As-DBCEFG strain was detected in As-DBCEFGH strain.

These results revealed that the reactions subsequent to ilicicolin A proceed by the sequential actions of AscF, AscG, and AscH proteins.

(In Vitro Analysis with Crude Enzyme Solution)

Any of the expression cassettes containing ascF, ascG, and ascH genes set forth in SEQ ID NOS: 22 to 24 which have been codon-optimized for the expression in the *Aspergillus* to generate As-F, As-G, and As-H strains was introduced into pyrG disruptant from *Aspergillus sojae* NBRC4239 strain. These strains were generated using the plasmid DNA, which was pUC19 having Ptef-asc gene-Talp-pyrG3 inserted, as a DNA for transformation.

Each of *Aspergillus sojae* NBRC4239 strain (wild-type strain), As-F strain, As-G strain, and As-H strain was cultured in GPY medium for a day. The cultured fungal cells were dehydrated followed by freezing in liquid nitrogen. The frozen fungal cells were disrupted by the Multi-beads Shocker. To the disrupted fungal cells was added 20 mM HEPES-NaOH (pH 7.0) to extract crude enzyme solutions from wild-type, As-F, As-G, and As-H strains.

The resulting crude enzyme solutions (obtained from 5 to 10 mg of fungal cells) were used to prepare the following reaction solutions (1) to (4):
(1) wild-type strain reaction solution: a mixture of the crude enzyme solution from wild-type strain, the standard preparation of ilicicolin A, 1 mM NADPH, 1 mM NADH, 1 mM ATP, and 3 mM $MgCl_2$;
(2) As-F reaction solution: a mixture of the crude enzyme solution from As-F strain, the standard preparation of ilicicolin A, 1 mM NADPH, 1 mM NADH, 1 mM ATP, and 3 mM $MgCl_2$;
(3) As-FG reaction solution: a mixture of the crude enzyme solution from As-F strain, the crude enzyme solution from As-G strain, the standard preparation of ilicicolin A, 1 mM NADPH, 1 mM NADH, 1 mM ATP, and 3 mM $MgCl_2$; and
(4) As-FGH reaction solution: a mixture of the crude enzyme solution from As-F strain, the crude enzyme solution from As-G strain, the crude enzyme solution from As-H strain, the standard preparation of ilicicolin A, 1 mM NADPH, 1 mM NADH, 1 mM ATP, and 3 mM $MgCl_2$.

Each of the reaction solutions (1) to (4) as described above was allowed to react at room temperature overnight. Each of the reaction solutions was then extracted with ethyl acetate. The resulting extracts were concentrated to dryness followed by LC/MS analysis.

The LC analysis was performed on a column, L-column2 ODS (particle size 3 µm, 2.1 mm×100 mm; Chemicals Evaluation Research Institute) using Liquid A: acetonitrile+0.1% (v/v) formic acid and Liquid B: water+0.1% (v/v) formic acid under the gradient condition of 40% to 100% Liquid A (for 50 min) at a flow rate of 0.25 ml/min while the MS analysis was performed in negative mode.

Figure 4A:
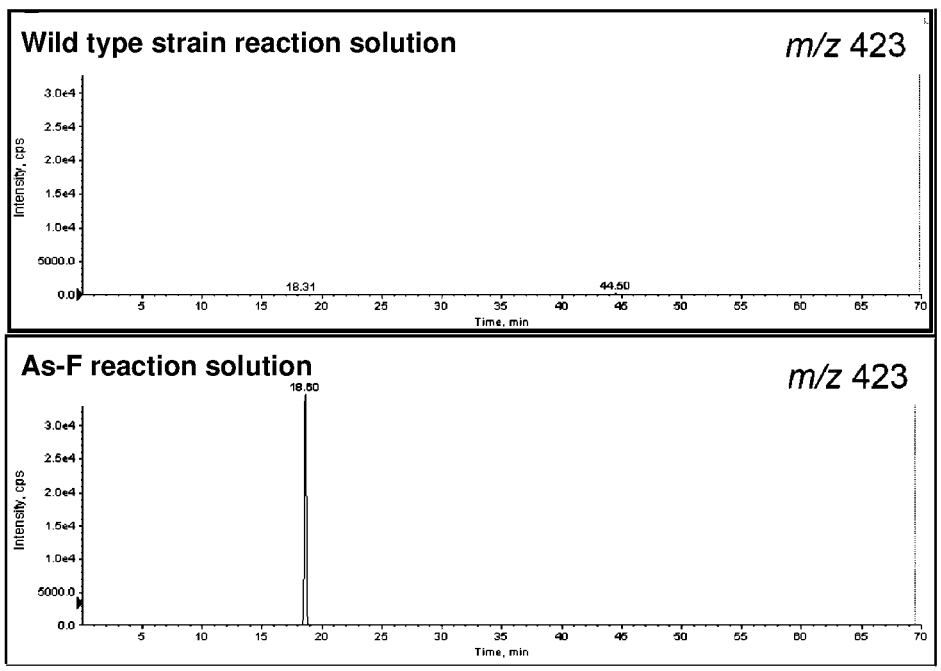
FIG. 4A shows the results from LC/MS analysis of the reaction products obtained by using wild-type strain and As-F reaction solutions as described in the Examples below.
Figure 4B:
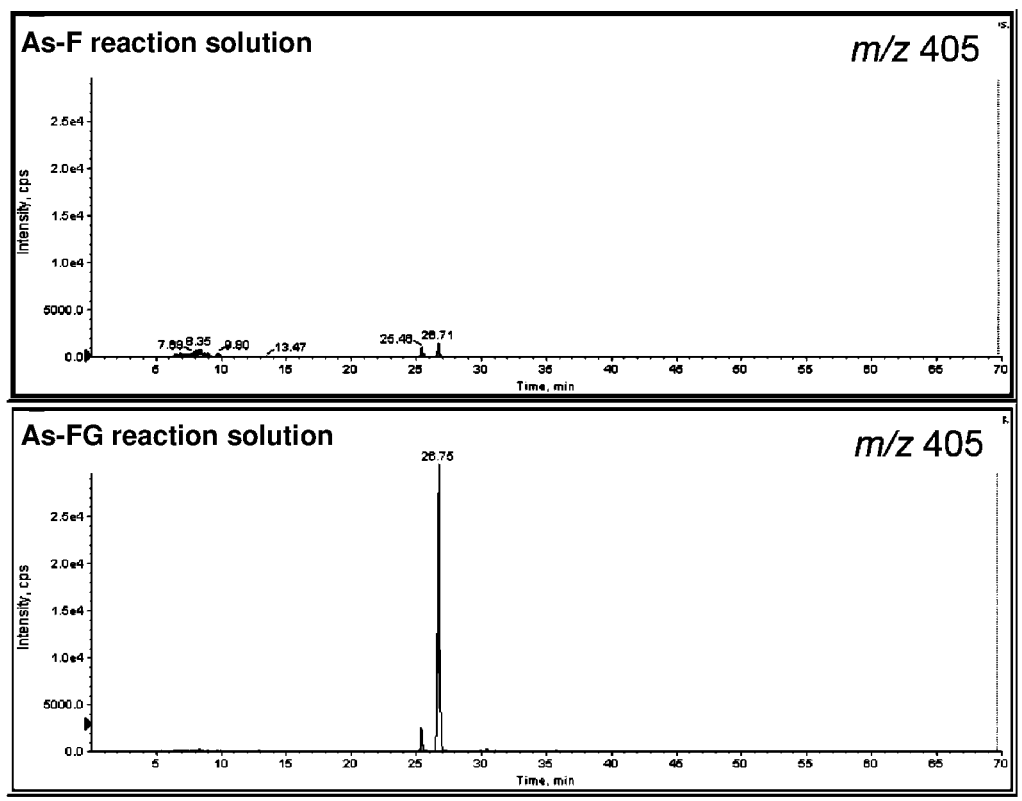
FIG. 4B shows the results from LC/MS analysis of the reaction products obtained by using As-F and As-FG reaction solutions as described in the Examples below.
Figure 5:
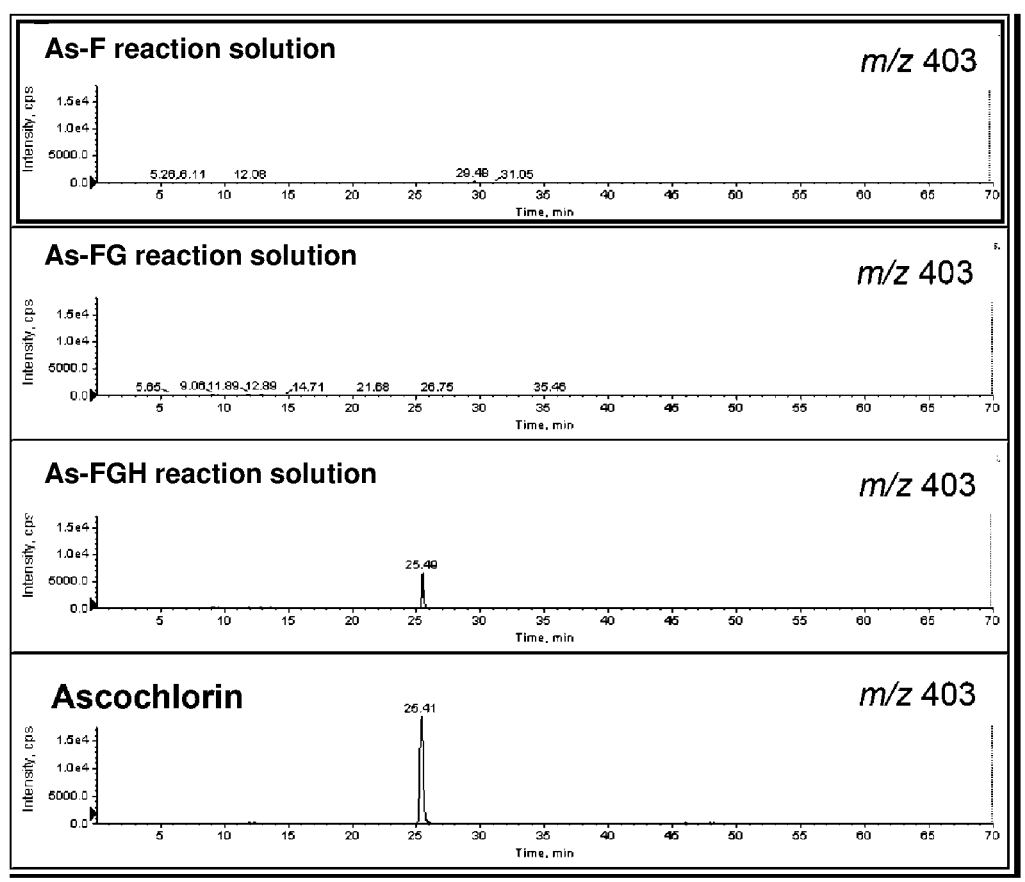
FIG. 5 shows the results from LC/MS analysis of the reaction products obtained by using As-FG and As-FGH reaction solutions as described in the Examples below.

As shown in FIG. 4A, the results showed that a new peak with an m/z value of 423 that was not observed in the wild-type strain reaction solution was detected in the As-F reaction solution. Also, as shown in FIG. 4B, a new peak with an m/z value of 405 that was not observed in the As-F reaction solution was detected in the As-FG reaction solution. Moreover, as shown in FIG. 5, a new peak with an m/z value of 403 that was not observed in As-FG and As-FG reaction solutions was detected in As-FGH reaction solution. These results revealed that ascochlorin was biosynthesized from ilicicolin A by the sequential actions of AscF, AscG, and AscH proteins because the elution time of the peak observed in As-FGH reaction corresponds with that of the peak observed in the standard preparation of ascochlorin and ascochlorin has an m/z value of 403.

Figure 6:
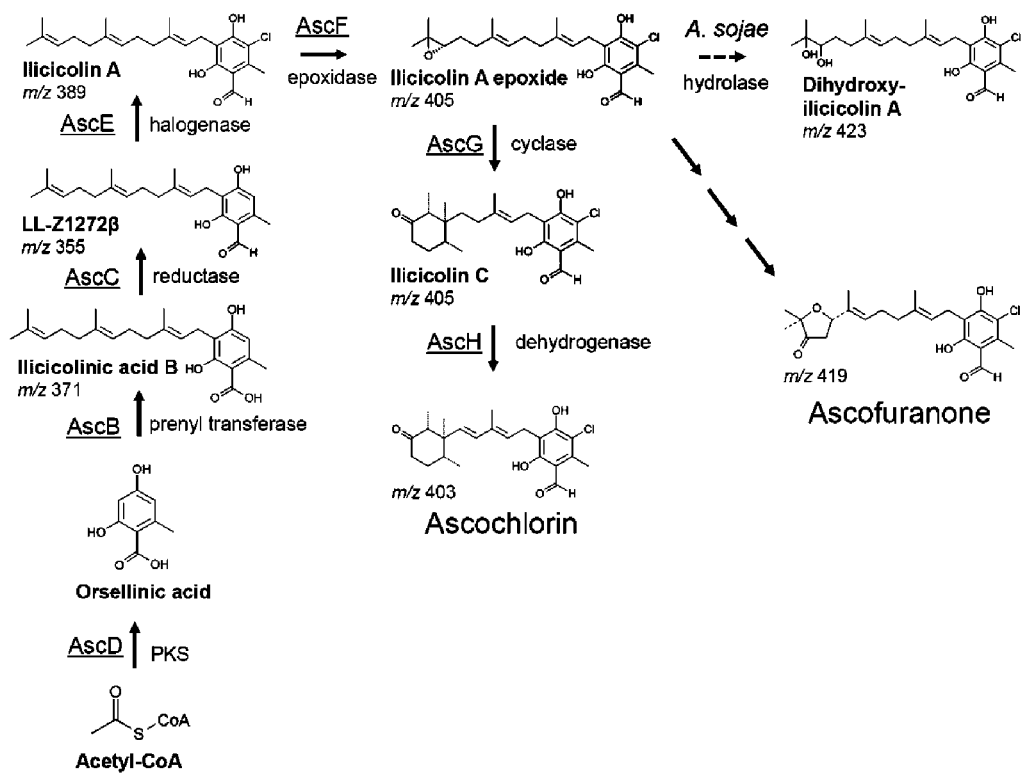
FIG. 6 shows the biosynthetic pathway of ilicicolin A and ascochlorin.

Thus, it was demonstrated that a gene cluster predicted to be involved in ascofuranone biosynthesis was the ascochlorin biosynthetic gene cluster. The biosynthesis scheme of ascochlorin to be expected is shown in FIG. 6. As shown in FIG. 6, it is found that the biosynthetic pathway to ascochlorin is partially overlapped with but different from the biosynthetic pathway to ascofuranone. This indicates that the product from transformants into which the ascochlorin biosynthetic gene cluster has been introduced is ascochlorin but not ascofuranone.

(Analysis of Strains Having Endogenous Epoxide Hydrolase Gene Disruptant)

The in vitro analysis as described above predicted that the reaction product obtained using the crude enzyme solution of AscF expressed in *Aspergillus sojae* NBRC4239 strain was dihydroxylated ilicicolin A because the peak with an m/z value of 423 was observed in As-F reaction (see FIG. 6). However, according to the literature described by Hosono et al. (J Antibiot (Tokyo). 2009 October; 62 (10): 571-4, incorporated herein by reference in its entirety), it was revealed that ilicicolin A epoxide (with an m/z value of 405) was accumulated in microorganisms belonging to the genus *Acremonium*. Therefore, it is expected that the actual reaction product from AscF is ilicicolin A epoxide. In other words, it was expected that ilicicolin A epoxide may be opened by endogenous epoxide hydrolase to produce dihydroxylated ilicicolin A in *Aspergillus sojae* NBRC4239 strain. As-DBCEF-ΔEH strain was generated by deleting the epoxide hydrolase gene (SEQ ID NO: 42) expressed at the highest expression level among genes predicted to encode epoxide hydrolase derived from *Aspergillus sojae* in As-DBCEF strain. The As-DBCEF-ΔEH strain was cultured in the same way as described above and analyzed by HPLC, which detected a new peak that was not observed in As-DBCEF strain. MS analysis also demonstrated that the peak has the m/z value corresponding to an epoxide compound. Thus, it is elucidated that AscF catalyzes an epoxidation reaction of ilicicolin A.

(Search for Ascofuranone Biosynthetic Genes)

Figure 7:
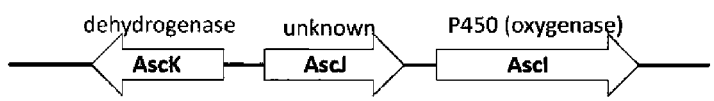
FIG. 7 shows an ascofuranone biosynthetic gene cluster predicted from transcriptome analysis.

As shown in FIG. 6, assuming that the biosynthesis of ascofuranone from ilicicolin A epoxide requires monooxygenation, it was predicted that another cytochrome P450 mono-oxygenase except for AscF was involved in this reaction. The results from RNA sequencing analysis as described above were utilized to search for P450 gene highly expressed in a sample having a high production level of ascofuranone. P450 gene expressing at about 60% of the expression level of AscF in the sample having a high production level of ascofuranone and is expressing at a minimal expression level in a sample having a low production level of ascofuranone was newly found from the results of the search. It was demonstrated that two genes adjacent to the P450 gene also highly expressed only in the sample having a high production level of ascofuranone, indicating that the three genes form a cluster (see FIG. 7). Blast Search and Domain Search using Pfam were performed for the proteins encoded by the two genes adjacent to the P450 gene, revealing that one was a function-unknown protein and the other was a dehydrogenase.

(Synthesis of Ascofuranone Using Crude Enzyme Solutions)

Three genes thus found, P450 gene (SEQ ID NO: 8), function-unknown gene (SEQ ID NO: 9) and dehydrogenase gene (SEQ ID NO: 10) were named ascI, ascJ, and ascK, respectively. Whether AscI protein (SEQ ID NO: 18), AscJ protein (SEQ ID NO: 19), and AscK protein (SEQ ID NO: 20) respectively encoded by these genes were biosynthetic enzymes of ascofuranone was determined by the in vitro analysis.

As-I, As-J, and As-K strains were generated by introducing any of the expression cassette containing ascI, ascJ, and ascK genes set forth in SEQ ID NOS: 8 to 10 into pyrG disruptants from *Aspergillus sojae* NBRC4239 strain. These strains were generated using the plasmid DNA, which is pUC19 having Ptef-asc gene-Talp-pyrG inserted, as a DNA for transformation.

Each of As-F, As-I, As-J, and As-K strains was cultured in GPY medium for a day. The cultured fungal cells were dehydrated followed by freezing in liquid nitrogen. The frozen fungal cells were disrupted by the Multi-beads Shocker. To the disrupted fungal cells was added 20 mM HEPES-NaOH (pH 7.4) to extract crude enzyme solutions from As-F, As-I, As-J, and As-K strains.

The resulting crude enzyme solutions (obtained from 5 to 7.5 mg of fungal cells) were used to prepare the following reaction solutions (1) to (7):

(1) As-F reaction solution: a mixture of the crude enzyme solution from As-F strain, the standard preparation of ilicicolin A, 1 mM NADPH, 1 mM NADH, 1 mM ATP, and 3 mM MgCl$_2$;
(2) As-FI reaction solution: a mixture of the crude enzyme solution from As-F strain, the crude enzyme solution from As-I strain, the standard preparation of ilicicolin A, 1 mM NADPH, 1 mM NADH, 1 mM ATP, and 3 mM MgCl$_2$;
(3) As-FIJ reaction solution: a mixture of the crude enzyme solution from As-F strain, the crude enzyme solution from As-I strain, the crude enzyme solution from As-J strain, the standard preparation of ilicicolin A, 1 mM NADPH, 1 mM NADH, 1 mM ATP, and 3 mM MgCl$_2$;
(4) As-FIK reaction solution: a mixture of the crude enzyme solution from As-F strain, the crude enzyme solution from As-I strain, the crude enzyme solution from As-K strain, the standard preparation of ilicicolin A, 1 mM NADPH, 1 mM NADH, 1 mM ATP, and 3 mM MgCl$_2$;
(5) As-FJK reaction solution: a mixture of the crude enzyme solution from As-F strain, the crude enzyme solution from As-J strain, the crude enzyme solution from As-K strain, the standard preparation of ilicicolin A, 1 mM NADPH, 1 mM NADH, 1 mM ATP, and 3 mM MgCl$_2$;
(6) As-IJK reaction solution: a mixture of the crude enzyme solution from As-I strain, the crude enzyme solution from As-J strain, the crude enzyme solution from As-K strain, the standard preparation of ilicicolin A, 1 mM NADPH, 1 mM NADH, 1 mM ATP, and 3 mM MgCl$_2$; and
(7) As-FIJK reaction solution: a mixture of the crude enzyme solution from As-F strain, the crude enzyme solution from As-G strain, the crude enzyme solution from As-H strain, the standard preparation of ilicicolin A, 1 mM NADPH, 1 mM NADH, 1 mM ATP, and 3 mM MgCl$_2$.

Each of the reaction solutions (1) to (7) as described above was allowed to react at 30° C. overnight. Each of the reaction solutions was then extracted with ethyl acetate. The resulting extracts were concentrated to dryness followed by LC/MS analysis.

The LC analysis was performed on a column, L-column2 ODS (particle size 3 μm, 2.1 mm×100 mm; Chemicals Evaluation Research Institute) using Liquid A: acetonitrile+ 0.1% (v/v) formic acid and Liquid B: water+0.1% (v/v) formic acid under the gradient condition of 40% to 100% Liquid A (for 50 min) at a flow rate of 0.25 ml/min while the MS analysis was performed in negative mode. The results from LC/MS analysis were shown in FIG. 8 and FIG. 10 and the results from MS/MS analysis were shown in FIG. 9.

Figure 8:
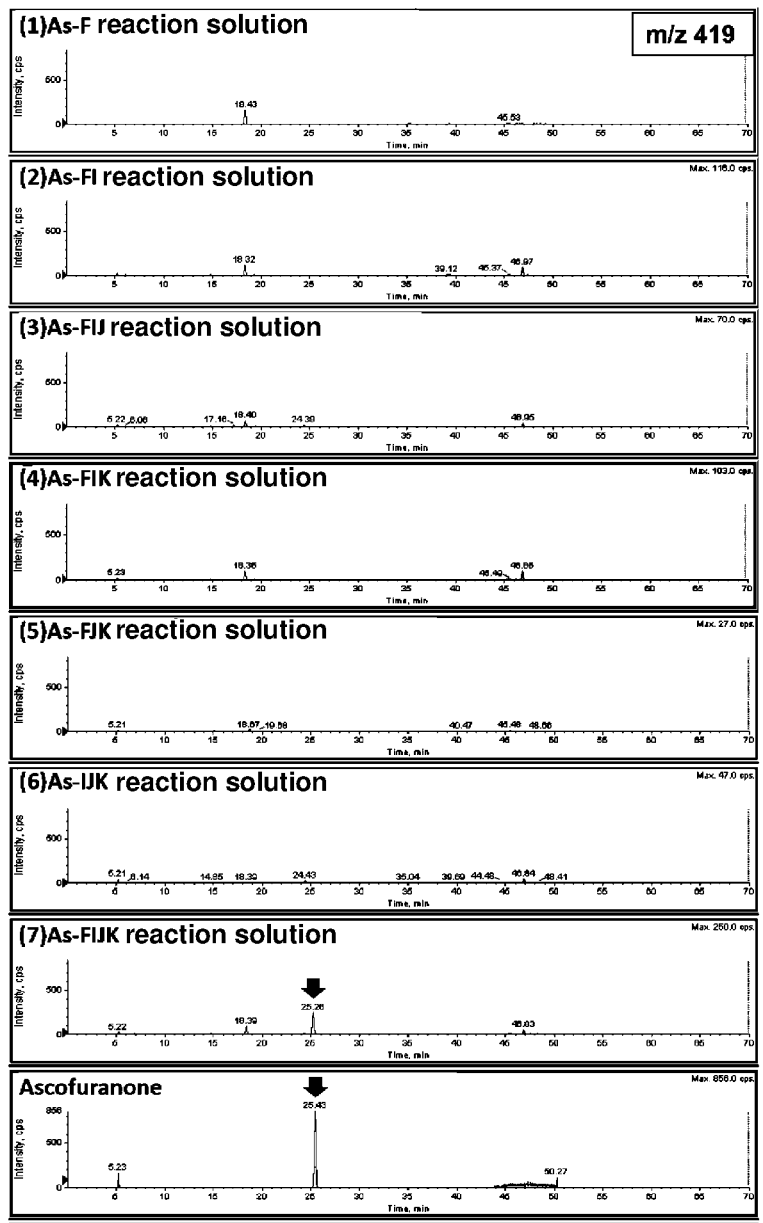
FIG. 8 shows the results from LC/MS analysis of the reaction products obtained by using As-F, As-FI, As-FU, As-FIK, As-FJK, As-UK, and As-FIJK reaction solutions as described in the Examples below.
Figure 9:
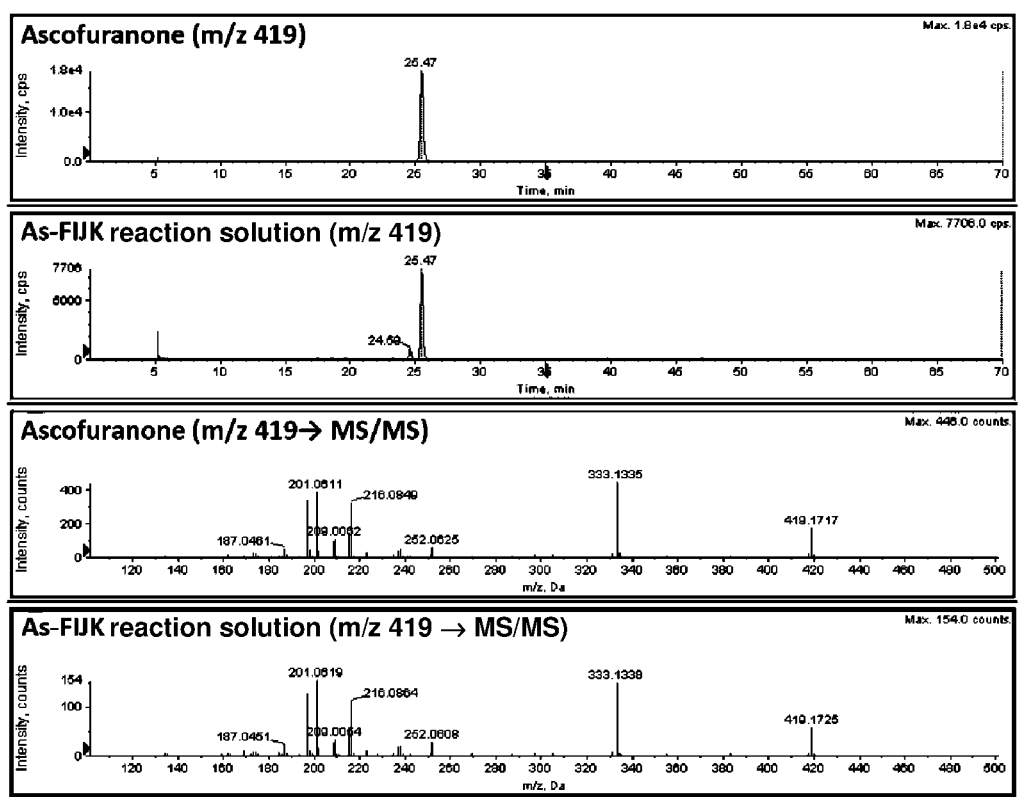
FIG. 9 shows the results from LC/MS and MS/MS analyses of the reaction products obtained by using As-FIJK reaction solution as described in the Examples below.

As shown in FIG. 8, the results showed that only in (7) As-FIJK reaction solution, the peak with an m/z value of 419, which is corresponding to ascofuranone, was detected at the same elution time as the peak detected in the standard preparation of ascofuranone. Moreover, the peak with an m/z value of 419 detected in (7) was analyzed by MS/MS at a collision energy of 45 ev, which resulted in a fragmentation pattern similar to that obtained in the standard preparation of ascofuranone as shown in FIG. 9.

Figure 10:
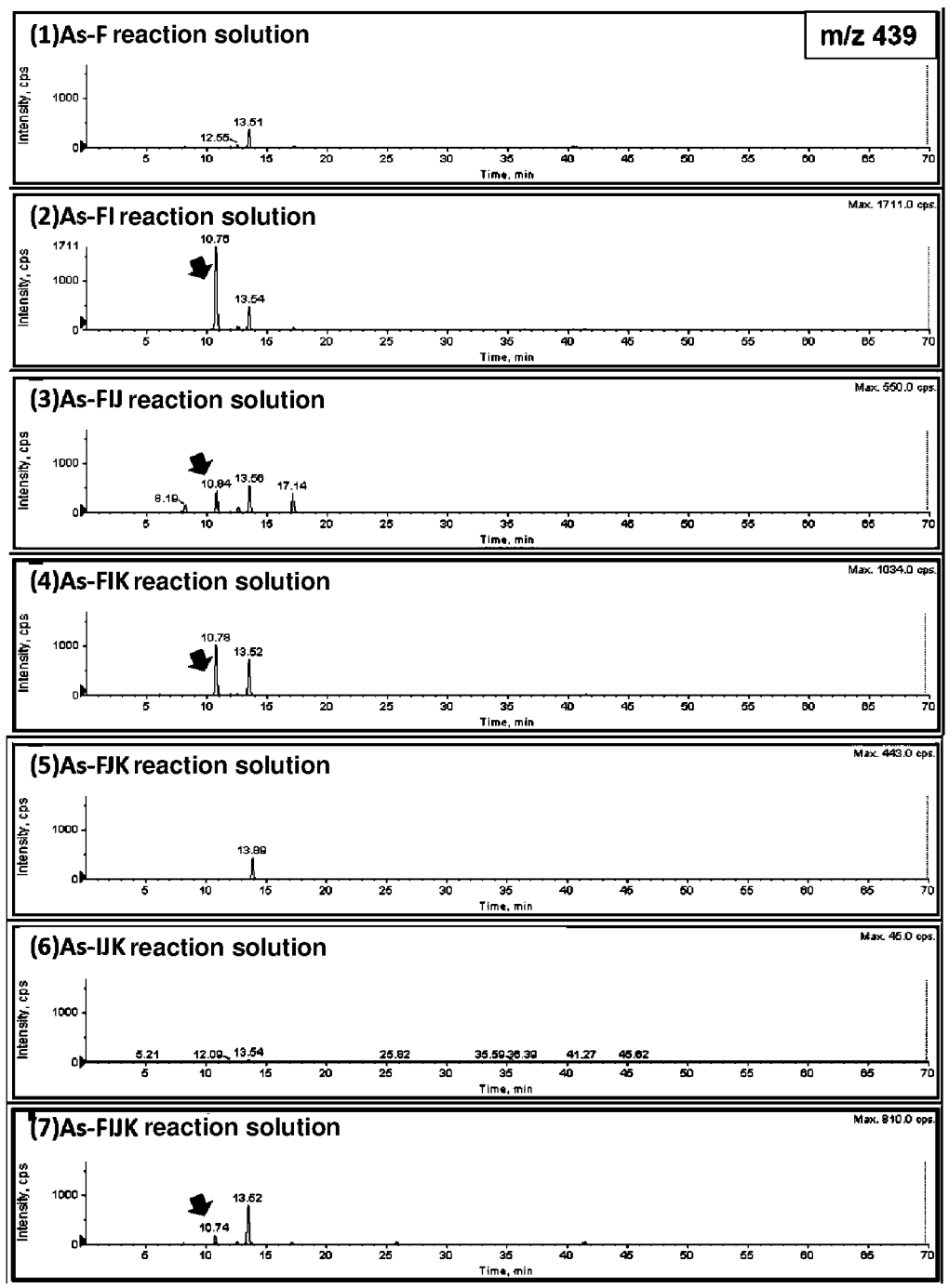
FIG. 10 shows the results from LC/MS analysis of the reaction products obtained by using As-F, As-FI, As-FU, As-FIK, As-FJK, As-UK, and As-FIJK reaction solutions as described in the Examples below.

Also, as shown in FIG. 10, a new peak with an m/z value of 439 that was not observed in (1) As-F reaction solution was detected in (2) As-FI reaction solution. The new peak was detected only in the presence of both AscF and AscI in the reaction solution. In other words, the peak with an m/z value of 439 was assumed to be derived from (a hydrolysate of) the compound produced in the reactions with AscF and AscI in this order using ilicicolin A as a substrate. Considering the difference of the m/z values and the fact that AscI is P450, it was strongly indicated that AscI functioned as an enzyme catalyzing monooxygenation (mono-oxygenase).

Figure 11:
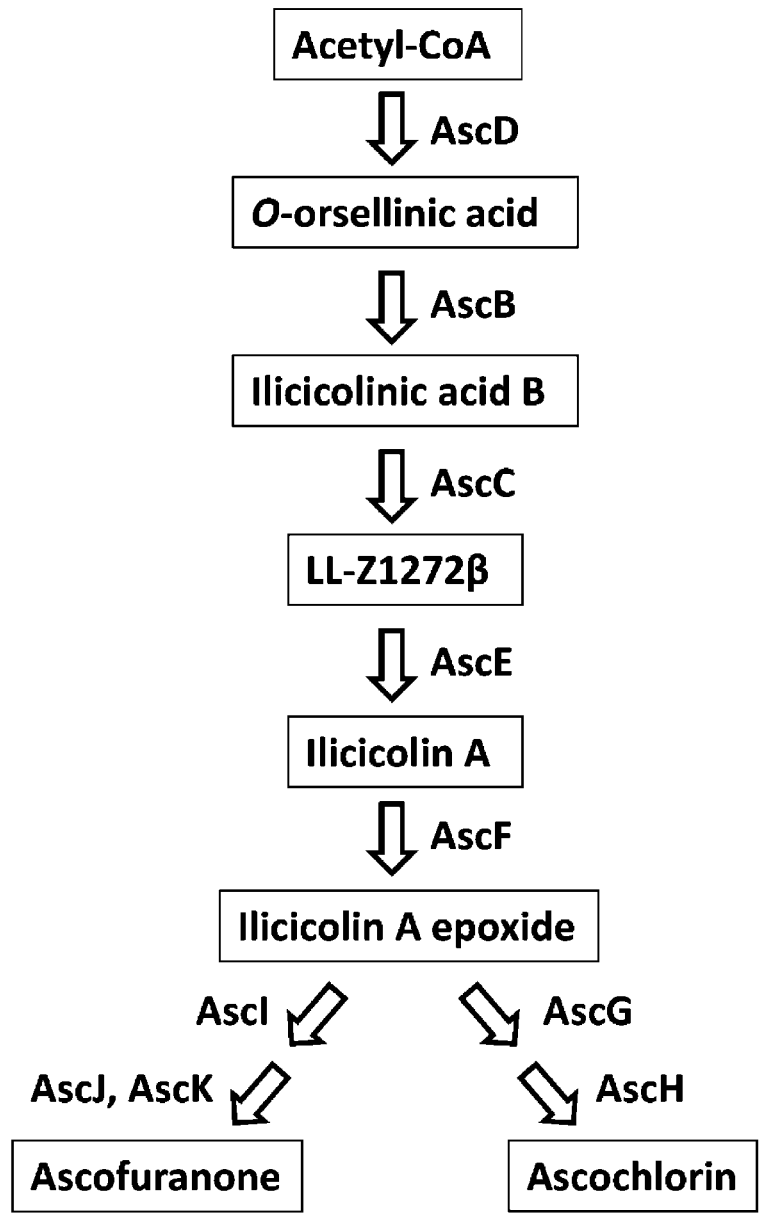
FIG. 11 shows the biosynthetic pathway of ascofuranone, ilicicolin A, and ascochlorin.

These results suggest that as shown in FIG. 11, ascofuranone was produced in a series of reactions in which ilicicolin A was used as a substrate to react with AscF, AscI, AscJ, and AscK.

(Generation of Transformants Expressing AscD, AscB, AscC, AscE, AscF, AscI, AscJ, and AscK)

In the same way as described above, the expression cassettes containing any of ascI, ascJ, and ascK genes set forth in SEQ ID NOS: 8 to 10 and P450 reductase gene derived from *A. sojae* NBRC4239 strain set forth in SEQ ID NO: 43 were sequentially introduced into As-DBCEF strain which had been subjected to pyrG marker recycling to generate As-DBCEFIred strain into which the expression cassettes for AscI and P450 reductase had been introduced; and As-DBCEFIJKred strain into which the expression cassettes for AscI, AscJ, AscK, and P450 reductase had been introduced. These strains were cultured in GPY medium supplemented with 5% (w/v) NaCl and analyzed by HPLC in the same way as described above.

The HPLC analysis was performed using Liquid A: acetonitrile+0.1% (v/v) formic acid and Liquid B: water+ 0.1% (v/v) formic acid under the gradient condition of 40 to 100% Liquid A (for 50 min) at a flow rate of 0.5 ml/min on TSK-gel ODS-100V 3 μm column (4.6 mm I.D.×150 mm). The results are shown in FIG. 12.

Figure 12:
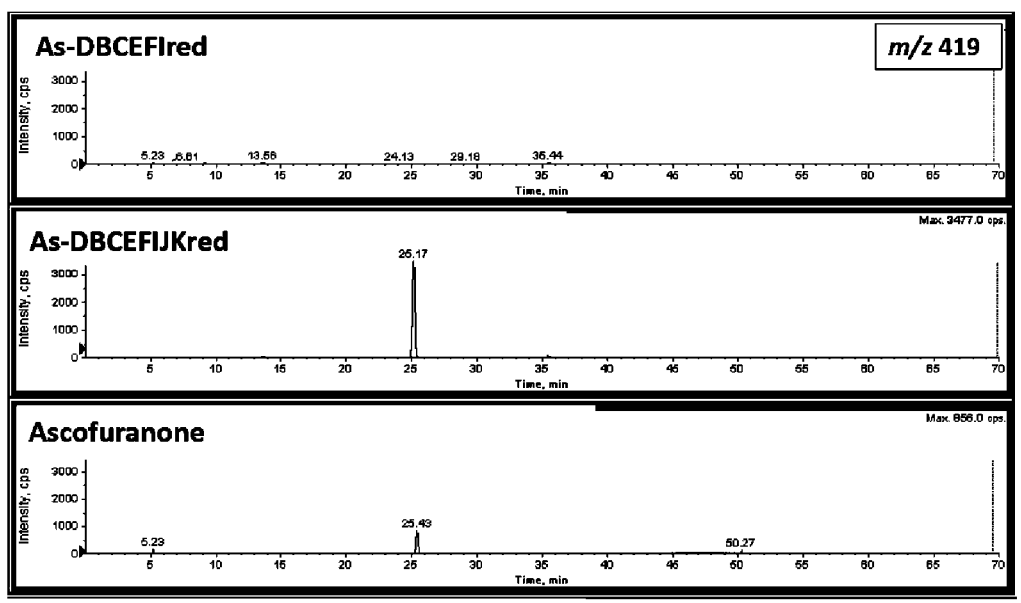
FIG. 12 shows the results from HPLC analysis of the extracts from As-DBCEFIred and As-DBCEFIJKred strains as described in the Examples below.

As shown in FIG. 12, a peak with an m/z value of 419 that was not observed in As-DBCEFIred strain and corresponded to ascofuranone was detected in As-DBCEFIJKred strain. The peak was also detected at the same elution time as the peak detected in the standard preparation of ascofuranone. These results revealed that ascB, ascC, ascD, ascE, ascF, ascI, ascJ, and ascK are ascofuranone biosynthetic genes.

Accordingly, it was demonstrated that the biosynthetic pathways to ascofuranone and ascochlorin share the reactions catalyzed by AscD, AscB, AscC, AscE, and AscF but have different reactions subsequent to ilicicolin A epoxide, as expected in FIG. 6. Specifically, it was demonstrated that the reaction of ilicicolin A epoxide with AscI leads to the biosynthesis of ascofuranone and the reaction of ilicicolin A epoxide with AscG leads to the biosynthesis of ascochlorin (see FIG. 11). Thus, ascG disruptants from a strain producing both ascofuranone and ascochlorin such as *Acremonium sclerotigenum* can produce only ascofuranone at a higher level while ascI disruptants from the strain can produce only ascochlorin at a higher level.

(Generation of pyrG Disruptants of *Acremonium sclerotigenum* F-1392 Strain)

The above-mentioned results reveal that the biosynthetic pathways to ascofuranone and ascochlorin share a common pathway to ilicicolin A epoxide and AscI competes with AscG for the same substrate. Thus, it was expected that ascG disruptants produce only ascofuranone and can use ilicicolin A epoxide that would have been supplied to the biosynthetic pathway to ascochlorin to produce ascofuranone, leading to an increased production level of ascofuranone. On the other hand, it was expected that ascI disruptants produce only ascochlorin and can use ilicicolin A epoxide that would have been supplied to the biosynthetic pathway to ascofuranone to produce ascochlorin, leading to an increased production level of ascochlorin. Accordingly, ascG disruptants and ascI disruptants were generated from *Acremonium sclerotigenum* to validate the hypotheses as described above.

For generation of various asc disruptants from *Acremonium sclerotigenum* F-1392 strain, ku70/pryG double disruptants were first generated. It is difficult to generate disruptants in filamentous fungi including *Acremonium sclerotigenum* because they generally have a very low efficiency of homologous recombination. Therefore, methods of increasing the efficiency of homologous recombination in filamentous fungi by abolishing the function of Ku70 or the like involved in gene insertion by non-homologous recombination are often used. The generation of ku70/pryG double disruptants was achieved by (1) generating pyrG disruptants, (2) generating ku70 disruptants using pyrG marker, and (3) generating ku70/pryG double disruptants by pyrG marker recycling.

First, for generation of pyrG disruptants, DNA fragments for generating pyrG disruptants were prepared as follows. PCR was performed using genomic DNA from *Acremonium sclerotigenum* F-1392 strain as a template to amplify the DNA fragment of about 3 kb upstream of pyrG ORF (5' pyrG), the DNA fragment of about 1.7 kb downstream of nucleotide position 147 of pyrG ORF (3' pyrG), and Ttef (SEQ ID NO: 44). Hygromycin resistance gene (hygr) was amplified by PCR using Linear Hygromycin Marker (Takara) as a template. Next, each of the amplified DNA fragments was ligated together in an In-fusion reaction to prepare the DNA fragment consisting of 5' pyrG-hygr-Ttef-3' pyrG for generating pyrG disruptants.

Subsequently, protoplasts of *Acremonium sclerotigenum* F-1392 strain were prepared according to the method as described in the literature (CYTOLOGIA, 82 (3): 317-320, June 2017, incorporated herein by reference in its entirety). pyrG disruptants were then generated by introducing 5' pyrG-hygr-Ttef-3' pyrG using the protoplast PEG method with polyethylene glycol and calcium chloride (see, for example, Mol. Gen. Genet. 218, 99-104, 1989, incorporated herein by reference in its entirety). The protoplasts treated with PEG were plated on agar medium for regeneration (3.5% Czapeck broth, 1.2 M sorbitol, 20 mM uracil, 20 mM uridine, 2% Agar) and cultured at 25° C. overnight. Five mL of agar medium for regeneration (0.7% Agar) containing 2 mg/L 5FOA and 100 mg/L hygromycin was further plated on the culture and cultured at 30° C. for 2 to 3 weeks. After subculturing multiple times, pyrG disruptants of interest were selected by colony PCR.

(Generation of Ku70 Disruptants from *Acremonium sclerotigenum* F-1392 Strain)

Subsequently, for generation of ku70 disruptants, DNA fragments for generating ku70 disruptants were prepared as follows. PCR was performed using genomic DNA from *Acremonium sclerotigenum* F-1392 strain as a template to amplify the DNA fragment of about 3 kb upstream of ku70 ORF (SEQ ID NO: 45) (5' ku70), the DNA fragment of about 2.3 kb downstream of base position 207 of ku70 ORF (3' ku70), the DNA fragment for pyrG marker recycling of about 1 kb downstream of 3' ku70 (LO), and pyrG gene (SEQ ID NO: 46). Next, each of the amplified DNA fragments was ligated together in an In-fusion reaction to prepare the DNA fragment consisting of 5' ku70-LO-pyrG-3' ku70 for generating ku70 disruptants. ku70 disruptants were generated by introducing the DNA fragment for generating ku70 disruptants into the pyrG disruptants generated above from *Acremonium sclerotigenum* F-1392 strain using protoplast-PEG method in the same way as described above. The protoplasts treated with PEG were plated on agar medium for regeneration (3.5% Czapek-Dox broth, 1.2 M sorbitol, 0.1% trace elements, 2% Agar) and cultured at 30° C. for about 5 days. After subculturing multiple times, ku70 disruptants of interest were selected by colony PCR.

(Generation of Ku70/pyrG Double Disruptants from *Acremonium sclerotigenum* F-1392 strain)

ku70/pyrG double disruptants were generated by collecting conidia of the generated ku70 disruptants and spreading $5 \times 10^5$ to $1 \times 10^6$ conidia on agar medium (3.5% Czapeck broth, 20 mM uracil, 20 mM uridine, 1.5% Agar) containing 1 mg/L 5FOA to perform pyrG marker recycling.

(Generation of ascG Disruptants from *Acremonium sclerotigenum* F-1392 Strain and Analysis of Production Levels of Ascofuranone)

Subsequently, for generation of ascG disruptants, DNA fragments for generating ascG disruptants were prepared as follows. PCR was performed using genomic DNA from *Acremonium sclerotigenum* F-1392 strain as a template to amplify the DNA fragment of about 2 kb upstream of base position 400 of ascG ORF (5' ascG), the DNA fragment of about 2.5 kb downstream of ascG ORF (3' ascG), the DNA fragment for pyrG marker recycling of about 0.9 kb upstream of 5' ascG (LO2), and pyrG gene (SEQ ID NO: 46). Next, each of the amplified DNA fragments was ligated together in an In-fusion reaction to prepare the DNA fragment consisting of 5' ascG-pyrG-LO2-3' ascG for generating ascG disruptants. ascG disruptants were generated by introducing the DNA fragment for generating ascG disruptants into the ku70/pyrG double disruptants generated above from *Acremonium* sclerotigenum F-1392 strain using protoplast-PEG method in the same way as described above. The protoplasts treated with PEG were plated on agar medium for regeneration (3.5% Czapek-Dox broth, 1.2 M sorbitol, 0.1% trace elements, 2% Agar) and cultured at 30° C. for about a week. After subculturing multiple times, ascG disruptants of interest were selected by colony PCR.

*Acremonium sclerotigenum* F-1392 strain (wild-type strain) and the generated ascG disruptants were cultured in GPY liquid medium at 25° C. for 3 days. 10% of the volume of the precultured liquid medium was inoculated into a medium for inducing high production of ascofuranone and cultured with shaking at 180 rpm at 28° C. for 4 days. One hundred mg of the cultured fungal cells was extracted with acetone and analyzed by HPLC. The results are shown in FIG. 13.

Figure 13:
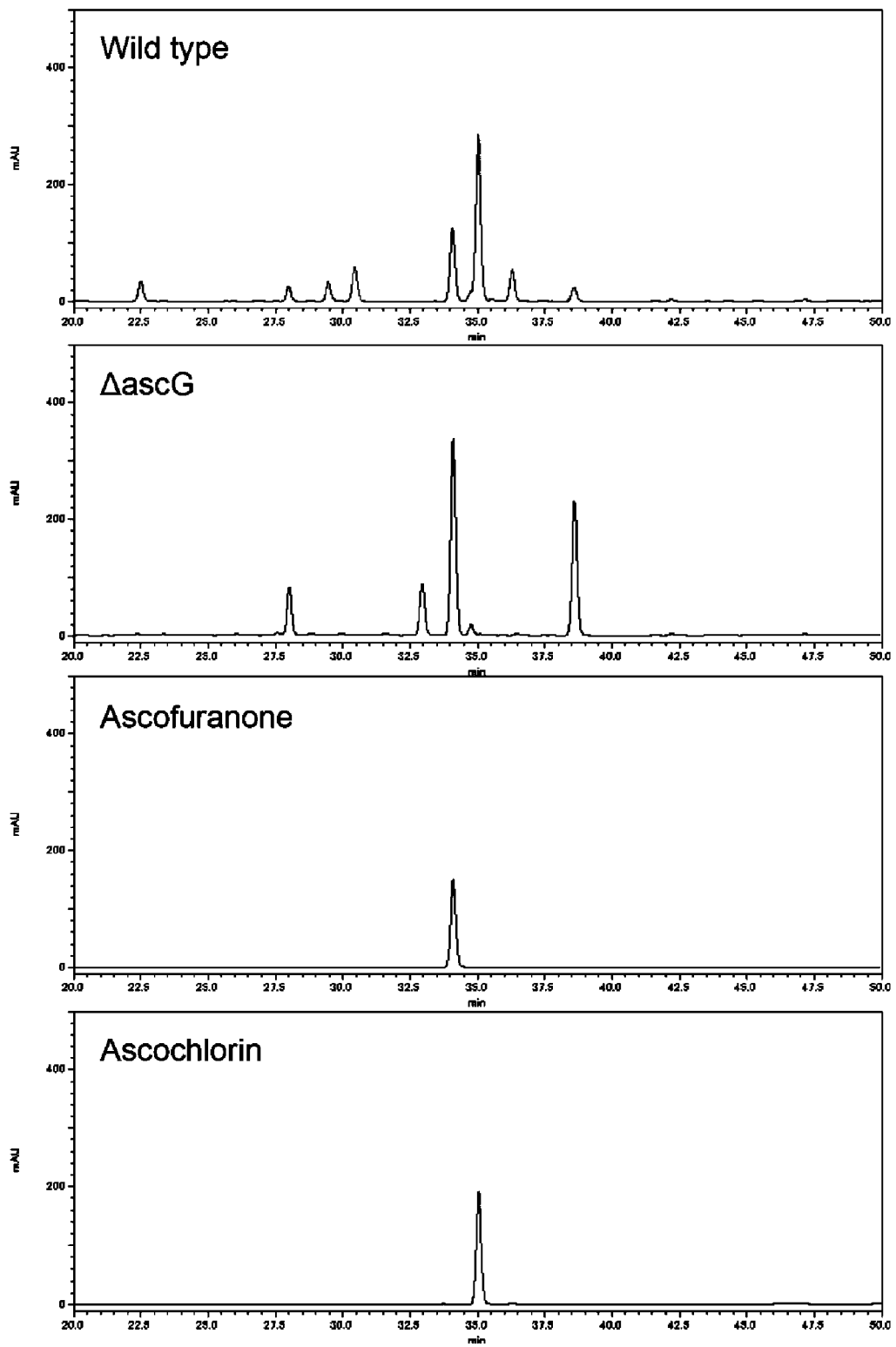
FIG. 13 shows the results from HPLC analysis of the extracts from ascG disruptant of *Acremonium sclerotigenum* F-1392 strain as described in the Examples below.

As shown in FIG. 13, ascG disruptants had no peak corresponding to ascochlorin, revealing that they produced only ascofuranone. It was also demonstrated that the ascofuranone production level per fungal cell in ascG disruptants was higher than in wild-type strain.

(Generation of ascI Disruptants from *Acremonium sclerotigenum* F-1392 Strain and Analysis of Production Levels of Ascochlorin)

Subsequently, for generation of ascI disruptants, DNA fragments for generating ascI disruptants were prepared as follows. PCR was performed using genomic DNA from *Acremonium sclerotigenum* F-1392 strain as a template to amplify the DNA fragment of about 2 kb upstream of ascI ORF (5' ascI), the DNA fragment of about 1.5 kb downstream of base position 905 of ascI ORF (3' ascI), and pyrG gene (SEQ ID NO: 46). Next, each of the amplified DNA fragments was ligated together in an In-fusion reaction to prepare the DNA fragment consisting of 5' ascI-pyrG-3' ascI for generating ascI disruptants. ascI disruptants were generated by introducing the DNA fragment for generating ascI disruptants into the ku70/pyrG double disruptants generated above from *Acremonium sclerotigenum* F-1392 strain using protoplast-PEG method in the same way as described above. The protoplasts treated with PEG were plated on agar medium for regeneration (3.5% Czapek-Dox broth, 1.2 M sorbitol, 0.1% trace elements, 2% Agar) and cultured at 30° C. for about a week. After subculturing multiple times, ascI disruptants of interest were selected by colony PCR.

*Acremonium sclerotigenum* F-1392 strain (wild-type strain) and the generated ascI disruptants were cultured in GPY liquid medium at 25° C. for 3 days. 10% of the volume of the precultured liquid medium was inoculated into a medium for inducing high production of ascofuranone and cultured with shaking at 180 rpm at 28° C. for 4 days. One hundred mg of the cultured fungal cells was extracted with acetone and analyzed by HPLC. The results showed that ascI disruptants had no peak corresponding to ascofuranone, revealing that they produced only ascochlorin. It was also demonstrated that the ascochlorin production level per fungal cell in ascI disruptants was higher than in wild-type strain.

(Generation of ascF Disruptants from *Acremonium sclerotigenum* F-1392 Strain and Analysis of Production Levels of Ilicicolin A)

Subsequently, for generation of ascF disruptants, DNA fragments for generating ascF disruptants were prepared as follows. PCR was performed using genomic DNA from *Acremonium sclerotigenum* F-1392 strain as a template to amplify the DNA fragment of about 1.5 kb upstream of ascF ORF (5' ascF), the DNA fragment of about 2 kb downstream of ascF ORF (3' ascF), the DNA fragment for pyrG marker recycling of about 1.5 kb downstream of 3' ascF (LO3), and pyrG gene (SEQ ID NO: 46). Next, each of the amplified DNA fragments was ligated together in an In-fusion reaction to prepare the DNA fragment consisting of 5' ascF-LO3-pyrG-3' ascF for generating ascF disruptants. ascF disruptants were generated by introducing the DNA fragment for generating ascF disruptants into the ku70/pyrG double disruptants generated above from *Acremonium sclerotigenum* F-1392 strain using protoplast-PEG method in the same way as described above. The protoplasts treated with PEG were plated on agar medium for regeneration (3.5% Czapek-Dox broth, 1.2 M sorbitol, 0.1% trace elements, 2% Agar) and cultured at 30° C. for about a week. After subculturing multiple times, ascF disruptants of interest were selected by colony PCR.

*Acremonium sclerotigenum* F-1392 strain (wild-type strain) and the generated ascF disruptants were cultured in GPY liquid medium at 25° C. for 3 days. 10% of the volume of the precultured liquid medium was inoculated into a medium for inducing high production of ascofuranone and cultured with shaking at 180 rpm at 28° C. for 4 days. One hundred mg of the cultured fungal cells was extracted with acetone and analyzed by HPLC. The results demonstrated that ascF disruptant accumulated a large amount of ilicicolin A.

(Functional Analysis of AscC Derived from *Trichoderma reesei*)

Blast Search was performed for amino acid sequences of AscB to AscE set forth in SEQ ID NOS: 11 to 14 derived from *Acremonium sclerotigenum*. The results suggested that *Trichoderma reesei* also had AscB to AscE homologs (having a sequence identity of 47%, 53%, 52%, 66% respectively) set forth in SEQ ID NOS: 47 to 50 and ascB to AscE genes encoding these homologs were adjacent to one another on its genome. The results predicted that the sequences set forth in SEQ ID NOS: 47 to 50 are also ilicicolin A biosynthetic enzymes. Accordingly, PCR was performed using genomic DNA of *Trichoderma reesei* NBRC31329 strain purchased from NITE as a template with primers set forth in SEQ ID NOS: 51 and 52 to clone ascC gene (Tr-ascC) set forth in SEQ ID NO: 53. Tr-ascC gene set forth in SEQ ID NO: 53, which is a nucleotide sequence with intron, was expected to encode AscC protein set forth in SEQ ID NO: 48 from intron prediction.

The DNA for transformation of 5' arm-Ptef-Tr-ascC-Talp-pyrG-3' arm was prepared by ligating the cloned Tr-ascC in the same way as described above. Subsequently, As-DB strain generated above which had ascD and ascB genes derived from *Acremonium* inserted thereinto and had been subjected to pyrG marker recycling was transformed with the DNA for transformation of 5' arm-Ptef-Tr-ascC-Talp-pyrG-3' arm to obtain As-DB-Tr-C strain into which one copy of the separate expression cassettes containing any of ascD and ascB derived from *Acremonium* and further ascC derived from *Trichoderma* was introduced.

Subsequently, As-DB-Tr-C strain was inoculated into GPY medium (2% (w/v) glucose, 1% (w/v) polypeptone, 0.5% (w/v) yeast extract, 0.5% (w/v) potassium dihydrogen phosphate, 0.05% (w/v) magnesium sulfate heptahydrate) and cultured at 30° C. for 4 days. The cultured fungal cells were collected on filter paper followed by dehydration via suction filtration.

The collected fungal cells were immersed in acetone overnight and filtered to obtain the acetone extract from As-DB-Tr-C strain. The resulting acetone extract was concentrated to dryness, dissolved in methanol, and then analyzed by HPLC. In As-DB-Tr-C strain, a new peak was detected at the same elution position as the peak detected in As-DBC strain with an m/z value of 355 corresponding to L-Z1272β. This demonstrates that as expected, Tr-ascC gene set forth in SEQ ID NO: 53 has the same function as ascC gene derived from *Acremonium* and therefore the sequences set forth in SEQ ID NOS: 47 to 50 derived from *Trichoderma* are ilicicolin A biosynthetic enzymes. Moreover, since AscB to AscH set forth in SEQ ID NOS: 35 to 41 derived from *Neonectria ditissima* have all 60% or more sequence identity to AscB to AscH derived from *Acremonium* and the genes encoding these are adjacent to one another on the genome, the enzyme group was expected to be ascochlorin biosynthetic enzymes.

(Functional Analysis of AscD and AscB Derived from *Trichoderma reesei*)

PCR was performed using genome of *Trichoderma reesei* NBRC31329 strain purchased from NITE as a template with primers set forth in SEQ ID NOS: 55 and 56 to clone ascD gene (Tr-ascD) set forth in SEQ ID NO: 57. In the same way, ascB gene (Tr-ascB) set forth in SEQ ID NO: 60 was cloned using primers set forth in SEQ ID NOS: 58 and 59. Tr-ascD gene set forth in SEQ ID NO: 57, which is a nucleotide sequence with intron, was expected to encode AscD protein set forth in SEQ ID NO: 49 from intron prediction.

The DNA for transformation of 5' arm-Ptef-Tr-ascD-Talp-loop out region-pyrG-3' arm and 5' arm-Ptef-Tr-ascB-Talp-loop out region-pyrG-3' arm were prepared by ligating the cloned Tr-ascD and Tr-ascB in the same way as described above. Subsequently, pyrG disruptant/ku70 disruptant from the *Aspergillus, Aspergillus sojae* was transformed with the DNA for transformation of 5' arm-Ptef-Tr-ascD-Talp-loop out region-pyrG-3' arm to obtain As-Tr-D strain having one copy of the expression cassette containing ascD derived from *Trichoderma* introduced thereinto. Moreover, As-Tr-D strain that had been subjected to pyrG recycling was transformed with 5' arm-Ptef-Tr-ascB-Talp-loop out region-pyrG-3' arm to obtain As-Tr-DB strain having one copy of the separate expression cassettes containing ascD and ascB derived from *Trichoderma* introduced thereinto.

Subsequently, As-Tr-DB strain (a strain having ascD and ascB genes derived from *Trichoderma* inserted thereinto) and As-DB strain (a strain having ascD and ascB genes derived from *Acremonium* inserted thereinto) were inoculated into GPY medium (2% (w/v) glucose, 1% (w/v) polypeptone, 0.5% (w/v) yeast extract, 0.5% (w/v) potassium dihydrogen phosphate, 0.05% (w/v) magnesium sulfate heptahydrate) and cultured at 30° C. for 4 days. The cultured fungal cells were collected on filter paper followed by dehydration via suction filtration.

Figure 14:
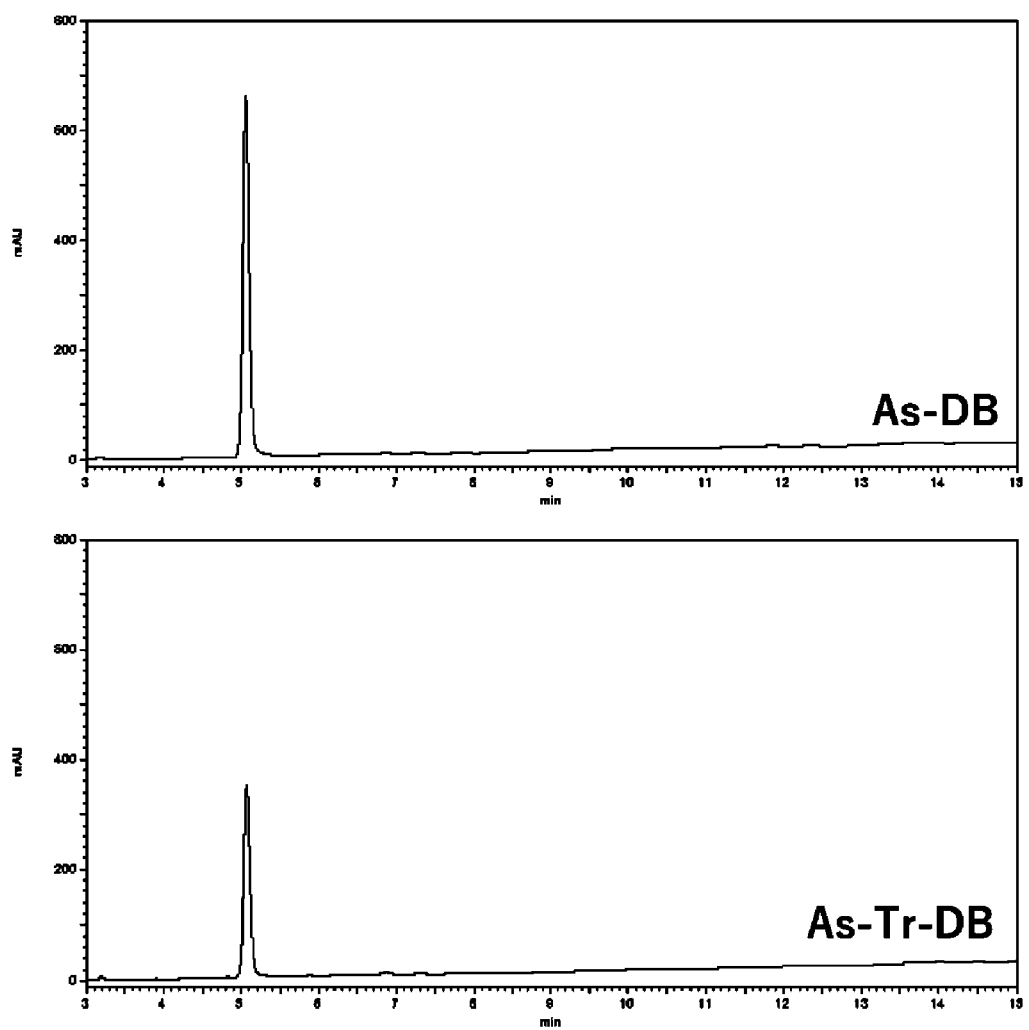
FIG. 14 shows the results from HPLC analysis of the extracts from As-Tr-DB and As-DB strains as described in the Examples below.

The collected fungal cells were immersed in acetone overnight and filtered to obtain the acetone extracts from As-Tr-DB and As-DB strains. The resulting acetone extracts were concentrated to dryness, dissolved in methanol, and then analyzed by HPLC. The HPLC analysis was performed using Liquid A: acetonitrile+0.1% (v/v) formic acid and Liquid B: water+0.1% (v/v) formic acid under the gradient condition of 80 to 95% Liquid A (for 15 min) at a flow rate of 1 ml/min on TSK-gel ODS-100V 3 μm column (4.6 mm I.D.×150 mm). As shown from the results in FIG. 14, a peak that was not observed in the parent strain was detected in As-Tr-DB strain as well as As-DB strain at the same elution position. This demonstrates that as expected, Tr-ascD and Tr-ascB genes set forth in SEQ ID NOS: 57 and 60 have the same function as ascD and ascB genes derived from *Acremonium*.

(Functional Analysis of AscE Derived from *Trichoderma reesei*)

An artificially synthesized gene (SEQ ID NO: 61) which encodes AscE set forth in SEQ ID NO: 50 and has been codon-optimized for expression in the *Aspergillus* was ligated in an In-Fusion reaction in the same way as described above to prepare a DNA for transformation of 5' arm-Ptef-Tr-ascE-Talp-pyrG-3' arm. Subsequently, As-DBC strain (a strain having one copy of each of the expression cassettes containing ascD, ascB, and ascC derived from *Acremonium* inserted thereinto) generated above that had been subjected to pyrG marker recycling was transformed with the DNA for transformation of 5' arm-Ptef-Tr-ascE-Talp-pyrG-3' arm to obtain As-DBC-Tr-E strain having one copy of the separate expression cassettes containing ascD, ascB, and ascC derived from *Acremonium* and further ascE derived from *Trichoderma* inserted thereinto.

Figure 15:
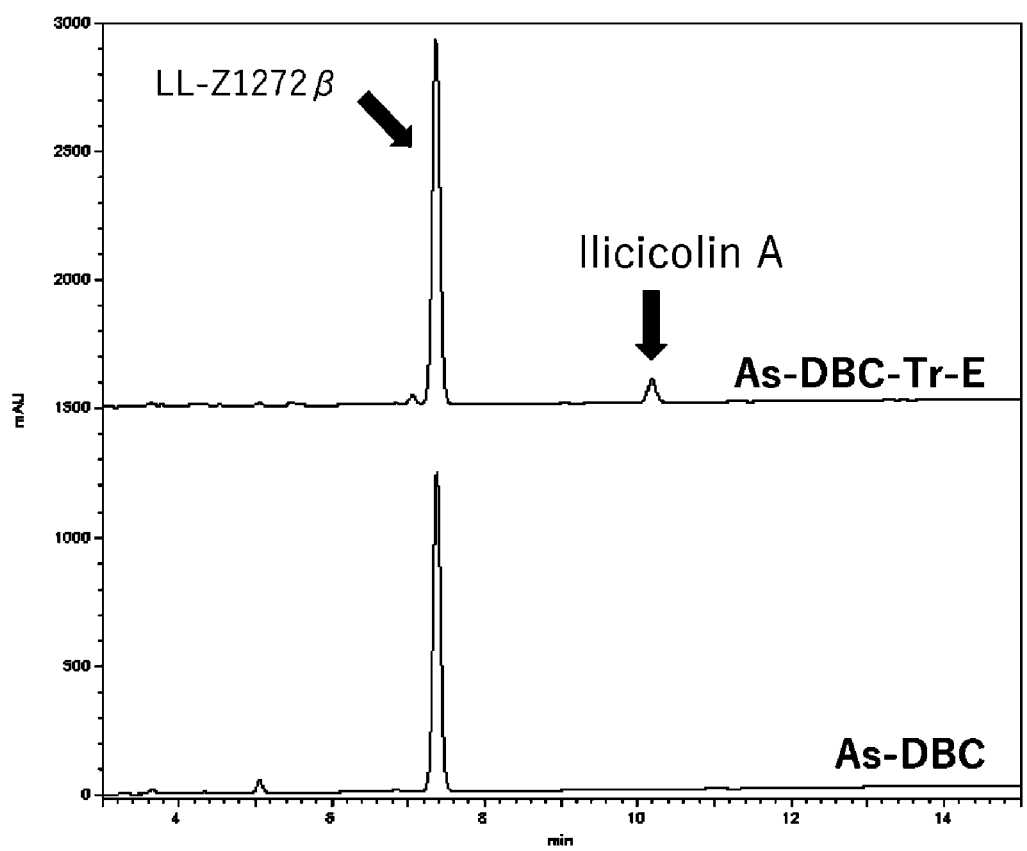
FIG. 15 shows the results from HPLC analysis of the extracts from As-DBC-Tr-E and As-DBC strains as described in the Examples below.

Subsequently, As-DBC-Tr-E and As-DBC strains were inoculated into GPY medium supplemented with 5% NaCl and cultured at 30° C. for 4 days. The cultured fungal cells were collected in the same way as described above and extracted with acetone. The acetone extract was analyzed by HPLC. The HPLC analysis was performed using Liquid A: acetonitrile+0.1% (v/v) formic acid and Liquid B: water+0.1% (v/v) formic acid under the gradient condition of 80 to 95% Liquid A (for 15 min) at a flow rate of 1 ml/min on TSK-gel ODS-100V 3 μm column (4.6 mm I.D.×150 mm). As shown from the results in FIG. 15, a new peak that was not observed in As-DBC strain was detected in As-DBC-Tr-E strain at the same elution position as the peak detected in the standard preparation of ilicicolin A. This demonstrated that AscE derived from *Trichoderma* as well as AscE derived from *Acremonium* was a halogenase which uses LL-Z1272β as a substrate. These results revealed that AscB, AscC, AscD, and AscE derived from *Trichoderma* set forth in SEQ ID NOS: 47 to 50 were ilicicolin A biosynthetic enzymes.

(Analysis of Ascofuranone Biosynthetic Pathway)

Figure 16:
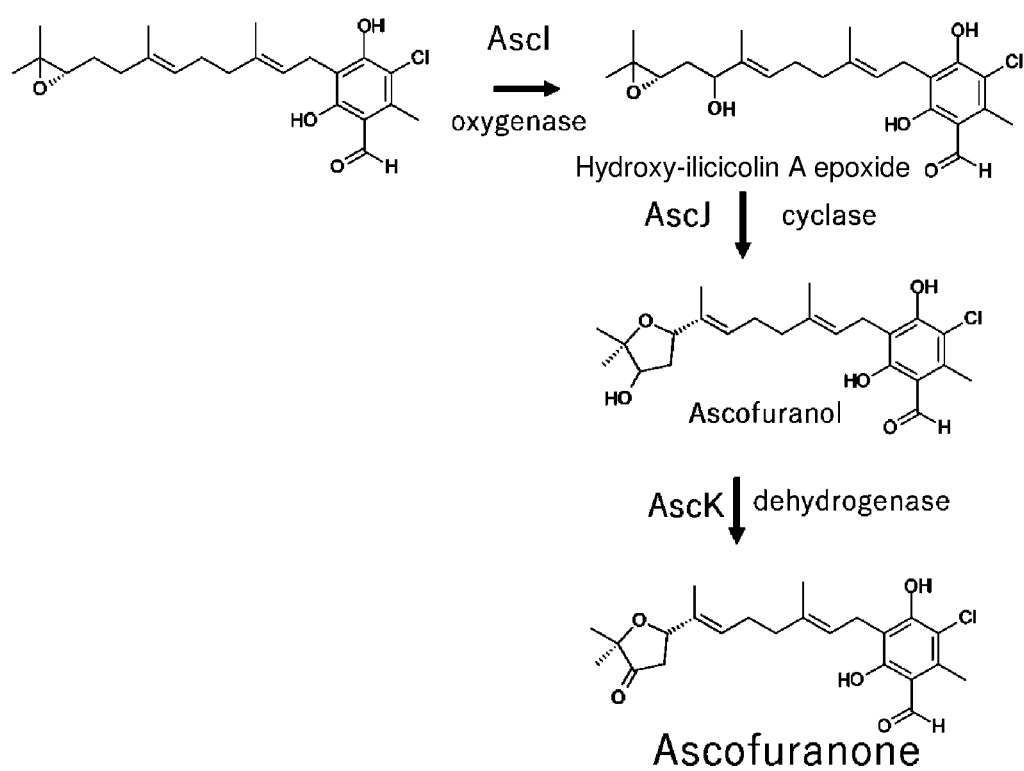
FIG. 16 shows the biosynthetic pathway from ilicicolin A epoxide to ascofuranone.

It is predicted that ascofuranone is biosynthesized by a series of reactions of ilicicolin A epoxide with AscI, AscJ, and AscK in this order in the ascofuranone biosynthetic pathway although products from the reactions with AscI and AscJ were unidentified. Accordingly, the ascG disruptant generated above which had been subjected to pyrG marker recycling was used as a parent strain to generate ascG disruptant/ascJ disruptant. A new peak that was not observed in the ascG disruptant was detected. The compound expected to be a product from the reaction with AscI was purified, analyzed by NMR, and identified as a novel compound having the structure shown in FIG. 16 (hydroxy-ilicicolin A epoxide). It was also found that the reaction of the product of AscI with AscJ produces ascofuranol. It was further found that ascofuranone was produced by reacting AscJ and AscK with the product from the reaction with AscI. These findings revealed that the ascofuranone biosynthetic pathway subsequent to ilicicolin A epoxide is as shown in FIG. 16.

(High Production of Ascofuranone by Forced Expression of AscI)

As mentioned above, the ascG disruptant produces only ascofuranone and has increased production of ascofuranone as compared to wild-type strain. However, as shown in FIG. 13, the peak at an elution time of about 38.5 min was detected in the ascG disruptant and the compound corresponding to this peak was identified as ilicicolin A epoxide. In other words, it was predicted that the reaction with AscI, which was a rate-determining step in the ascG disruptant, causes accumulation of ilicicolin A epoxide. Accordingly, the strain expressing at a high level ascI gene set forth in SEQ ID NO: 8 due to the presence of tef1 promoter derived from *Acremonium* set forth in SEQ ID NO: 62 and tef1 terminator derived from *Acremonium* set forth in SEQ ID NO: 63 (ΔascG-I strain) was generated from the ascG disruptant. The strain was cultured in a medium for inducing high production of ascofuranone in 100 mL bioreactor (Bio Jr. 8) manufactured by Biott at 28° C. for 4 days at 400 rpm at 0.5 vvm.

Figure 17:
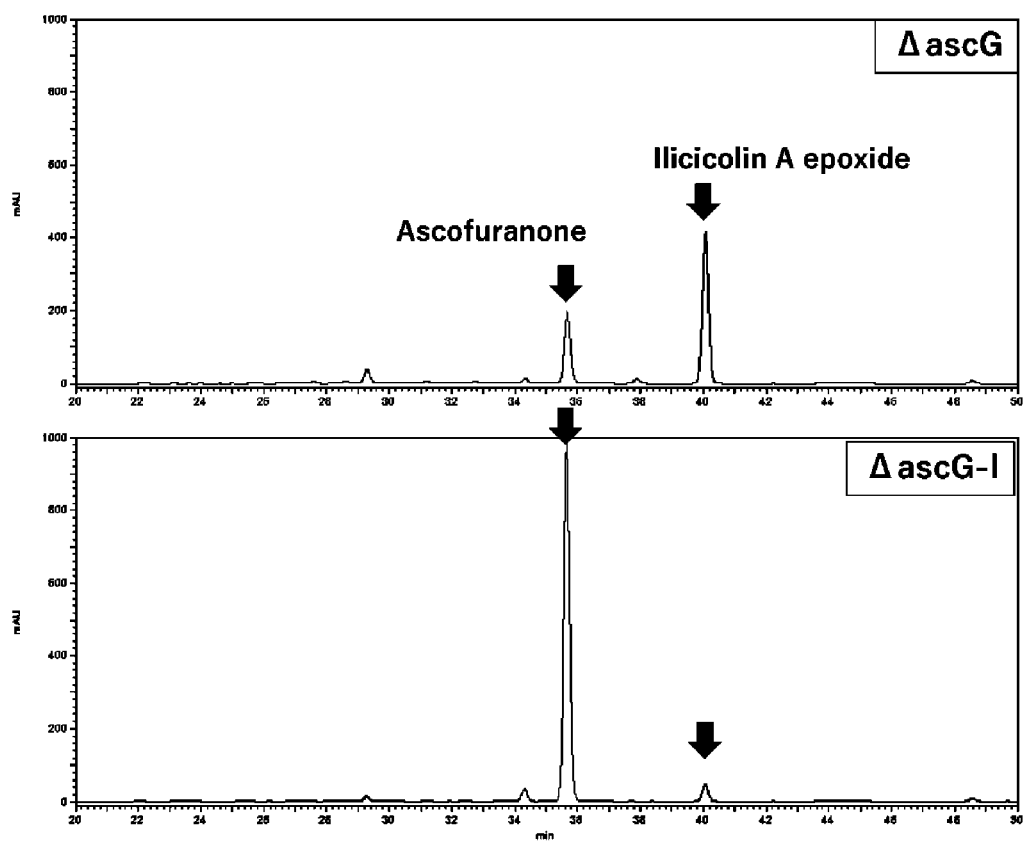
FIG. 17 shows the results from HPLC analysis of the extracts from ΔascG and ΔascG-I strains as described in the Examples below.

The cultured fungal cells were then collected from 10 mL of culture medium, extracted with acetone, and analyzed by HPLC. The HPLC analysis was performed using Liquid A:

acetonitrile+0.1% (v/v) formic acid and Liquid B: water+ 0.1% (v/v) formic acid under the gradient condition of 40 to 100% Liquid A (for 50 min) at a flow rate of 0.5 ml/min on TSK-gel ODS-100V 3 µm column (4.6 mm I.D.×150 mm). As shown from the results in FIG. 17, it was demonstrated that the amount of accumulated ilicicolin A epoxide was decreased and the yield of ascofuranone was greatly increased in ΔascG-I strain as compared to the ascG disruptant (ΔascG).

(Functional Analysis of Asc Homolog Derived from *Neonectria*)

The results from Blastp Search showed that *Neonectria ditissima* has genes, on its genome, encoding homologs of AscB to H (SEQ ID NOS: 35 to 41) having 60% or more sequence identity to AscB to H derived from *Acremonium* set forth in SEQ ID NOS: 11 to 17. Although gene sequences in the published database are not completely assembled, four genes encoding AscB, AscC, AscE, and AscF are at least located adjacent to one another, and two genes encoding AscG and AscH are also located adjacent to each other. Therefore, it was expected that these genes formed a cluster. In addition, the results from tblastn search demonstrated that a gene sequence having 50% or more sequence identity to ascA gene derived from *Acremonium* was located about 0.4 kb upstream of the gene encoding AscH. This suggests that homologs of AscB to H derived from *Neonectria* (SEQ ID NOS: 35 to 41) are ascochlorin biosynthetic enzymes.

It is expected that whether the sequences set forth in SEQ ID NOS: 35 to 41 are ascochlorin biosynthetic enzymes can be determined by analyzing the function of AscG set forth in SEQ ID NO: 40 because AscG which has a function as a terpene cyclase does not have any known domain and is a characteristic enzyme in the biosynthesis of ascochlorin. Accordingly, it was determined whether the expression of AscG derived from *Neonectria* set forth in SEQ ID NO: 40 in the ascG disruptant from *Acremonium sclerotigenum* F-1392 strain obtained above can complement the function of AscG derived from *Acremonium sclerotigenum*.

First, conidia were collected from the ascG disruptant from *Acremonium* sclerotigenum F-1392 strain and about $10^6$ conidia were grown on agar medium containing 5FOA to perform pyrG marker recycling. The strain subjected to marker recycling was ascG and ascH double gene-disrupted strain (ΔascG/ΔascH strain) because ascH gene was also concomitantly disrupted upon the excision of pyrG marker due to the design of the construct. The cassette was introduced into this strain, that allows the high expression of AscG derived from *Neonectria* set forth in SEQ ID NO: 40 using pyrG marker wherein the cassette is composed of tef1 promoter derived from *Acremonium* set forth in SEQ ID NO: 62 and tef1 terminator derived from *Acremonium* set forth in SEQ ID NO: 63. Nd-ascG gene (SEQ ID NO: 64), which is the gene sequence encoding AscG derived from *Neonectria* set forth in SEQ ID NO: 40, was obtained by artificial gene synthesis.

Figure 18:
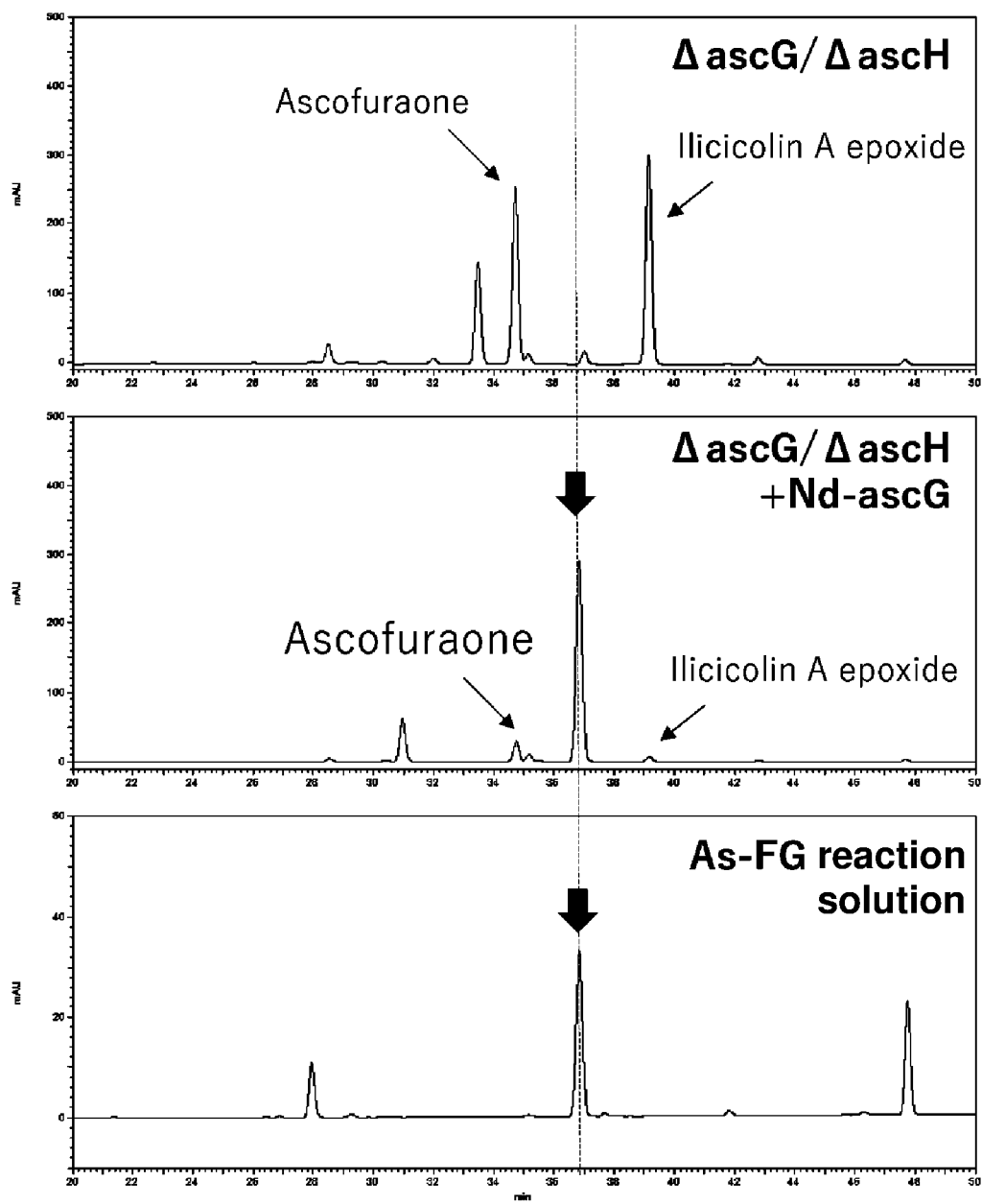
FIG. 18 shows the results from HPLC analysis of the extracts from ΔascG/AascH and ΔascG/AascH+Nd-ascG strains as well as As-FG reaction solution as described in the Examples below.

The ascG and ascH double gene-disrupted strain forced to express Nd-ascG gene (ΔascG/ΔascH+Nd-ascG strain) was cultured in a medium for inducing high production of ascofuranone in the same way as described above. The cultured fungal cells were extracted with acetone and the extract was analyzed by HPLC. As shown from the results in FIG. 18, the strain forced to express Nd-ascG gene had decreased production of ascofuranone and ilicicolin A epoxide while a new peak of compound that was not detected in the strain expressing no Nd-ascG gene was detected. It was demonstrated that this compound was detected at the same elution position as the compound with an m/z value of 405 specifically detected in the As-FG reaction in vitro as described above (ilicicolin C) and was analyzed by mass-spectrometry (MS) to identify a compound with an m/z value of 405. Therefore, AscG derived from *Neonectria* set forth in SEQ ID NO: 40 was demonstrated to have a function similar to that of AscG derived from *Acremonium*.

These results suggested that the AscB to H homologs derived from *Neonectria* set forth in SEQ ID NOS: 35 to 41 are ascochlorin biosynthetic enzymes.

It was revealed that the gene encoding Nd-AscI, which is AscI homolog (SEQ ID NO: 67) having 53% sequence identity to AscI derived from *Acremonium* was located about 6 kb upstream of the gene encoding AscH homolog derived from *Neonectria* (SEQ ID NO: 18). This indicates that the gene encoding Nd-AscI forms a cluster with genes encoding Nd-AscA, Nd-AscG, and Nd-AscH in *Neonectria ditissima*. Nd-AscI is likely to be an enzyme biosynthesizing compounds relevant to intermediates of ascochlorin and ascochlorin. In other words, it was expected that AscI homolog derived from *Neonectria* set forth in SEQ ID NO: 67 had a function similar to that of AscI derived from *Acremonium*. However, the genes encoding homologs of AscJ (SEQ ID NO: 19) and AscK (SEQ ID NO: 20) derived from *Acremonium* were not located near the cluster region of genes encoding Nd-AscI, Nd-AscA, Nd-AscG, and Nd-AscH in *Neonectria ditissima*.

Considering the results from Asc homologs derived from *Trichoderma* and *Neonectria*, it was suggested that when they have a high identity to Asc enzymes derived from *Acremonium*, have the same domain, and are located adjacent to one another on the genome to form a cluster, they are likely to have a function similar to that of Asc enzymes derived from *Acremonium*.

(Construction of a Vector for Forced Expression of AscA)

Whether ascA gene encoding the transcription factor present in the cluster shown in Table 1 regulates the expression of ascochlorin and ascofuranone biosynthetic genes was determined as follows.

The results from RNA sequencing revealed that ascA gene was expressed at a high level in a medium for inducing high production of ascofuranone. Therefore, it was expected that ascA gene positively regulates the ascochlorin and ascofuranone biosynthetic gene clusters. Accordingly, in order to determine whether the forced expression of ascA gene induce production of ascochlorin and ascofuranone in *Acremonium sclerotigenum*, a vector for forced expression of AscA was constructed as follows.

First, PCR was performed using genomic DNA of *Acremonium sclerotigenum* F-1392 strain as a template to clone tef1 gene promoter (Ptef) set forth in SEQ ID NO: 62, ascA gene set forth in SEQ ID NO: 65, tef1 gene terminator (Ttef) set forth in SEQ ID NO: 44, and pyrG gene set forth in SEQ ID NO: 46. These cloned fragments were ligated together in an In-fusion reaction to construct a vector for forced expression of AscA, which was pUC19 having the ascA forced expression cassette containing Ptef-ascA-Ttef-pyrG inserted.

The results from RNA sequencing revealed that AscA protein encoded by ascA gene consists of the amino acid sequence set forth in SEQ ID NO: 66 although ascA gene set forth in SEQ ID NO: 65 is a nucleotide sequence with intron.

(Evaluation of Production Levels of Ascochlorin and Ascofuranone in the Strain Forced to Express AscA)

The strain forced to express AscA was generated by introducing an AscA forced expression vector into the pyrG disruptant from *Acremonium sclerotigenum* F-1392 strain generated above.

*Acremonium sclerotigenum* F-1392 strain (wild-type strain) and the generated strain forced to express AscA were each cultured in GPY liquid medium at 30° C. for 4 days and analyzed by HPLC in the same way as described above. The results are shown in FIG. 19.

As shown in FIG. 19, wild-type strain did not produce ascochlorin and ascofuranone at all in GPY medium. In contrast, it was confirmed that the strain forced to express AscA produced both ascochlorin and ascofuranone.

So far, there have been problems that wild-type strains produce ascochlorin and ascofuranone only in a limited medium and slight differences in culture condition cause great variances of production. However, use of the strain forced to express AscA allows the production of ascochlorin and ascofuranone without the predetermined culture condition, achieving the stable industrial-scale production of isoprenoids such as ascochlorin, ascofuranone, and ilicicolin A. This is industrially very useful.

The sequences set forth in the Sequence Listing are as follows:
[SEQ ID NO: 1] ascB
[SEQ ID NO: 2] ascC
[SEQ ID NO: 3] ascD
[SEQ ID NO: 4] ascE
[SEQ ID NO: 5] ascF
[SEQ ID NO: 6] ascG
[SEQ ID NO: 7] ascH
[SEQ ID NO: 8] ascI
[SEQ ID NO: 9] ascJ
[SEQ ID NO: 10] ascK
[SEQ ID NO: 11] AscB protein
[SEQ ID NO: 12] AscC protein
[SEQ ID NO: 13] AscD protein
[SEQ ID NO: 14] AscE protein
[SEQ ID NO: 15] AscF protein
[SEQ ID NO: 16] AscG protein
[SEQ ID NO: 17] AscH protein
[SEQ ID NO: 18] AscI protein
[SEQ ID NO: 19] AscJ protein
[SEQ ID NO: 20] AscK protein
[SEQ ID NO: 21] Codon-optimized ascB
[SEQ ID NO: 22] Codon-optimized ascC
[SEQ ID NO: 23] Codon-optimized ascD
[SEQ ID NO: 24] Codon-optimized ascE
[SEQ ID NO: 25] Ptef
[SEQ ID NO: 26] Talp
[SEQ ID NO: 27] pyrG
[SEQ ID NO: 28] Codon-optimized ascF
[SEQ ID NO: 29] Codon-optimized ascG
[SEQ ID NO: 30] Codon-optimized ascH
[SEQ ID NO: 31] Ptef-Fw
[SEQ ID NO: 32] Ptef-Rv
[SEQ ID NO: 33] ascD-Fw
[SEQ ID NO: 34] ascD-Rv
[SEQ ID NO: 35] Nd-AscB protein
[SEQ ID NO: 36] Nd-AscC protein
[SEQ ID NO: 37] Nd-AscD protein
[SEQ ID NO: 38] Nd-AscE protein
[SEQ ID NO: 39] Nd-AscF protein
[SEQ ID NO: 40] Nd-AscG protein
[SEQ ID NO: 41] Nd-AscH protein
[SEQ ID NO: 42] Epoxide hydrolase gene derived from *A. sojae*
[SEQ ID NO: 43] P450 reductase gene derived from *A. sojae*
[SEQ ID NO: 44] Ttef
[SEQ ID NO: 45] ku70
[SEQ ID NO: 46] pyrG
[SEQ ID NO: 47] Tr-AscB protein
[SEQ ID NO: 48] Tr-AscC protein
[SEQ ID NO: 49] Tr-AscD protein
[SEQ ID NO: 50] Tr-AscE protein
[SEQ ID NO: 51] Tr-ascC-Fw
[SEQ ID NO: 52] Tr-ascC-Rv
[SEQ ID NO: 53] Tr-ascC
[SEQ ID NO: 54] pyrG3
[SEQ ID NO: 55] Tr-ascD-Fw
[SEQ ID NO: 56] Tr-ascC-Rv
[SEQ ID NO: 57] Tr-ascD
[SEQ ID NO: 58] Tr-ascB-Fw
[SEQ ID NO: 59] Tr-ascB-Rv
[SEQ ID NO: 60] Tr-ascB
[SEQ ID NO: 61] Codon-optimized Tr-ascE
[SEQ ID NO: 62] Ptef derived from *Acremonium*
[SEQ ID NO: 63] Ttef derived from *Acremonium*
[SEQ ID NO: 64] Nd-ascG
[SEQ ID NO: 65] ascA
[SEQ ID NO: 66] AscA protein
[SEQ ID NO: 67] Nd-AscI protein

INDUSTRIAL APPLICABILITY

The genes, transformants, knockout organisms, and production methods according to one aspect of the present invention can be used to produce a large amount of isoprenoids such as ascofuranone, ilicicolin A, and ascochlorin. Accordingly, the present invention is applicable to the industrial-scale production of isoprenoids such as ascofuranone, ilicicolin A, and ascochlorin.

The invention claimed is:

1. A transformant comprising an isolated gene inserted thereinto, and expressing the isolated gene, provided that the transformant is transformed isoprenoid-producing filamentous fungi, wherein the isolated gene comprises any one of nucleotide sequences of (1) to (4) below that encode an amino acid sequence of an enzyme having an activity of catalyzing monooxygenation of ilicicolin A epoxide:
   (1) a nucleotide sequence set forth in SEQ ID NO: 8;
   (2) a nucleotide sequence having 90% or more sequence identity to the nucleotide sequence set forth in SEQ ID NO: 8;
   (3) a nucleotide sequence encoding an amino acid sequence having 90% or more sequence identity to the amino acid sequence set forth in SEQ ID NO: 18; and
   (4) a nucleotide sequence encoding an amino acid sequence having 1, 2, 3, 4, 5, 6, 7, 8, 9, or 10 amino acids deleted, substituted, and/or added in the amino acid sequence set forth in SEQ ID NO: 18, provided that the amino acids are those per unit when 100 amino acids in the amino acid sequence are considered as one unit.

2. The transformant of claim 1, wherein the isolated gene comprises a nucleotide sequence having 95% or more sequence identity to the nucleotide sequence set forth in SEQ ID NO: 8.

3. The transformant of claim 1, wherein the isolated gene comprises a nucleotide sequence encoding an amino acid sequence having 95% or more sequence identity to the amino acid sequence set forth in SEQ ID NO: 18.

4. The transformant of claim 1, wherein the isolated gene comprises a nucleotide sequence encoding an amino acid sequence having 1, 2, 3, 4, or 5 amino acids deleted, substituted, and/or added in the amino acid sequence set forth in SEQ ID NO: 18, provided that the amino acids are those per unit when 100 amino acids in the amino acid sequence are considered as one unit.

5. The transformant of claim 1, wherein the isolated gene comprises a nucleotide sequence encoding an amino acid sequence having 1 or 2 amino acids deleted, substituted, and/or added in the amino acid sequence set forth in SEQ ID NO: 18, provided that the amino acids are those per unit when 100 amino acids in the amino acid sequence are considered as one unit.

6. A method for producing ascofuranone, comprising:
   providing the transformant according to claim 1,
   growing the transformant, and
   isolating ascofuranone from the transformant.

* * * * *